United States Patent
Bates et al.

(10) Patent No.: US 9,422,283 B2
(45) Date of Patent: Aug. 23, 2016

(54) SALTS AND POLYMORPHS OF A SUBSTITUTED IMIDAZOPYRIDINYL-AMINOPYRIDINE COMPOUND

(71) Applicant: ArQule, Inc., Burlington, MA (US)

(72) Inventors: Craig Bates, Pelham, NH (US); Jianmin Mao, Winchester, MA (US); David Reed, Pelham, NH (US)

(73) Assignee: ArQule, Inc., Burlington, MA (US)

( * ) Notice: Subject to any disclaimer, the term of this patent is extended or adjusted under 35 U.S.C. 154(b) by 0 days.

(21) Appl. No.: 14/693,015

(22) Filed: Apr. 22, 2015

(65) Prior Publication Data

US 2015/0299195 A1    Oct. 22, 2015

Related U.S. Application Data

(60) Provisional application No. 61/982,692, filed on Apr. 22, 2014.

(51) Int. Cl.
| | |
|---|---|
| *A61K 31/437* | (2006.01) |
| *C07D 471/02* | (2006.01) |
| *C07D 471/04* | (2006.01) |
| *C07C 309/04* | (2006.01) |
| *C07D 491/02* | (2006.01) |

(52) U.S. Cl.
CPC ............ *C07D 471/04* (2013.01); *A61K 31/437* (2013.01); *C07C 309/04* (2013.01); *C07B 2200/13* (2013.01); *C07D 471/02* (2013.01); *C07D 491/02* (2013.01)

(58) Field of Classification Search
CPC ......................... A61K 31/4188; A61K 31/437
USPC ........................................... 514/303; 546/118
See application file for complete search history.

(56) References Cited

U.S. PATENT DOCUMENTS

| | | | |
|---|---|---|---|
| 7,348,339 B2 * | 3/2008 | Bailey ................. | C07D 471/04 514/234.2 |
| 8,501,770 B2 | 8/2013 | Ashwell et al. | |
| 8,609,688 B2 | 12/2013 | Ashwell et al. | |
| 8,815,854 B2 | 8/2014 | Ashwell et al. | |
| 8,962,619 B2 | 2/2015 | Ashwell et al. | |
| 2002/0151549 A1 | 10/2002 | Hayakawa et al. | |

FOREIGN PATENT DOCUMENTS

WO    WO-2007111904 A2    10/2007

* cited by examiner

*Primary Examiner* — Kamal Saeed
*Assistant Examiner* — Janet L Coppins
(74) *Attorney, Agent, or Firm* — Cooley LLP; Ivor R. Elrifi; Matthew Pavao

(57) ABSTRACT

The present application relates to salts of Compound A, 3-(3-(4-(1-aminocyclobutyl) phenyl)-5-phenyl-3H-imidazo[4,5-b]pyridin-2-yl)pyridin-2-amine, solid state forms of Compound A free base or of salts of Compound A, amorphous forms of Compound A free base or of salts of Compound A, crystalline forms of Compound A free base or of salts of Compound A, polymorphs of Compound A free base or of salts of Compound A, and mesomorphs of Compound A free base or of salts of Compound A. The present application also relates to pharmaceutical compositions comprising these salts, solid state forms, amorphous forms, crystalline forms, polymorphs, or mesomorphs of Compound A free base or of salts of Compound A. The present application provides methods for preparing these salts, solid state forms, amorphous forms, crystalline forms, polymorphs, or mesomorphs of Compound A free base or of salts of Compound A.

40 Claims, 194 Drawing Sheets

2-D ISIS Draw and 3-D ball and stick representations

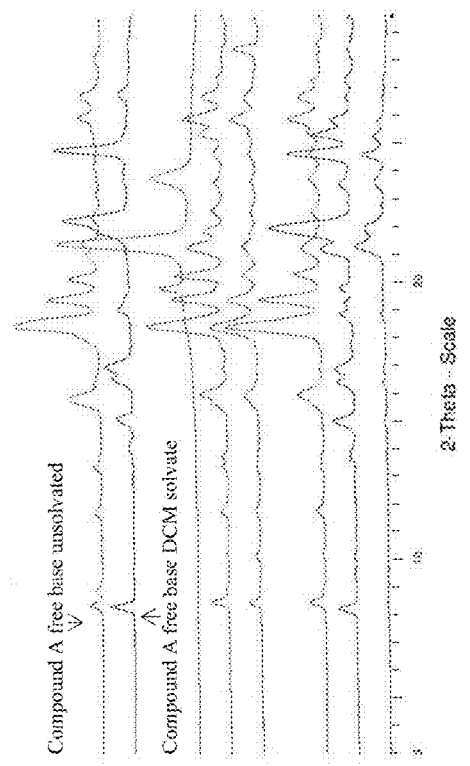
Figure 54
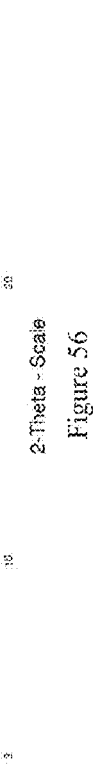
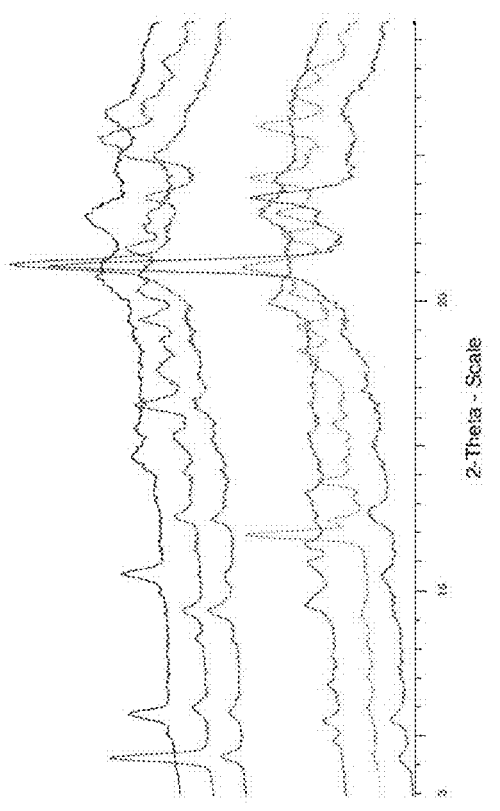
Figure 53
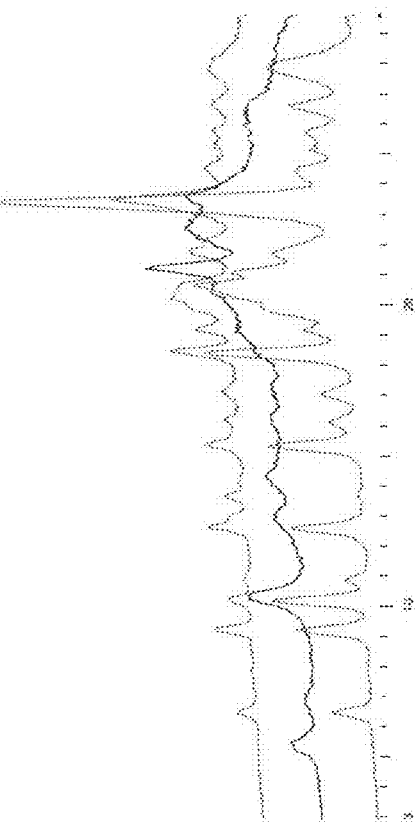
Figure 56
Figure 55

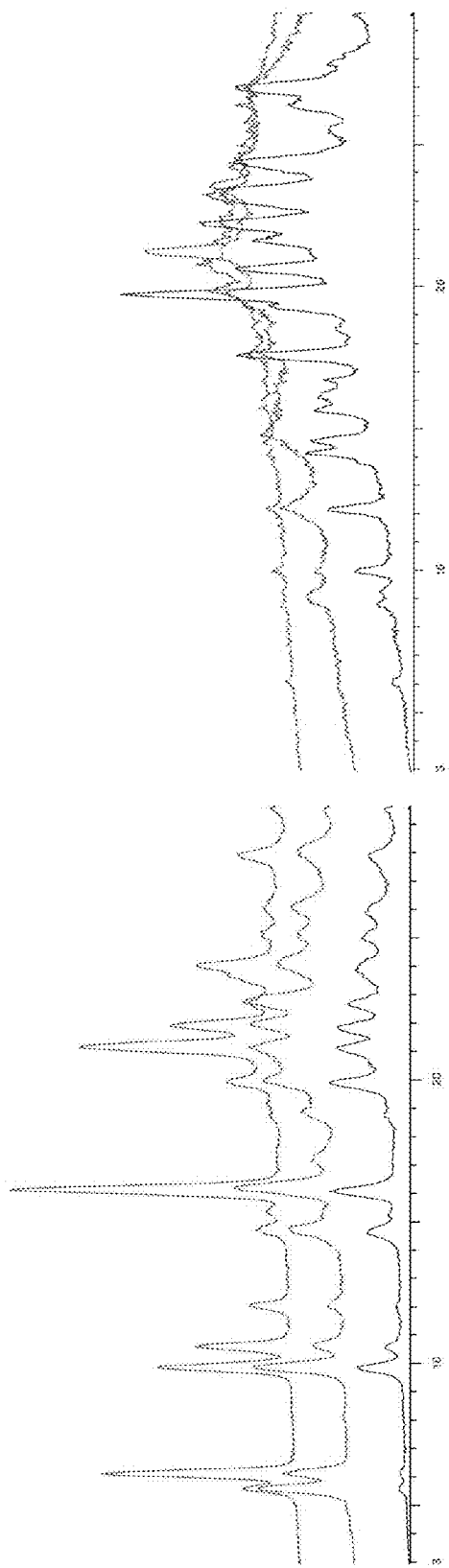
Figure 57
Figure 58
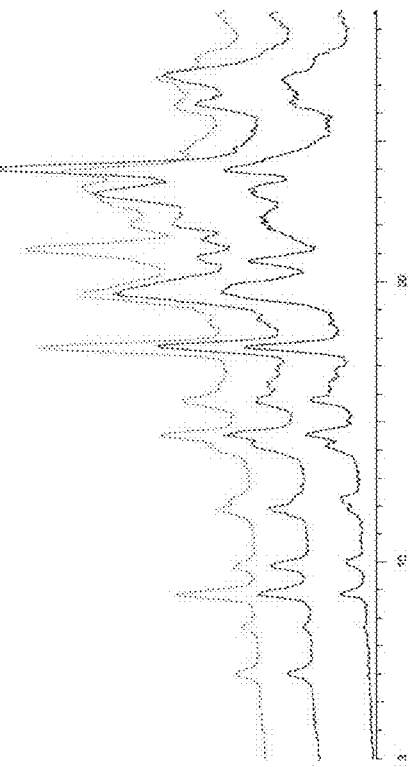
Figure 60
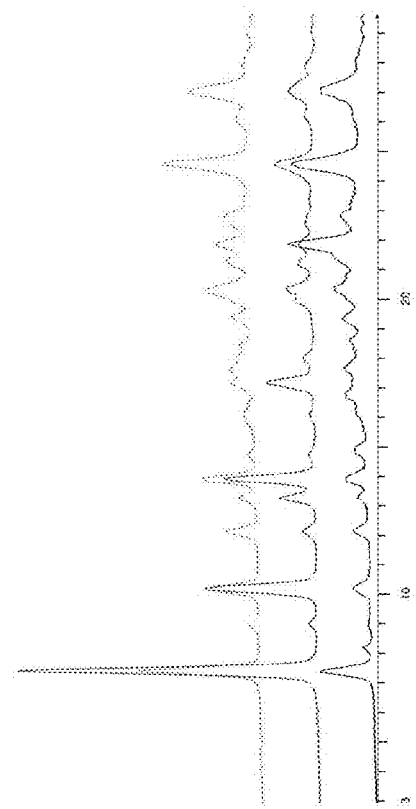
Figure 59

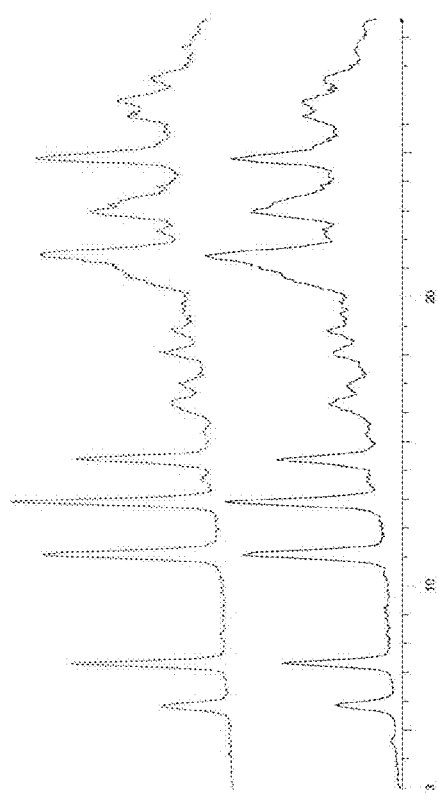
Figure 65
Figure 66
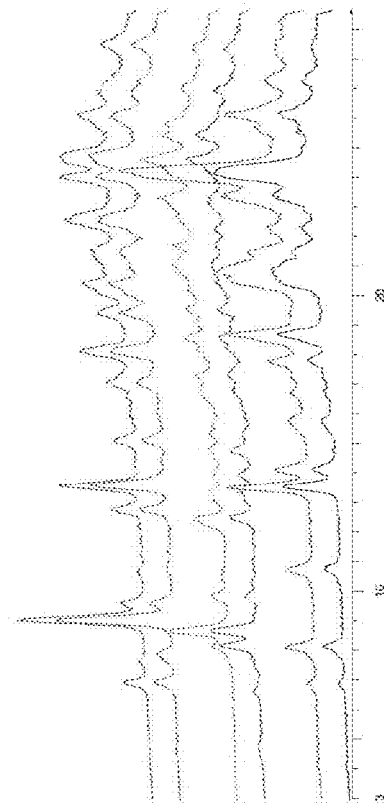
Figure 67
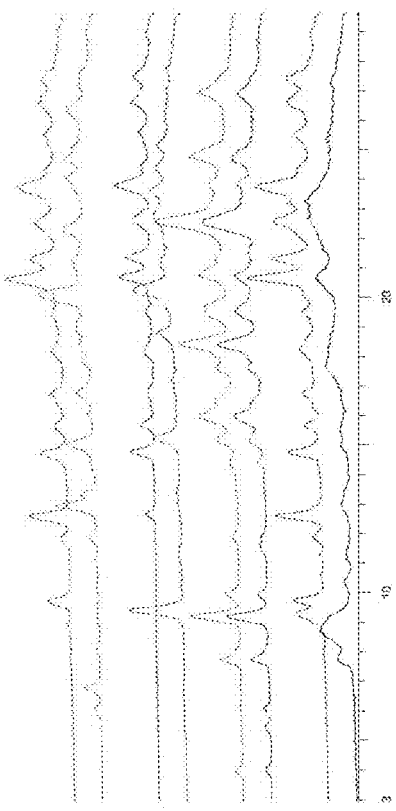
Figure 68

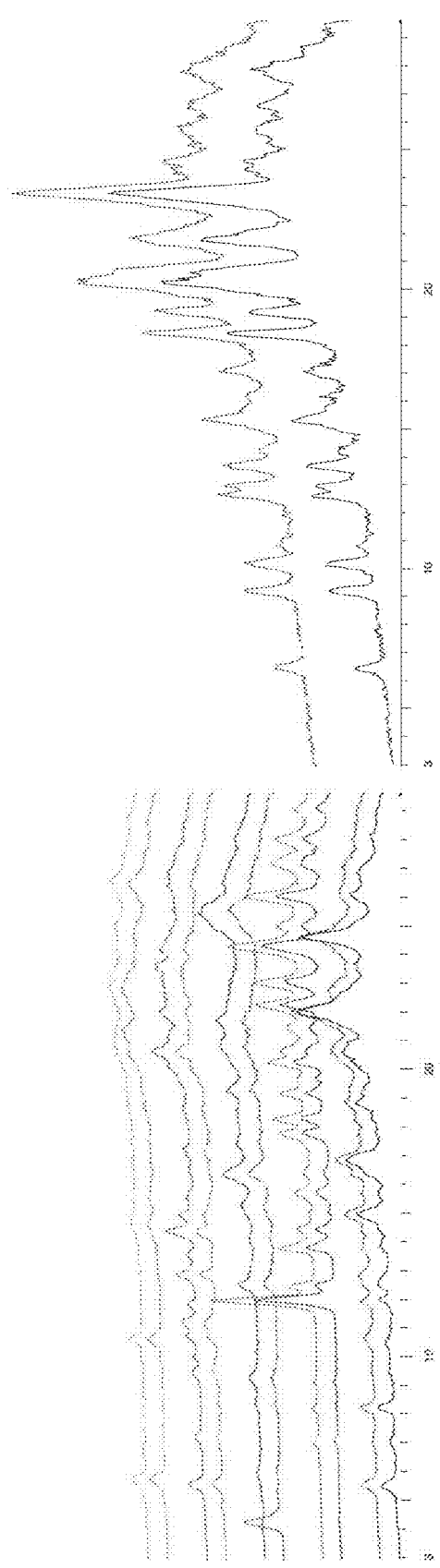
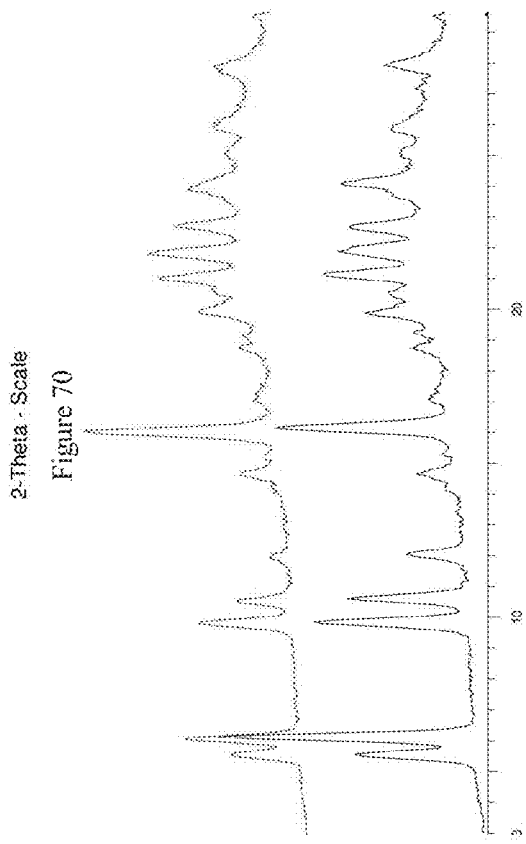
Figure 69
Figure 70
Figure 71
Figure 72

| Pos. [°2θ] | Height [cts] | Rel. Int. [%] |
|---|---|---|
| 3.7941 | 457.45 | 41.17 |
| 7.5782 | 404.98 | 36.45 |
| 7.8851 | 100.08 | 9.01 |
| 9.1234 | 1111.00 | 100.00 |
| 9.8745 | 486.99 | 43.83 |
| 11.8166 | 206.75 | 18.61 |
| 15.1479 | 280.98 | 25.29 |
| 15.9642 | 559.19 | 50.33 |
| 16.1378 | 538.59 | 48.48 |
| 16.4881 | 188.75 | 16.99 |
| 17.6322 | 284.66 | 25.62 |
| 18.4603 | 642.94 | 57.87 |
| 19.5760 | 130.31 | 11.73 |
| 20.9246 | 101.96 | 9.18 |
| 22.3197 | 152.01 | 13.68 |
| 22.7806 | 917.35 | 82.57 |
| 22.8709 | 770.35 | 69.34 |
| 23.1823 | 309.89 | 27.89 |
| 23.4652 | 211.40 | 19.03 |
| 24.8874 | 79.96 | 7.20 |
| 27.1402 | 115.37 | 10.38 |
| 27.6424 | 67.32 | 6.06 |
| 29.2701 | 41.11 | 3.70 |

Figure 112

| Pos. [°2θ] | Height [cts] | Rel. Int. [%] |
|---|---|---|
| 5.9683 | 2168.99 | 100.00 |
| 6.3985 | 1371.75 | 63.24 |
| 7.8862 | 232.17 | 10.70 |
| 9.6201 | 185.07 | 8.53 |
| 10.4244 | 290.56 | 13.40 |
| 11.1416 | 1728.92 | 79.71 |
| 12.0357 | 338.22 | 15.59 |
| 14.5842 | 240.48 | 11.09 |
| 15.1094 | 1161.91 | 53.57 |
| 16.7812 | 180.94 | 8.34 |
| 17.2659 | 448.48 | 20.68 |
| 18.7307 | 32.30 | 1.49 |
| 19.4562 | 243.93 | 11.25 |
| 19.9354 | 172.72 | 7.96 |
| 20.2600 | 49.48 | 2.28 |
| 20.8698 | 157.12 | 7.24 |
| 21.6779 | 78.81 | 3.63 |
| 22.4745 | 708.60 | 32.67 |
| 22.7231 | 695.85 | 32.08 |
| 23.6774 | 732.35 | 33.76 |
| 24.0600 | 99.48 | 4.59 |
| 24.2741 | 170.80 | 7.87 |
| 24.7896 | 205.75 | 9.49 |
| 25.4709 | 90.32 | 4.16 |
| 26.0836 | 125.44 | 5.78 |
| 26.4074 | 127.25 | 5.87 |
| 27.0267 | 433.60 | 19.99 |
| 28.2111 | 170.85 | 7.88 |
| 28.6473 | 205.61 | 9.48 |
| 29.4484 | 137.54 | 6.34 |

Figure 131

| Pos. [°2θ] | Height [cts] | Rel. Int. [%] |
|---|---|---|
| 5.8207 | 59.35 | 3.26 |
| 6.0000 | 53.92 | 2.96 |
| 8.6737 | 234.31 | 12.85 |
| 9.6042 | 180.06 | 9.88 |
| 9.9272 | 180.07 | 9.88 |
| 12.1578 | 259.09 | 14.21 |
| 12.5325 | 392.14 | 21.51 |
| 13.4636 | 235.75 | 12.93 |
| 14.5000 | 72.59 | 3.98 |
| 14.8273 | 87.55 | 4.80 |
| 16.5519 | 433.75 | 23.79 |
| 17.4558 | 359.10 | 19.70 |
| 18.2241 | 779.92 | 42.78 |
| 18.5184 | 191.05 | 10.48 |
| 19.0330 | 158.93 | 8.72 |
| 19.3358 | 224.18 | 12.30 |
| 19.5523 | 614.45 | 33.70 |
| 20.1292 | 1823.12 | 100.00 |
| 20.3760 | 346.74 | 19.02 |
| 21.2752 | 103.55 | 5.68 |
| 21.4215 | 155.94 | 8.55 |
| 21.7116 | 282.62 | 15.50 |
| 22.6349 | 702.94 | 38.56 |
| 22.9973 | 282.42 | 15.49 |
| 23.5896 | 352.55 | 19.34 |
| 23.9611 | 249.64 | 13.69 |
| 24.4081 | 208.88 | 11.46 |
| 24.8000 | 46.05 | 2.53 |
| 25.0795 | 227.37 | 12.47 |
| 25.3271 | 114.77 | 6.30 |
| 26.2607 | 61.78 | 3.39 |
| 26.6238 | 465.08 | 25.51 |
| 27.1667 | 250.55 | 13.74 |
| 27.4983 | 181.19 | 9.94 |
| 27.6400 | 90.23 | 4.95 |
| 28.1899 | 92.05 | 5.05 |
| 28.4503 | 166.40 | 9.13 |
| 29.0687 | 154.91 | 8.50 |
| 29.7014 | 56.59 | 3.10 |

Figure 147

Acetone:water (90:10)

Tetrahydrofuran:water (70:30)

Water

Acetone

Acetonitrile

2-Propanol

Acetone

Acetonitrile

Acetone

Acetonitrile

| Pos. [°2θ] | Height [cts] | Rel. Int. |
|---|---|---|
| 5.3834 | 389.47 | 37.49 |
| 5.9327 | 843.08 | 81.14 |
| 9.1787 | 143.44 | 13.81 |
| 10.8297 | 122.30 | 11.77 |
| 11.4709 | 894.85 | 86.13 |
| 11.9152 | 246.47 | 23.72 |
| 13.8445 | 121.40 | 11.68 |
| 14.5324 | 1038.98 | 100.00 |
| 15.4866 | 105.47 | 10.15 |
| 16.2854 | 26.79 | 2.58 |
| 17.0709 | 97.94 | 9.43 |
| 17.9070 | 355.32 | 34.20 |
| 18.4581 | 128.98 | 12.41 |
| 19.0700 | 32.97 | 3.17 |
| 19.5000 | 51.75 | 4.98 |
| 19.8136 | 127.97 | 12.32 |
| 20.2703 | 766.85 | 73.81 |
| 20.7622 | 158.23 | 15.23 |
| 21.4000 | 41.75 | 4.02 |
| 21.9239 | 94.93 | 9.14 |
| 22.6339 | 233.67 | 22.49 |
| 23.0314 | 1012.74 | 97.47 |
| 23.2800 | 147.63 | 14.21 |
| 23.6132 | 471.10 | 45.34 |
| 24.0146 | 356.66 | 34.33 |
| 24.2851 | 192.35 | 18.51 |
| 24.8004 | 101.34 | 9.75 |
| 25.6987 | 66.74 | 6.42 |
| 26.2402 | 395.80 | 38.09 |
| 27.2663 | 186.16 | 17.92 |
| 27.3305 | 192.76 | 18.55 |
| 27.8485 | 327.51 | 31.52 |
| 28.6886 | 122.06 | 11.75 |
| 28.9250 | 347.91 | 33.49 |
| 29.2400 | 71.75 | 6.91 |
| 29.7544 | 126.02 | 12.13 |

Figure 241

| Pos. [°2θ] | Height [cts] | Rel. Int. [%] |
|---|---|---|
| 5.5400 | 41.47 | 5.87 |
| 5.7574 | 142.44 | 20.16 |
| 7.0563 | 170.28 | 24.10 |
| 8.9421 | 380.10 | 53.80 |
| 9.5861 | 299.17 | 42.35 |
| 11.3337 | 376.18 | 53.25 |
| 13.7350 | 681.45 | 96.45 |
| 15.2141 | 142.05 | 20.11 |
| 16.5184 | 385.60 | 54.58 |
| 16.9493 | 74.23 | 10.51 |
| 17.5400 | 37.47 | 5.30 |
| 17.7600 | 37.47 | 5.30 |
| 18.1137 | 178.24 | 25.23 |
| 19.2826 | 399.21 | 56.51 |
| 19.7142 | 217.86 | 30.84 |
| 19.8348 | 174.43 | 24.69 |
| 20.6141 | 625.06 | 88.47 |
| 20.9145 | 688.30 | 97.42 |
| 21.3756 | 125.20 | 17.72 |
| 21.9381 | 706.50 | 100.00 |
| 22.6487 | 332.61 | 47.08 |
| 22.9562 | 648.91 | 91.85 |
| 23.2707 | 210.89 | 29.85 |
| 23.7510 | 358.48 | 50.74 |
| 24.5449 | 171.06 | 24.21 |
| 24.9263 | 165.20 | 23.38 |
| 25.2628 | 160.60 | 22.73 |
| 26.2424 | 387.69 | 54.87 |
| 26.6329 | 330.71 | 46.81 |
| 27.3162 | 98.47 | 13.94 |
| 27.4834 | 118.91 | 16.83 |
| 27.9470 | 96.76 | 13.70 |
| 28.3260 | 315.00 | 44.59 |
| 28.6344 | 189.05 | 26.76 |
| 29.3200 | 80.94 | 11.46 |

Figure 244

| Pos. [°2θ] | Height [cts] | Rel. Int. [%] |
|---|---|---|
| 4.8431 | 242.03 | 39.39 |
| 7.2089 | 260.61 | 42.41 |
| 9.5400 | 11.51 | 1.87 |
| 11.2608 | 162.36 | 26.42 |
| 12.0534 | 121.96 | 19.85 |
| 12.9109 | 112.07 | 18.24 |
| 14.2584 | 82.50 | 13.43 |
| 14.9742 | 45.30 | 7.37 |
| 15.5678 | 195.62 | 31.84 |
| 16.7364 | 453.94 | 73.88 |
| 16.9771 | 614.48 | 100.00 |
| 19.4968 | 486.69 | 79.20 |
| 20.3243 | 331.76 | 53.99 |
| 20.7549 | 100.65 | 16.38 |
| 20.9930 | 94.59 | 15.39 |
| 21.6517 | 194.48 | 31.65 |
| 23.0578 | 169.04 | 27.51 |
| 24.0330 | 329.71 | 53.66 |
| 24.4015 | 391.30 | 63.68 |
| 25.2871 | 122.23 | 19.89 |
| 25.5997 | 98.70 | 16.06 |
| 27.1028 | 33.67 | 5.48 |
| 28.9886 | 49.34 | 8.03 |

Figure 247

| Pos. [°2θ] | Height [cts] | Rel. Int. [%] |
|---|---|---|
| 5.7794 | 730.13 | 100.00 |
| 6.1717 | 45.61 | 6.25 |
| 10.8269 | 120.78 | 16.54 |
| 14.8754 | 150.55 | 20.62 |
| 16.3195 | 178.09 | 24.39 |
| 16.7821 | 43.70 | 5.98 |
| 17.7081 | 94.48 | 12.94 |
| 18.5000 | 13.36 | 1.83 |
| 19.1961 | 37.39 | 5.12 |
| 22.1056 | 352.58 | 48.29 |
| 23.0640 | 105.81 | 14.49 |
| 23.7344 | 296.85 | 40.66 |
| 24.5429 | 52.88 | 7.24 |
| 25.4325 | 30.74 | 4.21 |
| 26.0600 | 24.59 | 3.37 |
| 26.5453 | 72.94 | 9.99 |

Figure 250

| Pos. [°2θ] | Height [cts] | Rel. Int. [%] |
|---|---|---|
| 6.1202 | 241.52 | 50.61 |
| 7.8800 | 40.29 | 8.44 |
| 10.0633 | 118.75 | 24.89 |
| 10.9307 | 351.33 | 73.63 |
| 12.3580 | 200.86 | 42.09 |
| 14.9337 | 62.12 | 13.02 |
| 15.6612 | 166.22 | 34.83 |
| 15.9208 | 200.17 | 41.95 |
| 16.4433 | 141.26 | 29.60 |
| 16.7062 | 94.97 | 19.90 |
| 17.3969 | 64.10 | 13.43 |
| 18.5444 | 64.85 | 13.59 |
| 19.8025 | 95.13 | 19.94 |
| 20.3722 | 181.14 | 37.96 |
| 20.7600 | 180.17 | 37.76 |
| 22.8191 | 477.18 | 100.00 |
| 24.0858 | 78.86 | 16.53 |
| 24.8619 | 78.51 | 16.45 |
| 25.7424 | 57.41 | 12.03 |
| 26.7252 | 108.80 | 22.80 |
| 27.9847 | 88.71 | 18.59 |
| 28.3600 | 58.26 | 12.21 |
| 28.7419 | 75.91 | 15.91 |

Figure 253

| Pos. [°2θ] | Height [cts] | Rel. Int. [%] |
|---|---|---|
| 5.1895 | 196.38 | 69.18 |
| 5.9744 | 88.35 | 31.13 |
| 6.2267 | 146.71 | 51.68 |
| 10.5063 | 283.86 | 100.00 |
| 11.1000 | 125.42 | 44.18 |
| 13.6424 | 161.78 | 56.99 |
| 15.1200 | 37.63 | 13.26 |
| 16.5355 | 58.39 | 20.57 |
| 18.8455 | 55.65 | 19.60 |
| 20.1730 | 180.28 | 63.51 |
| 21.1955 | 92.16 | 32.47 |
| 22.0146 | 117.18 | 41.28 |
| 22.2750 | 124.73 | 43.94 |
| 22.9587 | 148.08 | 52.17 |
| 23.8192 | 136.17 | 47.97 |
| 24.7203 | 73.62 | 25.94 |
| 25.5000 | 40.68 | 14.33 |
| 26.1291 | 58.45 | 20.59 |
| 27.4329 | 72.91 | 25.69 |
| 28.4400 | 25.34 | 8.93 |

Figure 256

| Pos. [°2θ] | Height [cts] | Rel. Int. [%] |
|---|---|---|
| 6.1049 | 52.72 | 26.82 |
| 6.8454 | 47.11 | 23.96 |
| 10.1539 | 33.09 | 16.84 |
| 14.5938 | 110.95 | 56.44 |
| 17.0474 | 128.82 | 65.53 |
| 18.4898 | 34.24 | 17.42 |
| 19.7007 | 88.13 | 44.83 |
| 20.3812 | 83.77 | 42.62 |
| 21.8652 | 99.40 | 50.56 |
| 22.8358 | 196.58 | 100.00 |
| 24.7587 | 108.26 | 55.07 |
| 25.3363 | 76.56 | 38.95 |
| 26.7084 | 81.81 | 41.62 |
| 27.7159 | 63.68 | 32.39 |
| 29.0174 | 51.08 | 25.98 |

Figure 259

| Pos. [°2θ] | Height [cts] | Rel. Int. [%] |
|---|---|---|
| 4.0579 | 1774.53 | 62.84 |
| 7.5015 | 1531.15 | 54.22 |
| 7.8239 | 598.00 | 21.18 |
| 9.2076 | 2823.72 | 100.00 |
| 9.9907 | 2489.52 | 88.16 |
| 12.0903 | 464.99 | 16.47 |
| 14.8351 | 758.11 | 26.85 |
| 15.3500 | 1072.73 | 37.99 |
| 15.7176 | 2405.15 | 85.18 |
| 16.4012 | 1008.92 | 35.73 |
| 16.7162 | 1170.28 | 41.44 |
| 17.5453 | 1675.56 | 59.34 |
| 17.8940 | 1246.03 | 44.13 |
| 18.5538 | 1308.18 | 46.33 |
| 19.3000 | 1557.44 | 55.16 |
| 19.9743 | 2327.01 | 82.41 |
| 20.6146 | 1438.72 | 50.95 |
| 21.4944 | 1893.01 | 67.04 |
| 22.2597 | 1310.37 | 46.41 |
| 23.1670 | 1806.52 | 63.98 |
| 23.7869 | 2161.85 | 76.56 |
| 24.1887 | 966.77 | 34.24 |
| 24.5332 | 805.33 | 28.52 |
| 25.5372 | 526.45 | 18.64 |
| 26.0639 | 1229.82 | 43.55 |
| 26.5022 | 718.12 | 25.43 |

Figure 262

SALTS AND POLYMORPHS OF A SUBSTITUTED IMIDAZOPYRIDINYL-AMINOPYRIDINE COMPOUND

RELATED APPLICATION

This application claims priority to, and the benefit of, U.S. Ser. No. 61/982,692, filed on Apr. 22, 2014, the contents of which are incorporated herein by reference in its entirety.

BACKGROUND

Cancer is the second leading cause of death in the United States, exceeded only by heart disease (Cancer Facts and Figures 2004, American Cancer Society, Inc.) Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

Cancer cells are by definition heterogeneous. For example, within a single tissue or cell type, multiple mutational 'mechanisms' may lead to the development of cancer. As such, heterogeneity frequently exists between cancer cells taken from tumors of the same tissue and same type that have originated in different individuals. Frequently observed mutational 'mechanisms' associated with some cancers may differ between one tissue type and another (e.g., frequently observed mutational 'mechanisms' leading to colon cancer may differ from frequently observed 'mechanisms' leading to leukemia). It is therefore often difficult to predict whether a particular cancer will respond to a particular chemotherapeutic agent (Cancer Medicine, 5th Edition, Bast et al. eds., B. C. Decker Inc., Hamilton, Ontario).

Components of cellular signal transduction pathways that regulate the growth and differentiation of normal cells can, when dysregulated, lead to the development of cellular proliferative disorders and cancer. Mutations in cellular signaling proteins may cause such proteins to become expressed or activated at inappropriate levels or at inappropriate times during the cell cycle, which in turn may lead to uncontrolled cellular growth or changes in cell-cell attachment properties. For example, dysregulation of receptor tyrosine kinases by mutation, gene rearrangement, gene amplification, and overexpression of both receptor and ligand has been implicated in the development and progression of human cancers.

AKT protein family, whose members are also called protein kinases B (PKB), plays an important role in mammalian cellular signaling. In humans, there are three genes in the AKT family: Akt1, Akt2, and Akt3. These genes code for enzymes that are members of the serine/threonine-specific protein kinase family. Akt1 is involved in cellular survival pathways, by inhibiting apoptotic processes. Akt1 is also able to induce protein synthesis pathways, and is therefore a key signaling protein in the cellular pathways that lead to skeletal muscle hypertrophy, and general tissue growth. Akt2 is an important signaling molecule in the insulin signaling pathway and is required to induce glucose transport. The role of Akt3 is less clear, though it appears to be predominantly expressed in brain.

The AKT family regulates cellular survival and metabolism by binding and regulating many downstream effectors, e.g., Nuclear Factor-κB, Bcl-2 family proteins and murine double minute 2 (MDM2). Akt1 is known to play a role in the cell cycle. Moreover, activated Akt1 may enable proliferation and survival of cells that have sustained a potentially mutagenic impact and, therefore, may contribute to acquisition of mutations in other genes. Akt1 has also been implicated in angiogenesis and tumor development. Studies have shown that deficiency of Akt1 enhanced pathological angiogenesis and tumor growth associated with matrix abnormalities in skin and blood vessels. Since it can block apoptosis, and thereby promote cell survival, Akt1 is a major factor in many types of cancer.

Accordingly, new compounds and methods for modulating AKT genes and treating proliferation disorders, including cancer, are needed. Identification of free base and salts of these compounds, and solid forms, such as amorphous forms, crystalline forms and mesomorphic forms, of the free base or salts of these compounds with optimal physical and chemical properties will advance the development of these compounds as pharmaceuticals. The most useful of such physical and chemical properties include: easy and reproducible preparation, crystallinity, non-hygroscopicity, aqueous solubility, stability to visible and ultraviolet light, low rate of degradation under accelerated stability conditions of temperature and humidity, low rate of isomerization between isomeric forms, and safety for long-term administration to humans. The present application addresses these needs.

SUMMARY

The application pertains, at least in part, to a solid state form of a substituted imidazopyridinyl-aminopyridine compound, Compound A:

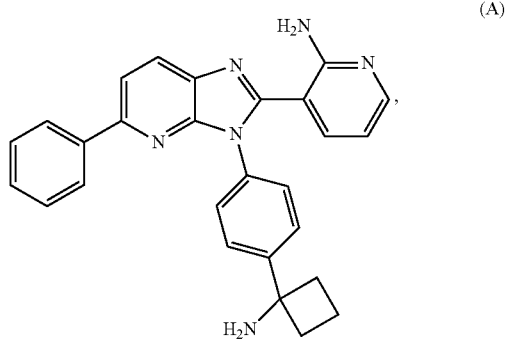 [SMILES: Nc1ncccc1-c1nc2ccc(-c3ccccc3)nc2n1-c1ccc(C2(N)CCC2)cc1]

(A)

3-(3-(4-(1-aminocyclobutyl)phenyl)-5-phenyl-3H-imidazo[4,5-b]pyridin-2-yl)pyridin-2-amine The application also pertains, at least in part, to a salt of Compound A.

The application also pertains, at least in part, to a solid state form of Compound A free base or of a salt of Compound A.

In one embodiment, the salt of Compound is a mono-salt, a bis-salt, or a tris-salt.

In one embodiment, the application pertains to an HCl salt of Compound A. In one embodiment, the HCl salt of Compound A is a mono-, bis-, or tris-HCl salt. In one embodiment, the HCl salt of Compound A is a tris-HCl salt.

In one embodiment, the application pertains to a mesylate (i.e., methane sulfonic acid salt) of Compound A. In one embodiment, the mesylate of Compound A is a mono-, bis-, or tris-salt. In one embodiment, the mesylate of Compound A is a bis-mesylate.

In one embodiment, the solid state form is an amorphous form. In another embodiment, the solid state form is a crystalline form. In another embodiment, the solid state form is a mesomorphic form. In a further embodiment, the solid state form is unsolvated. In a further embodiment, the solid state form is a solvate.

In a further embodiment, the solid of Compound A free base or of a salt of Compound A is in multiple polymorphic forms.

In one embodiment, the solid state form of Compound A free base or of a salt of Compound A is a stable solid state form. In one embodiment, the solid state form of Compound A free base or of a salt of Compound A is a stable amorphous form. In another embodiment, the solid state form of Compound A free base or of a salt of Compound A is a stable crystalline form. In another embodiment, the solid state form of Compound A free base or of a salt of Compound A is a stable polymorph. In one embodiment, the solid state form of Compound A free base or of a salt of Compound A is a stable mesomorph.

In one embodiment, the polymorphs of Compound A free base are unsolvated. In another embodiment, the polymorphs of Compound A free base are solvate. In one embodiment, the polymorphs of a Compound A salt are unsolvated. In another embodiment, the polymorphs of a Compound A salt are solvate.

The application also pertains, at least in part, to polymorphs of Compound A free base. In one embodiment, the polymorph of Compound A free base is Form 1. In some embodiments, Form 1 has X-ray powder diffraction peaks at approximately 22.0 and 25.0°2θ using Cu Kα radiation. In some embodiments, Form 1 has X-ray powder diffraction peaks at approximately 8.3, 17.1, 22.0, and 25.0°2θ using Cu Kα radiation. In some embodiments, Form 1 has X-ray powder diffraction peaks at approximately 8.3, 9.5, 12.9, 14.1, 15.2, 16.6, 17.1, 19.2, 19.4, 19.6, 21.2, 22.0, 22.4 and 25.0°2θ using Cu Kα radiation. In some embodiments, Form 1 is a solvate. In further embodiments, Form 1 is a dichloromethane (DCM) or methyl ethyl ketone (MEK) solvate. In further embodiments, Form 1 is a DCM hemi solvate or a MEK hemi solvate.

In another embodiment, the polymorph of Compound A free base is Form 2. In some embodiments, Form 2 has X-ray powder diffraction peaks at approximately 18.4 and 19.3°2θ using Cu Kα radiation. In some embodiments, Form 2 has X-ray powder diffraction peaks at approximately 15.8, 18.4, 19.3, and 20.1°2θ using Cu Kα radiation. In some embodiments, Form 2 has X-ray powder diffraction peaks at approximately 8.3, 8.8, 11.6, 13.3, 15.8, 18.4, 19.3, 20.1, 20.9, 21.4, 23.2, 25.9 and 26.6°2θ using Cu Kα radiation. In some embodiments, Form 2 is unsolvated.

In another embodiment, the polymorph of Compound A free base is Form 3. In some embodiments, Form 3 has X-ray powder diffraction peaks at approximately 15.1 and 23.4°2θ using Cu Kα radiation. In some embodiments, Form 3 has X-ray powder diffraction peaks at approximately 15.1, 18.8, 21.0, and 23.4°2θ using Cu Kα radiation. In some embodiments, Form 3 has X-ray powder diffraction peaks at approximately 6.4, 7.6, 8.4, 11.7, 15.1, 16.7, 18.8, 21.0, and 23.4°2θ using Cu Kα radiation. In some embodiments, Form 3 is unsolvated.

In another embodiment, the polymorph of Compound A free base is Form 4. In some embodiments, Form 4 has X-ray powder diffraction peaks at approximately 17 and 23°2θ using Cu Kα radiation. In some embodiments, Form 4 has X-ray powder diffraction peaks at approximately 15, 17, 23, and 26°2θ using Cu Kα radiation. In some embodiments, Form 4 has X-ray powder diffraction peaks at approximately 8, 14, 15, 17, 22, 23, and 26°2θ using Cu Kα radiation. In some embodiments, Form 4 is a solvate. In further embodiments, Form 4 is a tetrahydrofuran (THF) solvate. In further embodiments, Form 4 is a THF hemi solvate.

The application also pertains, at least in part, to polymorphs of Compound A mesylate. In one embodiment, the polymorph of Compound A mesylate is Form A. In some embodiments, Form A has X-ray powder diffraction peaks at approximately 9.4 and 23.0°2θ using Cu Kα radiation. In some embodiments, Form A has X-ray powder diffraction peaks at approximately 9.4, 15.5, 18.8, and 23.0°2θ using Cu Kα radiation. In some embodiments, Form A has X-ray powder diffraction peaks at approximately 4.1, 7.8, 9.4, 10.1, 12.1, 15.5, 16.2, 18.8, 19.9, 21.1, 23.0, 25.1 and 27.4°2θ using Cu Kα radiation.

In another embodiment, the polymorph of Compound A mesylate is Form B. In some embodiments, Form B has X-ray powder diffraction peaks at approximately 6.2 and 14.3°2θ using Cu Kα radiation. In some embodiments, Form B has X-ray powder diffraction peaks at approximately 6.2, 6.6, 14.3, and 15.3°2θ using Cu Kα radiation. In some embodiments, Form B has X-ray powder diffraction peaks at approximately 6.2, 6.6, 11.3, 14.3, 15.3, 22.8, and 26.9°2θ using Cu Kα radiation.

In another embodiment, the polymorph of Compound A mesylate is Form C. In some embodiments, Form C has X-ray powder diffraction peaks at approximately 20.3 and 22.8°2θ using Cu Kα radiation. In some embodiments, Form C has X-ray powder diffraction peaks at approximately 17.6, 18.4, 19.3, 19.7 and 22.8°2θ using Cu Kα radiation. In some embodiments, Form C has X-ray powder diffraction peaks at approximately 6.2, 8.9, 9.8, 10.1, 13.7, 18.4, 19.3, 19.7, 22.8, and 26.8°2θ using Cu Kα radiation.

In another embodiment, the polymorph of Compound A mesylate is Form D. In some embodiments, Form D has X-ray powder diffraction peaks at approximately 14.5 and 23.0°2θ using Cu Kα radiation. In some embodiments, Form D has X-ray powder diffraction peaks at approximately 5.9, 11.5, 14.5, 20.3, and 23.0°2θ using Cu Kα radiation. In some embodiments, Form D has X-ray powder diffraction peaks at approximately 5.4, 5.9, 11.5, 14.5, 17.9, 20.3, 23.0, 23.6, 24.0, 26.2, 27.8, and 28.9°2θ using Cu Kα radiation.

In another embodiment, the polymorph of Compound A mesylate is Form E. In some embodiments, Form E has X-ray powder diffraction peaks at approximately 20.9 and 21.9°2θ using Cu Kα radiation. In some embodiments, Form E has X-ray powder diffraction peaks at approximately 13.7, 20.6, 20.9, 21.9, and 23.0°2θ using Cu Kα radiation. In some embodiments, Form E has X-ray powder diffraction peaks at approximately 8.9, 11.3, 13.7, 16.5, 19.3, 20.6, 20.9, 21.9, 23.0, 23.8, and 26.2°2θ using Cu Kα radiation.

In another embodiment, the polymorph of Compound A mesylate is Form F. In some embodiments, Form F has X-ray powder diffraction peaks at approximately 16.7 and 17.0°2θ using Cu Kα radiation. In some embodiments, Form F has X-ray powder diffraction peaks at approximately 16.7, 17.0, 19.5, 20.3, and 24.4°2θ using Cu Kα radiation. In some embodiments, Form F has X-ray powder diffraction peaks at approximately 4.8, 7.2, 15.6, 16.7, 17.0, 19.5, 20.3, 21.7, 24.0, and 24.4°2θ using Cu Kα radiation.

In another embodiment, the polymorph of Compound A mesylate is Form G. In some embodiments, Form G has X-ray powder diffraction peaks at approximately 5.8 and 22.1°2θ using Cu Kα radiation. In some embodiments, Form G has X-ray powder diffraction peaks at approximately 5.8, 14.9, 16.3, 22.1, and 23.7°2θ using Cu Kα radiation. In some embodiments, Form G has X-ray powder diffraction peaks at approximately 5.8, 10.8, 14.9, 16.3, 17.7, 22.1, 23.1, 23.7, 24.5, and 26.5°2θ using Cu Kα radiation.

In another embodiment, the polymorph of Compound A mesylate is Form H. In some embodiments, Form H has X-ray powder diffraction peaks at approximately 10.9 and 22.8°2θ using Cu Kα radiation. In some embodiments, Form H has X-ray powder diffraction peaks at approximately 6.1, 10.9, 12.4, 15.9, and 22.8°2θ using Cu Kα radiation. In some embodiments, Form H has X-ray powder diffraction peaks at approximately 6.1, 10.1, 10.9, 12.4, 15.7, 15.9, 16.4, 20.4, 20.8, and 22.8°2θ using Cu Kα radiation.

In another embodiment, the polymorph of Compound A mesylate is Form I. In some embodiments, Form I has X-ray powder diffraction peaks at approximately 5.2 and 10.5°2θ using Cu Kα radiation. In some embodiments, Form I has X-ray powder diffraction peaks at approximately 5.2, 6.2, 10.5, 20.2, and 23.0°2θ using Cu Kα radiation. In some embodiments, Form I has X-ray powder diffraction peaks at approximately 5.2, 6.2, 10.5, 11.1, 13.6, 20.2, 22.0, 22.3, 23.0, and 23.8°2θ using Cu Kα radiation.

In another embodiment, the polymorph of Compound A mesylate is Form J. In some embodiments, Form J has X-ray powder diffraction peaks at approximately 17.0 and 22.8°2θ using Cu Kα radiation. In some embodiments, Form J has X-ray powder diffraction peaks at approximately 14.6, 17.0, 21.9, 22.8, and 24.8°2θ using Cu Kα radiation. In some embodiments, Form J has X-ray powder diffraction peaks at approximately 14.6, 17.0, 19.7, 20.4, 21.9, 22.8, 24.8, 25.3, 26.7, and 27.7°2θ using Cu Kα radiation.

In another embodiment, the polymorph of Compound A mesylate is Form K. In some embodiments, Form K has X-ray powder diffraction peaks at approximately 9.2 and 10.0°2θ using Cu Kα radiation. In some embodiments, Form K has X-ray powder diffraction peaks at approximately 9.2, 10.0, 15.7, 20.0, and 23.8°2θ using Cu Kα radiation. In some embodiments, Form K has X-ray powder diffraction peaks at approximately 4.1, 9.2, 10.0, 15.7, 17.5, 19.3, 20.0, 21.5, 23.2, and 23.8°2θ using Cu Kα radiation.

The application also pertains, at least in part, to pharmaceutical compositions comprising Compound A and a pharmaceutically acceptable diluent, excipient or carrier. The application also pertains, at least in part, to pharmaceutical compositions comprising Compound A free base or a salt of Compound A and a pharmaceutically acceptable diluent, excipient or carrier. In one embodiment, the salt is an HCl salt or mesylate.

The application also pertains, at least in part, to pharmaceutical compositions comprising a stable solid state form of Compound A free base and a pharmaceutically acceptable diluent, excipient or carrier. The application also pertains, at least in part, to pharmaceutical compositions comprising a stable solid state form of a salt of Compound A and a pharmaceutically acceptable diluent, excipient or carrier. In one embodiment, the solid state form is an amorphous form. In another embodiment, the solid state form is a crystalline form. In another embodiment, the solid state form is a mesomorphic form. In a further embodiment, the solid state form is unsolvated. In a further embodiment, the solid state form is a solvate.

The application also pertains, at least in part, to pharmaceutical compositions comprising a crystalline form of Compound A free base or of a salt of Compound A, and a pharmaceutically acceptable diluent, excipient or carrier. The application also pertains, at least in part, to pharmaceutical compositions comprising a polymorph of Compound A free base or of a salt of Compound A, and a pharmaceutically acceptable diluent, excipient or carrier. In one embodiment, the polymorph is Form 1, 2, 3, or 4, or Form A, B, C, D, E, F, G, H, I, J or K.

The application also pertains, at least in part, to a method of preparing a salt of Compound A, a solid state of Compound A free base or of a salt of Compound A, an amorphous form of Compound A free base or of a salt of Compound A, a polymorph of Compound A free base or of a salt of Compound A, or a mesomorph of Compound A free base or of a salt of Compound A.

The application pertains, at least in part, to a method for preparing a polymorph of Compound A free base, comprising: dissolving Compound A free base in a solvent to form a solution; and isolating Compound A from said solution. In one embodiment, the method further comprises warming said solution during the dissolvation of Compound A. In one embodiment, the method further comprises stirring said solution during the dissolvation of Compound A. In one embodiment, the method further comprises cooling said solution to facilitate isolation of Compound A from said solution. In one embodiment, the method further comprises evaporating said solution to facilitate isolation of Compound A from said solution. In one embodiment, the method further comprises adding a Compound A seed polymorph to said solution before isolating Compound A from said solution.

The application pertains, at least in part, to a method for preparing a polymorph of a salt of Compound A, comprising: dissolving Compound A free base in a first solvent to form a first solution; mixing an acid with said first solution. In one embodiment, said acid is dissolved in a second solvent to form a second solution before said acid being mixed with said first solution. In one embodiment, the first and the second solvents are the same; in another embodiment, the first and the second solvents are different. In one embodiment, said mixing comprises adding said acid or said second solution to said first solution; in another embodiment, said mixing comprises adding said first solution to said acid or said second solution. In one embodiment, said mixing forms a third solution. In one embodiment, said mixing forms a first slurry. In one embodiment, the method further comprises, warming said first solution. In one embodiment, the method further comprises warming said third solution or said first slurry. In one embodiment, the method further comprises stirring said third solution or said first slurry. In one embodiment, the method further comprises cooling said third solution or said first slurry. In one embodiment, the method further comprises stirring said third solution or said first slurry after said cooling. In one embodiment, the method further comprises evaporating said third solution. In one embodiment, the method further comprises adding a seed polymorph to said third solution to form a second slurry. In one embodiment, the method further comprises stirring said second slurry. In one embodiment, the method further comprises cooling said second slurry. In one embodiment, the method further comprises stirring said second slurry after said cooling. In one embodiment, the method further comprises filtering said third solution, said first slurry, or said second slurry. In one embodiment, the method further comprises drying said third solution, said first slurry, or said second slurry.

The application also pertains, at least in part, to a method for preparing a polymorph of a salt of Compound A, comprising: dissolving Compound A free base in a first solvent to form a Compound A slurry; adding an acid to said Compound A slurry. In one embodiment, said acid is dissolved in a second solvent to form a second solution before said acid being added to said Compound A slurry. In one embodiment, the first and the second solvents are the same; in another embodiment, the first and the second solvents are different. In one embodiment, adding said acid or said second solution to said Compound A slurry forms a third solution. In one embodiment, adding said acid or said second solution to said Compound A slurry forms a first slurry. In one embodiment, the method further comprises, warming said Compound A slurry. In one embodiment, the method further comprises warming said third solution or said first slurry. In one embodiment, the method further comprises stirring said third solution or said first slurry. In one embodiment, the method further comprises cooling said third solution or said first slurry. In one embodiment, the method further comprises stirring said third solution or said first slurry after said cooling. In one embodiment, the method further comprises evaporating said third solution. In one embodiment, the method further comprises adding a third solvent to said third solution to form a second slurry. In one embodiment, the method further comprises adding a seed polymorph to said third solution to form a third slurry. In one embodiment, the method further comprises stirring said second slurry or said third slurry. In one embodiment, the method further comprises cooling said second slurry or said third slurry. In one embodiment, the method further comprises stirring said second slurry or said third slurry after said cooling. In one embodiment, the method further comprises filtering said third solution, said first slurry, said second slurry, or said third slurry. In one embodiment, the method further comprises drying said third solution, said first slurry, said second slurry, or said third slurry.

Unless otherwise defined, all technical and scientific terms used herein have the same meaning as commonly understood by one of ordinary skill in the art to which this application belongs. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art. In the case of conflict, the present specification, including definitions, will control. In addition, the materials, methods, and examples are illustrative only and are not intended to be limiting.

Other features and advantages of the application will be apparent from the following detailed description and claims.

BRIEF DESCRIPTION OF THE FIGURES

FIG. 53: XRPD of Compound A phosphoric acid salts FIG. 54: XRPD of Compound A L-glutamic acid salts FIG. 55: XRPD of Compound A L-tartaric acid salts FIG. 56: XRPD of Compound A mucic acid salts FIG. 57: XRPD of Compound A citric acid salts FIG. 58: XRPD of Compound A D-glucuronic acid salts FIG. 59: XRPD of Compound A hippuric acid salts FIG. 60: XRPD of Compound A D-gluconic acid salts FIG. 65: XRPD of Compound A HCl salts pre- and post-storage at 40° C. and 75% RH (4 pairs of curves shown, with the lower curve of each curve pair showing pre-storage XRPD)

FIG. 66: XRPD of Compound A sulfuric acid salts pre- and post-storage at 40° C. and 75% RH (the lower curve showing pre-storage XRPD)

FIG. 67: XRPD of Compound A methane sulfonic acid salts pre- and post-storage at 40° C. and 75% RH (4 pairs of curves shown, with the lower curve of each curve pair showing pre-storage XRPD)

FIG. 68: XRPD of Compound A maleic acid salts pre- and post-storage at 40° C. and 75% RH (3 pairs of curves shown, with the lower curve of each curve pair showing pre-storage XRPD)

FIG. 69: XRPD of Compound A phosphoric acid salts pre- and post-storage at 40° C. and 75% RH (5 pairs of curves shown, with the lower curve of each curve pair showing pre-storage XRPD)

FIG. 70: XRPD of Compound A L-tartaric acid salts pre- and post-storage at 40° C. and 75% RH (the lower curve showing pre-storage XRPD)

FIG. 71: XRPD of Compound A mucic acid salts pre- and post-storage at 40° C. and 75% RH (2 pairs of curves shown, with the lower curve of each curve pair showing pre-storage XRPD)

FIG. 72: XRPD of Compound A citric acid salts pre- and post-storage at 40° C. and 75% RH (the lower curve showing pre-storage XRPD)

FIG. 112: Form A Compound A bis-mesylate—XRPD—Peak List

FIG. 131: Form B Compound A bis-mesylate—XRPD—Peak List

FIG. 147: Form C Compound A bis-mesylate—XRPD—Peak List

Figure 197:
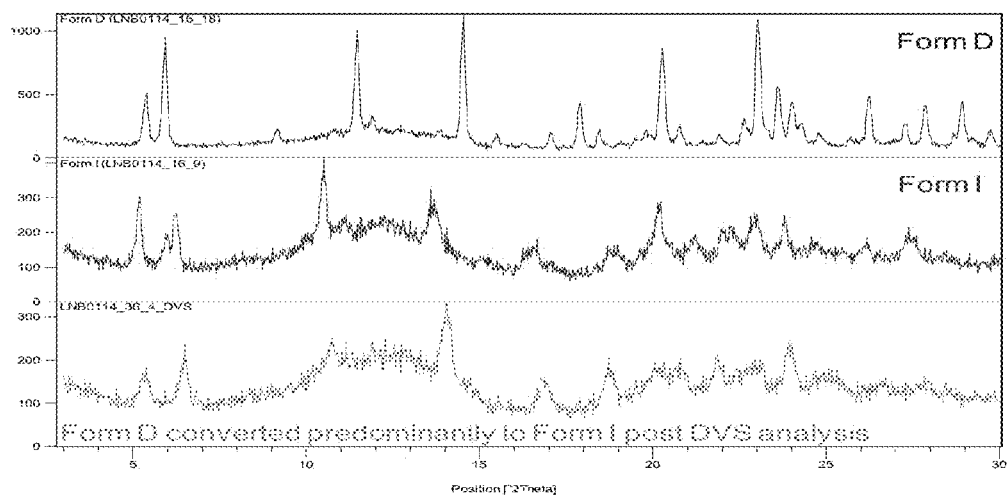

FIG. 197: Form D Compound A bis-mesylate—XRPD Analysis: Post-DVS Analysis

Figure 198:
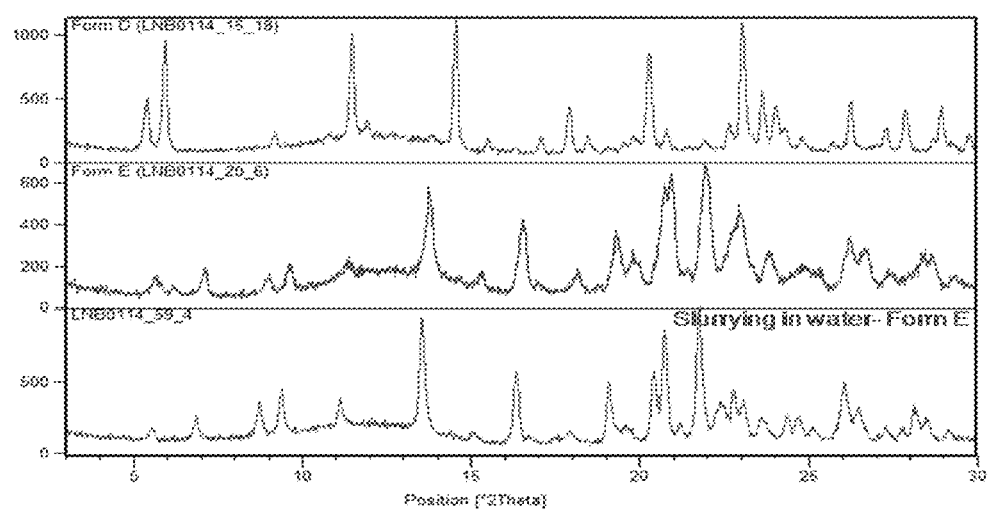

FIG. 198: Form D Compound A bis-mesylate—XRPD Analysis: Slurry in Deionized Water FIG. 199: Form D Compound A bis-mesylate—HPLC Purity Analysis FIG. 200: Form D Compound A bis-mesylate—HPLC Purity: Stability Study at 40° C. and 75% RH FIG. 201: Form D Compound A bis-mesylate—HPLC Purity: Stability Study at Ambient Temperature FIG. 202: Form D Compound A bis-mesylate—HPLC Purity: Stability Study at 80° C.

Figure 203:
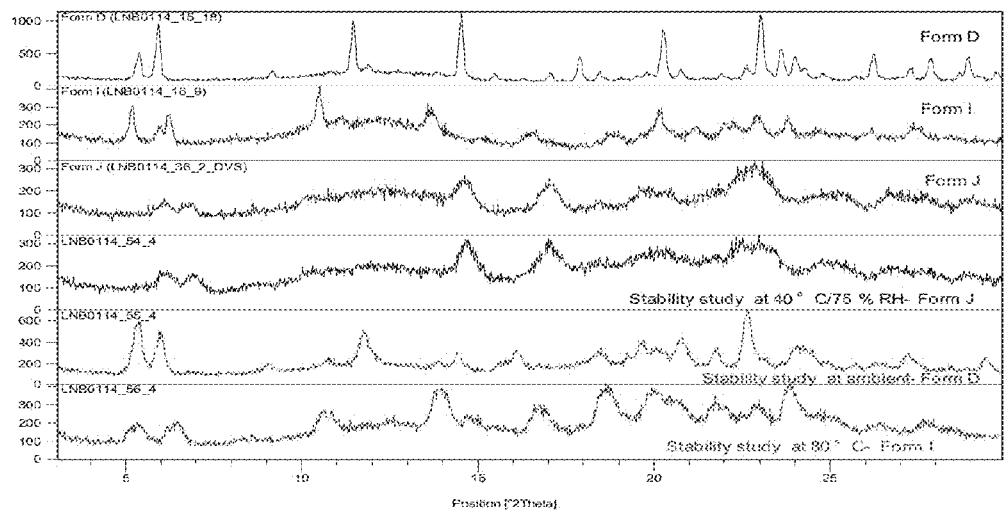

FIG. 203: Form D Compound A bis-mesylate—XRPD Analysis: Stability Testing at 40° C. and 75% RH, Ambient Temperature, and 80° C.

Figure 204:
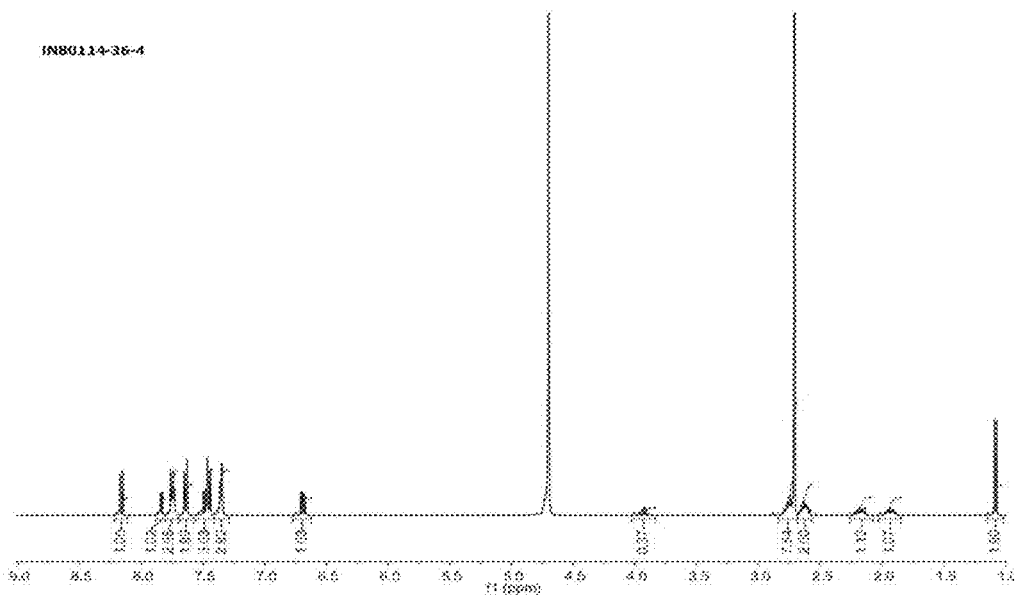

FIG. 204: Form D Compound A bis-mesylate—$^1$H NMR Spectroscopy

Figure 205:
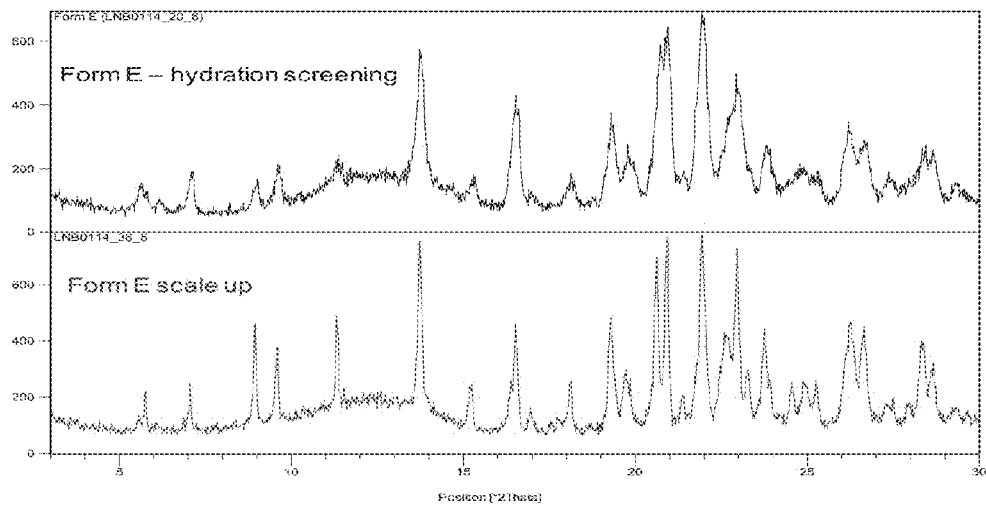

FIG. 205: Form E Compound A bis-mesylate—XRPD Analysis: Hydration Screen and Scale-Up FIG. 206: Form E Compound A bis-mesylate—PLM Analysis FIG. 207: Form E Compound A bis-mesylate—TG/DTA Analysis after air drying at ambient temperature for about 3 days FIG. 208: Form E Compound A bis-mesylate—TG/DTA Analysis after drying under vacuum at ambient temperature for further about 1 day FIG. 209: Form E Compound A bis-mesylate—TG/DTA Analysis after heating experiment (150° C.)

Figure 210:
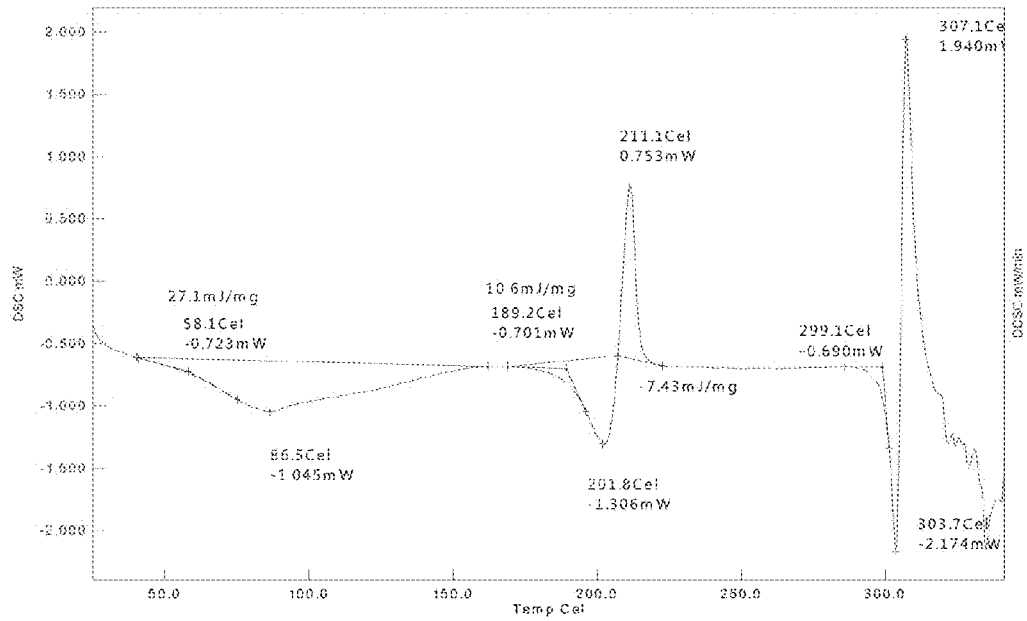

FIG. 210: Form E Compound A bis-mesylate—DSC Analysis

Figure 211:
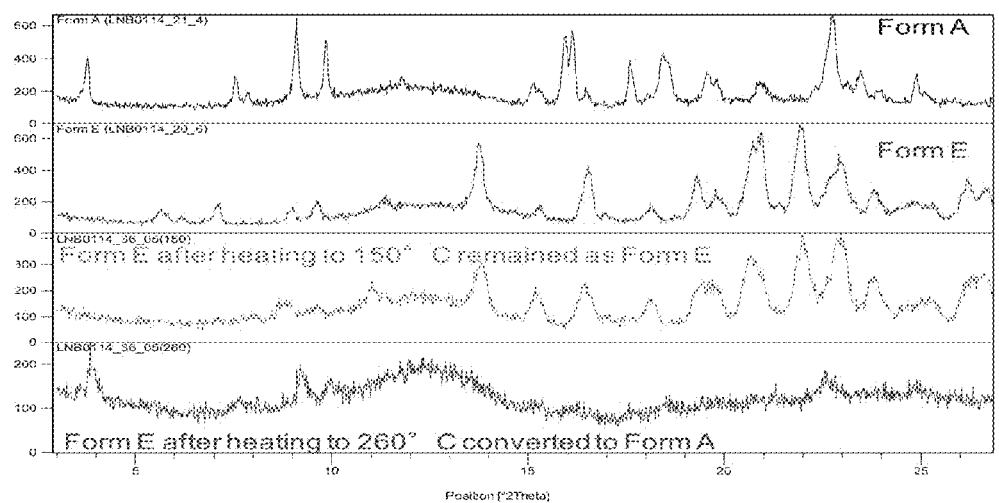

FIG. 211: Form E Compound A bis-mesylate—XRPD Analysis: Form A, Form E, Form E after heating to 150° C., and Form E after heating to 260° C.

Figure 212:
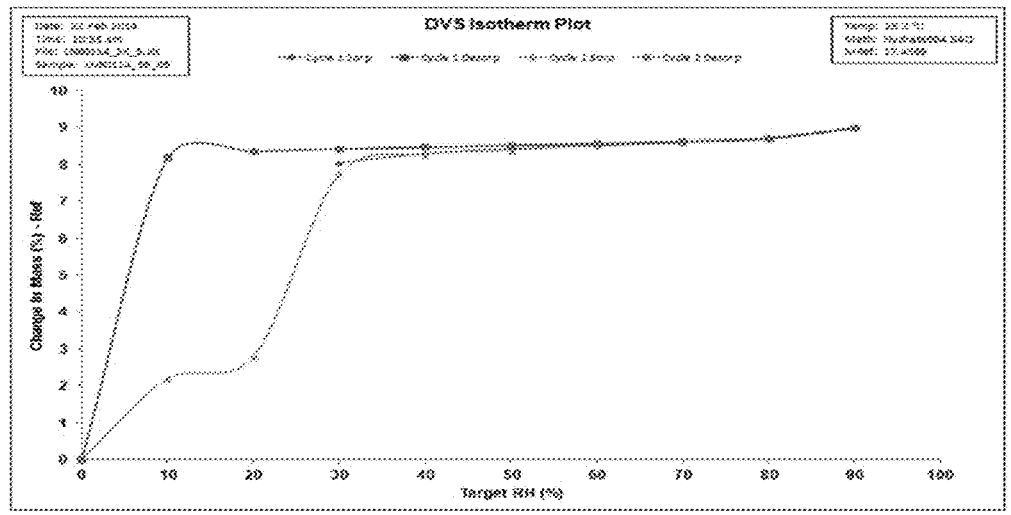

FIG. 212: Form E Compound A bis-mesylate—DVS Analysis

Figure 213:
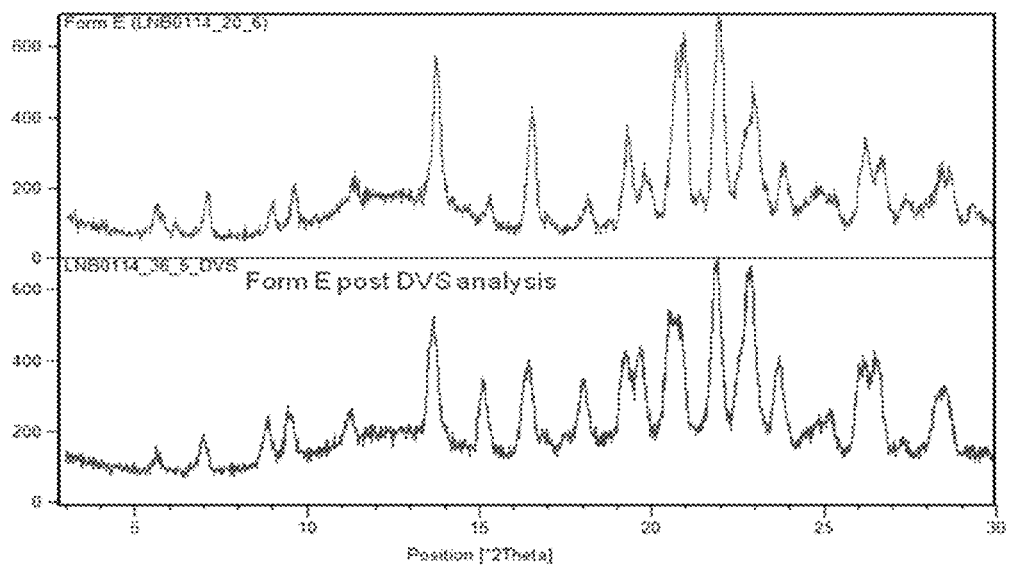

FIG. 213: Form E Compound A bis-mesylate—XRPD Analysis: Post-DVS Analysis

Figure 214:
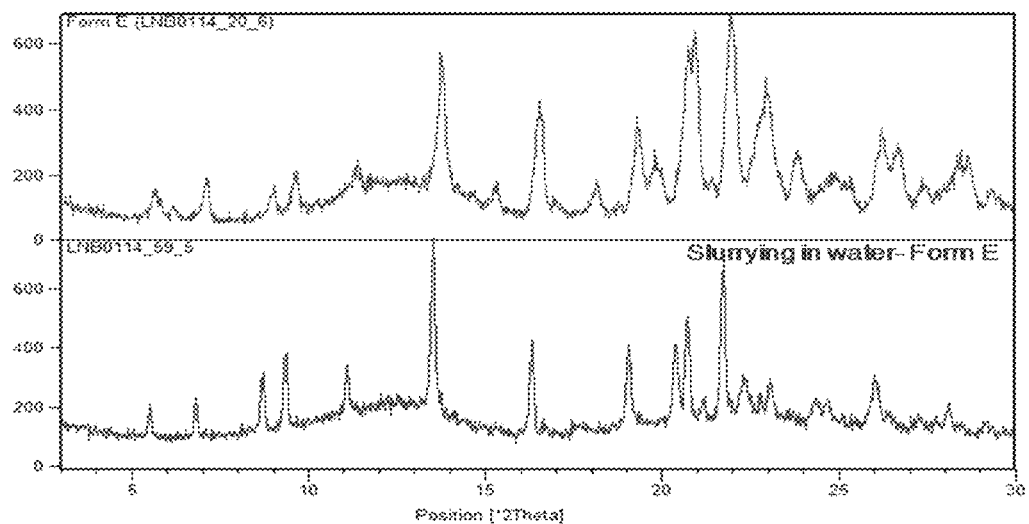

FIG. 214: Form E Compound A bis-mesylate—XRPD Analysis: Slurry in Deionized Water FIG. 215: Form E Compound A bis-mesylate—HPLC Purity Analysis FIG. 216: Form E Compound A bis-mesylate—HPLC Purity: Stability Study at 40° C. and 75% RH FIG. 217: Form E Compound A bis-mesylate—HPLC Purity: Stability Study at Ambient Temperature FIG. 218: Form E Compound A bis-mesylate—HPLC Purity: Stability Study at 80° C.

Figure 219:
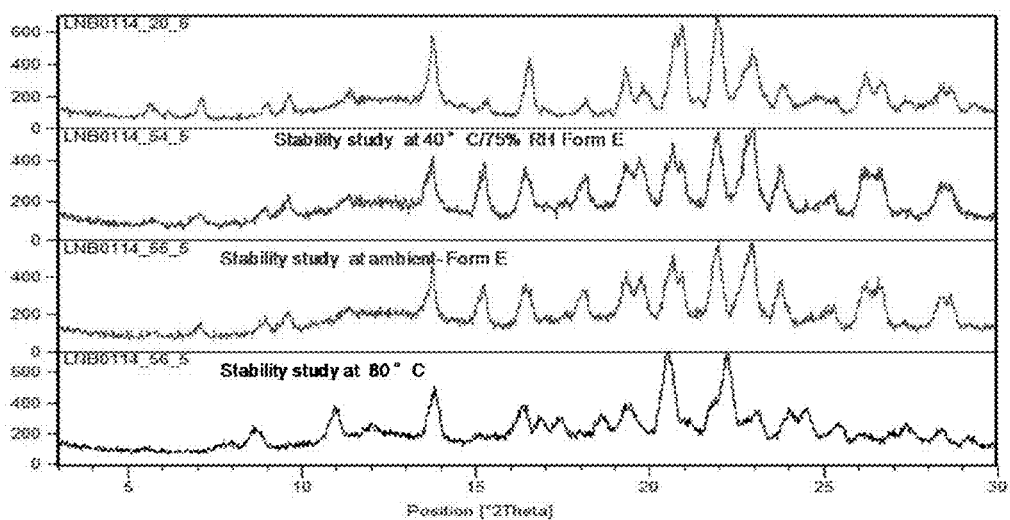

FIG. 219: Form E Compound A bis-mesylate—XRPD Analysis: Stability Testing at 40° C. and 75% RH, Ambient Temperature, and 80° C.

Figure 220:
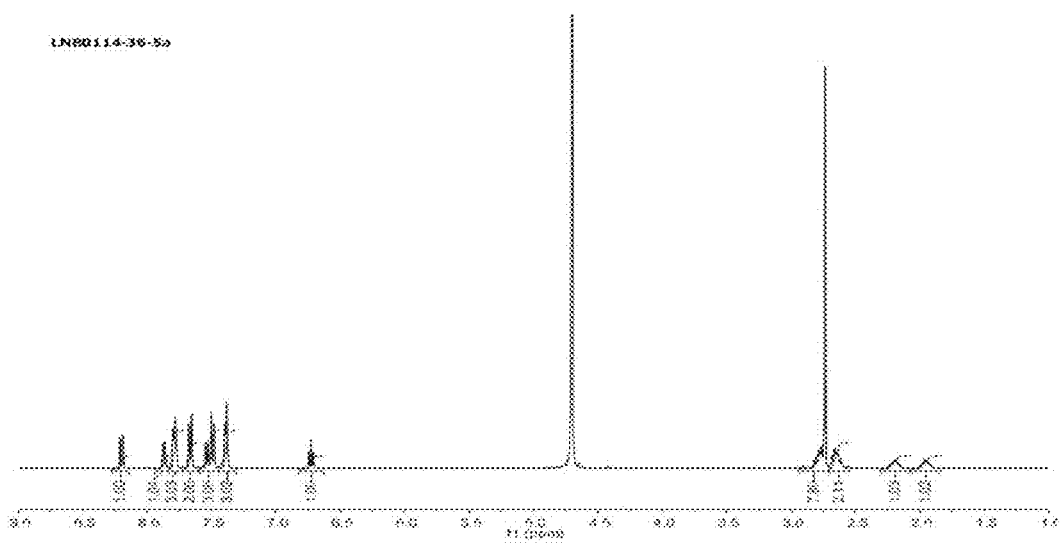

FIG. 220: Form E Compound A bis-mesylate—$^1$H NMR Spectroscopy

Figure 221:
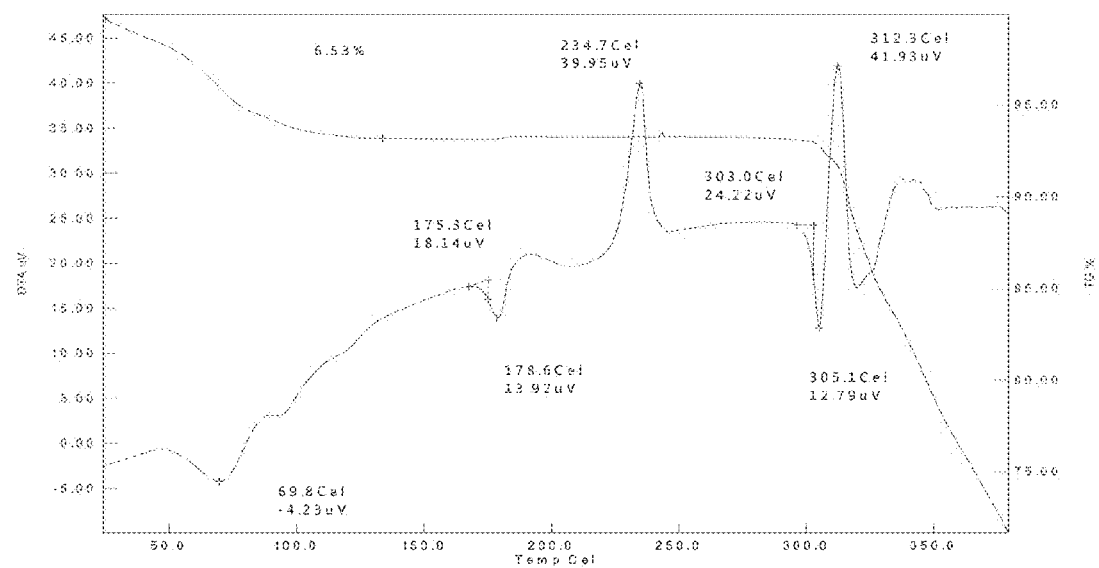

FIG. 221: Form F Compound A bis-mesylate—TG/DTA Analysis

Figure 222:
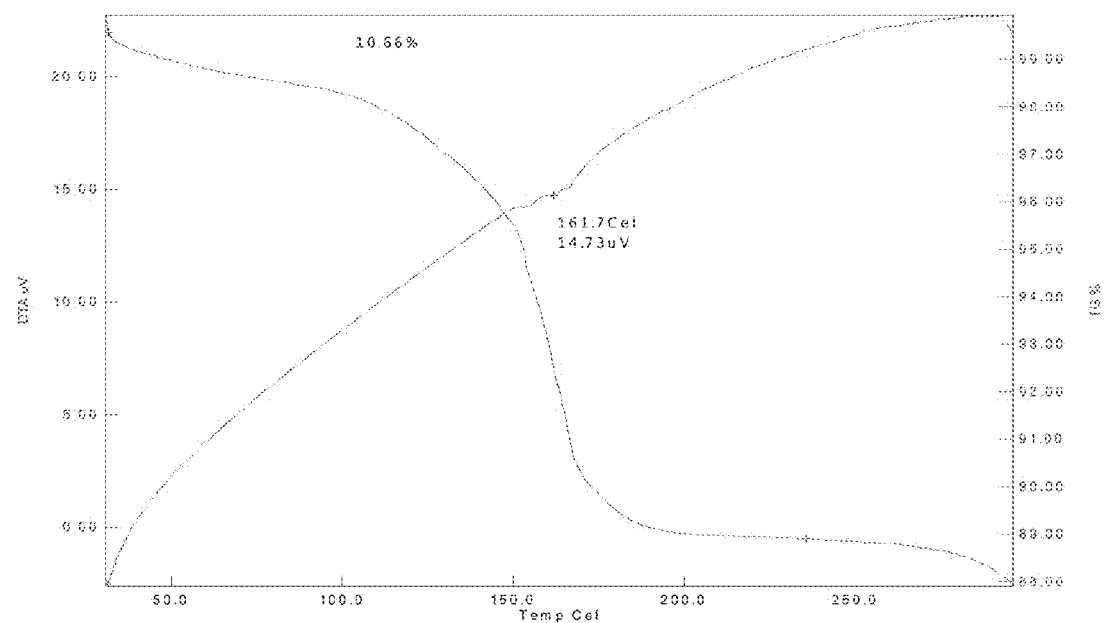

FIG. 222: Form G Compound A bis-mesylate—TG/DTA Analysis

Figure 223:
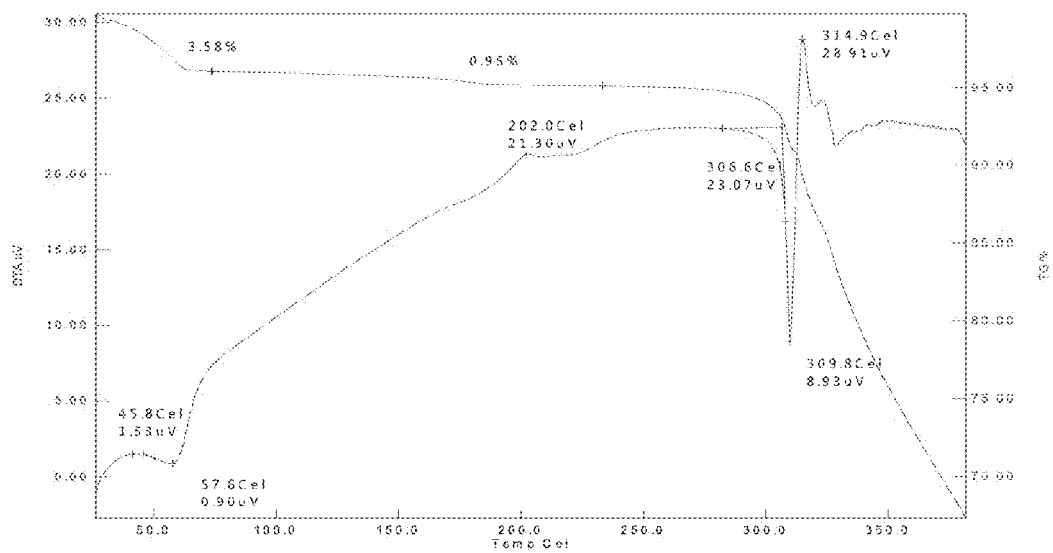

FIG. 223: Form H Compound A bis-mesylate—TG/DTA Analysis

Figure 224:
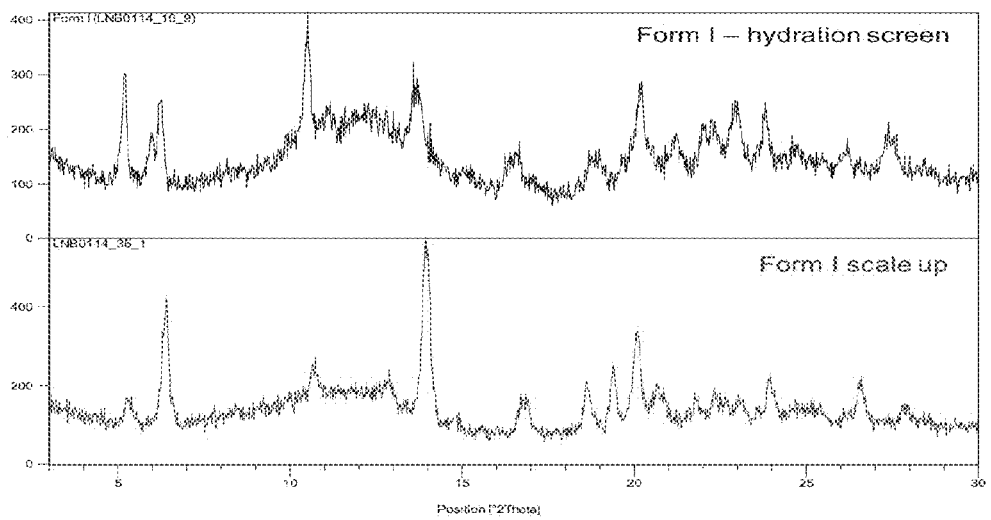

FIG. 224: Form I Compound A bis-mesylate—XRPD Analysis: Hydration Screen and Scale-Up FIG. 225: Form I Compound A bis-mesylate—PLM Analysis FIG. 226: Form I Compound A bis-mesylate—TG/DTA Analysis FIG. 227: Form I Compound A bis-mesylate—DSC Analysis FIG. 228: Form I Compound A bis-mesylate—DVS Analysis FIG. 229: Form I Compound A bis-mesylate—XRPD Analysis: Post-DVS Analysis FIG. 230: Form I Compound A bis-mesylate—XRPD Analysis: Slurry in Deionized Water FIG. 231: Form I Compound A bis-mesylate—HPLC Purity Analysis FIG. 232: Form I Compound A bis-mesylate—HPLC Purity: Stability Study at 40° C. and 75% RH FIG. 233: Form I Compound A bis-mesylate—HPLC Purity: Stability Study at Ambient Temperature FIG. 234: Form I Compound A bis-mesylate—HPLC Purity: Stability Study at 80° C.

Figure 235:
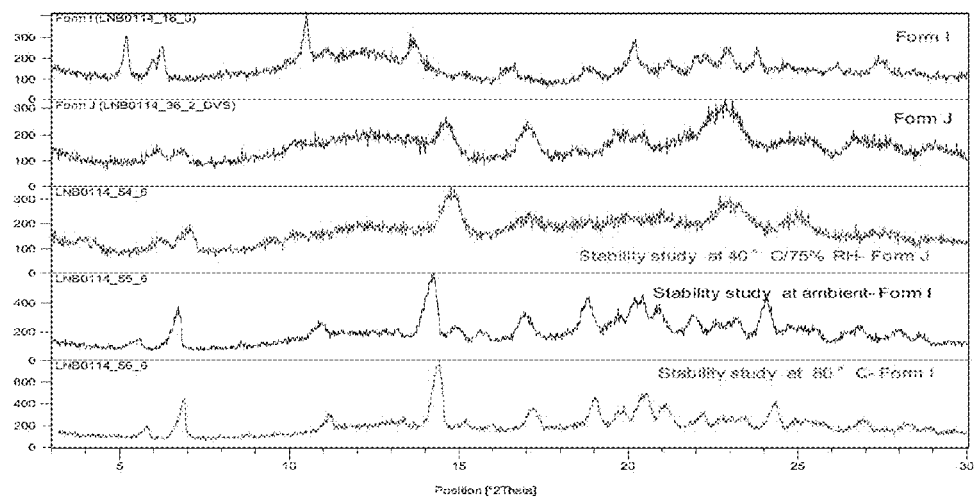

FIG. 235: Form I Compound A bis-mesylate—XRPD Analysis: Stability Testing at 40° C. and 75% RH, Ambient Temperature, and 80° C.

Figure 236:
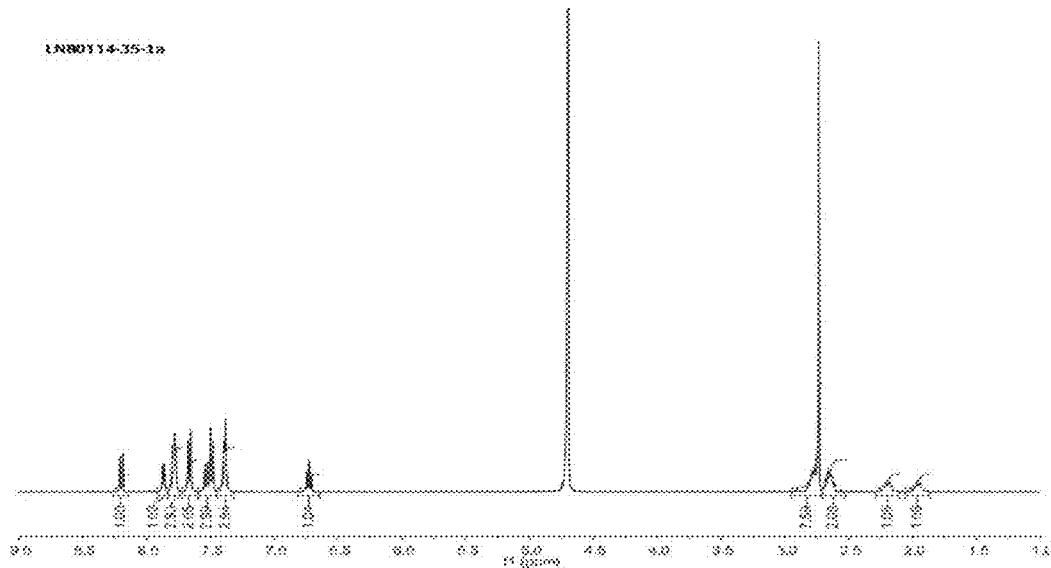

FIG. 236: Form I Compound A bis-mesylate—$^1$H NMR Spectroscopy

Figure 237:
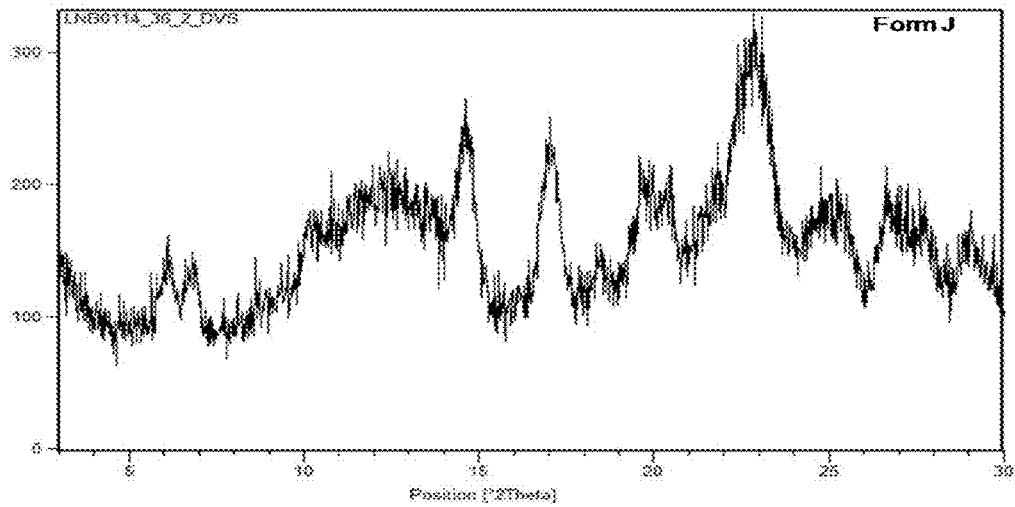

FIG. 237: Form J Compound A bis-mesylate—XRPD Analysis

Figure 238:
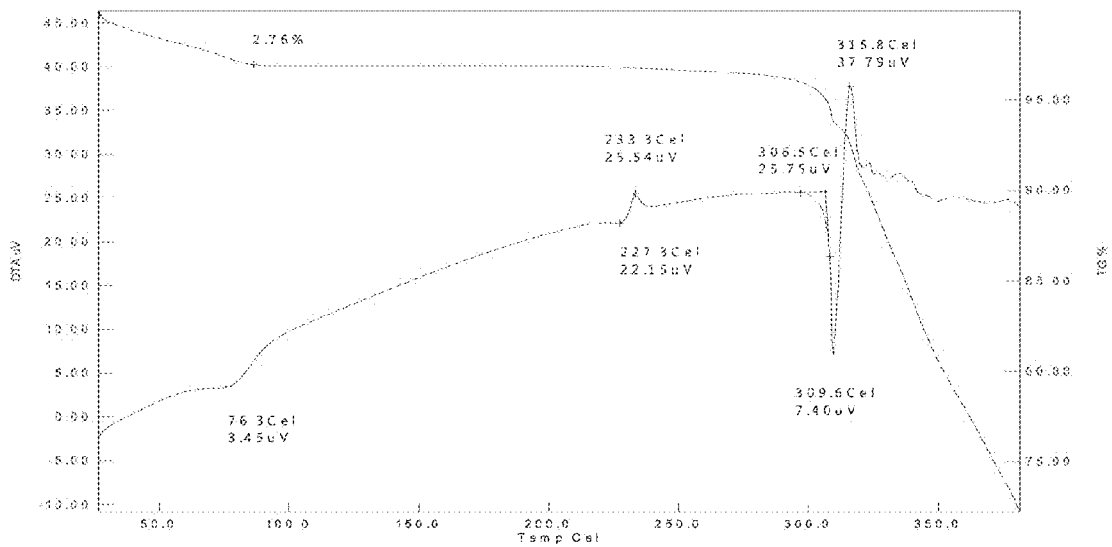

FIG. 238: Form J Compound A bis-mesylate—TG/DTA Analysis

Figure 239:
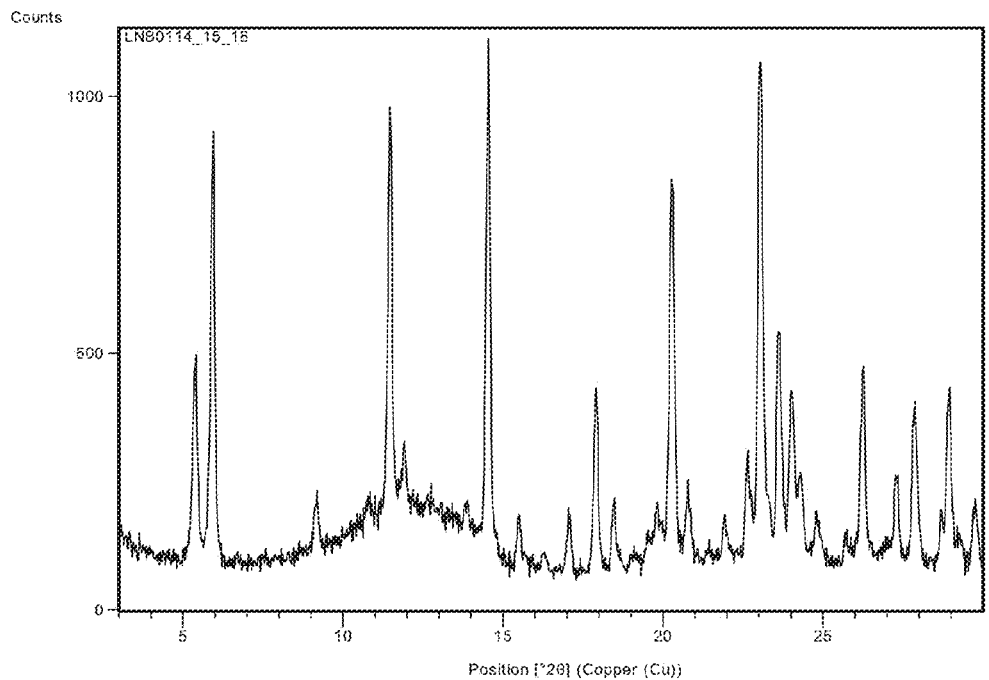

FIG. 239: Form D Compound A bis-mesylate—XRPD

Figure 240:
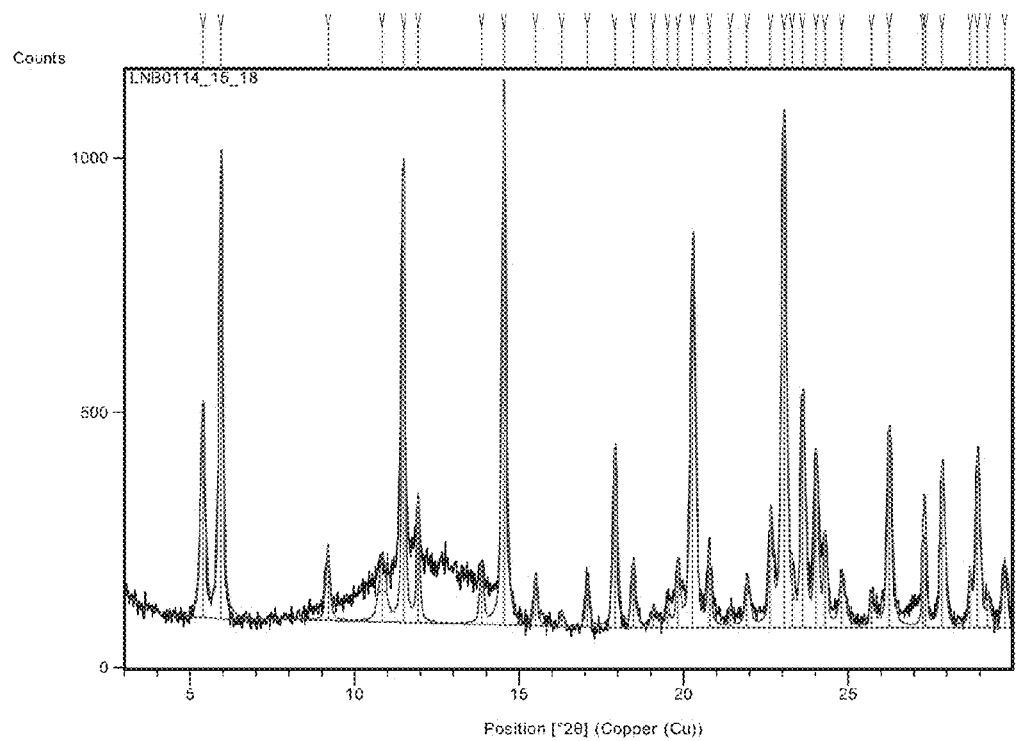

FIG. 240: Form D Compound A bis-mesylate—XRPD—Peaks Indicated

FIG. 241: Form D Compound A bis-mesylate—XRPD—Peak List

Figure 242:
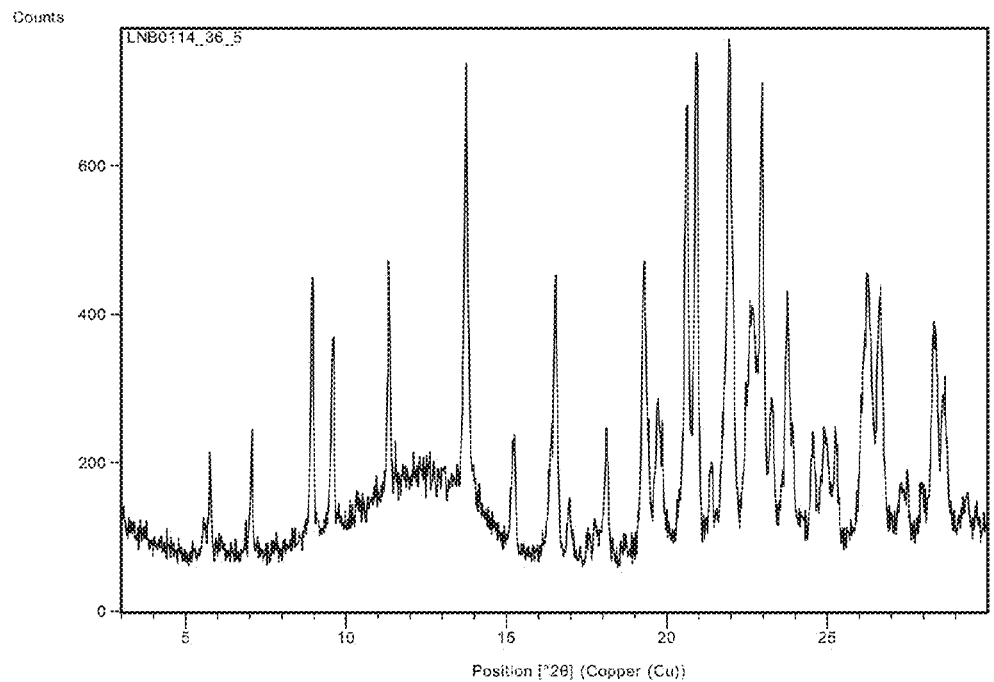

FIG. 242: Form E Compound A bis-mesylate—XRPD

Figure 243:
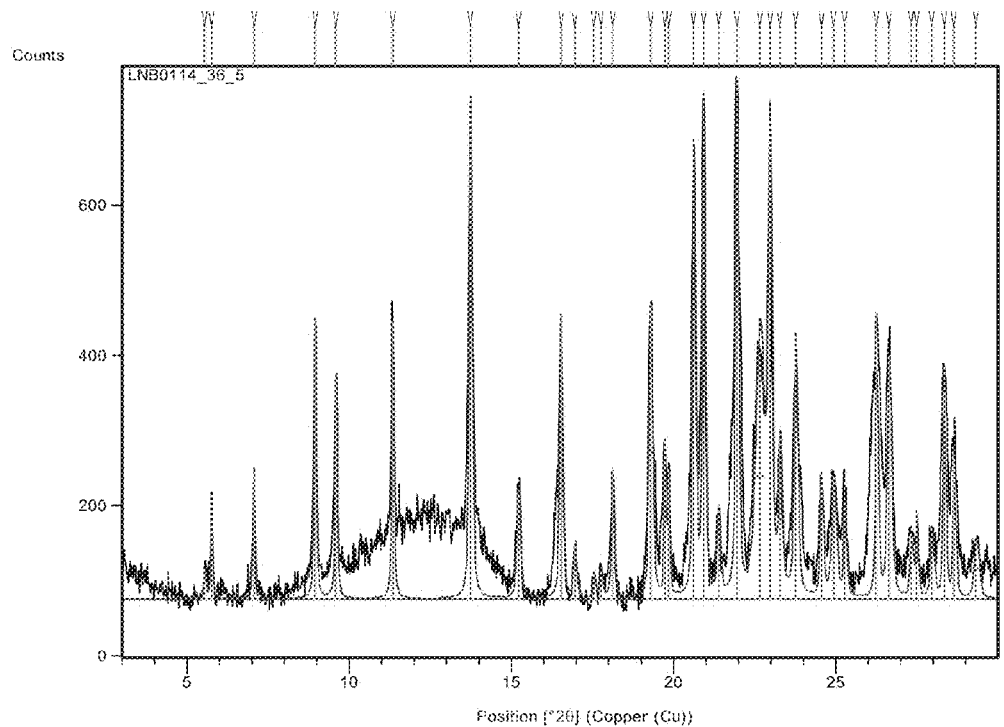

FIG. 243: Form E Compound A bis-mesylate—XRPD—Peaks Indicated

FIG. 244: Form E Compound A bis-mesylate—XRPD—Peak List

Figure 245:
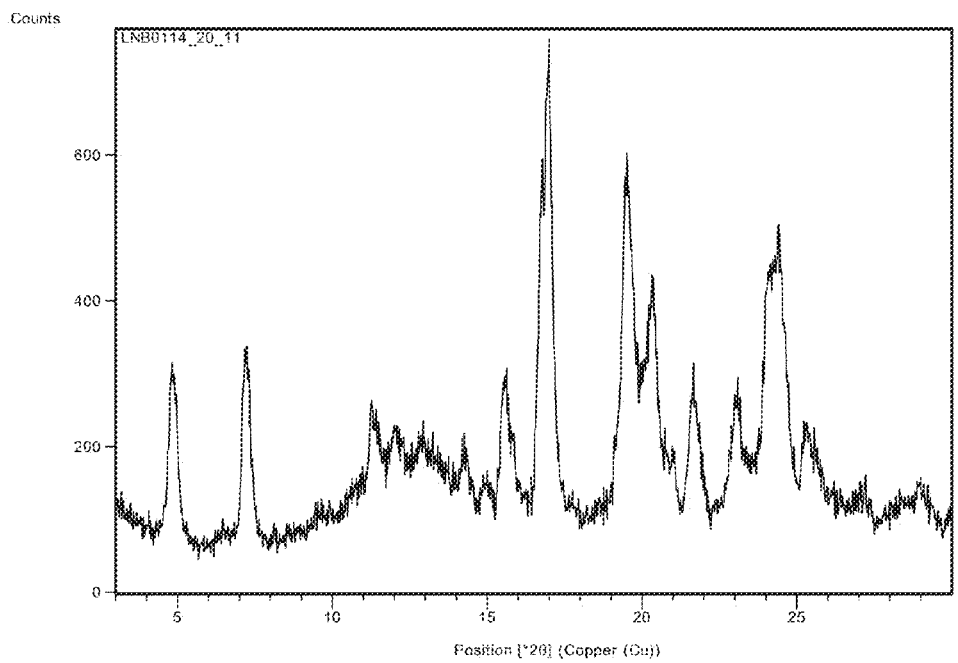

FIG. 245: Form F Compound A bis-mesylate—XRPD

Figure 246:
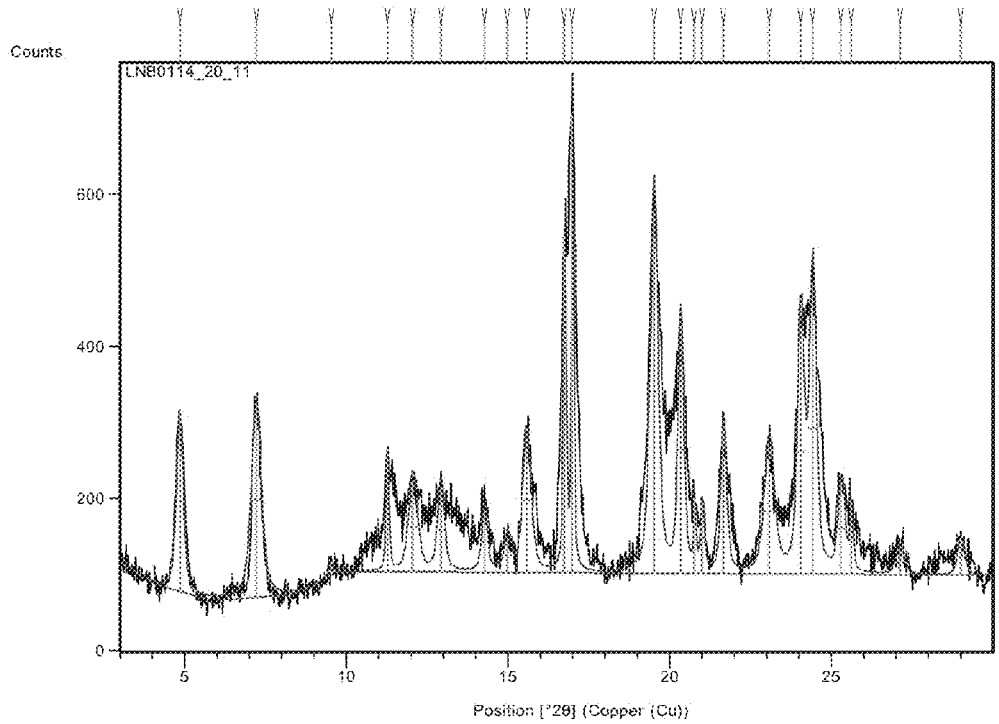

FIG. 246: Form F Compound A bis-mesylate—XRPD—Peaks Indicated

FIG. 247: Form F Compound A bis-mesylate—XRPD—Peak List

Figure 248:
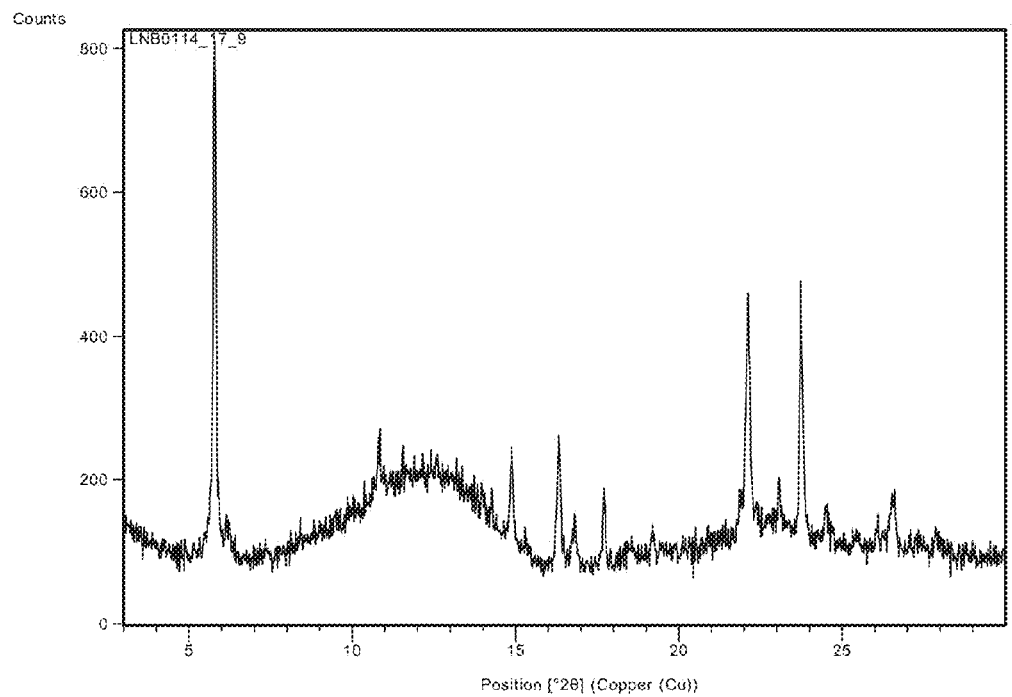

FIG. 248: Form G Compound A bis-mesylate—XRPD

Figure 249:
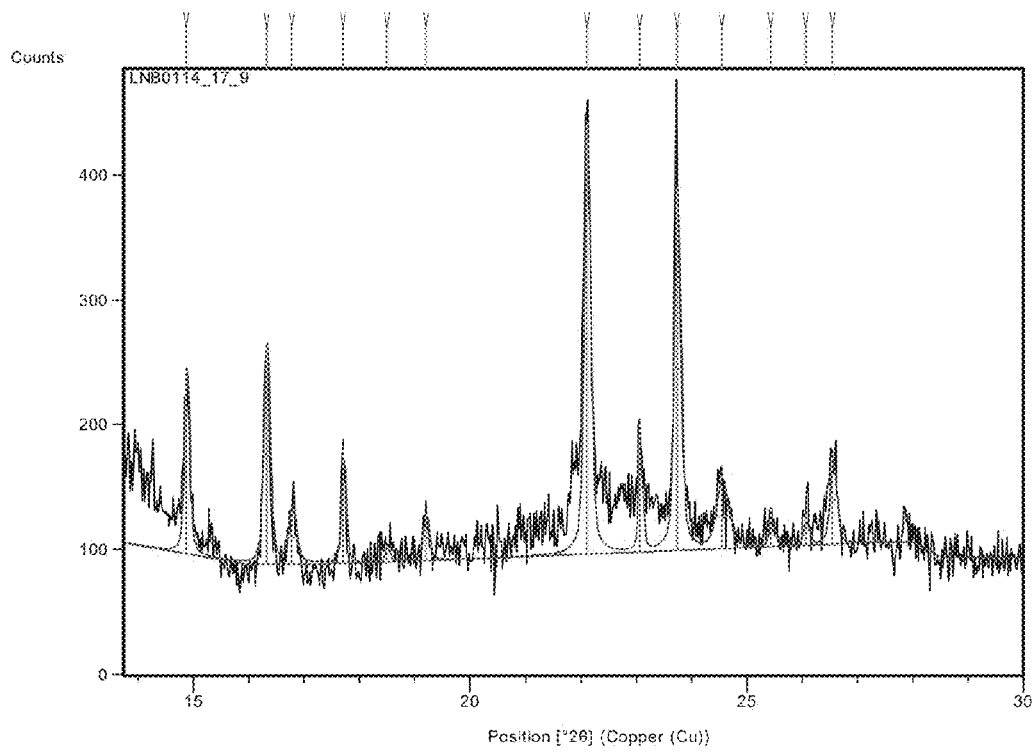

FIG. 249: Form G Compound A bis-mesylate—XRPD—Peaks Indicated

FIG. 250: Form G Compound A bis-mesylate—XRPD—Peak List

Figure 251:
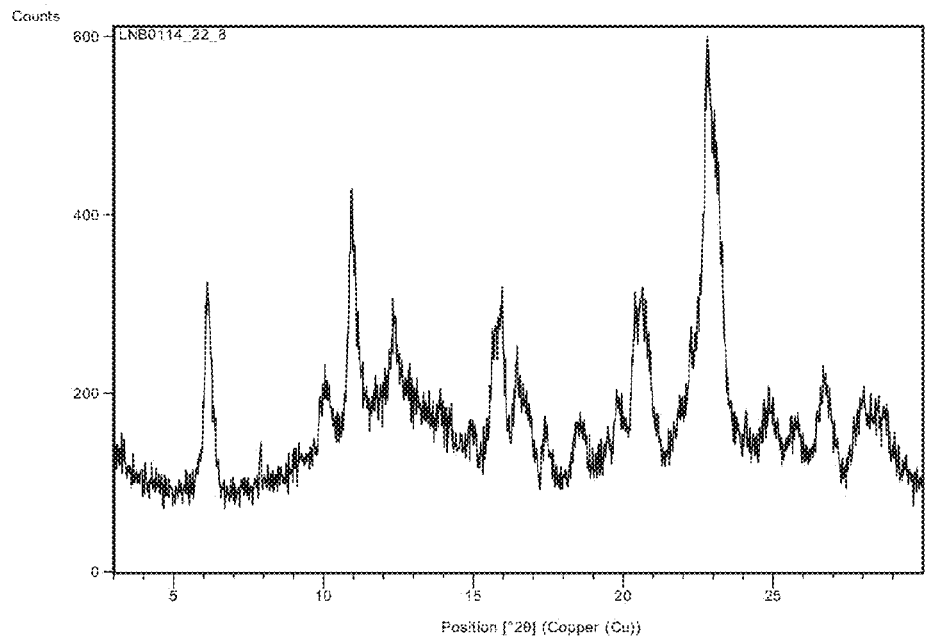

FIG. 251: Form H Compound A bis-mesylate—XRPD

Figure 252:
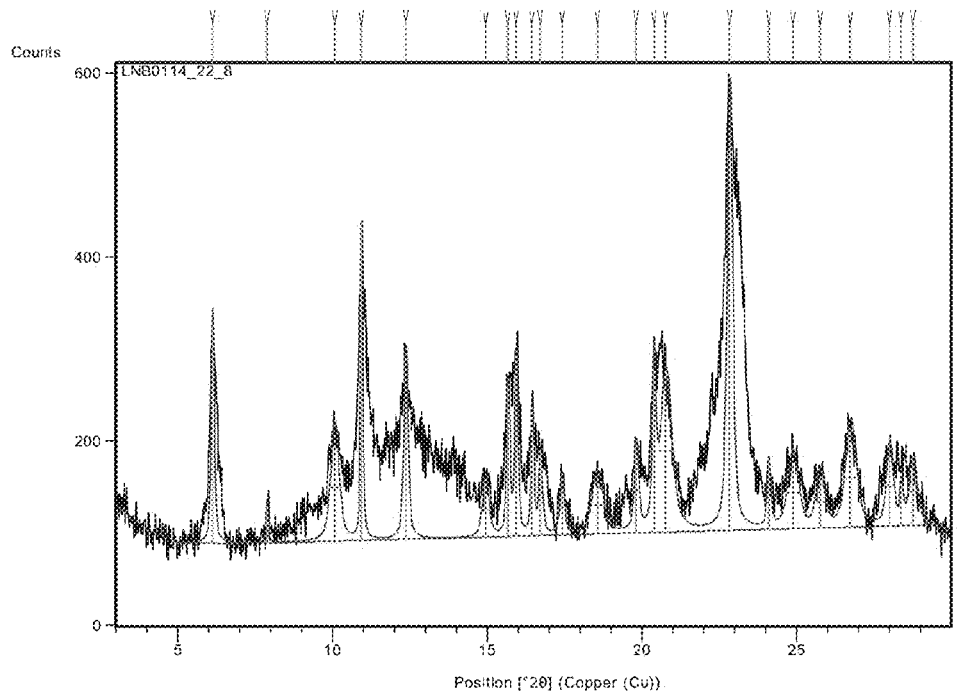

FIG. 252: Form H Compound A bis-mesylate—XRPD—Peaks Indicated

FIG. 253: Form H Compound A bis-mesylate—XRPD—Peak List

Figure 254:
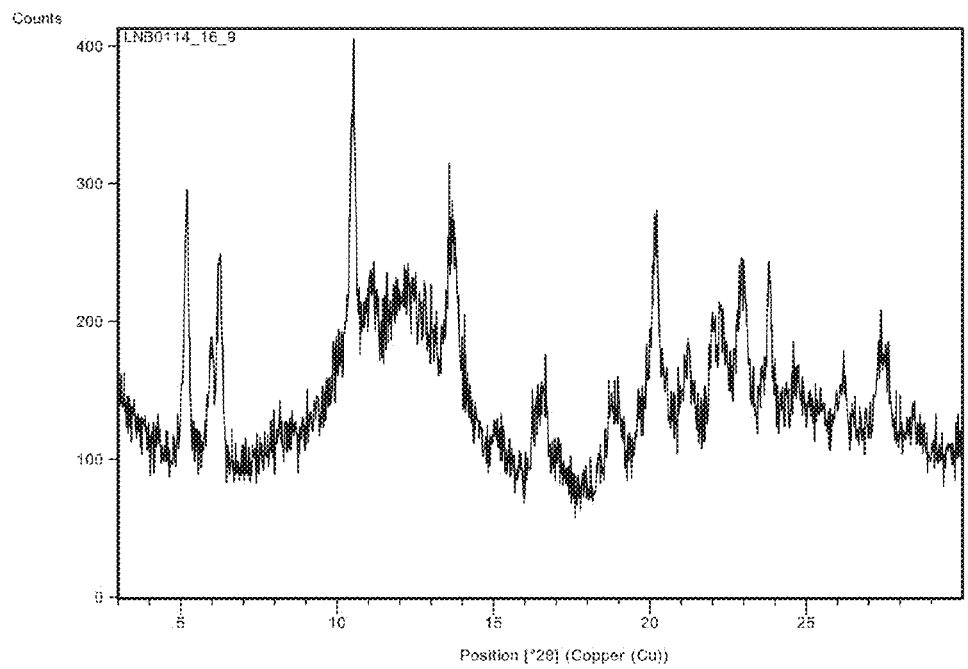

FIG. 254: Form I Compound A bis-mesylate—XRPD

Figure 255:
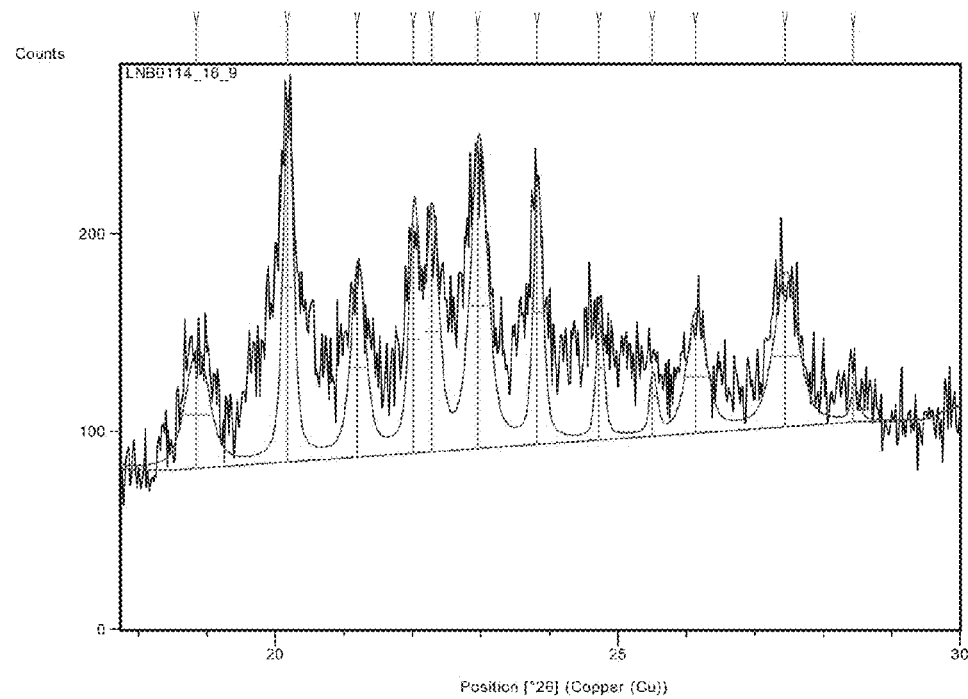

FIG. 255: Form I Compound A bis-mesylate—XRPD—Peaks Indicated

FIG. 256: Form I Compound A bis-mesylate—XRPD—Peak List

Figure 257:
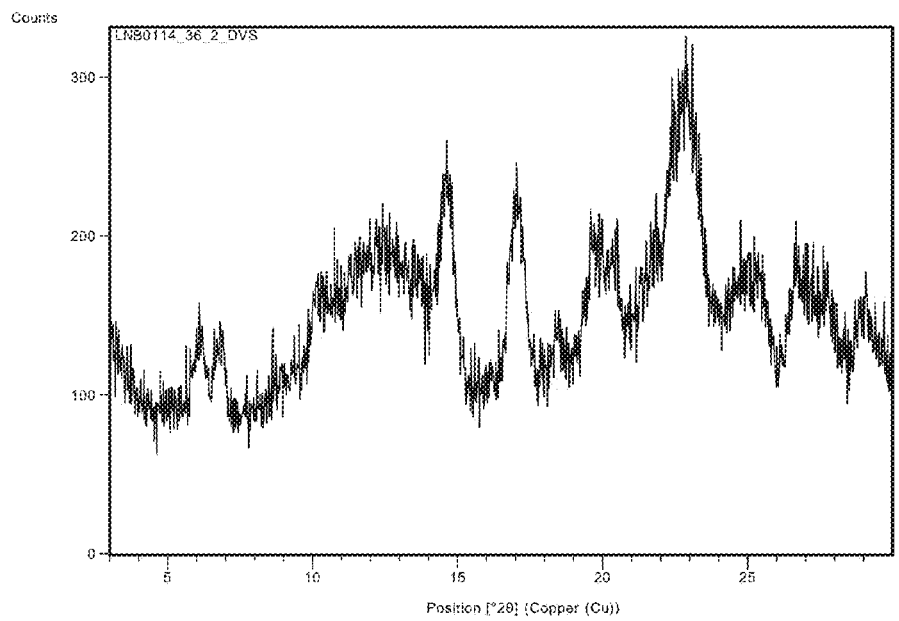

FIG. 257: Form J Compound A bis-mesylate—XRPD

Figure 258:
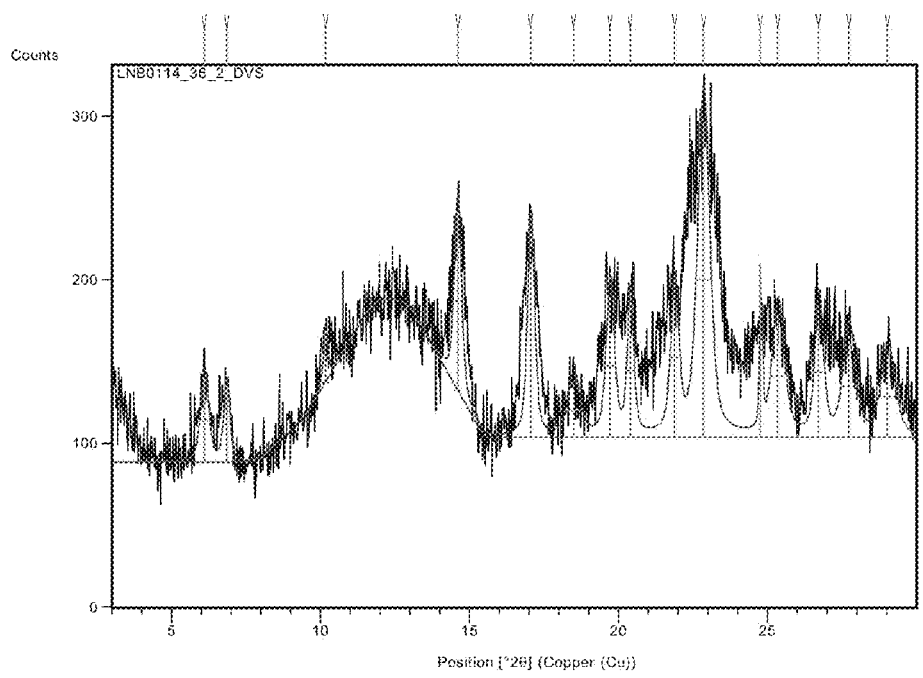

FIG. 258: Form J Compound A bis-mesylate—XRPD—Peaks Indicated

FIG. 259: Form J Compound A bis-mesylate—XRPD—Peak List

Figure 260:
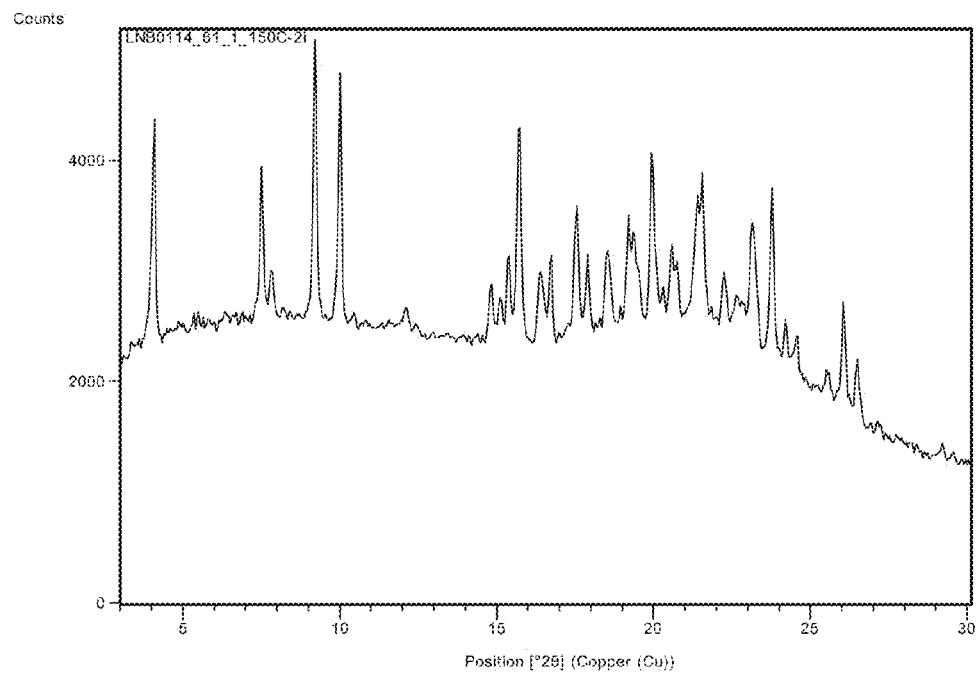

FIG. 260: Form K Compound A bis-mesylate—XRPD

Figure 261:
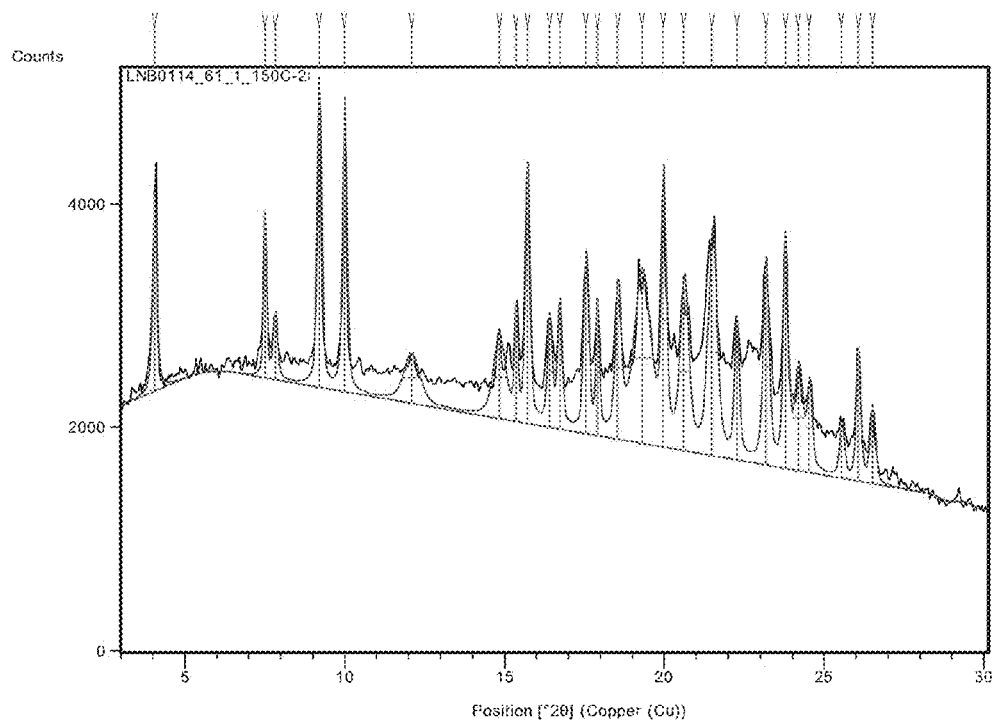

FIG. 261: Form K Compound A bis-mesylate—XRPD—Peaks Indicated

FIG. 262: Form K Compound A bis-mesylate—XRPD—Peak List

Figure 263:
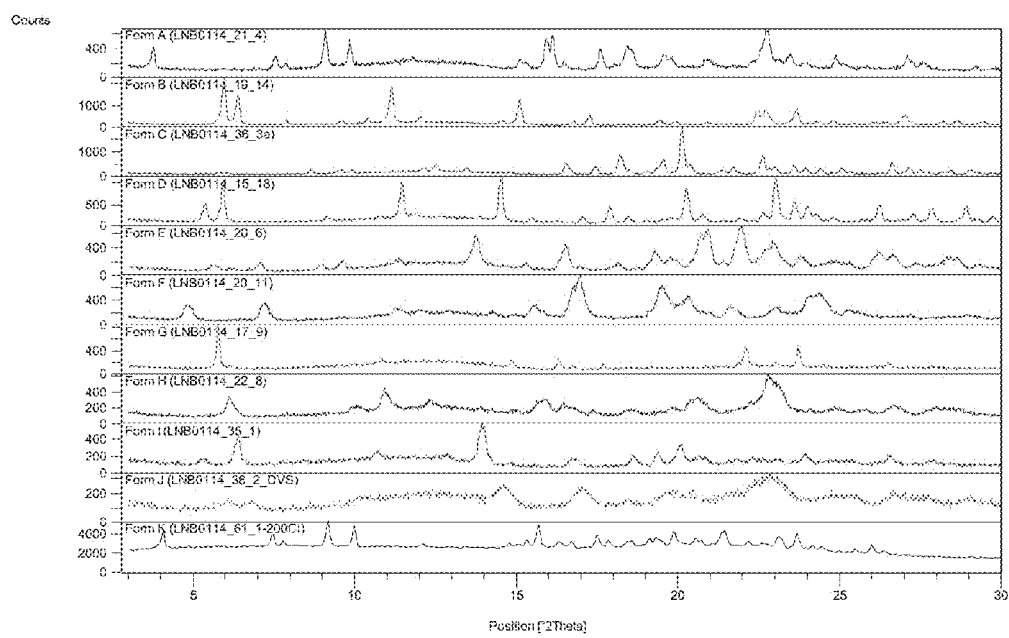

FIG. 263: XRPD Comparison of all Polymorphic Forms of Compound A bis-mesylate Identified during the Polymorph Screen, Hydration Screen and Scale-up Assessment

DETAILED DESCRIPTION

Polymorphs of Compound a Free Base

Compound A can be dissolved and then crystallized from a solvent or a mixture thereof described below to yield the polymorphic forms of the application. In some embodiments, a polymorph of Compound A free base is prepared by: dissolving Compound A free base in a solvent or a mixture of solvents to form a solution, and isolating Compound A free base from said solution. In particular embodiments of the application, the solvent or a mixture thereof is evaporated to produce Compound A free base polymorphs. The solvents suitable for preparing polymorphs of Compound A free base include, but are not limited to, DCM, THF, dioxane, ethyl acetate, ethanol, IPAc, IPA, MEK, acetone, acetonitrile, nitromethane, water, and a mixture thereof. In particular embodiments, the solvents suitable for preparing polymorphs of Compound A free base are DCM, IPA, MEK, acetone, THF, IPAc, acetonitrile, dioxane, ethylacetate, and ethanol. For example, Compound A free base is dissolved and then crystallized from DCM, IPA, MEK, acetone, THF, IPAc, or acetonitrile. The solvents may be anhydrous or may contain various amount of water (e.g., 0.1-0.5%, 0.5-1%, 1-5%, 5-10%, 10-20%, 20-30%, 30-40%, 40-50%, 50-60%, 60-70%, 70-80%, and 80-90%).

In one embodiment, the method for preparing a polymorph of Compound A free base further comprises warming said solution during the dissolvation of Compound A. For example, the solution can be warmed to 20-30° C., 30-40° C., 40-50° C., 50-60° C., 60-70° C., 70-80° C., 80-90° C., 90-100° C., 100-150° C., or 150-200° C., or above 200° C. In one embodiment, the method further comprises stirring said solution during the dissolvation of Compound A. For example, the solution can be stirred for at least 5 min, 10 min, 15 min, 20 min, 30 min, 60 min, 2 hrs, 4 hrs, 8 hrs, 12 hrs, 24 hrs, 36 hrs, or 48 hrs. In one embodiment, the method further comprises cooling said solution to facilitate isolation of Compound A from said solution. For example, the solution can be cooled to 100-90° C., 90-80° C., 80-70° C., 70-60° C., 60-50° C., 50-40° C., 40-30° C., 30-20° C., 20-10° C., or 10-0° C., or below 0° C. In one embodiment, the method further comprises evaporating said solution to facilitate isolation of Compound A free base from said solution. In one embodiment, the method further comprises, adding a Compound A seed polymorph to said solution before isolating Compound A free base from said solution. In one embodiment, said isolation comprises filtering Compound A free base from said solution. In one embodiment, said isolation further comprises drying Compound A free base. For example, said drying can be conducted at any appropriate conditions (e.g., appropriate temperatures (e.g., below 0° C., 0-10° C., 10-20° C., 20-30° C., 30-40° C., 40-50° C., 50-60° C., 60-70° C., 70-80° C., 80-90° C., 90-100° C., 100-150° C., or 150-200° C., or above 200° C.)

Figure 2:
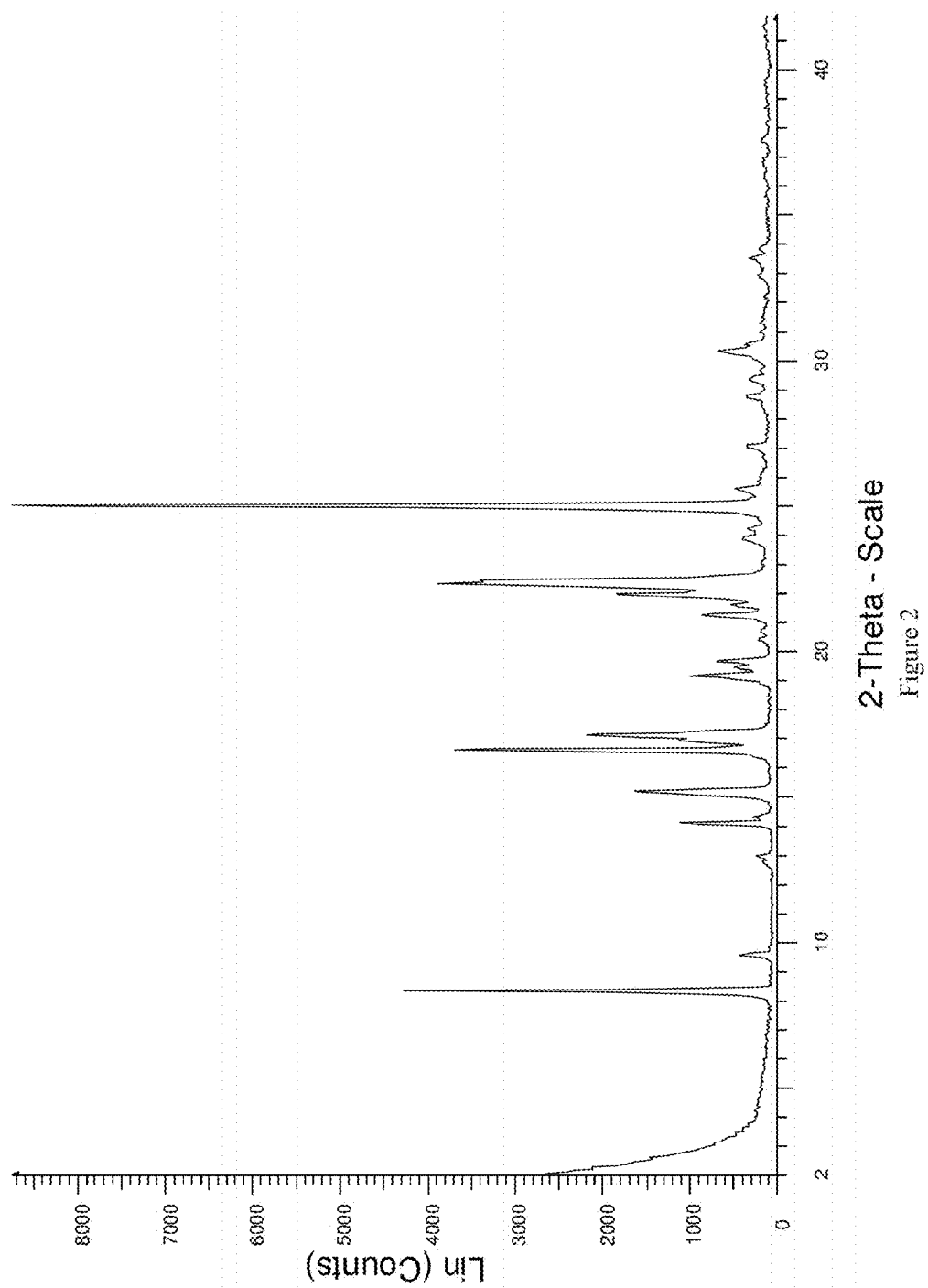
FIG. 2: XRPD of Form 1 polymorph of Compound A free base

In one embodiment, the polymorph of Compound A free base is Form 1. In some embodiments, Form 1 has X-ray powder diffraction peaks at approximately 22.0 and 25.0°2θ using Cu Kα radiation. In some embodiments, Form 1 has X-ray powder diffraction peaks at approximately 8.3, 17.1, 22.0, and 25.0°2θ using Cu Kα radiation. In some embodiments, Form 1 has X-ray powder diffraction peaks at approximately 8.3, 9.5, 12.9, 14.1, 15.2, 16.6, 17.1, 19.2, 19.4, 19.6, 21.2, 22.0, and 25.0°2θ using Cu Kα radiation. In one embodiment, Form 1 has a X-ray powder diffraction pattern substantially similar to that shown in FIG. 2.

In one embodiment, Form 1 can be a solvate. In some embodiments, Form 1 can be a dichloromethane (DCM) or methyl ethyl ketone (MEK) solvate. In a further embodiment, Form 1 can be a DCM hemi solvate or a MEK hemi solvate.

In one embodiment, Form 1 can be isolated from IPA, MEK, or acetone.

In some embodiments, Form 1 is stable at a temperature at or below 150° C., 140° C., 130° C., 120° C., 100° C., 90° C., 80° C., 70° C., 60° C., 50° C., 40° C., or 30° C. For example, Form 1 is stable at 25° C. In some embodiments, Form 1 is stable at or above 50% RH, 60% RH, 70% RH, 80% RH, or 90% RH. For example, Form 1 is stable in a range of 0-96% RH. For example, Form 1 is stable at 96% RH.

In one embodiment, Form 1 can convert to other polymorphic forms. For example, Form 1, when heated, may convert to Form 2.

In another embodiment, the polymorph of Compound A free base is Form 2. In some embodiments, Form 2 has X-ray powder diffraction peaks at approximately 18.4 and 19.3°2θ using Cu Kα radiation. In some embodiments, Form 2 has X-ray powder diffraction peaks at approximately 15.8, 18.4, 19.3, and 20.1°2θ using Cu Kα radiation. In some embodiments, Form 2 has X-ray powder diffraction peaks at approximately 8.3, 8.8, 11.6, 13.3, 15.8, 18.4, 19.3, 20.1, 20.9, 21.4, 23.2, 25.9, and 26.6°2θ using Cu Kα radiation. In one embodiment, Form 2 has a X-ray powder diffraction pattern substantially similar to that shown in FIG. 3.

In some embodiments, Form 2 is unsolvated.

In one embodiment, Form 2 can be isolated from IPAc or acetonitrile.

In some embodiments, Form 2 is stable at a temperature at or below 250° C., 240° C., 230° C., 220° C., 210° C., 200° C., 190° C., 180° C., 170° C., 160° C., 150° C., 140° C., 130° C., 120° C., 100° C., 90° C., 80° C., 70° C., 60° C., 50° C., 40° C., or 30° C. In some embodiments, Form 2 is stable at or above 50% RH, 60% RH, 70% RH, 80% RH, or 90% RH. For example, Form 2 is stable in a range of 0-96% RH. For example, Form 2 is stable at 96% RH.

In one embodiment, Form 2 can convert to other polymorphic forms. For example, Form 2, when melted and then cooled, may convert to Form 3.

In another embodiment, the polymorph of Compound A free base is Form 3. In some embodiments, Form 3 has X-ray powder diffraction peaks at approximately 15.1 and 23.4°2θ using Cu Kα radiation. In some embodiments, Form 3 has X-ray powder diffraction peaks at approximately 15.1, 18.8, 21.0, and 23.4°2θ using Cu Kα radiation. In some embodiments, Form 3 has X-ray powder diffraction peaks at approximately 6.4, 7.6, 8.4, 11.7, 15.1, 16.7, 18.8, 21.0, and 23.4°2θ using Cu Kα radiation. In one embodiment, Form 3 has a X-ray powder diffraction pattern substantially similar to that shown in FIG. 3.

In some embodiments, Form 3 is unsolvated.

In some embodiments, Form 3 is stable at a temperature at or below 250° C., 240° C., 230° C., 220° C., 210° C., 200° C., 190° C., 180° C., 170° C., 160° C., 150° C., 140° C., 130° C., 120° C., 100° C., 90° C., 80° C., 70° C., 60° C., 50° C., 40° C., or 30° C. In some embodiments, Form 3 is stable at or above 50% RH, 60% RH, 70% RH, 80% RH, or 90% RH. For example, Form 3 is stable in a range of 0-96% RH. For example, Form 3 is stable at 96% RH.

In another embodiment, the polymorph of Compound A free base is Form 4. In some embodiments, Form 4 has X-ray powder diffraction peaks at approximately 17 and 23°2θ using Cu Kα radiation. In some embodiments, Form 4 has X-ray powder diffraction peaks at approximately 15, 17, 23, and 26°2θ using Cu Kα radiation. In some embodiments, Form 4 has X-ray powder diffraction peaks at approximately 8, 14, 15, 17, 22, 23, and 26°2θ using Cu Kα radiation. In one embodiment, Form 4 has a X-ray powder diffraction pattern substantially similar to that shown in FIG. 14.

In one embodiment, Form 4 can be a solvate. In some embodiments, Form 4 is a tetrahydrofuran (THF) solvate. In a further embodiment, Form 4 is a THF hemi solvate.

In one embodiment, Form 4 can be isolated from THF. For example, Form 4 can be isolated from THF containing 5% water.

In some embodiments, Form 4 is stable at a temperature at or below 250° C., 240° C., 230° C., 220° C., 210° C., 200° C., 190° C., 180° C., 170° C., 160° C., 150° C., 140° C., 130° C., 120° C., 100° C., 90° C., 80° C., 70° C., 60° C., 50° C., 40° C., or 30° C. In some embodiments, Form 4 is stable at or above 50% RH, 60% RH, 70% RH, 80% RH, or 90% RH. For example, Form 4 is stable in a range of 0-96% RH. For example, Form 4 is stable at 96% RH.

Salts of Compound A

Compound A free base has three pKa values: 7.84, 4.69, and 2.82. Compound A can form mono-, bis-, and tris-salts. The acids that form salts with Compound A include, but are not limited to, HCl, $H_2SO_4$, methane sulfonic acid, maleic acid, phosphoric acid, L-glutamic acid, L-tartaric acid, galactaric acid, citric acid, D-glucuronic acid, hippuric acid, D-gluconic acid, L-lactic acid, L-ascorbic acid, succinic acid, and acetic acid. These acids form mono-, bis-, and tris-salt with Compound A free base.

Salts of Compound A can be prepared in appropriate solvents or mixtures thereof. The solvents include, but are not limited to, THF, dioxane, ethyl acetate, ethanol, isopropyl acetate (IPAc), isopropanol (IPA), MEK, acetone, acetonitrile, and nitromethane. Factors to consider in the selection of the appropriate solvent include, but are not limited to, the solubility of Compound A free base, the stability of the salt in the solvent, the solubility of the salt, and the type of salt (i.e., mono-, bis-, or tris-salt) to be formed.

Salts of Compound A can be formed by mixing Compound A free base with an acid in appropriate solvents or mixtures thereof. The mixture may be heated, for example, to facilitate the dissolution of Compound A free base or the reaction between Compound A free base and the acid. The mixture may also be cooled, for example, to decrease undesirable side reactions or lessen salt degradation. The amount of acid used for the reaction is determined according to the type of salt (i.e., mono-, bis-, or tris-salt) to be formed. Reaction time may be adjusted to complete the reaction. For example, the reaction type can be 5 min, 10 min, 20 min, 30 min, 45 min, 60 min, 2 hours, 3 hours, 4 hours, 6 hours, 8 hours, 10 hours, 12 hours, 18 hours, 24 hours, 36 hours, 48 hours, 60 hours, or 72 hours. The reaction mixture may be cooled to facilitate salt precipitation and isolation.

Salts of Compound A may be purified through simple filtration or other purification methods (e.g., HPLC) known in the art.

Salts of Compound A may be water soluble. For example, the solubility of a salt of Compound A may be in the range of 0.01-0.05 mg/ml, 0.05-0.1 mg/ml, 0.1-0.5 mg/ml, 0.5-1.0 mg/ml, 1-5 mg/ml, 5-10 mg/ml, 10-20 mg/ml, 20-30 mg/ml, 30-40 mg/ml, 40-50 mg/ml, 50-75 mg/ml, or 75-100 mg/ml, or above 100 mg/ml.

Salts of Compound A may be amorphous or crystalline. Salts of Compound A may form multiple polymorphs. An amorphous salt of Compound A may convert to a polymorph. For example, upon heating or under humid conditions (e.g., >50% RH), an amorphous salt of Compound A may convert to a crystalline form. An amorphous salt may also lose the counter-ion (e.g., a tris-salt turning into a bis- and/or mono-salt) and convert to a crystalline form. A polymorph of a salt of Compound A may convert to another polymorph.

Polymorphs of Salts of Compound A

Polymorphs of salts of Compound A can be formed by mixing Compound A free base with an acid or a solution of acid. In some embodiments, polymorphs of salts of Compound A can be prepared by: dissolving Compound A free base in a first solvent to form a first solution; mixing an acid with said first solution. In one embodiment, said acid is dissolved in a second solvent to form a second solution before said acid being mixed with said first solution. For example, said acid includes, but are not limited to, HCl, $H_2SO_4$, methane sulfonic acid, maleic acid, phosphoric acid, L-glutamic acid, L-tartaric acid, galactaric acid, citric acid, D-glucuronic acid, hippuric acid, D-gluconic acid, L-lactic acid, L-ascorbic acid, succinic acid, and acetic acid. For example, said acid is HCl or methane sulfonic acid.

In one embodiment, the first and the second solvents are the same; in another embodiment, the first and the second solvents are different. For example, said first solvent is selected from THF, dioxane, ethyl acetate, ethanol, IPAc, IPA, MEK, acetone, acetonitrile, nitromethane, and methanol. The solvents may be anhydrous or may contain various amount of water (e.g., 0.1-0.5%, 0.5-1%, 1-5%, 5-10%, 10-20%, 20-30%, 30-40%, 40-50%, 50-60%, 60-70%, 70-80%, and 80-90%). For example, said first solvent is THF, ethyl acetate, ethanol, or methanol. For example, said first solvent is methanol containing water (e.g., 0.1-0.5%, 0.5-1%, 1-5%, 5-10%, 10-20%). For example, said second solvent is selected from THF, dioxane, ethyl acetate, ethanol, IPAc, IPA, MEK, acetone, acetonitrile, nitromethane, and methanol. For example, said second solvent is THF, ethyl acetate, ethanol, or methanol. The solvents may be anhydrous or may contain various amount of water (e.g., 0.1-0.5%, 0.5-1%, 1-5%, 5-10%, 10-20%, 20-30%, 30-40%, 40-50%, 50-60%, 60-70%, 70-80%, and 80-90%). For example, said first solvent and second solvent are the same and are each THF, ethyl acetate, ethanol, or methanol.

In one embodiment, the method further comprises, warming said first solution. For example, said first solution can be warmed to 20-30° C., 30-40° C., 40-50° C., 50-60° C., 60-70° C., 70-80° C., 80-90° C., 90-100° C., 100-150° C., or 150-200° C., or above 200° C.

In one embodiment, said mixing comprises adding said acid or said second solution to said first solution; in anther embodiment, said mixing comprises adding said first solution to said acid or said second solution. In one embodiment, said mixing forms a third solution. In one embodiment, said mixing forms a first slurry. In one embodiment, the method further comprises warming said third solution or said first slurry. For example, said third solution or said first slurry can be warmed to 20-30° C., 30-40° C., 40-50° C., 50-60° C., 60-70° C., 70-80° C., 80-90° C., 90-100° C., 100-150° C., or 150-200° C., or above 200° C. In one embodiment, the method further comprises stirring said third solution or said first slurry. For example, said stirring lasts for at least 5 min, 10 min, 15 min, 20 min, 30 min, 60 min, 2 hrs, 4 hrs, 8 hrs, 12 hrs, 24 hrs, 36 hrs, or 48 hrs. In one embodiment, the method further comprises cooling said third solution or said first slurry. For example, said third solution or said first slurry can be cooled to 100-90° C., 90-80° C., 80-70° C., 70-60° C., 60-50° C., 50-40° C., 40-30° C., 30-20° C., 20-10° C., or 10-0° C., or below 0° C. In one embodiment, the method further comprises stirring said third solution or said first slurry after said cooling. For example, said stirring lasts for at least 5 min, 10 min, 15 min, 20 min, 30 min, 60 min, 2 hrs, 4 hrs, 8 hrs, 12 hrs, 24 hrs, 36 hrs, or 48 hrs.

In one embodiment, the method further comprises evaporating said third solution.

In one embodiment, the method further comprises adding a seed polymorph to said third solution to form a second slurry. In one embodiment, the method further comprises stirring said second slurry. For example, said stirring lasts for at least 5 min, 10 min, 15 min, 20 min, 30 min, 60 min, 2 hrs, 4 hrs, 8 hrs, 12 hrs, 24 hrs, 36 hrs, or 48 hrs. In one embodiment, the method further comprises cooling said second slurry. For example, said second slurry can be cooled to 100-90° C., 90-80° C., 80-70° C., 70-60° C., 60-50° C., 50-40° C., 40-30° C., 30-20° C., 20-10° C., or 10-0° C., or below 0° C. In one embodiment, the method further comprises stirring said second slurry after said cooling. For example, said stirring lasts for at least 5 min, 10 min, 15 min, 20 min, 30 min, 60 min, 2 hrs, 4 hrs, 8 hrs, 12 hrs, 24 hrs, 36 hrs, or 48 hrs.

In one embodiment, the method further comprises filtering said third solution, said first slurry, or said second slurry. Said filtering can be conducted at any conditions. For example, said filtering can be conducted at an ambient temperature or at other appropriate temperatures (e.g., below 0° C., 0-10° C., 10-20° C., 20-30° C., 30-40° C., 40-50° C., 50-60° C., 60-70° C., 70-80° C., 80-90° C., 90-100° C., 100-150° C., or 150-200° C., or above 200° C.). In one embodiment, the method further comprises drying said third solution, said first slurry, or said second slurry. Said drying can be conducted at any appropriate conditions (e.g., appropriate temperatures (e.g., below 0° C., 0-10° C., 10-20° C., 20-30° C., 30-40° C., 40-50° C., 50-60° C., 60-70° C., 70-80° C., 80-90° C., 90-100° C., 100-150° C., or 150-200° C., or above 200° C.), appropriate duration (e.g., less than 5 min, 10 min, 20 min, 30 min, 60 min, 2 hrs, 4 hrs, 8 hrs, 12 hrs, and 24 hrs), and pressure (e.g., atmospheric pressure and under vacuum)).

In another embodiment, polymorphs of salts of Compound A can be prepared by: dissolving Compound A free base in a first solvent to form a Compound A slurry; adding an acid to said Compound A slurry. In one embodiment, said acid is dissolved in a second solvent to form a second solution before said acid being added to said Compound A slurry. For example, said acid includes, but are not limited to, HCl, H$_2$SO$_4$, methane sulfonic acid, maleic acid, phosphoric acid, L-glutamic acid, L-tartaric acid, galactaric acid, citric acid, D-glucuronic acid, hippuric acid, D-gluconic acid, L-lactic acid, L-ascorbic acid, succinic acid, and acetic acid. For example, said acid is HCl or methane sulfonic acid.

In one embodiment, the first and the second solvents are the same; in another embodiment, the first and the second solvents are different. For example, said first solvent is selected from THF, dioxane, ethyl acetate, ethanol, IPAc, IPA, MEK, acetone, acetonitrile, nitromethane, and methanol. The solvents may be anhydrous or may contain various amount of water (e.g., 0.1-0.5%, 0.5-1%, 1-5%, 5-10%, 10-20%, 20-30%, 30-40%, 40-50%, 50-60%, 60-70%, 70-80%, and 80-90%). For example, said first solvent is THF, ethyl acetate, ethanol, or methanol. For example, said first solvent is methanol containing water (e.g., 0.1-0.5%, 0.5-1%, 1-5%, 5-10%, 10-20%). For example, said second solvent is selected from THF, dioxane, ethyl acetate, ethanol, IPAc, IPA, MEK, acetone, acetonitrile, nitromethane, and methanol. For example, said second solvent is THF, ethyl acetate, ethanol, or methanol. The solvents may be anhydrous or may contain various amount of water (e.g., 0.1-0.5%, 0.5-1%, 1-5%, 5-10%, 10-20%, 20-30%, 30-40%, 40-50%, 50-60%, 60-70%, 70-80%, and 80-90%). For example, said first solvent and second solvent are the same and are each THF, ethyl acetate, ethanol, or methanol.

In one embodiment, the method further comprises, warming said Compound A slurry. For example, said Compound A slurry can be warmed to 20-30° C., 30-40° C., 40-50° C., 50-60° C., 60-70° C., 70-80° C., 80-90° C., 90-100° C., 100-150° C., or 150-200° C., or above 200° C. For example, said Compound A slurry can be warmed to 55° C.

In one embodiment, adding said acid or said second solution to said Compound A slurry forms a third solution. In one embodiment, adding said acid or said second solution to said Compound A slurry forms a first slurry. In one embodiment, the method further comprises warming said third solution or said first slurry. For example, said third solution or said first slurry can be warmed to 20-30° C., 30-40° C., 40-50° C., 50-60° C., 60-70° C., 70-80° C., 80-90° C., 90-100° C., 100-150° C., or 150-200° C., or above 200° C. In one embodiment, the method further comprises stirring said third solution or said first slurry. For example, said stirring lasts for at least 5 min, 10 min, 15 min, 20 min, 30 min, 60 min, 2 hrs, 4 hrs, 8 hrs, 12 hrs, 24 hrs, 36 hrs, or 48 hrs. In one embodiment, the method further comprises cooling said third solution or said first slurry. For example, said third solution or said first slurry can be cooled to 100-90° C., 90-80° C., 80-70° C., 70-60° C., 60-50° C., 50-40° C., 40-30° C., 30-20° C., 20-10° C., or 10-0° C., or below 0° C. In one embodiment, the method further comprises stirring said third solution or said first slurry after said cooling. For example, said stirring lasts for at least 5 min, 10 min, 15 min, 20 min, 30 min, 60 min, 2 hrs, 4 hrs, 8 hrs, 12 hrs, 24 hrs, 36 hrs, or 48 hrs.

In one embodiment, the method further comprises evaporating said third solution.

In one embodiment, the method further comprises adding a third solvent to said third solution to form a second slurry. For example, said third solvent can be any solvent that induces the formation of a slurry. For example, said third solvent is selected from THF, dioxane, ethyl acetate, ethanol, IPAc, IPA, MEK, acetone, acetonitrile, nitromethane, and methanol. Said third solvent may be anhydrous or may contain various amount of water (e.g., 0.1-0.5%, 0.5-1%, 1-5%, 5-10%, 10-20%, 20-30%, 30-40%, 40-50%, 50-60%, 60-70%, 70-80%, and 80-90%). For example, said third solvent is IPAc.

In one embodiment, the method further comprises adding a seed polymorph to said third solution to form a third slurry. In one embodiment, the method further comprises stirring said second slurry or said third slurry. For example, said stirring lasts for at least 5 min, 10 min, 15 min, 20 min, 30 min, 60 min, 2 hrs, 4 hrs, 8 hrs, 12 hrs, 24 hrs, 36 hrs, or 48 hrs. In one embodiment, the method further comprises cooling said second slurry or said third slurry. For example, said second slurry or third slurry can be cooled to 100-90° C., 90-80° C., 80-70° C., 70-60° C., 60-50° C., 50-40° C., 40-30° C., 30-20° C., 20-10° C., or 10-0° C., or below 0° C. In one embodiment, the method further comprises stirring said second slurry or said third slurry after said cooling. For example, said stirring lasts for at least 5 min, 10 min, 15 min, 20 min, 30 min, 60 min, 2 hrs, 4 hrs, 8 hrs, 12 hrs, 24 hrs, 36 hrs, or 48 hrs.

In one embodiment, the method further comprises filtering said third solution, said first slurry, said second slurry, or said third slurry. Said filtering can be conducted at any conditions. For example, said filtering can be conducted at an ambient temperature or at other appropriate temperatures (e.g., below 0° C., 0-10° C., 10-20° C., 20-30° C., 30-40° C., 40-50° C., 50-60° C., 60- 70° C., 70-80° C., 80-90° C., 90-100° C., 100-150° C., or 150-200° C., or above 200° C.). In one embodiment, the method further comprises drying said third solution, said first slurry, said second slurry, or said third slurry. Said drying can be conducted at any appropriate conditions (e.g., appropriate temperatures (e.g., below 0° C., 0-10° C., 10-20° C., 20-30° C., 30-40° C., 40-50° C., 50-60° C., 60-70° C., 70-80° C., 80-90° C., 90-100° C., 100-150° C., or 150-200° C., or above 200° C.), appropriate duration (e.g., less than 5 min, 10 min, 20 min, 30 min, 60 min, 2 hrs, 4 hrs, 8 hrs, 12 hrs, and 24 hrs), and pressure (e.g., atmospheric pressure and under vacuum)).

Figure 32:
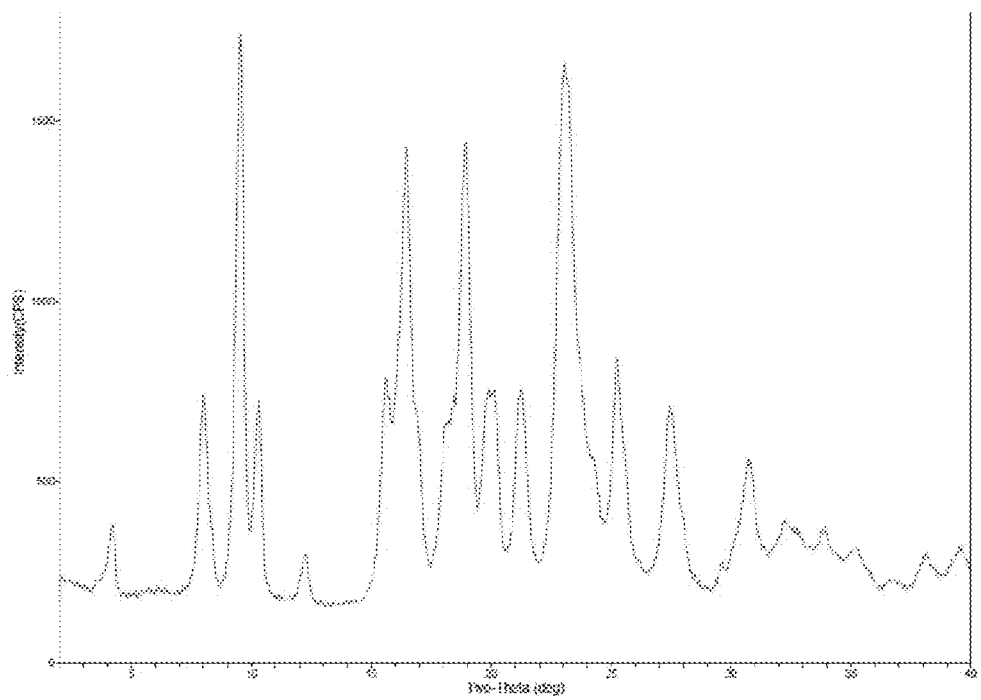
FIG. 32: XRPD of Form A of Compound A methane sulfonic acid salt
Figure 33:
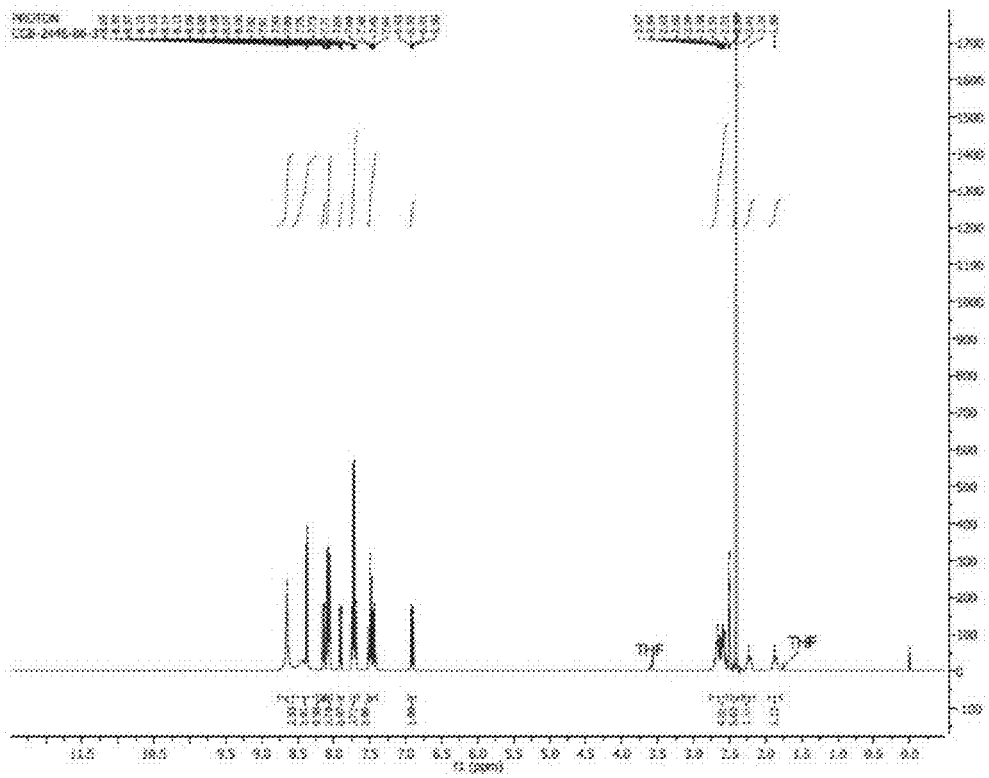
FIG. 33: $^1$H NMR of Form A of Compound A methane sulfonic acid salt

The application also pertains, at least in part, to polymorphs of Compound A mesylate. In one embodiment, the polymorph of Compound A mesylate is Form A. In some embodiments, Form A has X-ray powder diffraction peaks at approximately 9.4 and 23.0°2θ using Cu Kα radiation. In some embodiments, Form A has X-ray powder diffraction peaks at approximately 9.4, 15.5, 18.8, and 23.0°2θ using Cu Kα radiation. In some embodiments, Form A has X-ray powder diffraction peaks at approximately 4.1, 7.8, 9.4, 10.1, 12.1, 15.5, 16.2, 18.8, 19.9, 21.1, 23.0, 25.1 and 27.4°2θ using Cu Kα radiation. In one embodiment, Form A has a X-ray powder diffraction pattern substantially similar to that shown in FIG. 32.

In one embodiment, Form A is Compound A bis-mesylate.

In some embodiments, Form A is stable at a temperature at or below 350° C., 325° C., 300° C., 275° C., 250° C., 200° C., 150° C., 100° C., or 50° C. In some embodiments, Form A is stable at or below 325° C. In some embodiments, Form A is stable at or above 50% RH, 60% RH, 70% RH, 80% RH, or 90% RH. For example, Form A is stable in a range of 0-96% RH.

Figure 34:
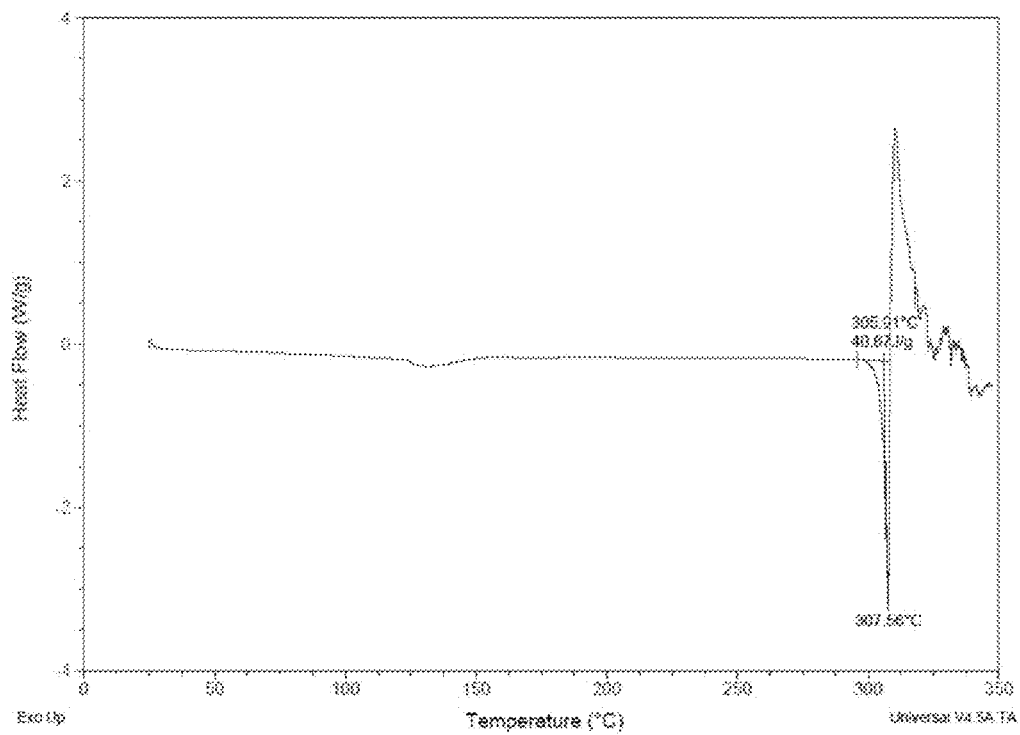
FIG. 34: DSC of Form A of Compound A methane sulfonic acid salt
Figure 35:
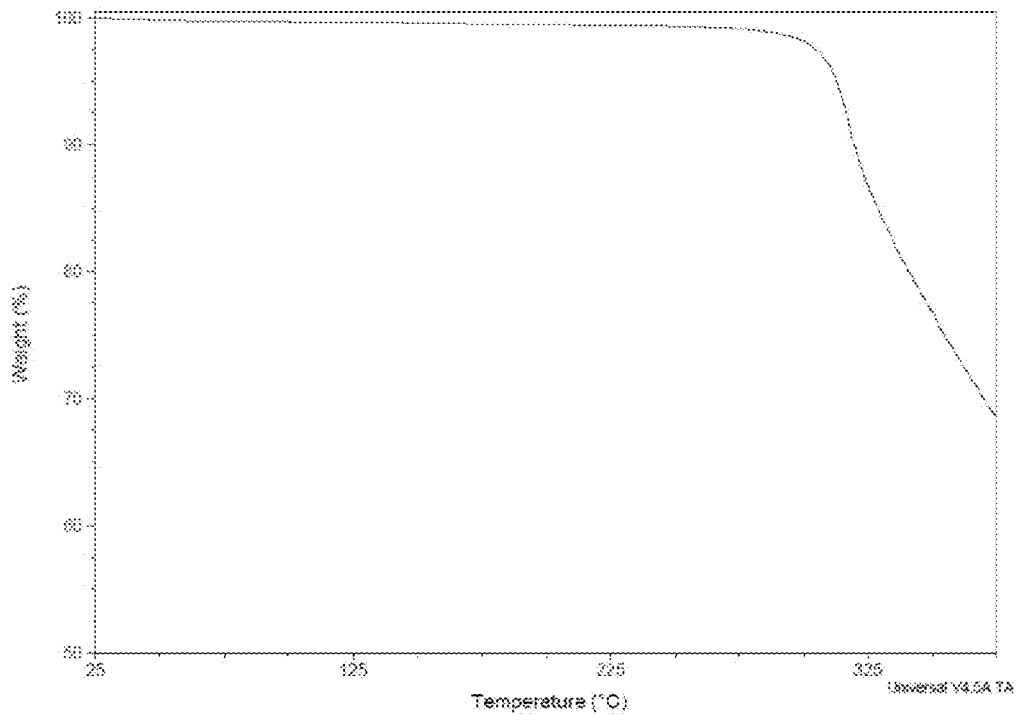
FIG. 35: TGA of Form A of Compound A methane sulfonic acid salt
Figure 36:
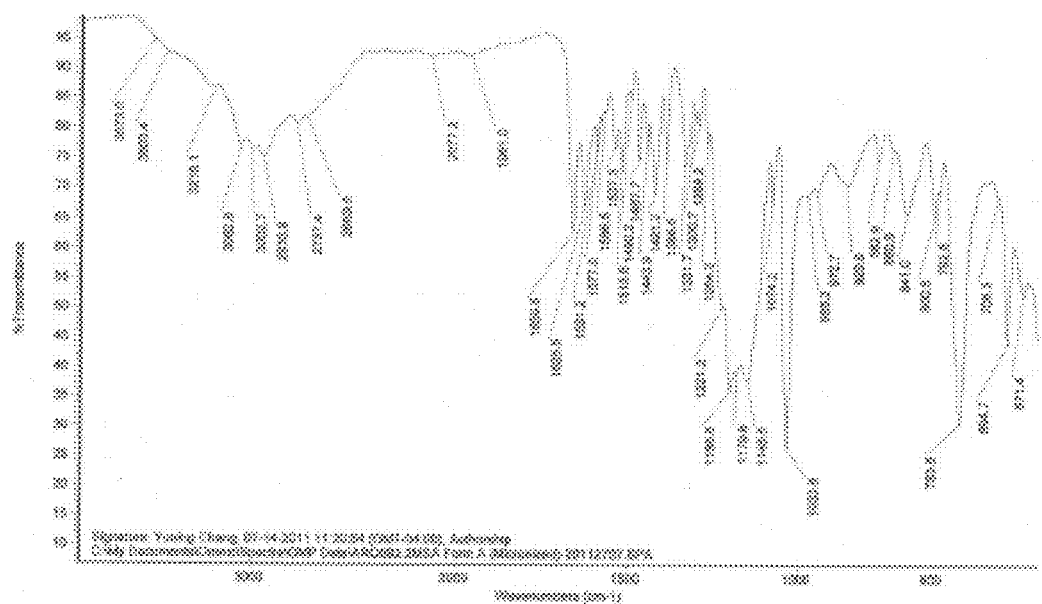
FIG. 36: IR of Form A of Compound A methane sulfonic acid salt

In some embodiments, Form A shows a sharp endotherm with an onset temperature of 305.9° C. and a melt at 307.6° C. (FIG. 34). In some embodiments, Form A shows no significant weight loss until the melting (FIG. 35).

In one embodiment, Form A can be produced by: dissolving Compound A free base in THF; adding a solution of methane sulfonic acid in THF to the Compound A free base solution to form a slurry; and filtering and drying said slurry.

In another embodiment, Form A can be produced by: adding dry methanol to the amorphous form of Compound A bis-mesylate to prepare a slurry. The slurry was stirred at about 22° C. for about 2 days before the sample was filtered and allowed to dry at ambient temperature.

Figure 37:
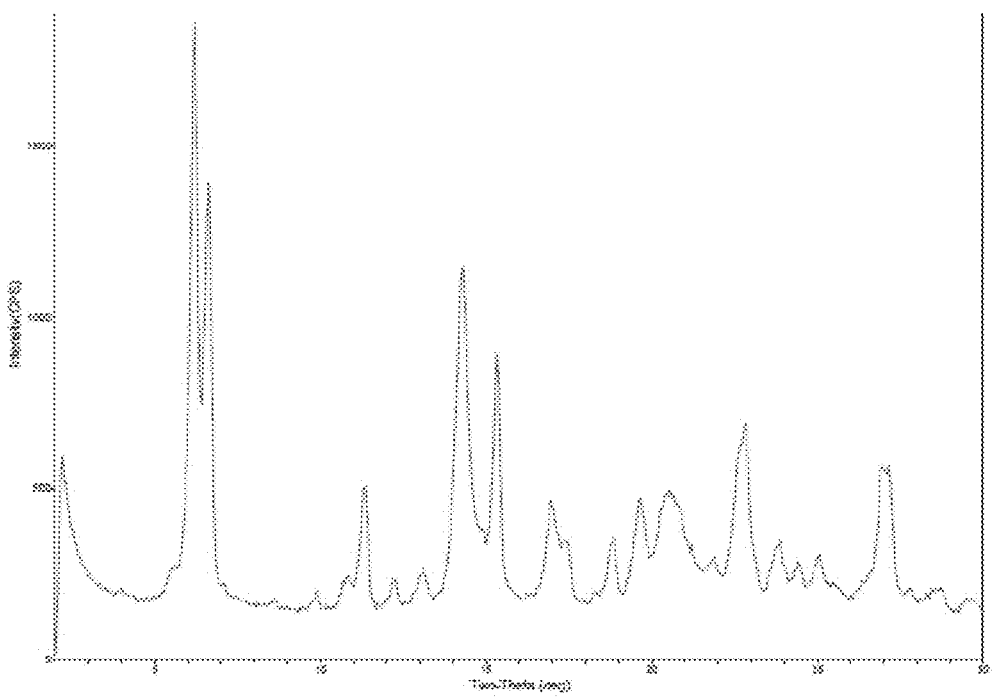
FIG. 37: XRPD of Form B of Compound A methane sulfonic acid salt
Figure 38:
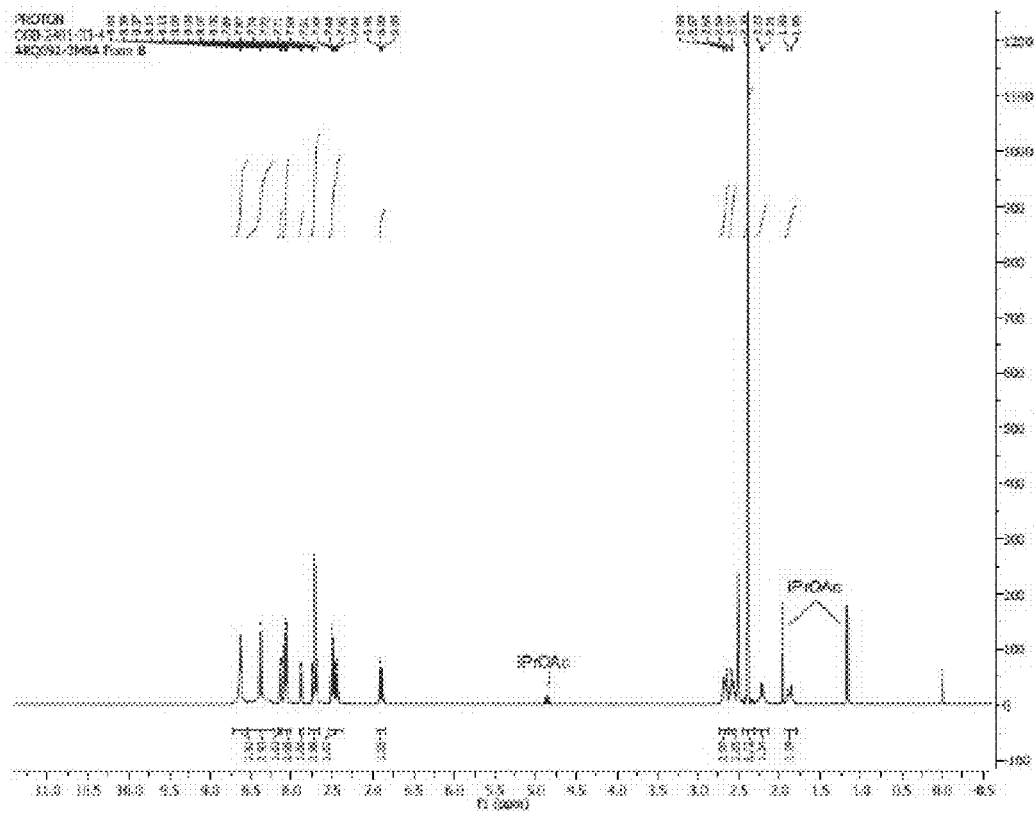
FIG. 38: $^1$H NMR of Form B of Compound A methane sulfonic acid salt

In one embodiment, the polymorph of Compound A mesylate is Form B. In some embodiments, Form B has X-ray powder diffraction peaks at approximately 6.2 and 14.3°2θ using Cu Kα radiation. In some embodiments, Form B has X-ray powder diffraction peaks at approximately 6.2, 6.6, 14.3, and 15.3°2θ using Cu Kα radiation. In some embodiments, Form B has X-ray powder diffraction peaks at approximately 6.2, 6.6, 11.3, 14.3, 15.3, 22.8, and 26.9°2θ using Cu Kα radiation. In one embodiment, Form B has a X-ray powder diffraction pattern substantially similar to that shown in FIG. 37.

In one embodiment, Form B is Compound A bis-mesylate.

In some embodiments, Form B is stable at a temperature at or below 210° C., 205° C., 200° C., 150° C., 100° C., or 50° C. In some embodiments, Form B is stable at or below 205° C. In some embodiments, Form B is stable at or above 50% RH, 60% RH, 70% RH, 80% RH, or 90% RH. For example, Form B is stable in a range of 0-96% RH.

Figure 39:
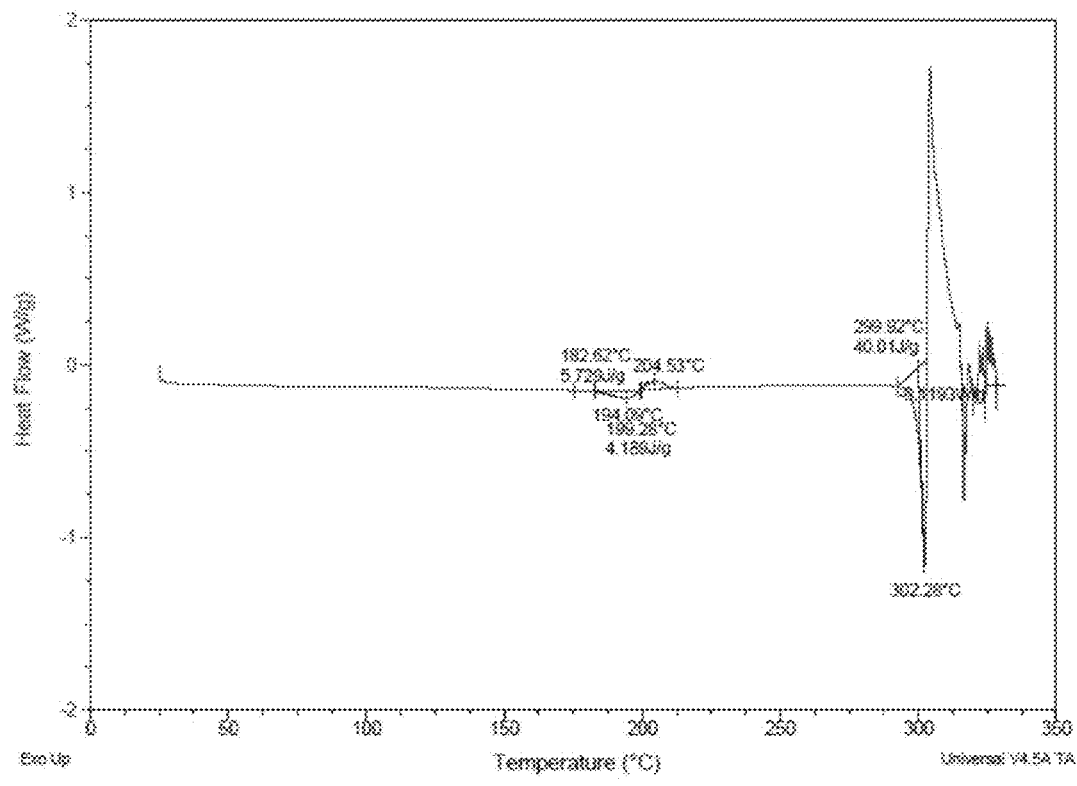
FIG. 39: DSC of Form B of Compound A methane sulfonic acid salt
Figure 40:
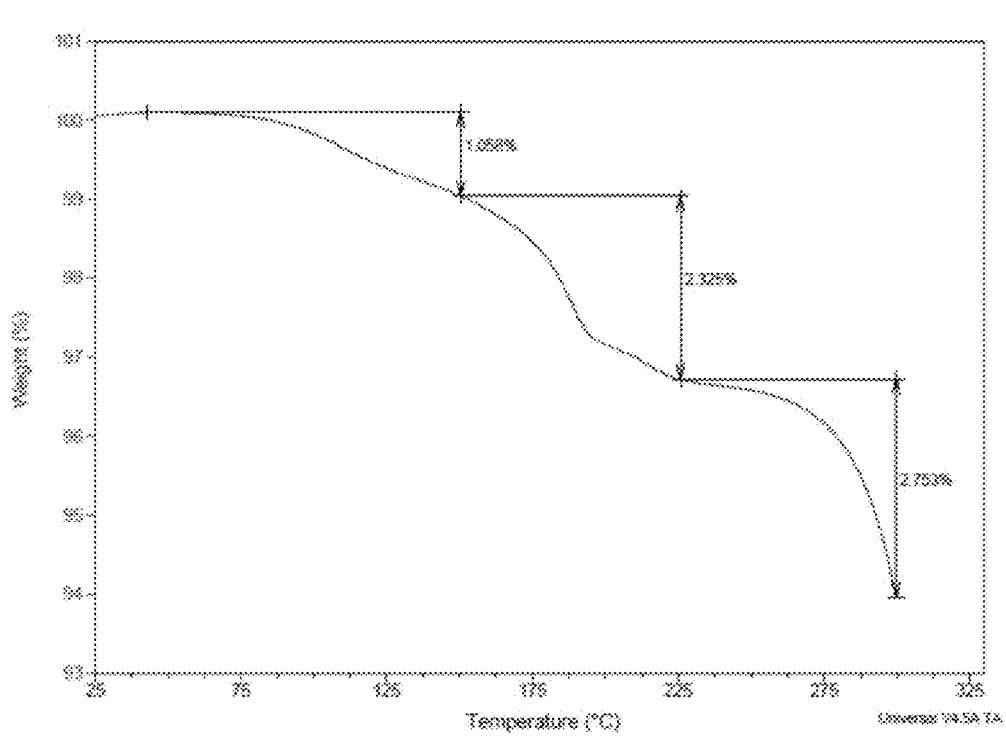
FIG. 40: TGA of Form B of Compound A methane sulfonic acid salt
Figure 41:
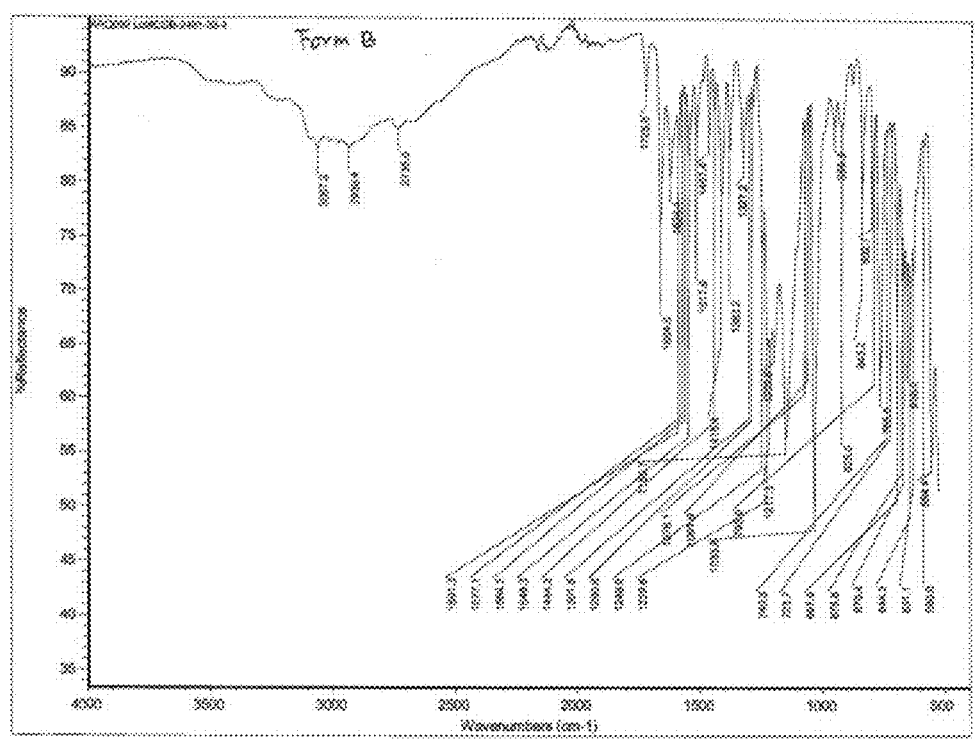
FIG. 41: IR of Form B of Compound A methane sulfonic acid salt

In some embodiments, Form B shows a broad endotherm with an onset temperature of 182.6° C. and a melt at 194.1° C. (FIG. 39). In some embodiments, Form B shows an exotherm at an onset temperature of 199.3° C. with a peak at 204.5° C. (FIG. 39). In some embodiments, Form B shows a second endotherm with an onset temperature of 299.9° C. and a second melt at 302.3° C. (FIG. 39). In some embodiments, Form B shows weight loss at multiple temperatures (FIG. 40).

In one embodiment, Form B can be produced by: dissolving Compound A free base in aqueous methanol to form a first slurry; adding methane sulfonic acid to said first slurry to form a solution; adding IPAc to said solution to form a second slurry; and filtering and drying said second slurry. For example, said methane sulfonic acid is neat methane sulfonic acid. For example, the aqueous methanol may contain 2% water.

In another embodiment, Form B can be produced by: adding 2-propanol with 0.35 water activity to the amorphous form of Compound A bis-mesylate salt to prepare a slurry. The slurry was stirred at about 22° C. for about 3 days before the sample was filtered and allowed to dry at ambient temperature prior to characterization.

Figure 42:
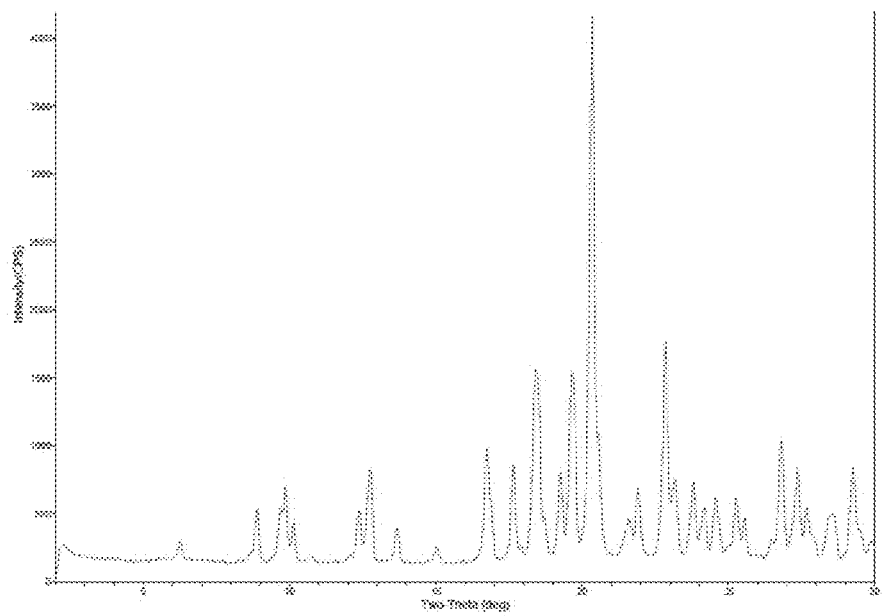
FIG. 42: XRPD of Form C of Compound A methane sulfonic acid salt
Figure 43:
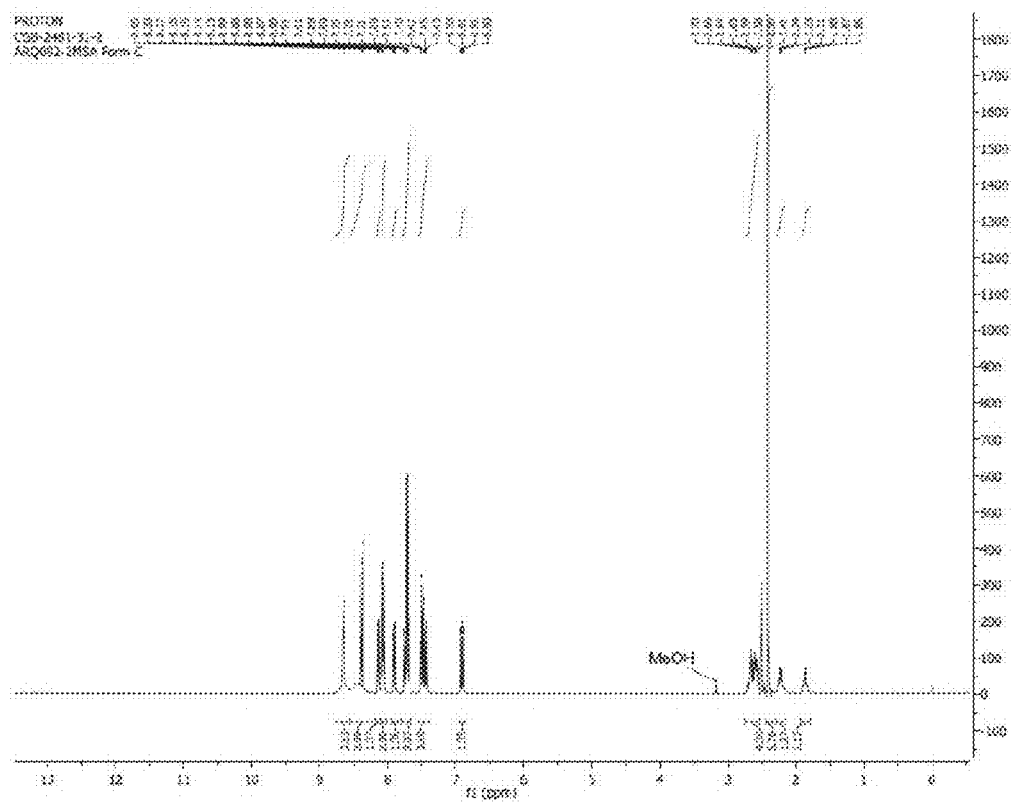
FIG. 43: $^1$H NMR of Form C of Compound A methane sulfonic acid salt

In one embodiment, the polymorph of Compound A mesylate is Form C. In some embodiments, Form C has X-ray powder diffraction peaks at approximately 20.3 and 22.8°2θ using Cu Kα radiation. In some embodiments, Form C has X-ray powder diffraction peaks at approximately 17.6, 18.4, 19.3, 19.7, 20.3, and 22.8°2θ using Cu Kα radiation. In some embodiments, Form C has X-ray powder diffraction peaks at approximately 6.2, 8.9, 9.8, 10.1, 13.7, 17.6, 18.4, 19.3, 19.7, 20.3, 22.8, and 26.8°2θ using Cu Kα radiation. In one embodiment, Form C has a X-ray powder diffraction pattern substantially similar to that shown in FIG. 42.

In one embodiment, Form C is Compound A bis-mesylate.

In some embodiments, Form C is stable at a temperature at or below 400° C., 375° C., 350° C., 325° C., 300° C., 275° C., 250° C., 200° C., 150° C., 100° C., or 50° C. In some embodiments, Form C is stable at or below 310° C. In some embodiments, Form C is stable at or above 50% RH, 60% RH, 70% RH, 80% RH, or 90% RH. For example, Form C is stable in a range of 0-96% RH.

Figure 44:
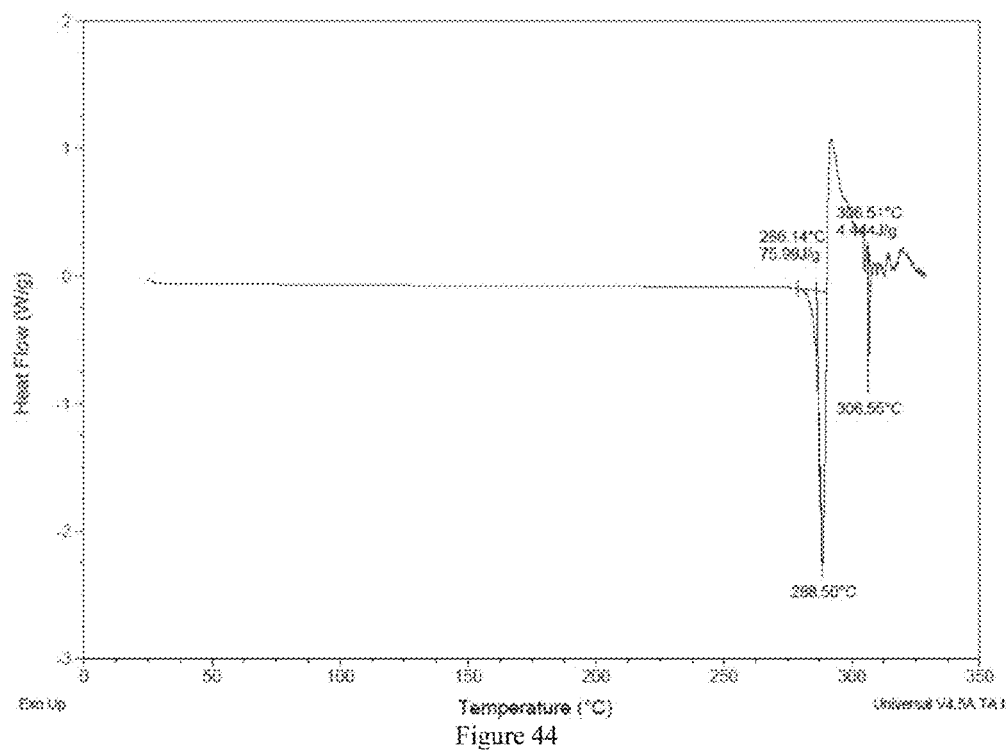
FIG. 44: DSC of Form C of Compound A methane sulfonic acid salt
Figure 45:
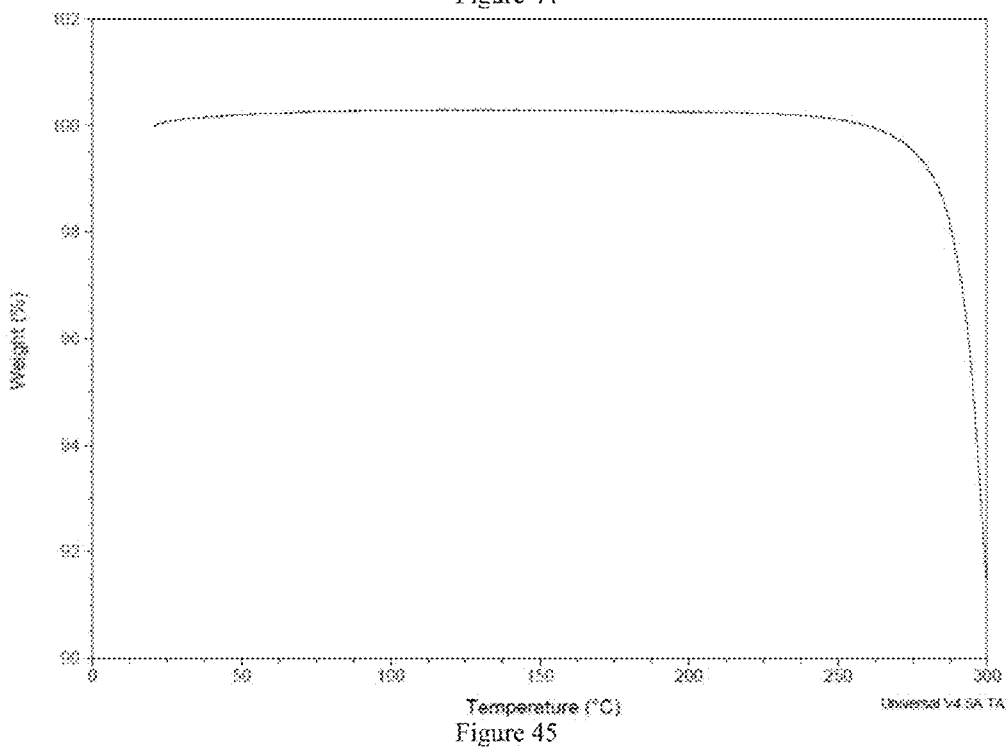
FIG. 45: TGA of Form C of Compound A methane sulfonic acid salt
Figure 46:
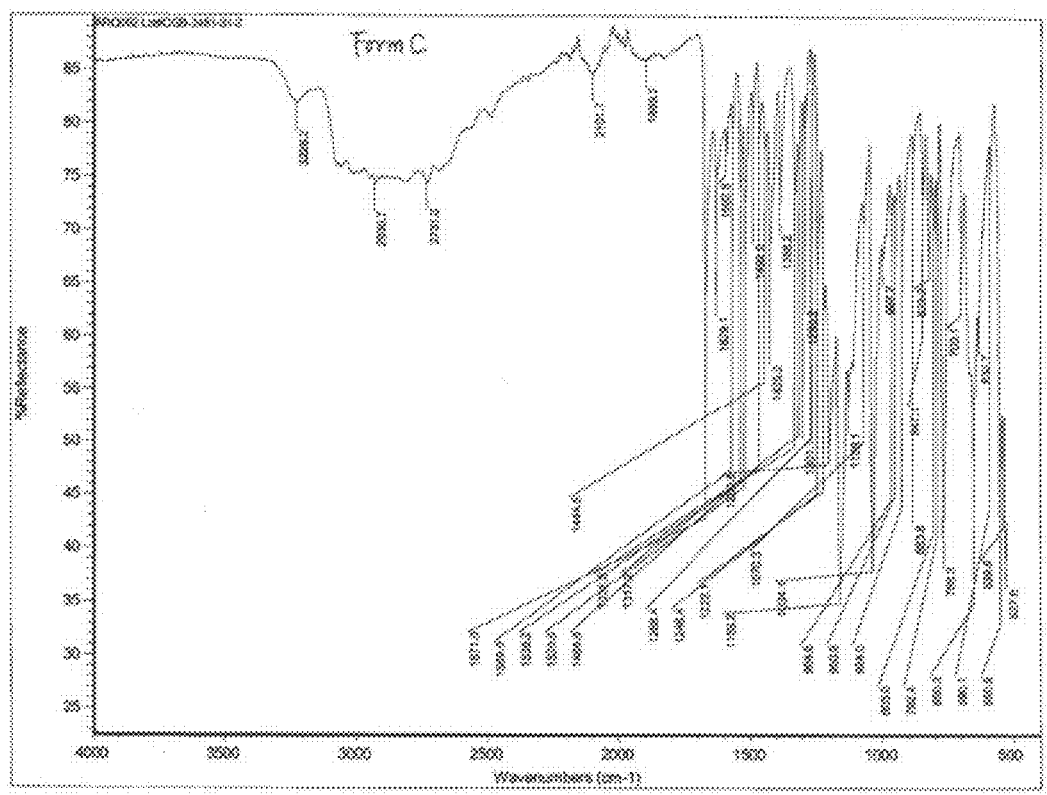
FIG. 46: IR of Form C of Compound A methane sulfonic acid salt

In some embodiments, Form C shows a sharp endotherm with an onset temperature of 286.1° C. and a melt at 288.5° C. (FIG. 44). In some embodiments, Form C shows no significant weight loss until the melting (FIG. 45).

In one embodiment, Form C can be produced by: dissolving Compound A free base in aqueous methanol to form a solution; adding methane sulfonic acid to said solution; adding Compound A mesylate seed crystal (e.g., seed Form C crystal) to said solution to form a slurry; and filtering and drying said slurry. For example, said methane sulfonic acid is neat methane sulfonic acid. For example, the aqueous methanol may contain 2% water.

In another embodiment, Form C can be produced by: adding 2% aqueous methanol to Form A to form a slurry, stirring the slurry, and filtering and drying the slurry.

As is well known in the art, due to fluctuations in the instrument and experimental conditions, results obtained from the characterization of polymorphs of the present application (e.g., by TGA, DSC, XRPD, PLM) may have slight differences from one measurement to another. For example, the X-ray powder diffraction peaks of a polymorph may shift from one measurement to another. That is, from one measurement to another, the X-ray powder diffraction peaks may have slightly different numeric values. However, the X-ray powder diffraction patterns (e.g., the positions, intensities, and shapes of the peaks) of the polymorph are substantially similar (e.g., at least 80%, 85%, 90%, or 95% of the patterns match one another).

Figure 110:
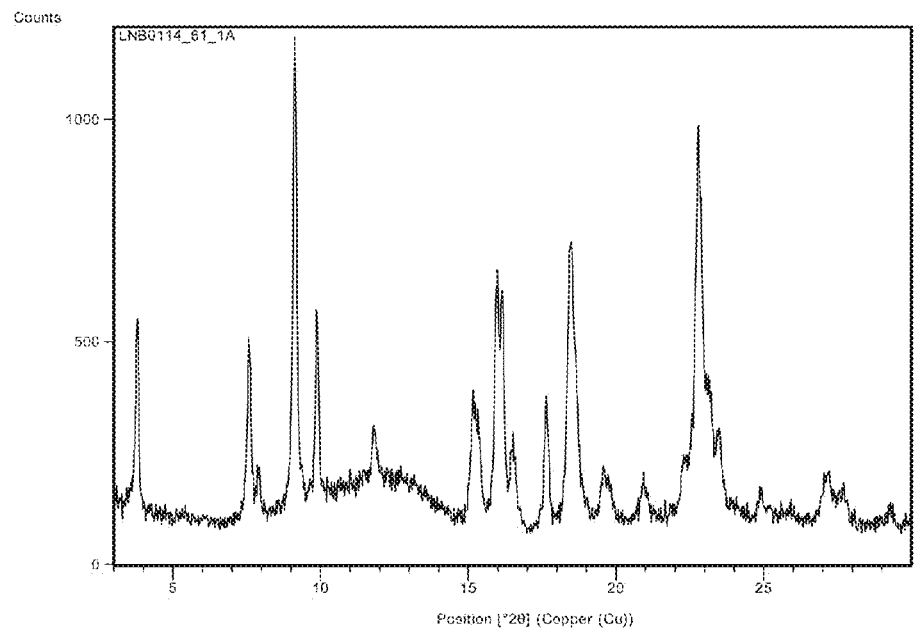
FIG. 110: Form A Compound A bis-mesylate—XRPD
Figure 111:
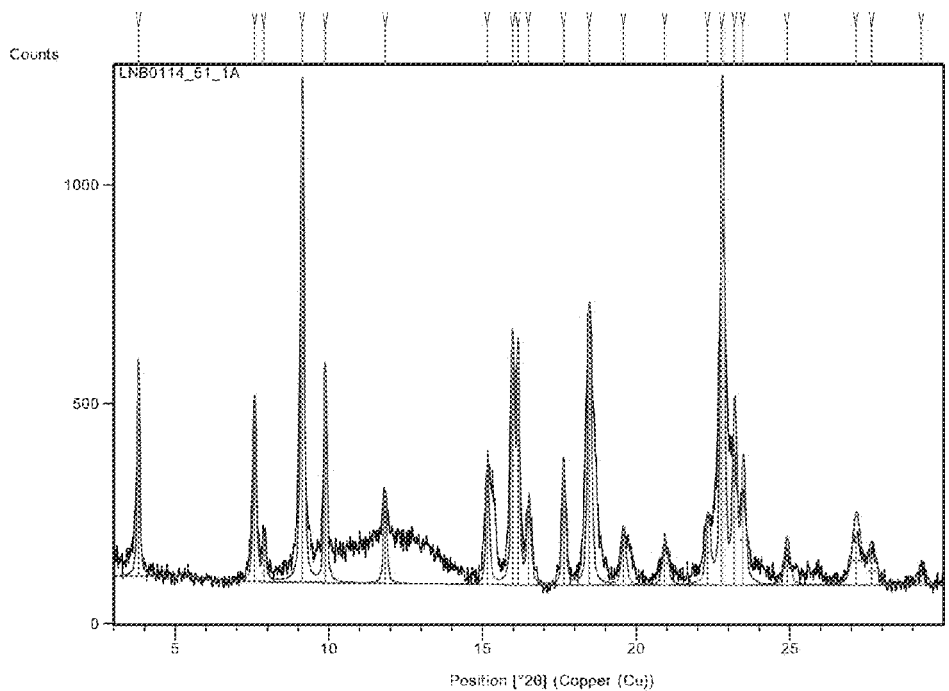
FIG. 111: Form A Compound A bis-mesylate—XRPD—Peaks Indicated
Figure 113:
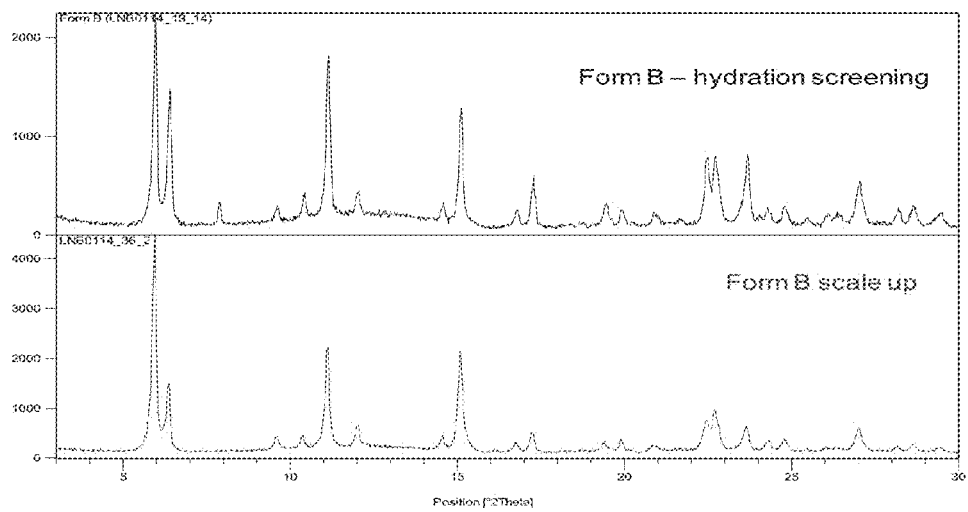
FIG. 113: Form B Compound A bis-mesylate—XRPD Analysis: Hydration Screen and Scale-Up
Figure 114:
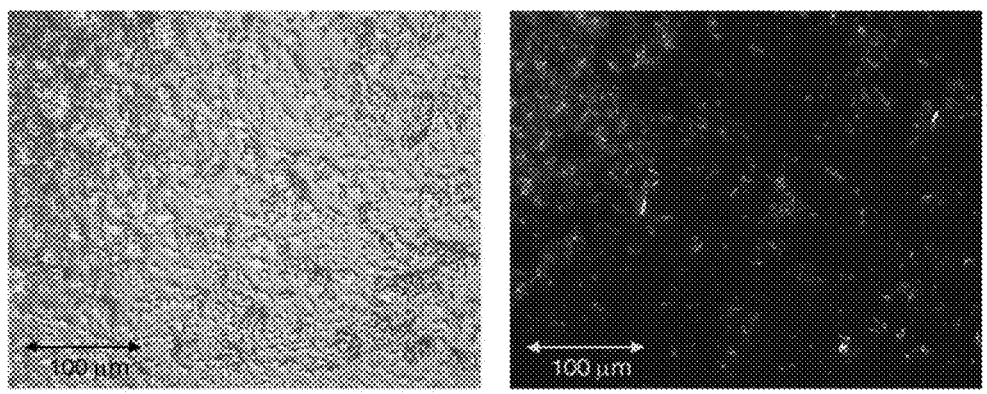
FIG. 114: Form B Compound A bis-mesylate—PLM Analysis
Figure 115:
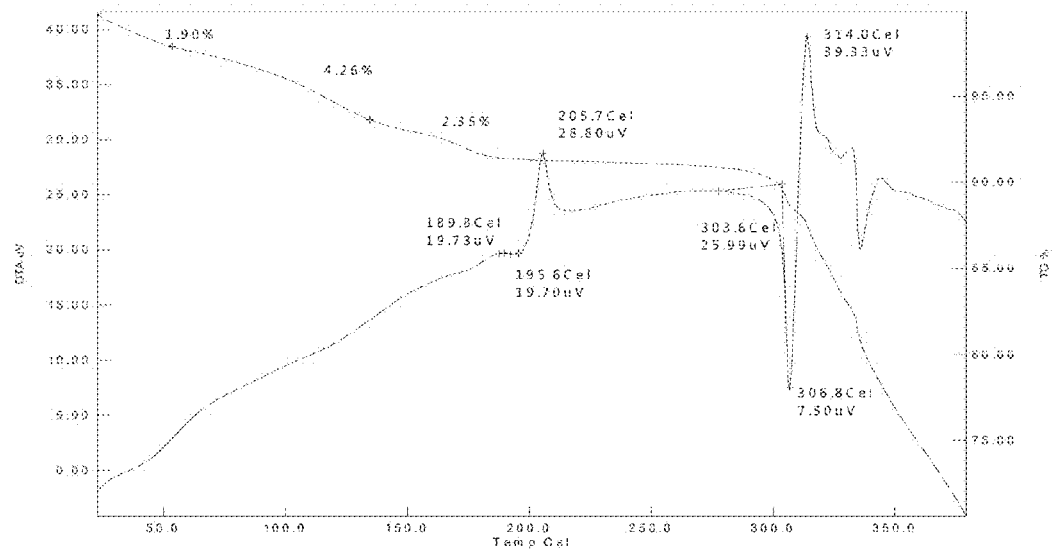
FIG. 115: Form B Compound A bis-mesylate—TG/DTA Analysis: After air drying for 2-3 days
Figure 116:
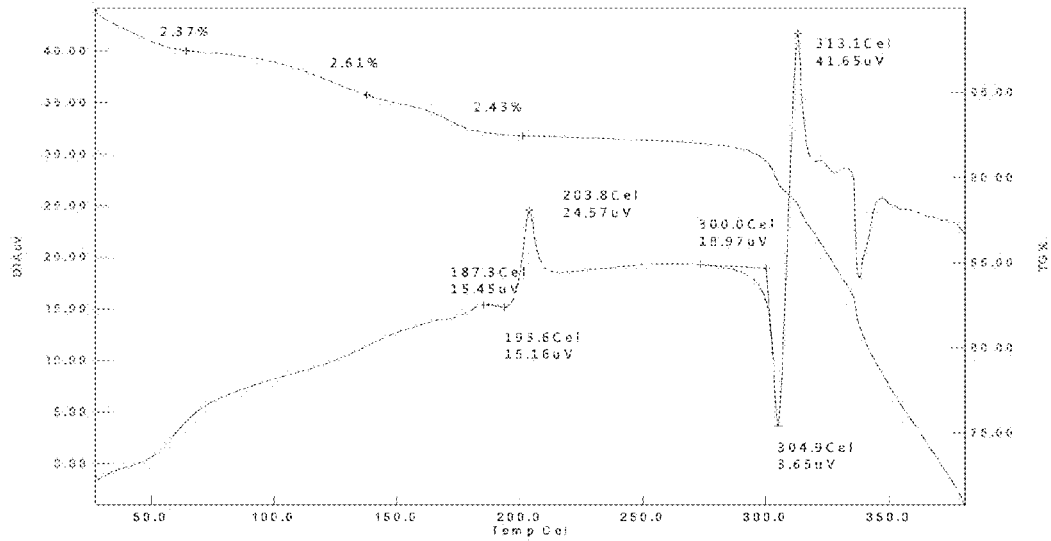
FIG. 116: Form B Compound A bis-mesylate—TG/DTA Analysis: After drying under vacuum for 1 day
Figure 117:
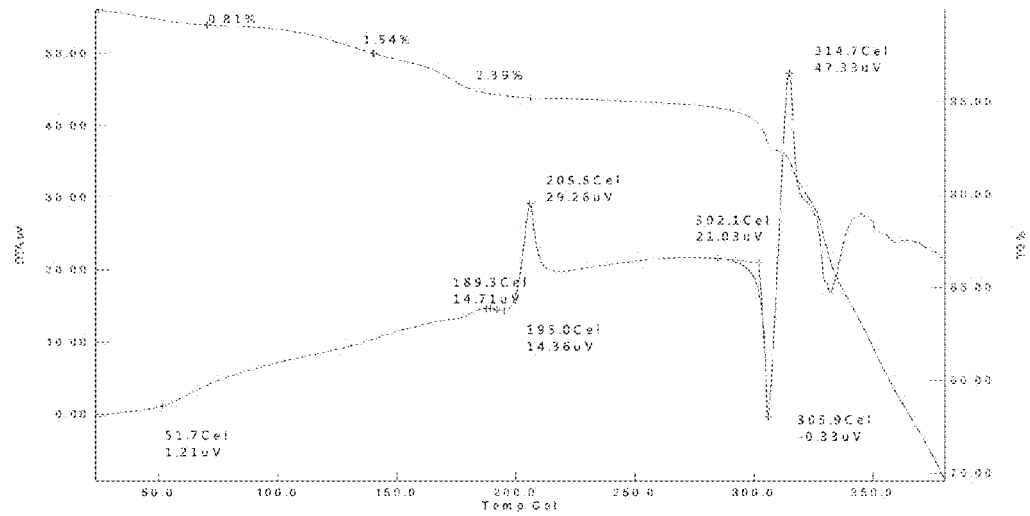
FIG. 117: Form B Compound A bis-mesylate—TG/DTA Analysis: After drying at 50° C. for a further day
Figure 118:
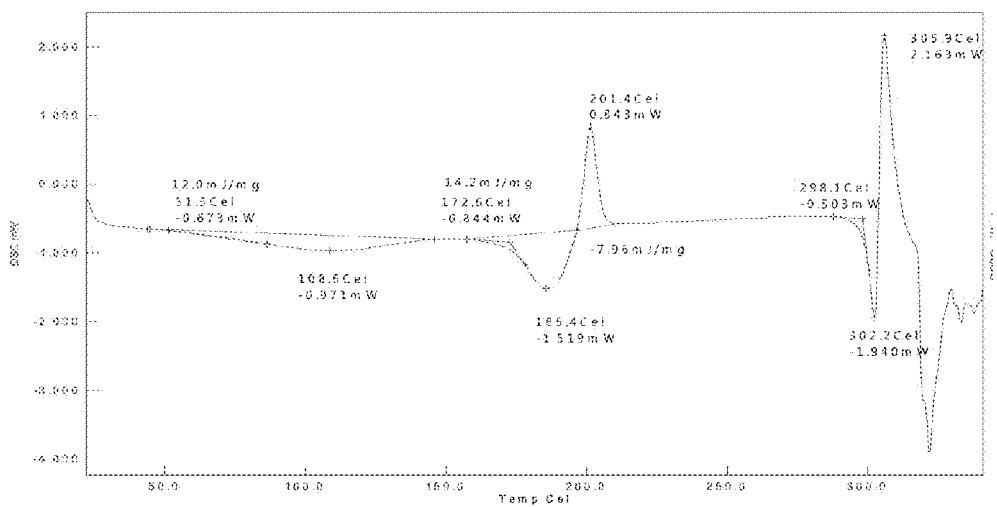
FIG. 118: Form B Compound A bis-mesylate—DSC Analysis
Figure 119:
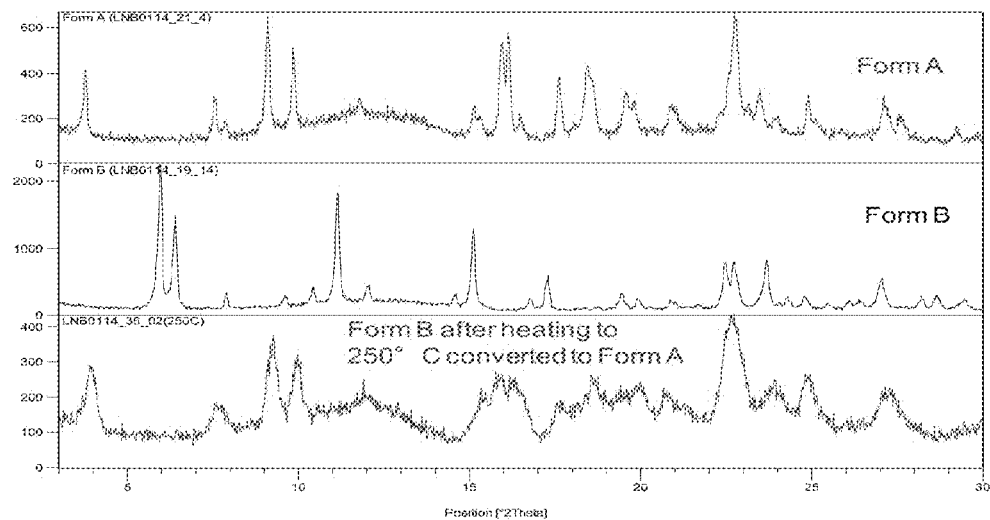
FIG. 119: Form B Compound A bis-mesylate—XRPD Analysis: Form A Compared to Form B compared to Form B after heating to 250° C.
Figure 120:
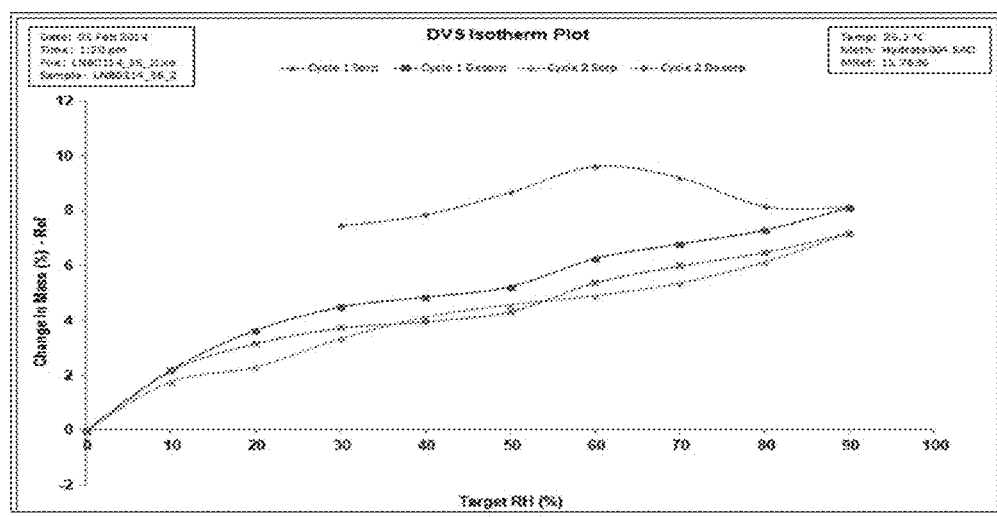
FIG. 120: Form B Compound A bis-mesylate—DVS Analysis
Figure 121:
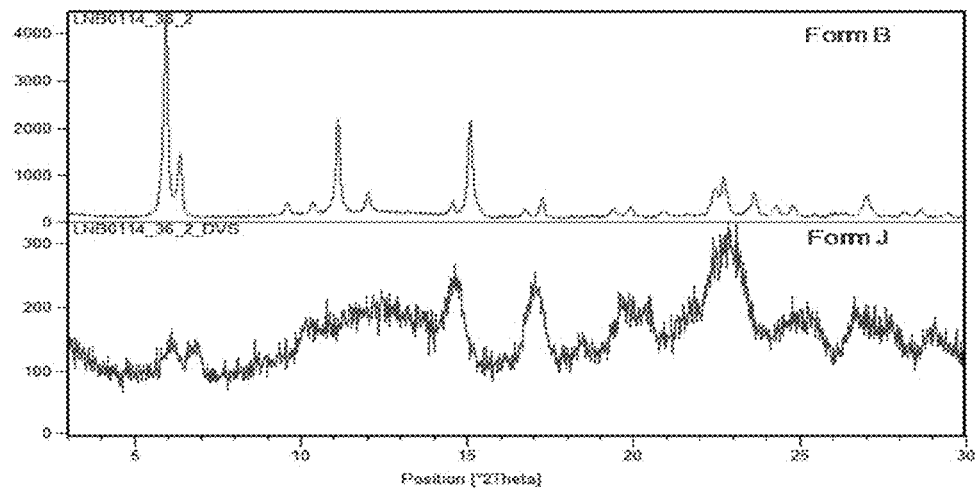
FIG. 121: Form B Compound A bis-mesylate—XRPD Analysis: Post-DVS Analysis
Figure 122:
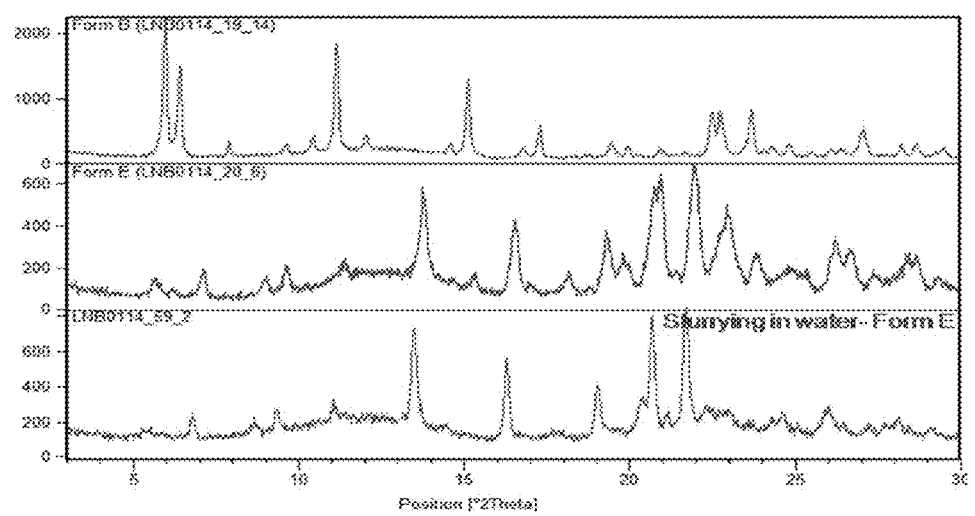
FIG. 122: Form B Compound A bis-mesylate—XRPD Analysis: Slurry in Deionized Water
Figure 123:
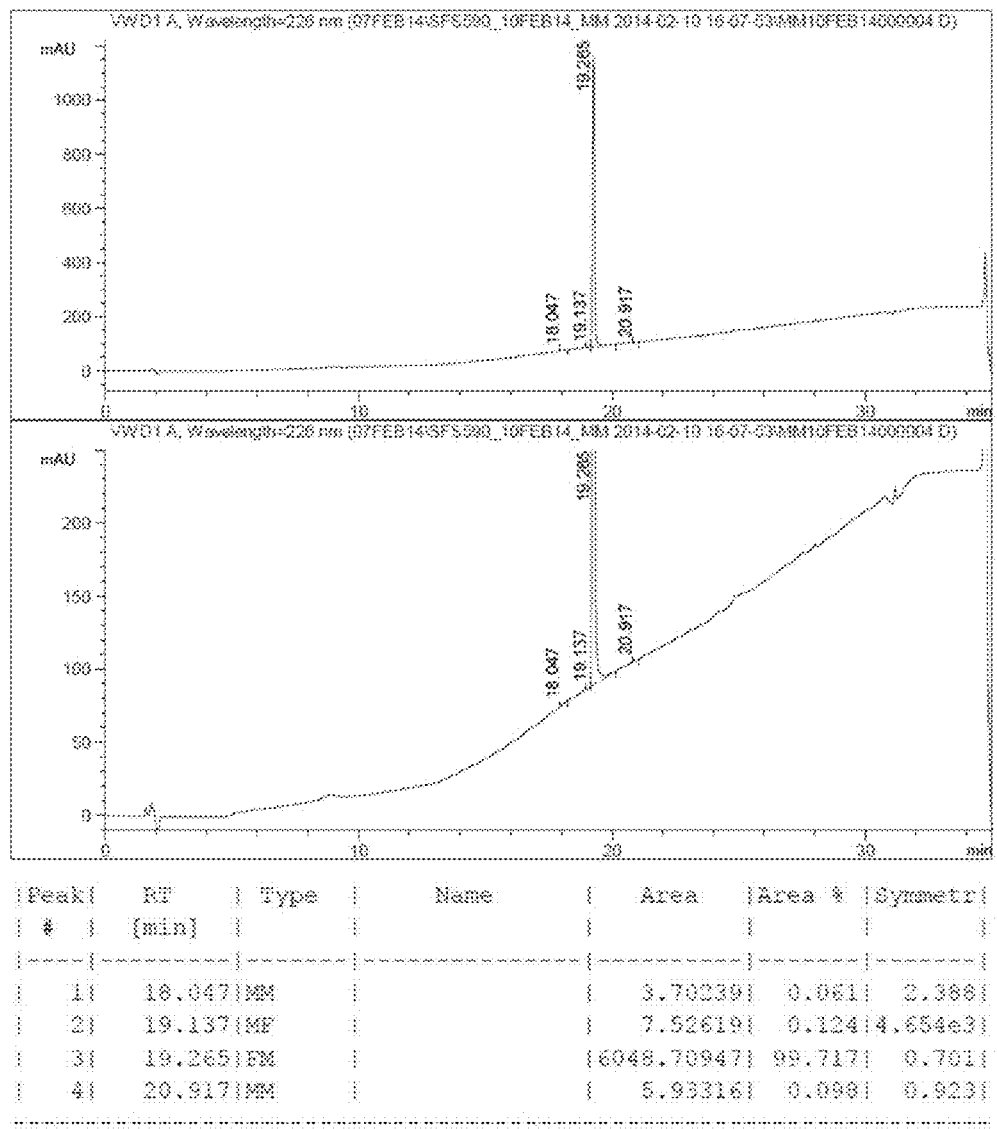
FIG. 123: Form B Compound A bis-mesylate—HPLC Purity Analysis
Figure 124:
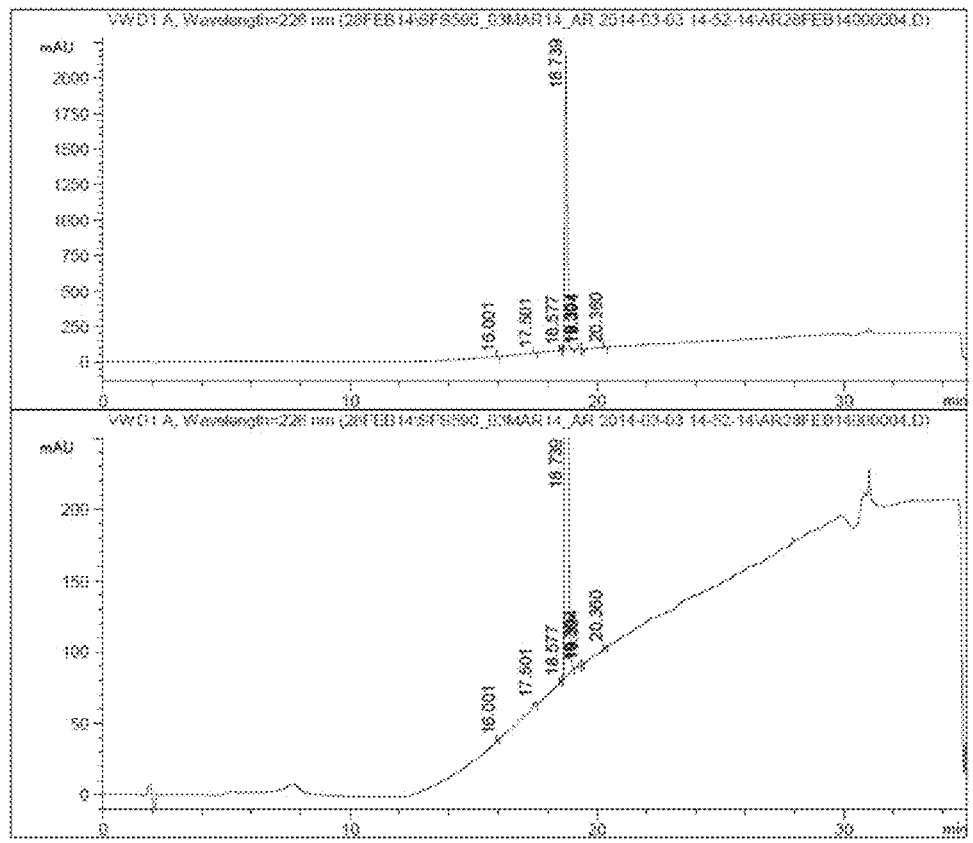
FIG. 124: Form B Compound A bis-mesylate—HPLC Purity: Stability Study at 40° C. and 75% RH
Figure 125:
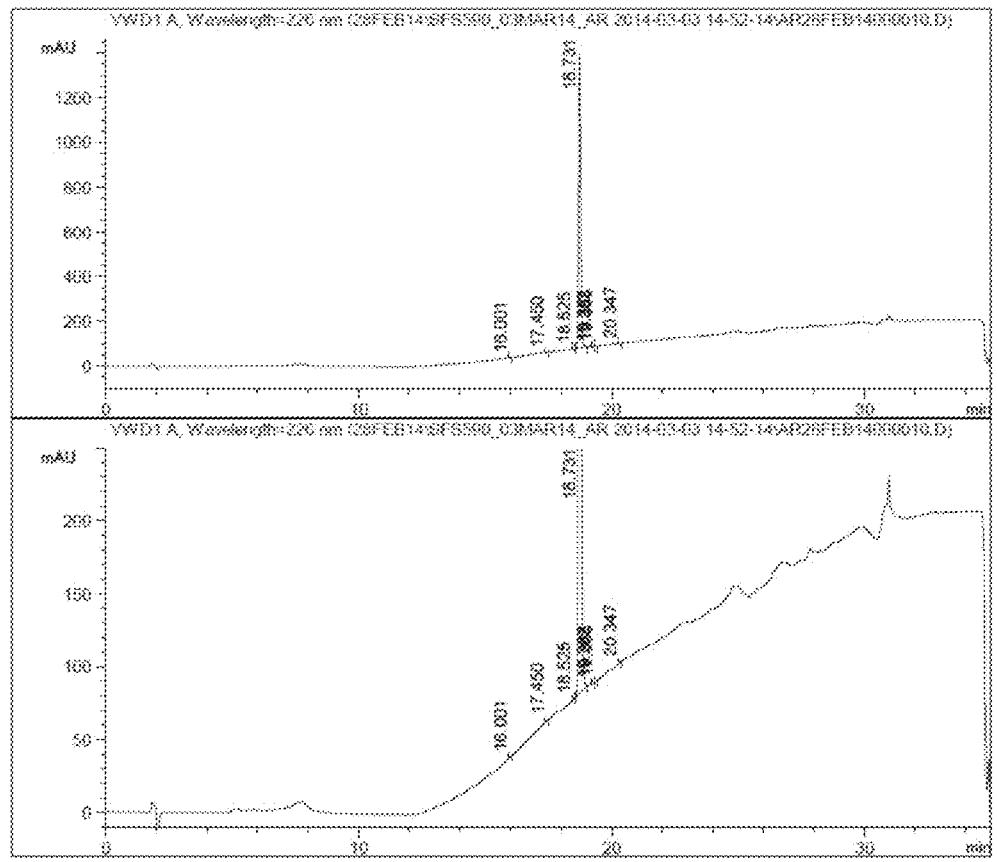
FIG. 125: Form B Compound A bis-mesylate—HPLC Purity: Stability Study at Ambient Temperature
Figure 126:
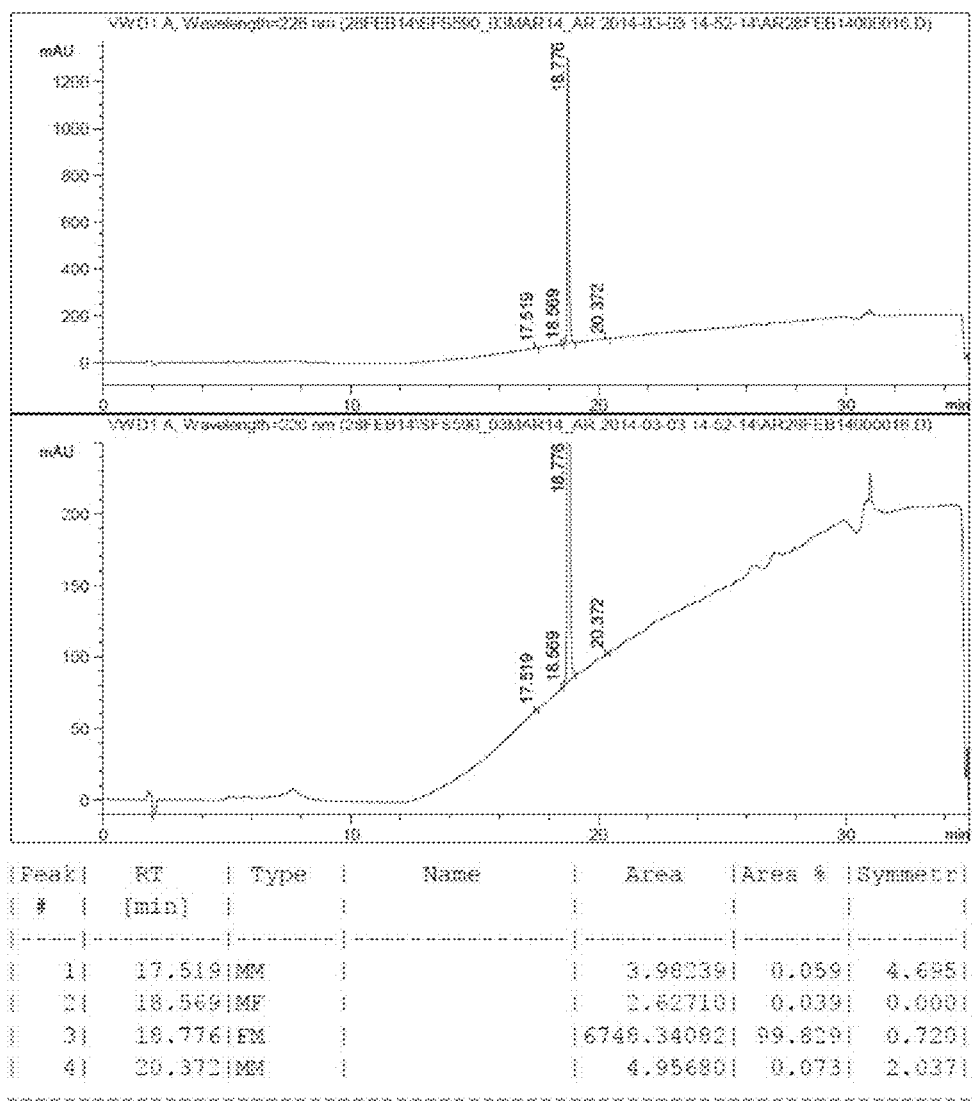
FIG. 126: Form B Compound A bis-mesylate—HPLC Purity: Stability Study at 80° C.
Figure 127:
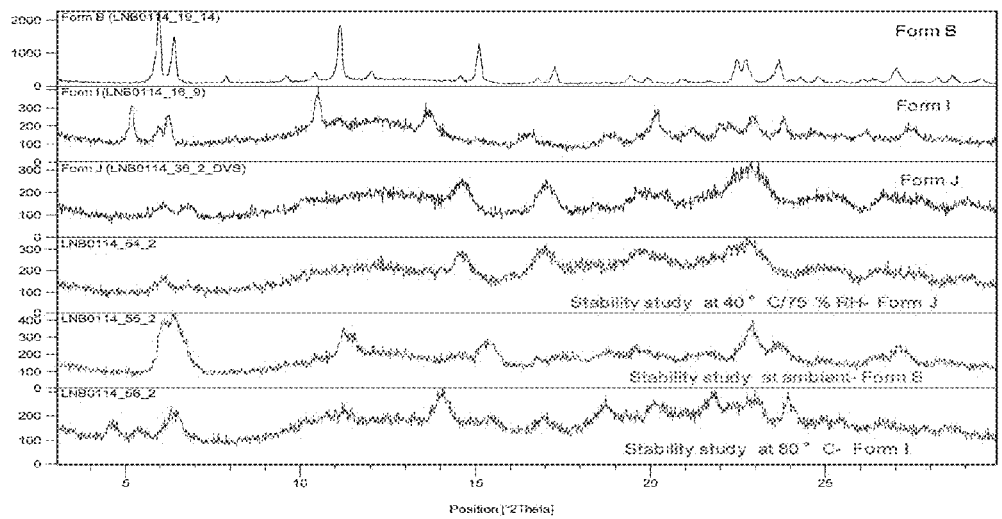
FIG. 127: Form B Compound A bis-mesylate—XRPD Analysis: Stability Testing—Forms B, I, and J Compared to Form B at 40° C. and 75% RH, Ambient Temperature, and 80° C.
Figure 128:
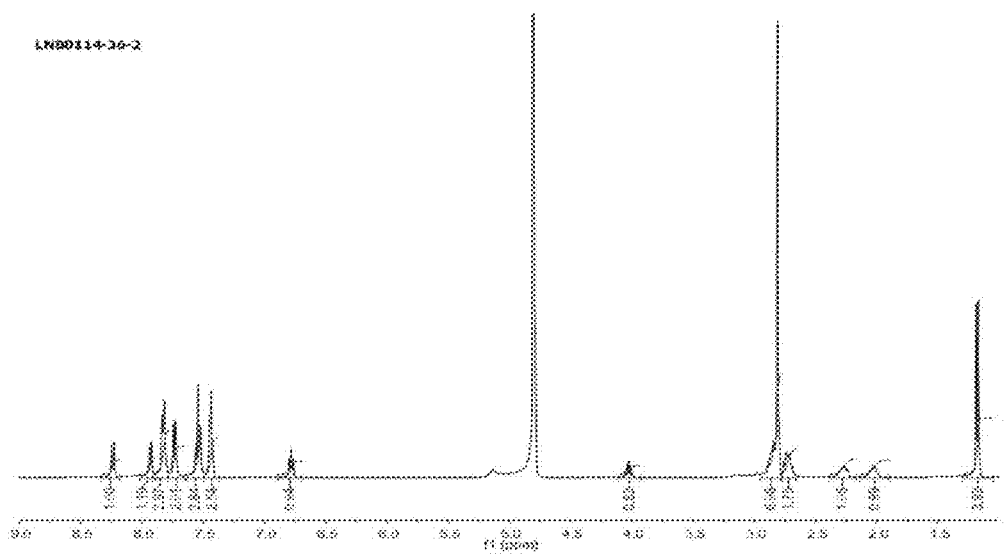
FIG. 128: Form B Compound A bis-mesylate—$^1$H NMR Spectroscopy

In one embodiment, Form A has X-ray powder diffraction peaks at approximately 9.1 and 22.8°2θ using Cu Kα radiation. In some embodiments, Form A has X-ray powder diffraction peaks at approximately 9.1, 15.1, 16.0, 18.5, 22.8, and 22.9°2θ using Cu Kα radiation. In some embodiments, Form A has X-ray powder diffraction peaks at approximately 3.8, 7.6, 9.1, 9.9, 15.1, 16.0, 16.1, 18.5, 22.8, 22.9, and 23.2°2θ using Cu Kα radiation. In one embodiment, Form A has X-ray powder diffraction pattern substantially similar to that shown in FIG. 110. In one embodiment, Form A has X-ray powder diffraction peaks as shown in FIG. 112.

Figure 129:
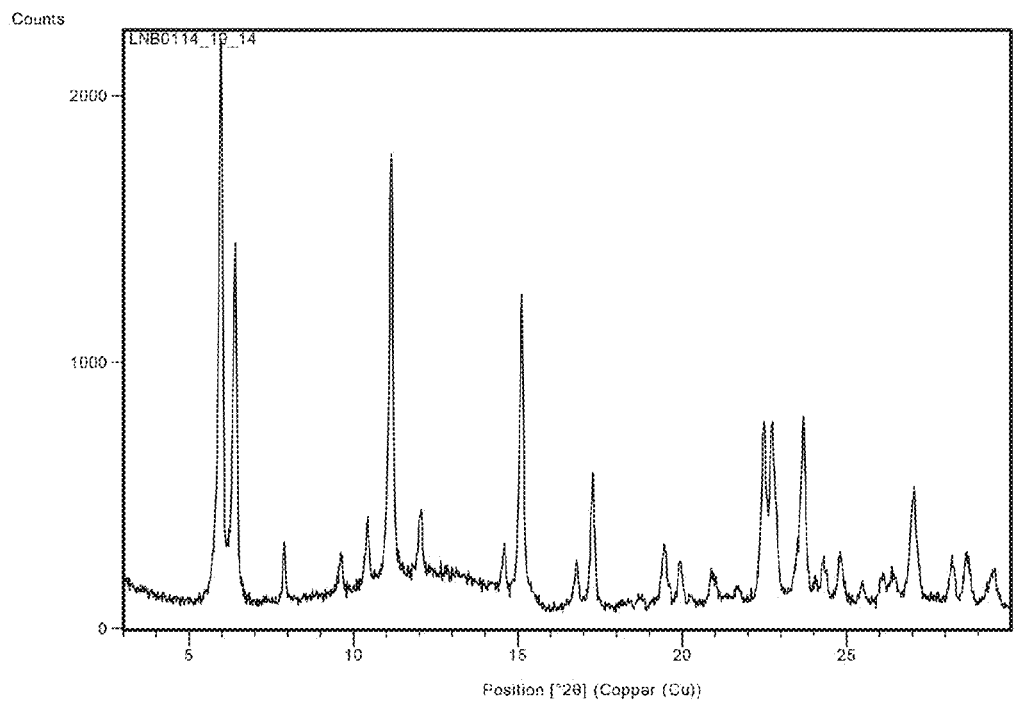
FIG. 129: Form B Compound A bis-mesylate—XRPD
Figure 130:
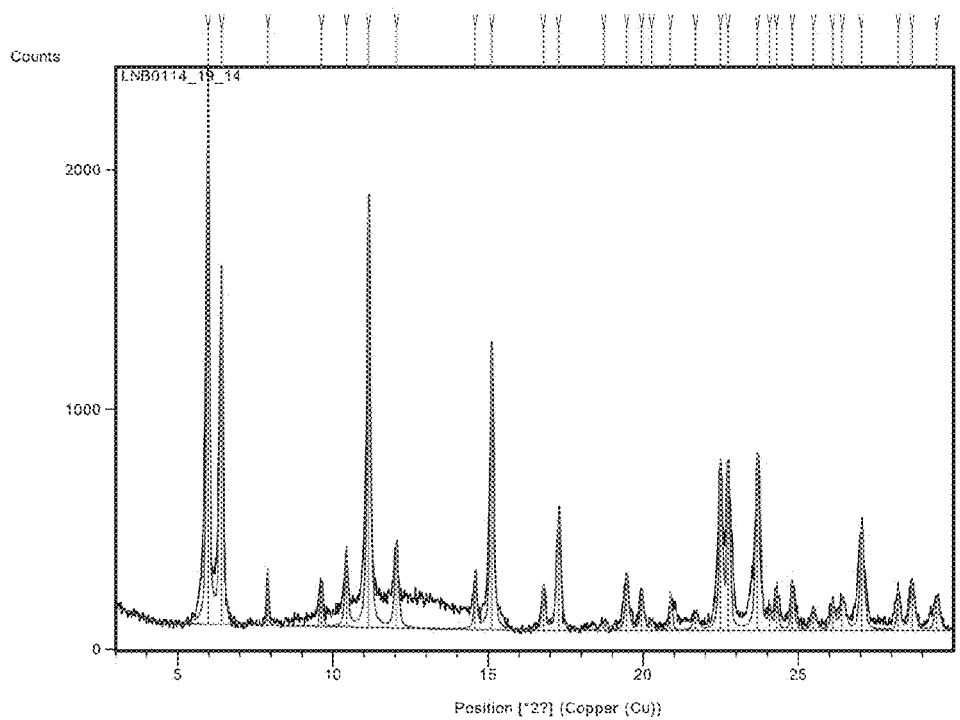
FIG. 130: Form B Compound A bis-mesylate—XRPD—Peaks Indicated
Figure 132:
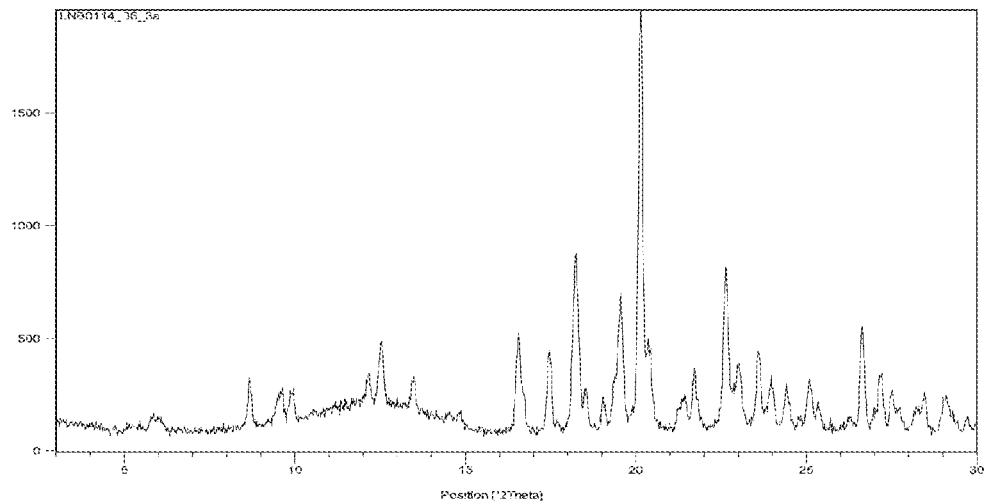
FIG. 132: Form C Compound A bis-mesylate—XRPD Analysis
Figure 133:
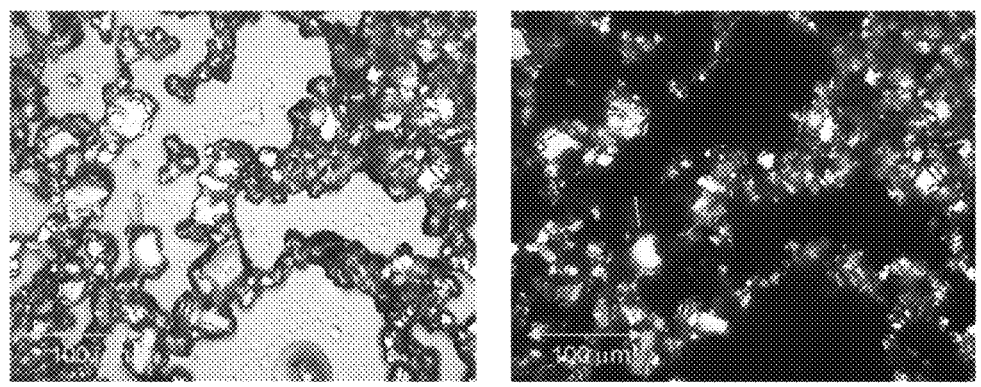
FIG. 133: Form C Compound A bis-mesylate—PLM Analysis
Figure 134:
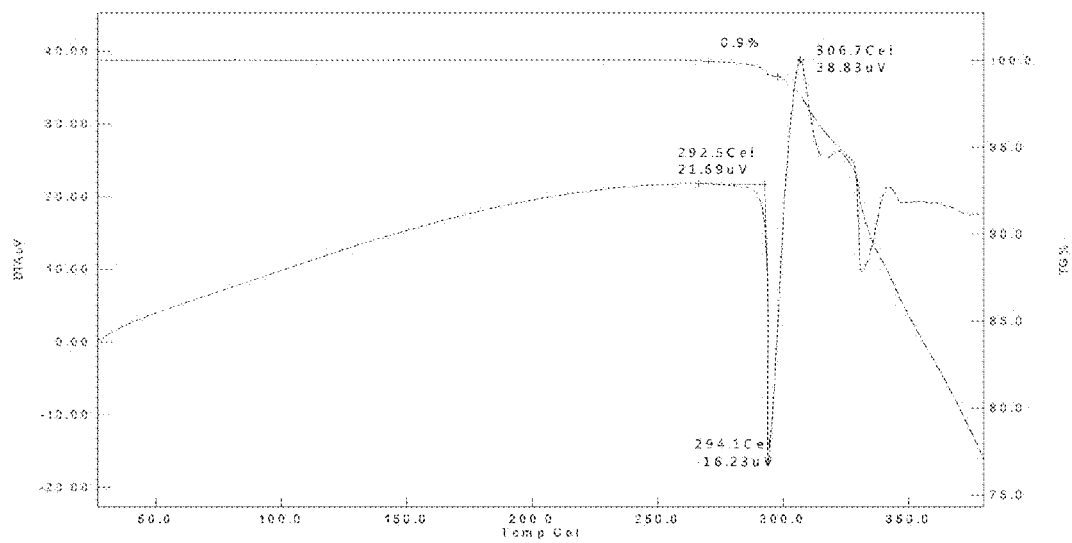
FIG. 134: Form C Compound A bis-mesylate—TG/DTA Analysis
Figure 135:
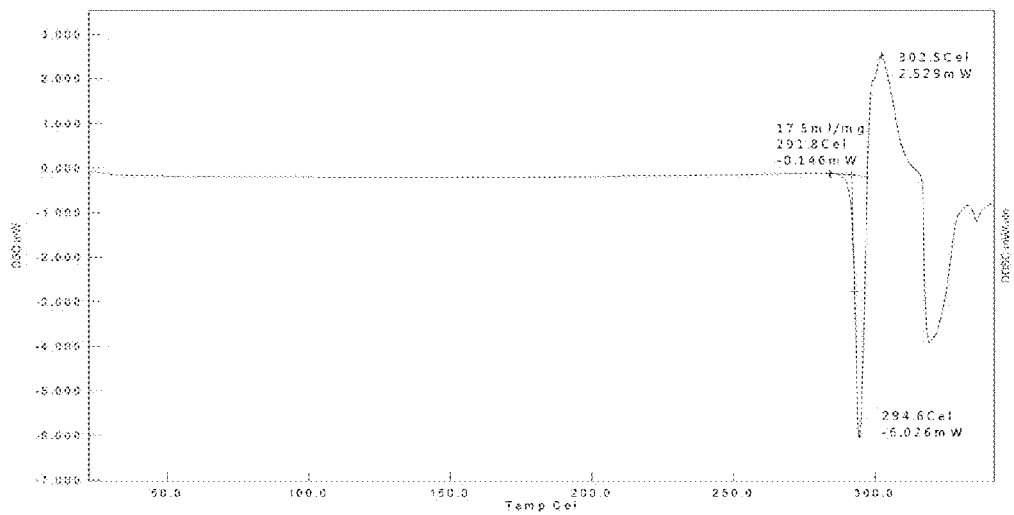
FIG. 135: Form C Compound A bis-mesylate—DSC Analysis
Figure 136:
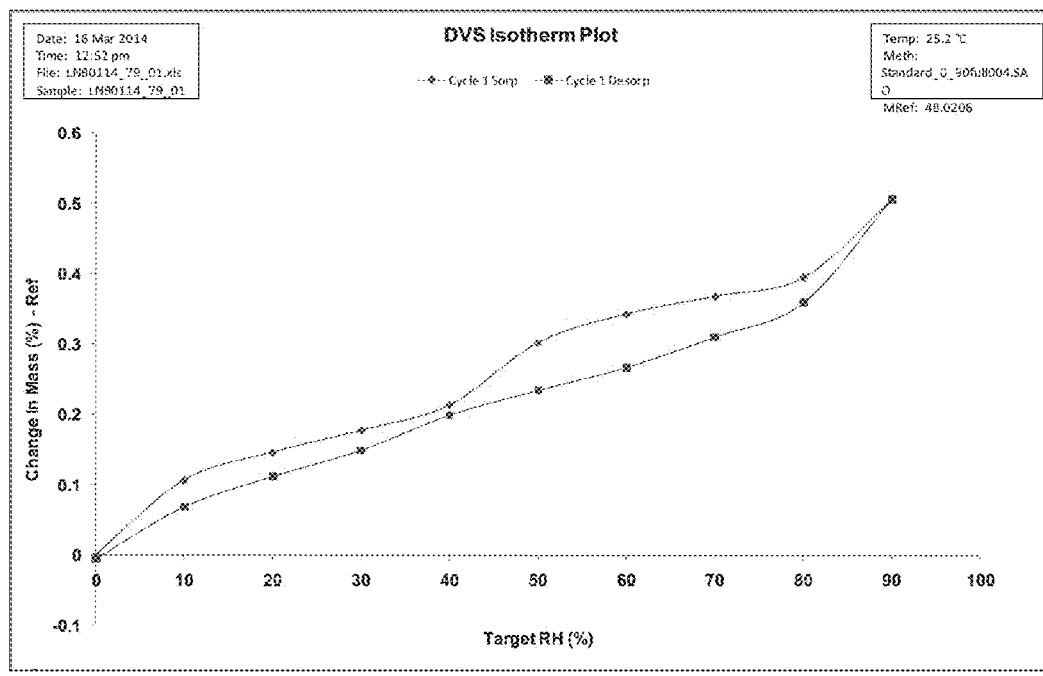
FIG. 136: Form C Compound A bis-mesylate—DVS Analysis
Figure 137:
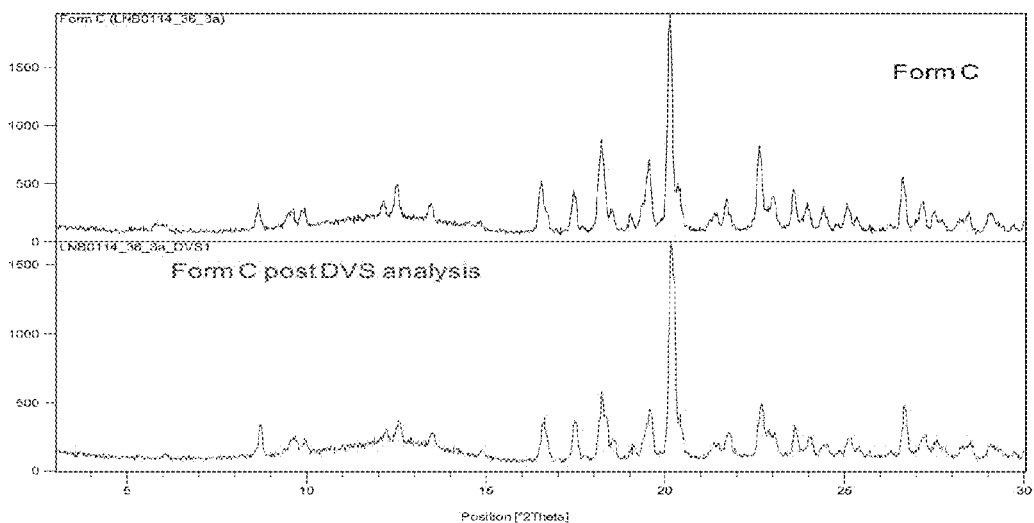
FIG. 137: Form C Compound A bis-mesylate—XRPD Analysis: Post-DVS Analysis
Figure 138:
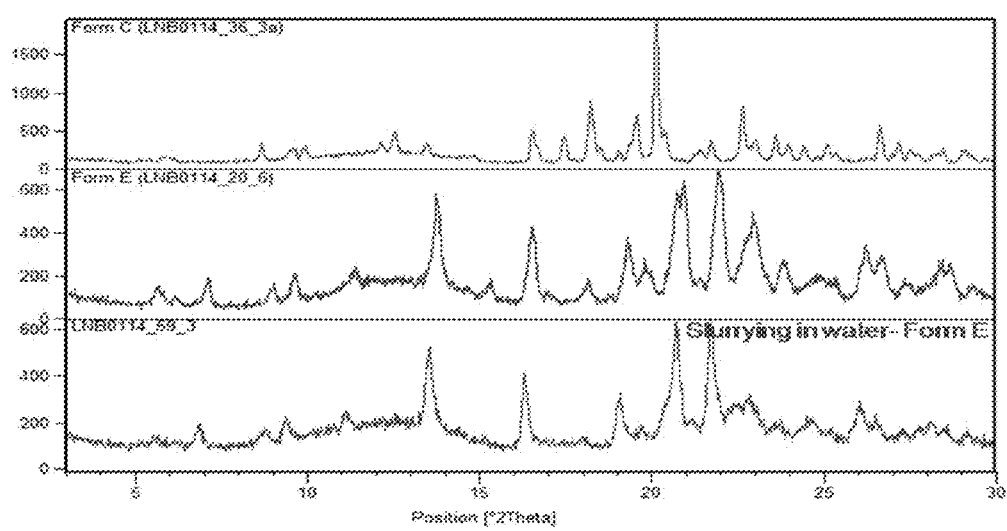
FIG. 138: Form C Compound A bis-mesylate—XRPD Analysis: Slurry in Deionized Water
Figure 139:
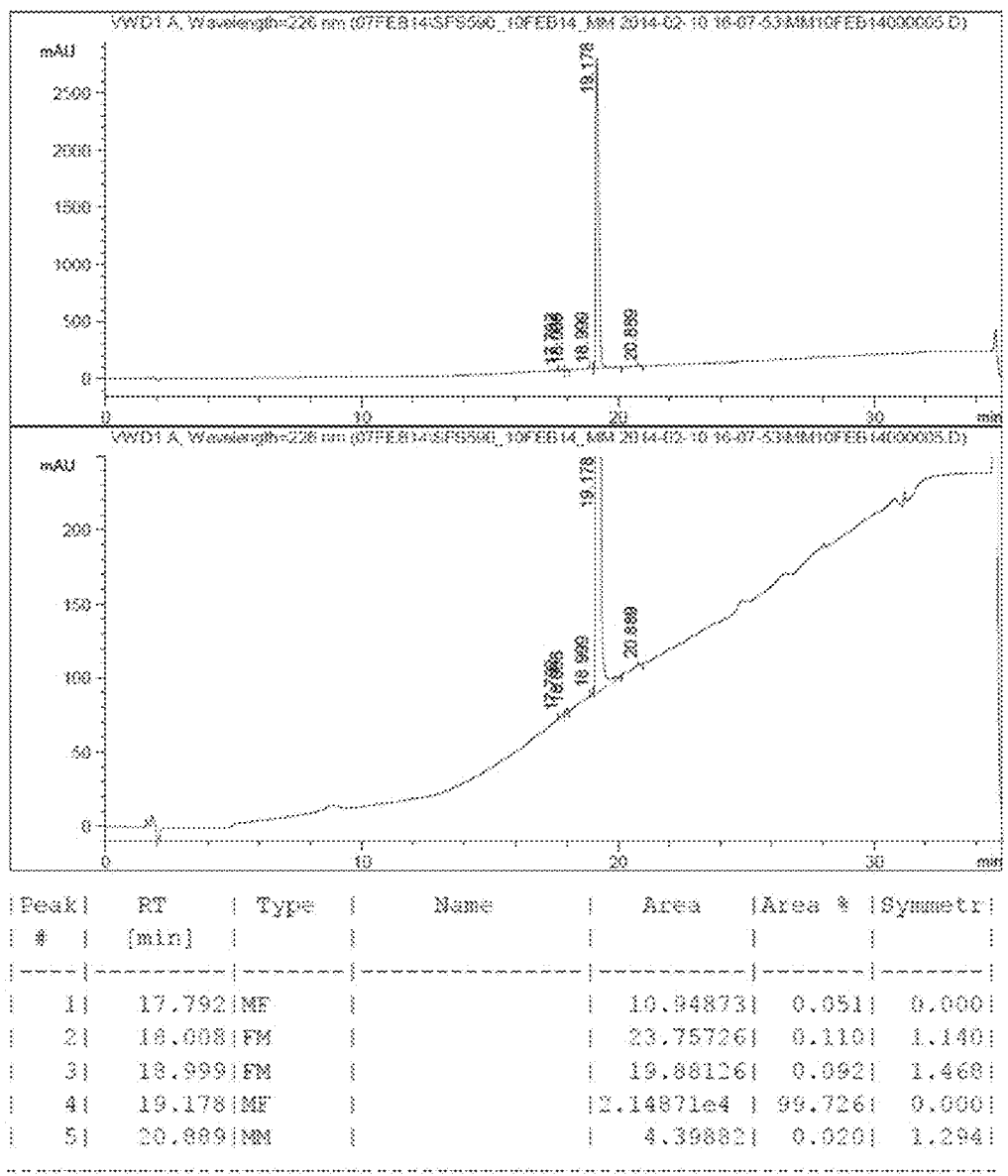
FIG. 139: Form C Compound A bis-mesylate—HPLC Purity Analysis
Figure 140:
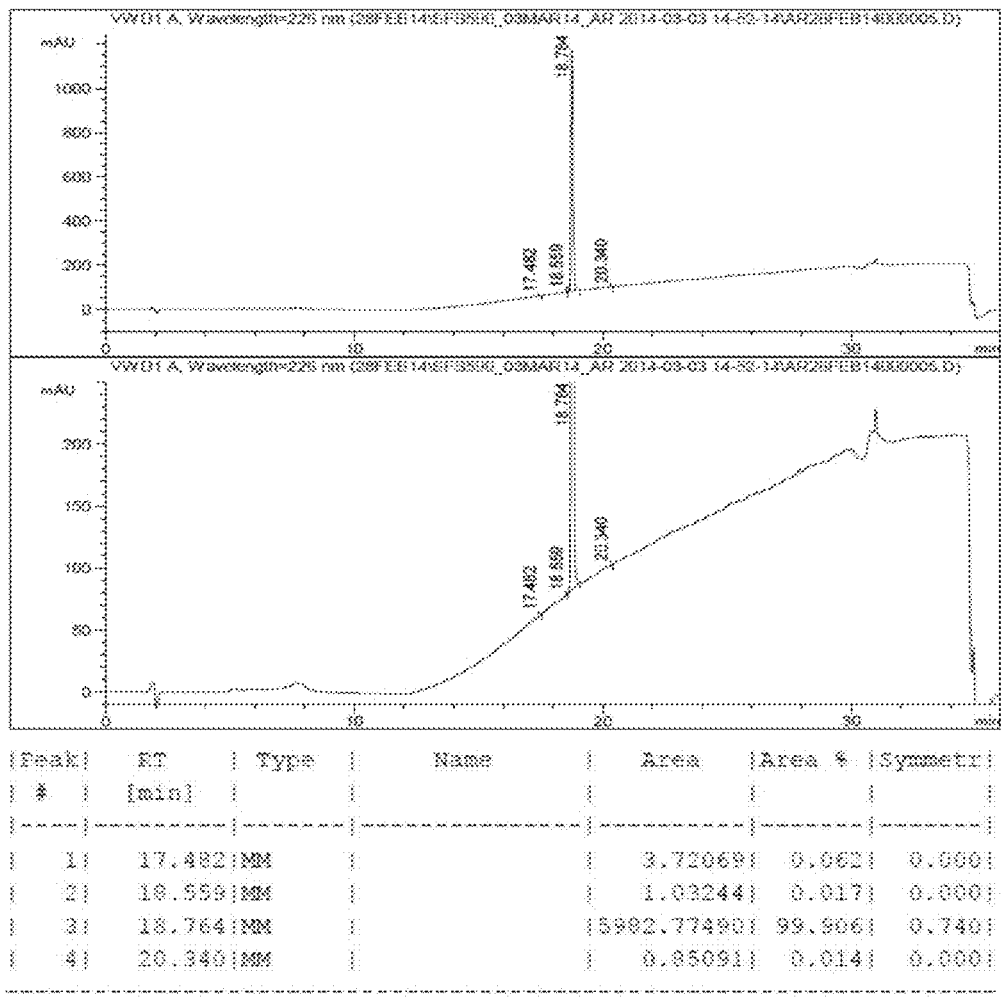
FIG. 140: Form C Compound A bis-mesylate—HPLC Purity: Stability Study at 40° C. and 75% RH
Figure 141:
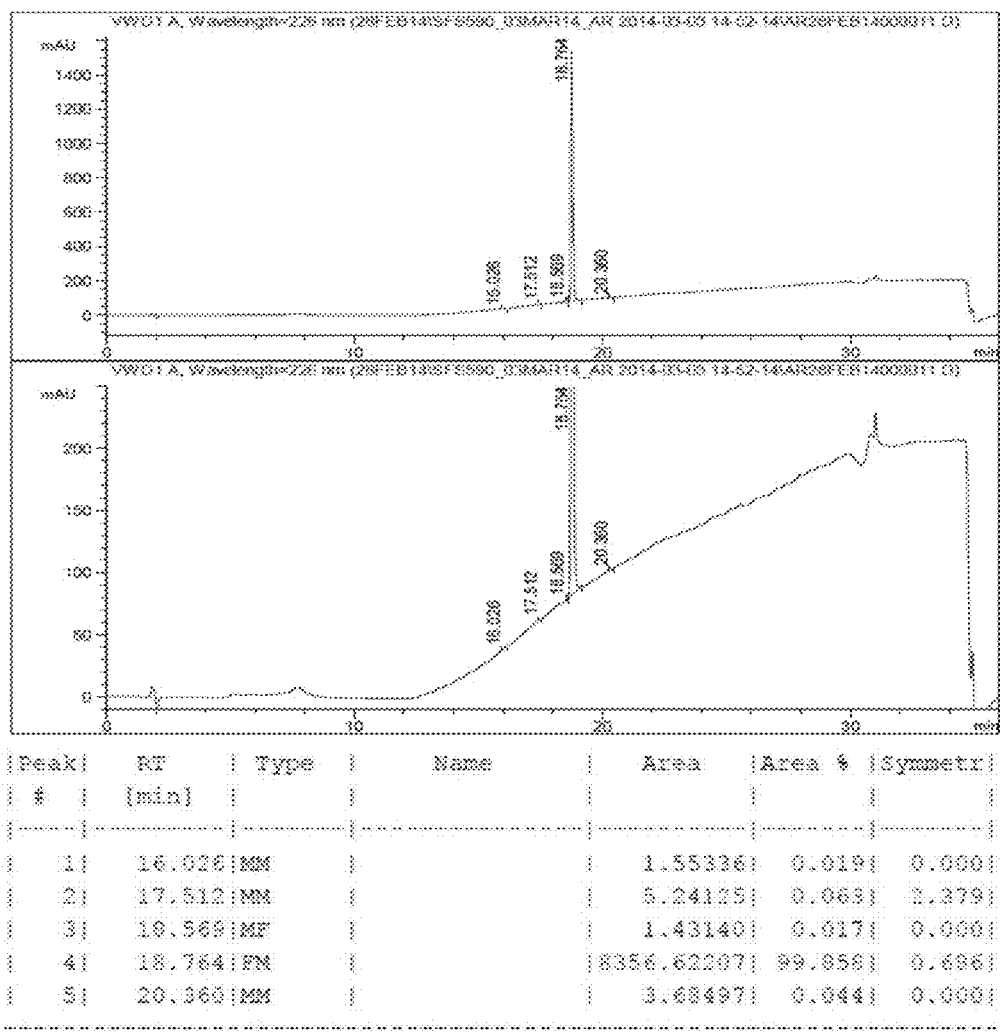
FIG. 141: Form C Compound A bis-mesylate—HPLC Purity: Stability Study at Ambient Temperature
Figure 142:
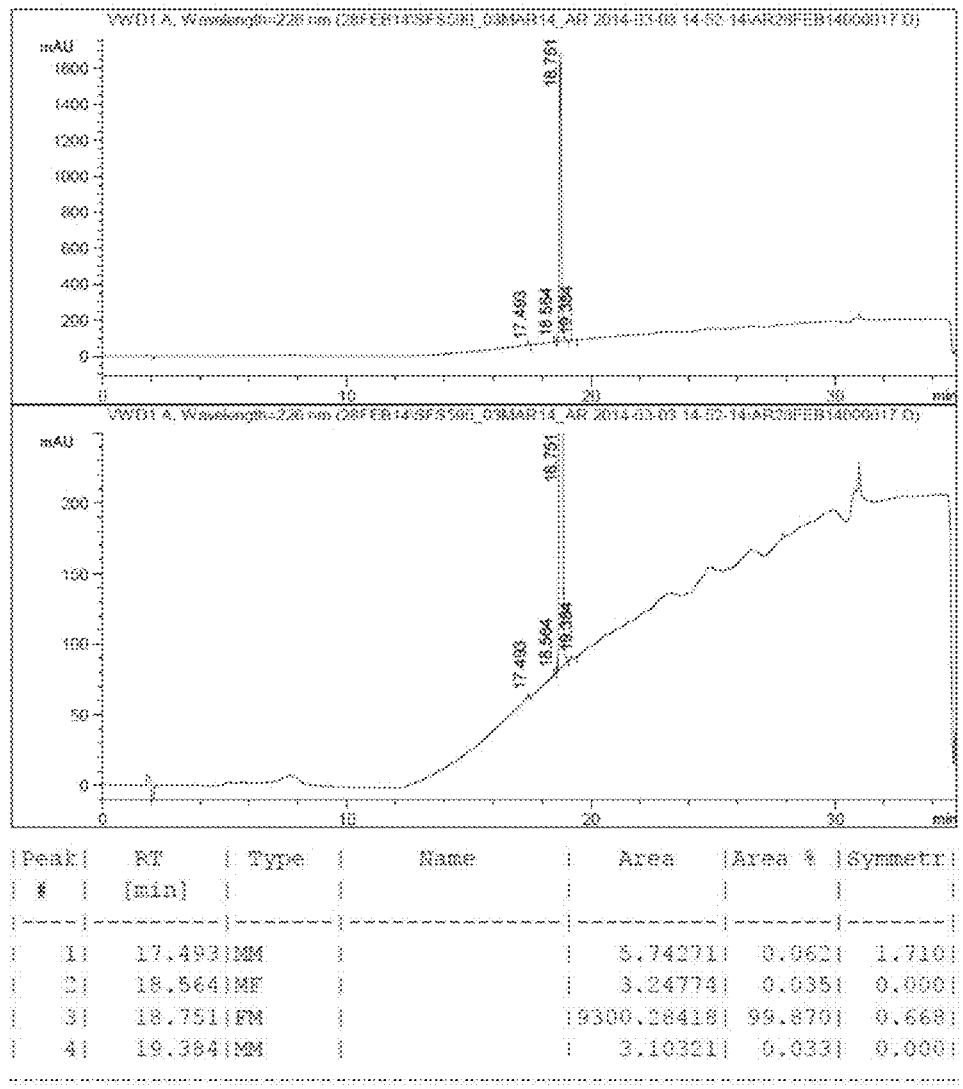
FIG. 142: Form C Compound A bis-mesylate—HPLC Purity: Stability Study at 80° C.
Figure 143:
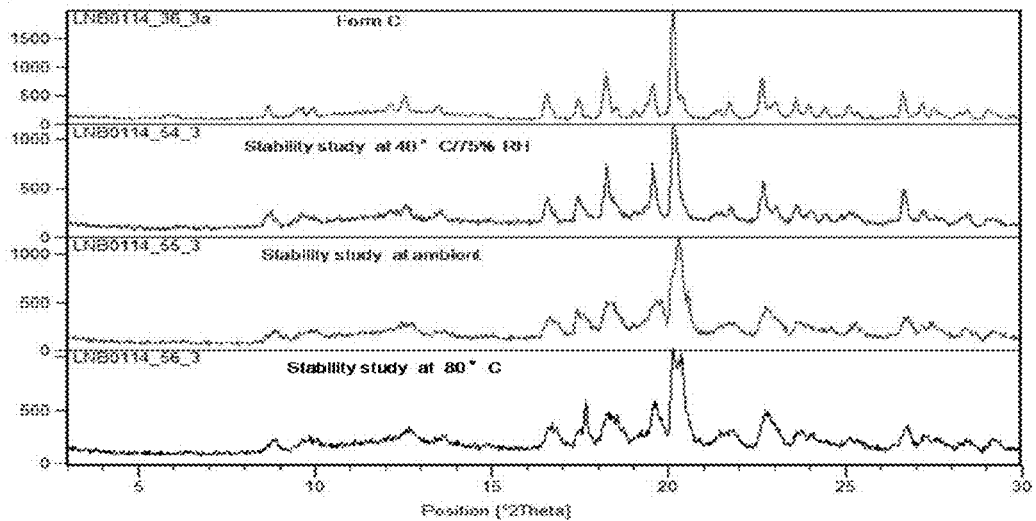
FIG. 143: Form C Compound A bis-mesylate—XRPD Analysis: Stability Testing at 40° C. and 75% RH, Ambient Temperature, and 80° C.
Figure 144:
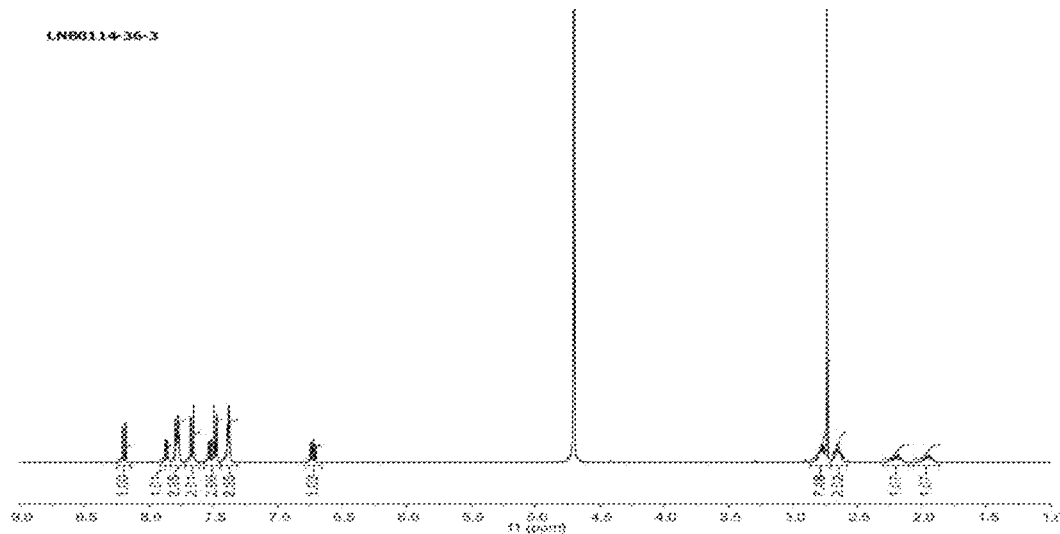
FIG. 144: Form C Compound A bis-mesylate—$^1$H NMR Spectroscopy

In one embodiment, Form B has X-ray powder diffraction peaks at approximately 6.0 and 14.6°2θ using Cu Kα radiation. In some embodiments, Form B has X-ray powder diffraction peaks at approximately 6.0, 6.4, 11.1, 14.6, 15.1, and 23.7°2θ using Cu Kα radiation. In some embodiments, Form B has X-ray powder diffraction peaks at approximately 6.0, 6.4, 11.1, 14.6, 15.1, 17.3, 22.5, 22.7, 23.7, and 27.0°2θ using Cu Kα radiation. In one embodiment, Form B has X-ray powder diffraction pattern substantially similar to that shown in FIG. 129. In one embodiment, Form B has X-ray powder diffraction peaks as shown in FIG. 131.

Figure 145:
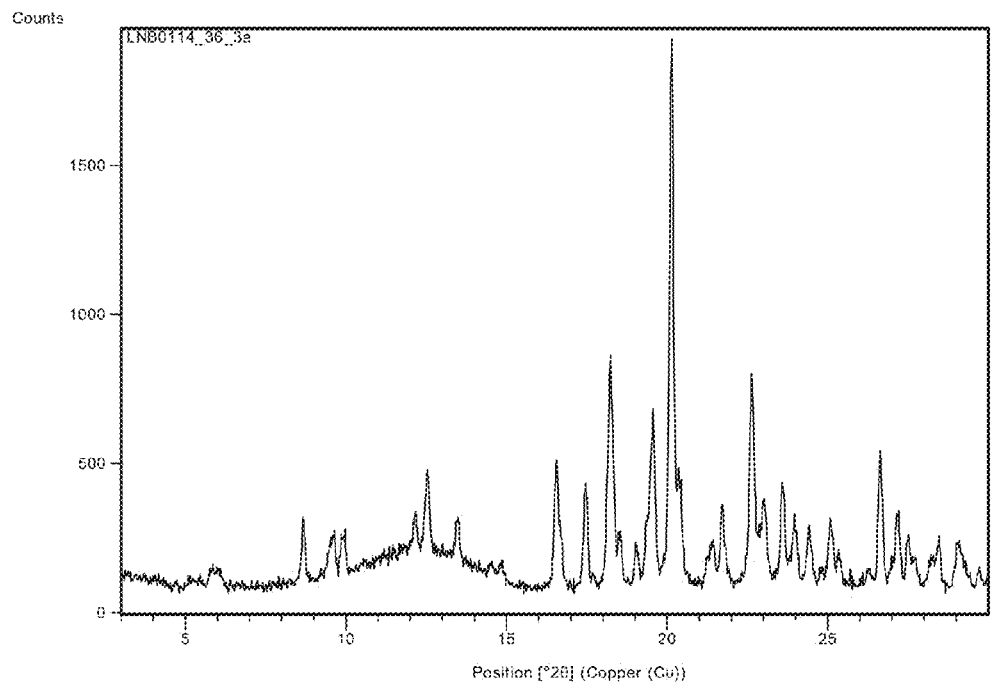
FIG. 145: Form C Compound A bis-mesylate—XRPD
Figure 146:
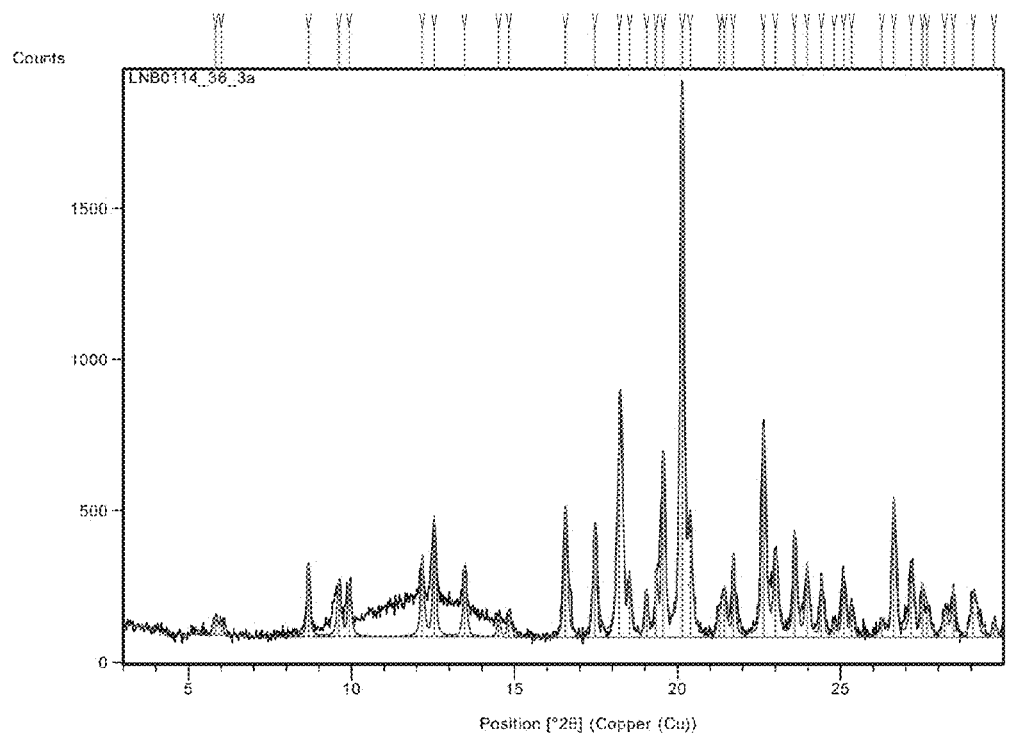
FIG. 146: Form C Compound A bis-mesylate—XRPD—Peaks Indicated
Figure 148:
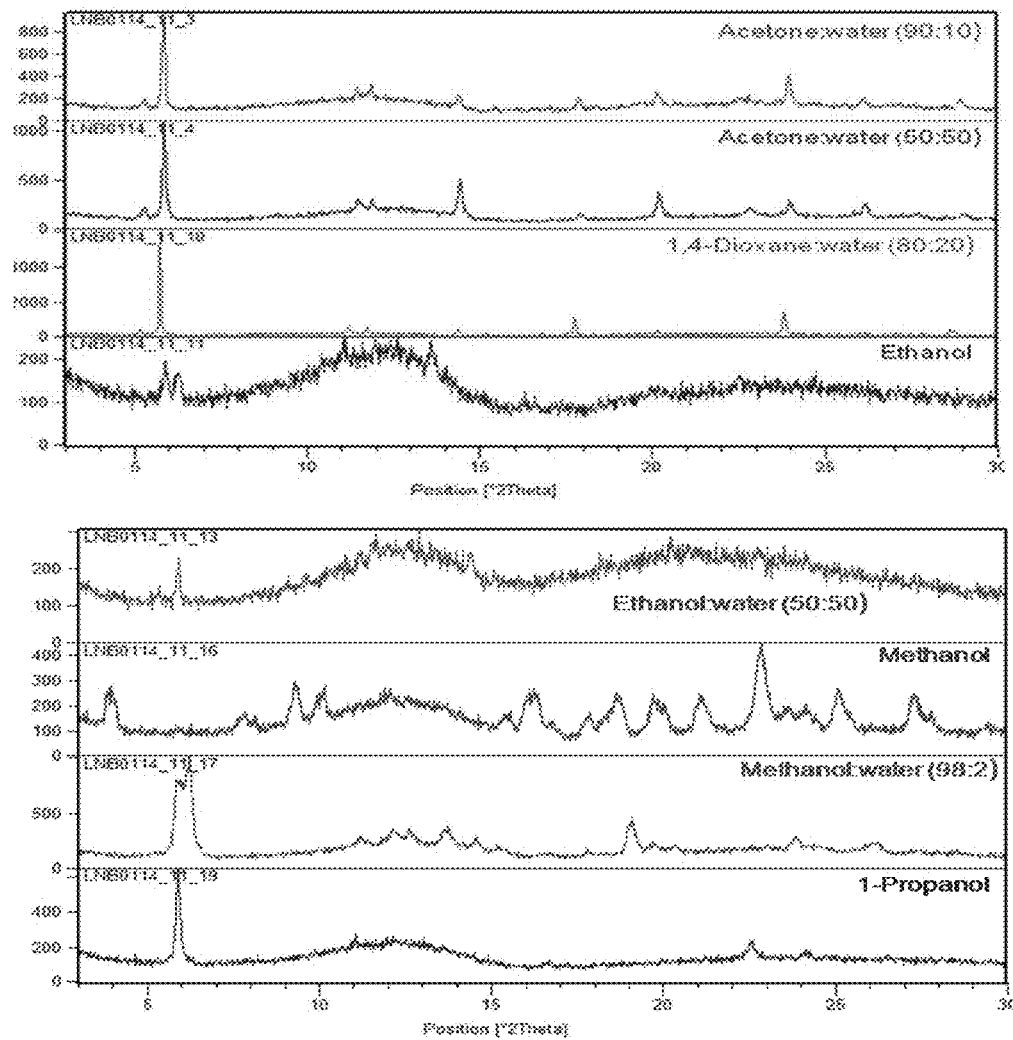
FIG. 148: Crash Cooling Experiments at −18° C.—XRPD Analysis of solid states of Compound A bis-mesylate in Various Solvents
Figure 149:
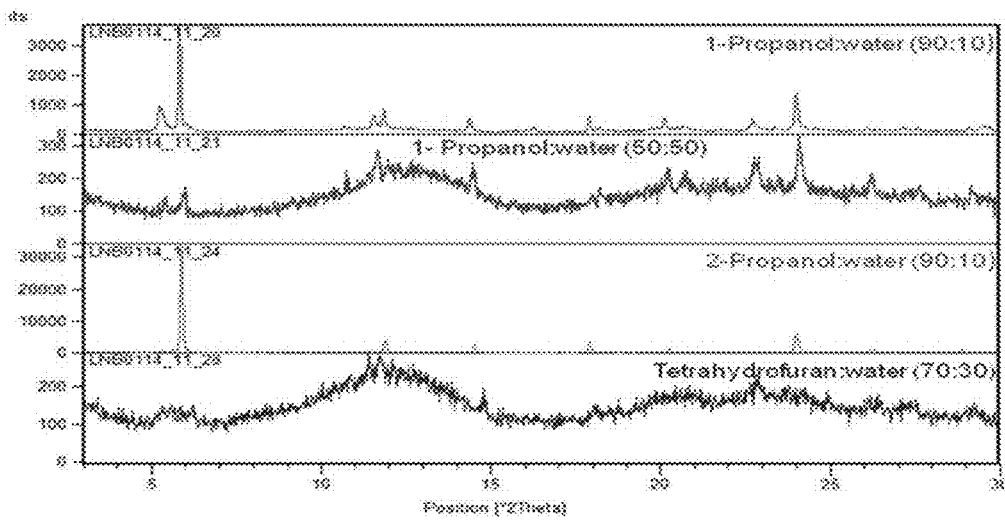
FIG. 149: Crash Cooling Experiments at −18° C.—XRPD Analysis of solid states of Compound A bis-mesylate in Various Solvents
Figure 150:
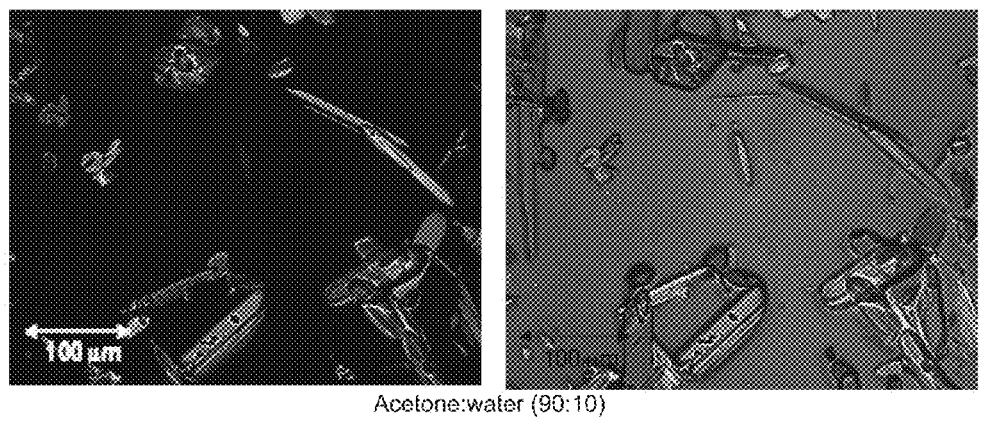
FIG. 150: Crash Cooling Experiments at −18° C.—PLM Analysis of solid states of Compound A bis-mesylate—Acetone:water (90:10)
Figure 151:
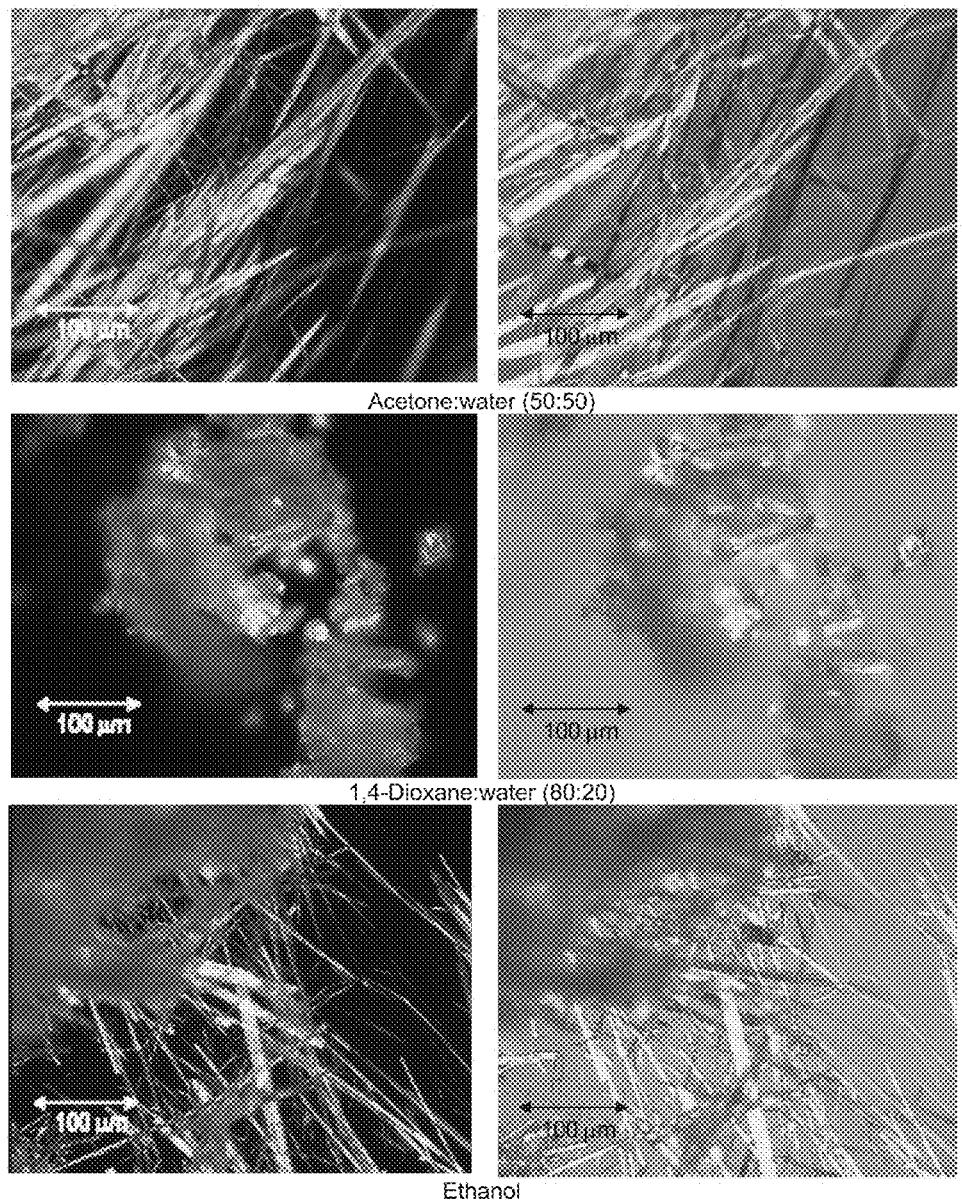
FIG. 151: Crash Cooling Experiments at −18° C.—PLM Analysis of solid states of Compound A bis-mesylate—Acetone:water (50:50), 1,4-Dioxane:water (80:20), and Ethanol
Figure 152:
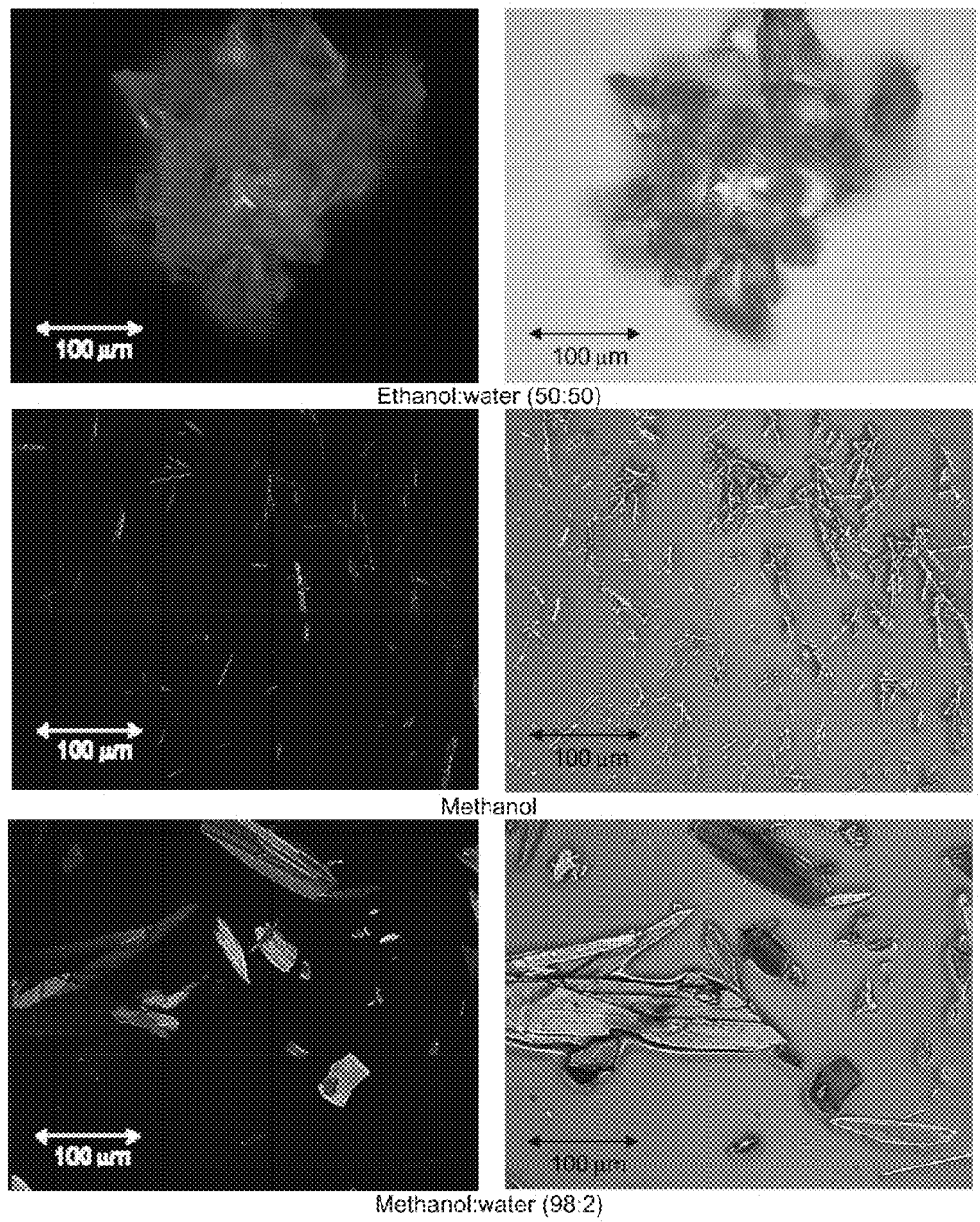
FIG. 152: Crash Cooling Experiments at −18° C.—PLM Analysis of solid states of Compound A bis-mesylate—Ethanol:water (50:50), Methanol, and Methanol:water (98:2)
Figure 153:
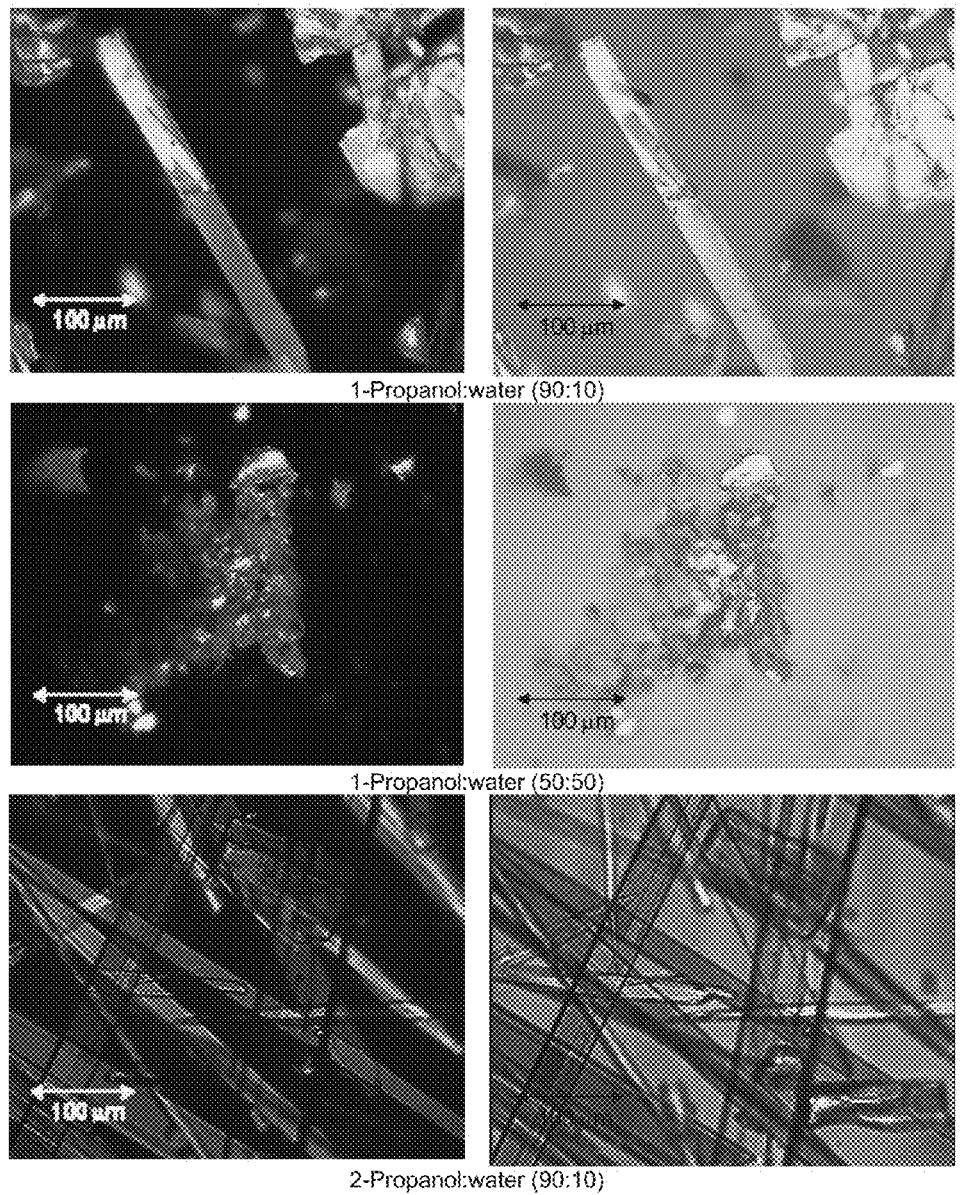
FIG. 153: Crash Cooling Experiments at −18° C.—PLM Analysis of solid states of Compound A bis-mesylate—1-propanol:water (90:10), 1-propanol:water (50:50), and 2-propanol:water (90:10)
Figure 154:
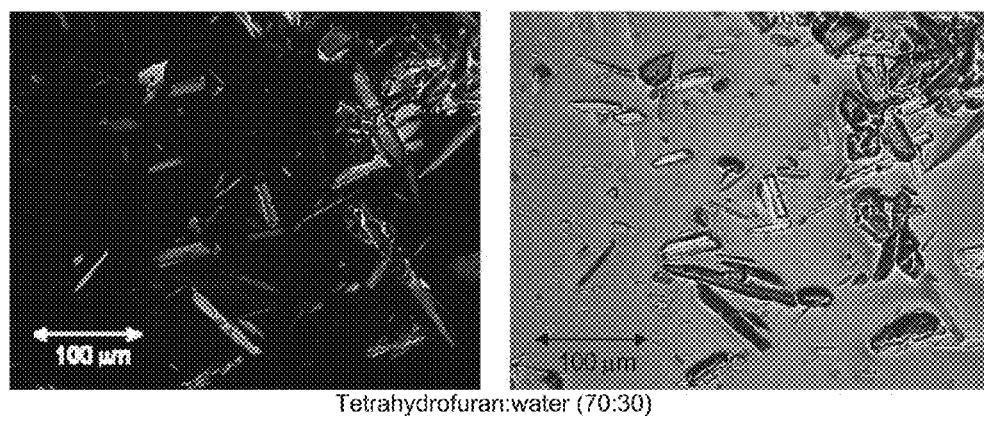
FIG. 154: Crash Cooling Experiments at −18° C.—PLM Analysis of solid states of Compound A bis-mesylate—Tetrahydrofuran:water (70:30)
Figure 155:
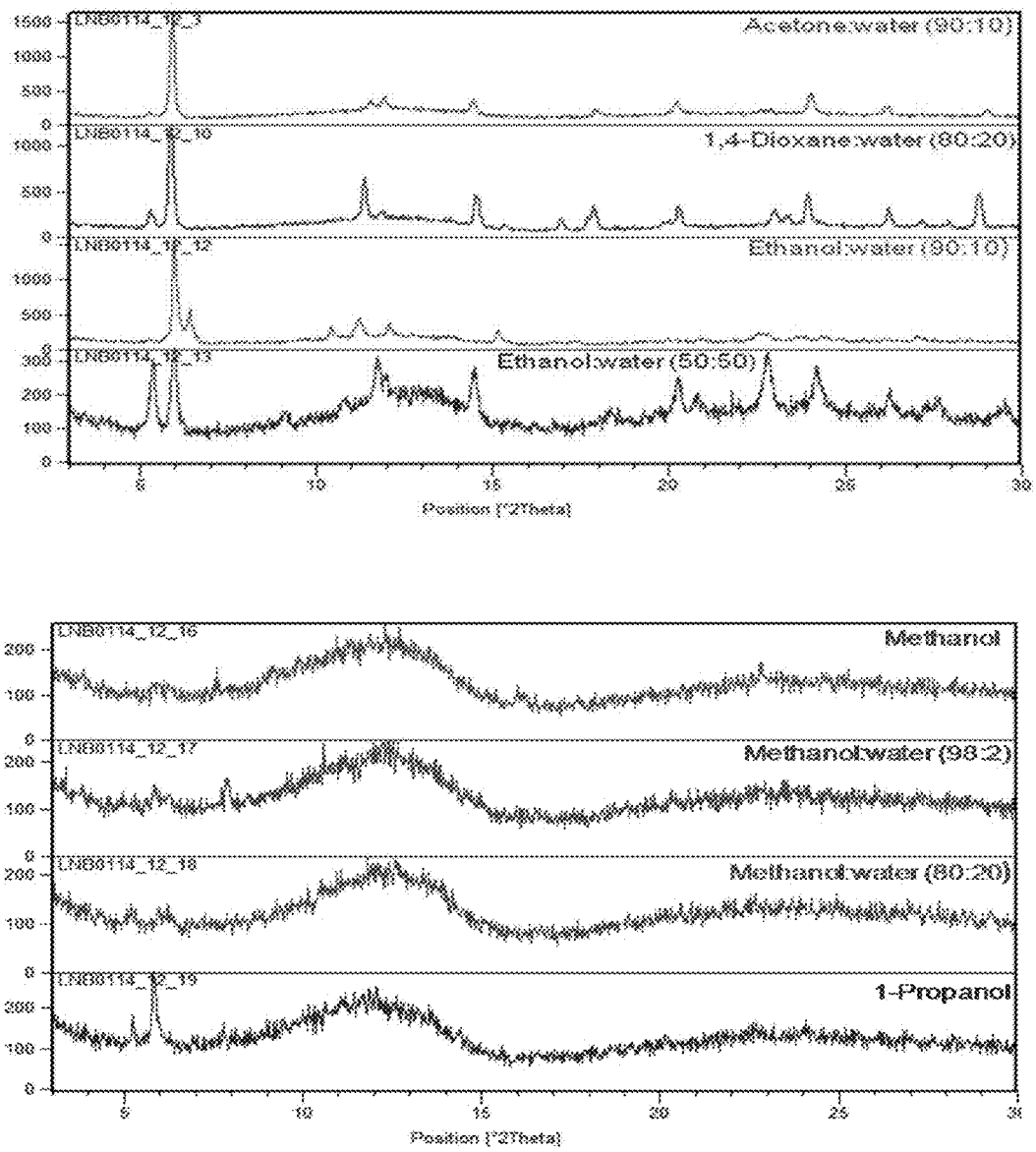
FIG. 155: Slow Cooling Experiments (from 60° C. to 5° C. at 0.3° C./min)—XRPD Analysis of solid states of Compound A bis-mesylate in Various Solvents
Figure 156:
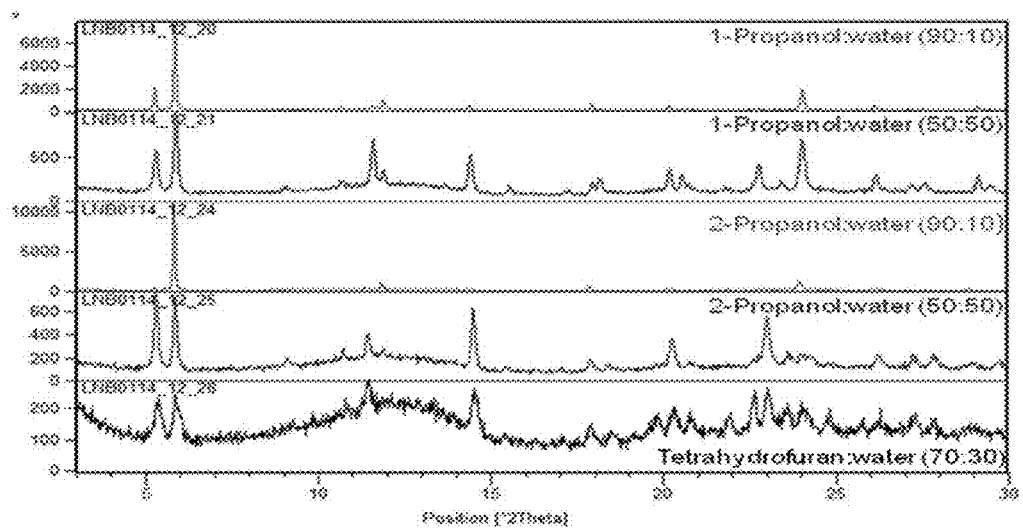
FIG. 156: Slow Cooling Experiments (from 60° C. to 5° C. at 0.3° C./min)—XRPD Analysis of solid states of Compound A bis-mesylate in Various Solvents
Figure 157:
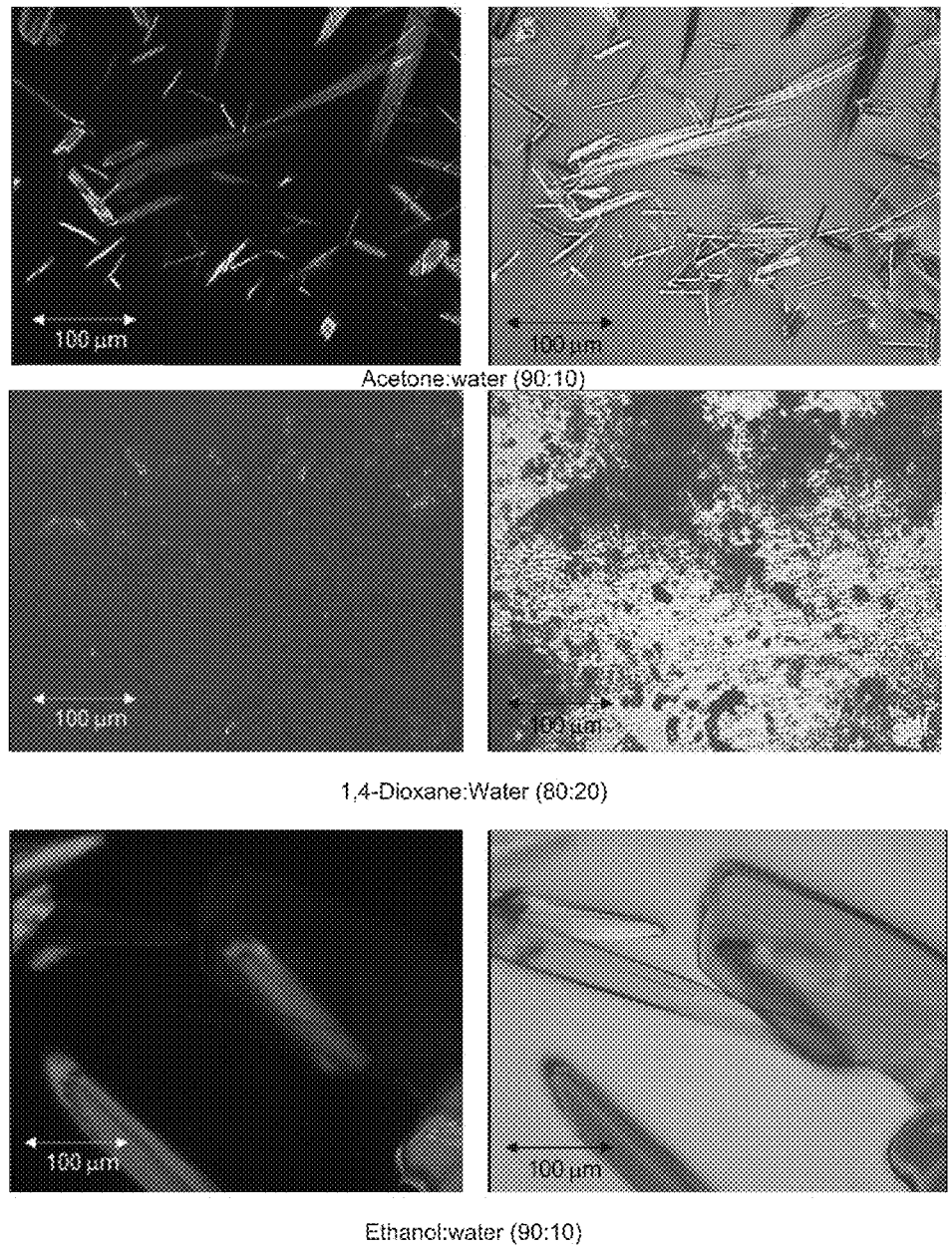
FIG. 157: Slow Cooling Experiments (from 60° C. to 5° C. at 0.3° C./min)—PLM Analysis of solid states of Compound A bis-mesylate—Acetone:water (90:10), 1,4-Dioxane:water (80:20), and Ethanol:water (90:10)
Figure 158:
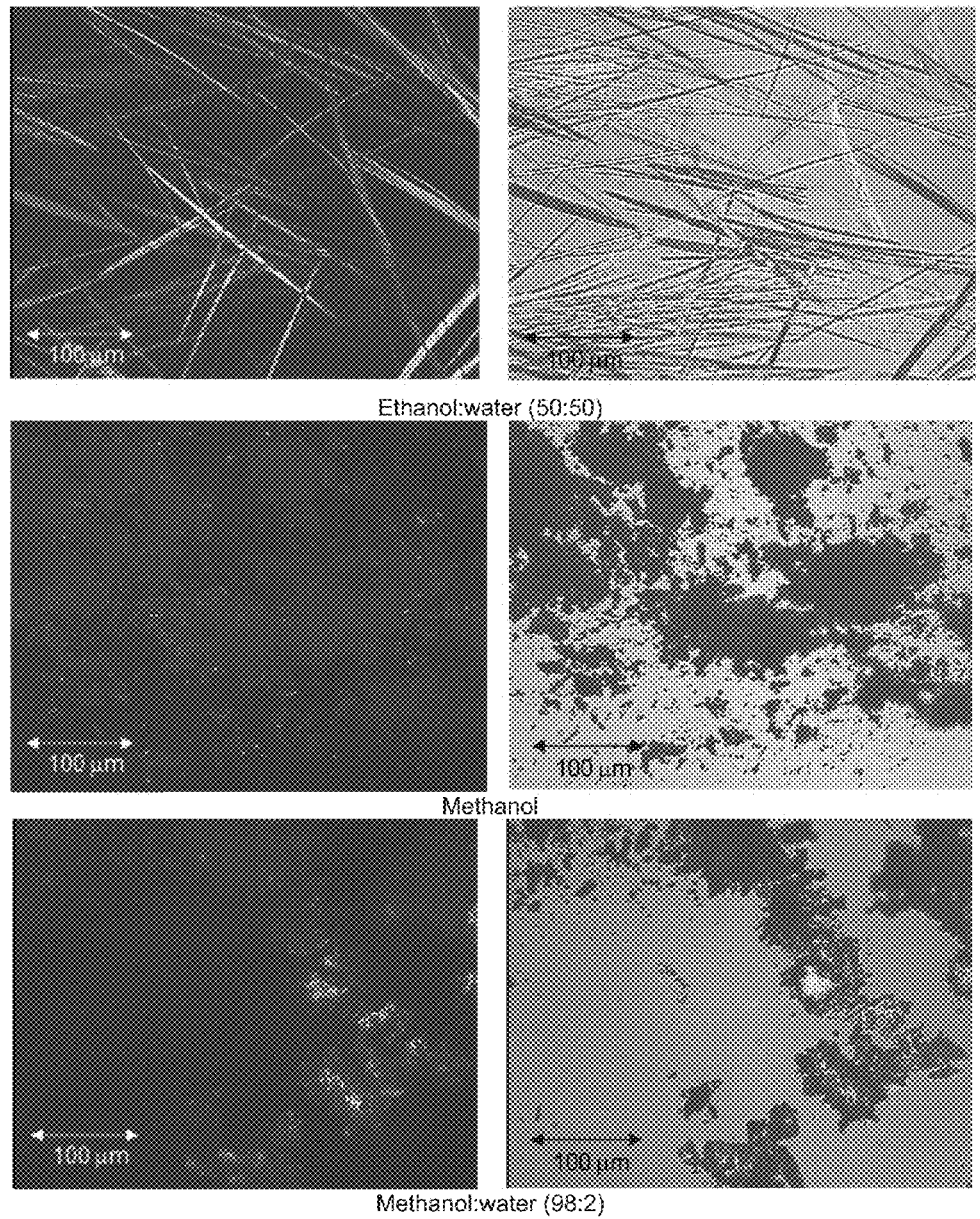
FIG. 158: Slow Cooling Experiments (from 60° C. to 5° C. at 0.3° C./min)—PLM Analysis of solid states of Compound A bis-mesylate—Ethanol:water (50:50), Methanol, and Methanol:water (98:2)
Figure 159:
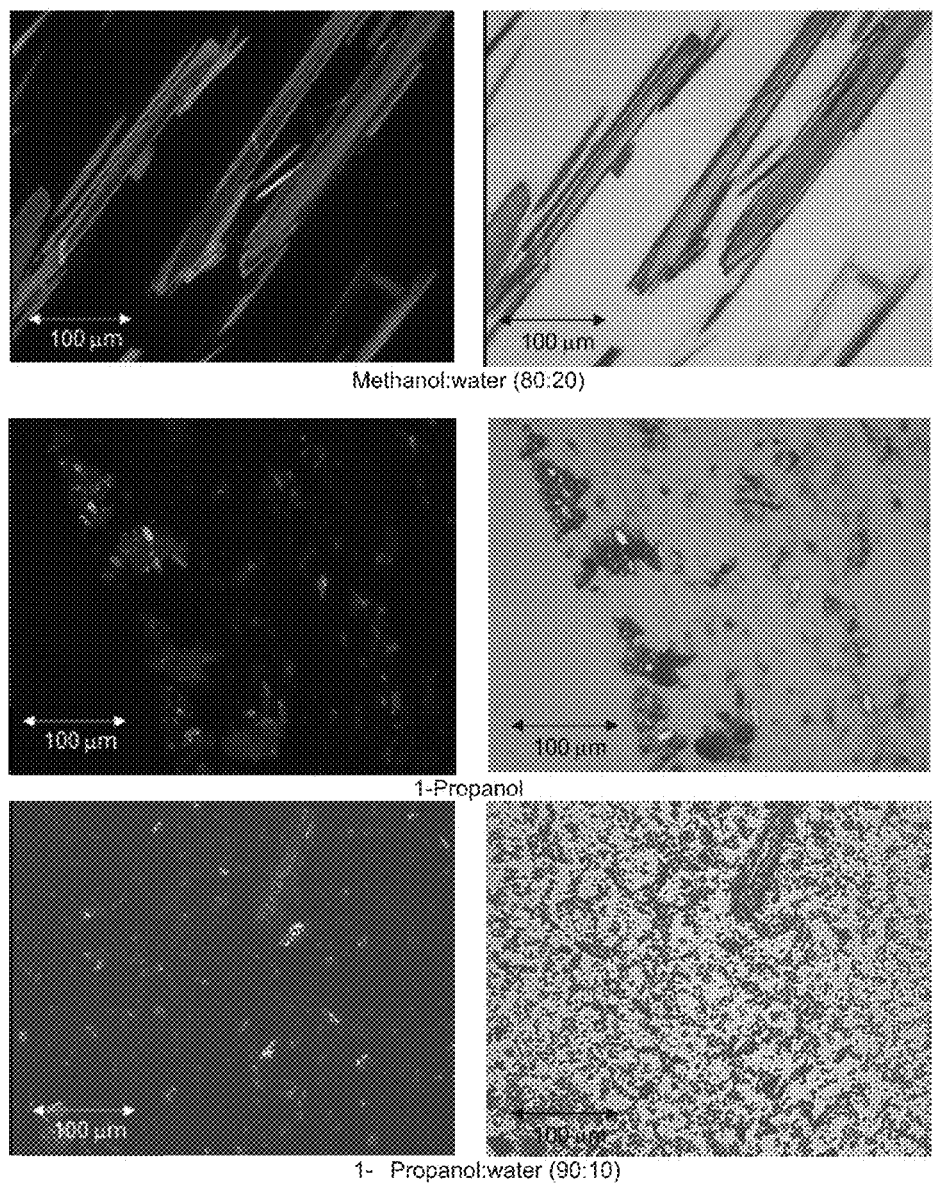
FIG. 159: Slow Cooling Experiments (from 60° C. to 5° C. at 0.3° C./min)—PLM Analysis of solid states of Compound A bis-mesylate—Methanol:water (80:20), 1-propanol, and 1-propanol:water (90:10)
Figure 160:
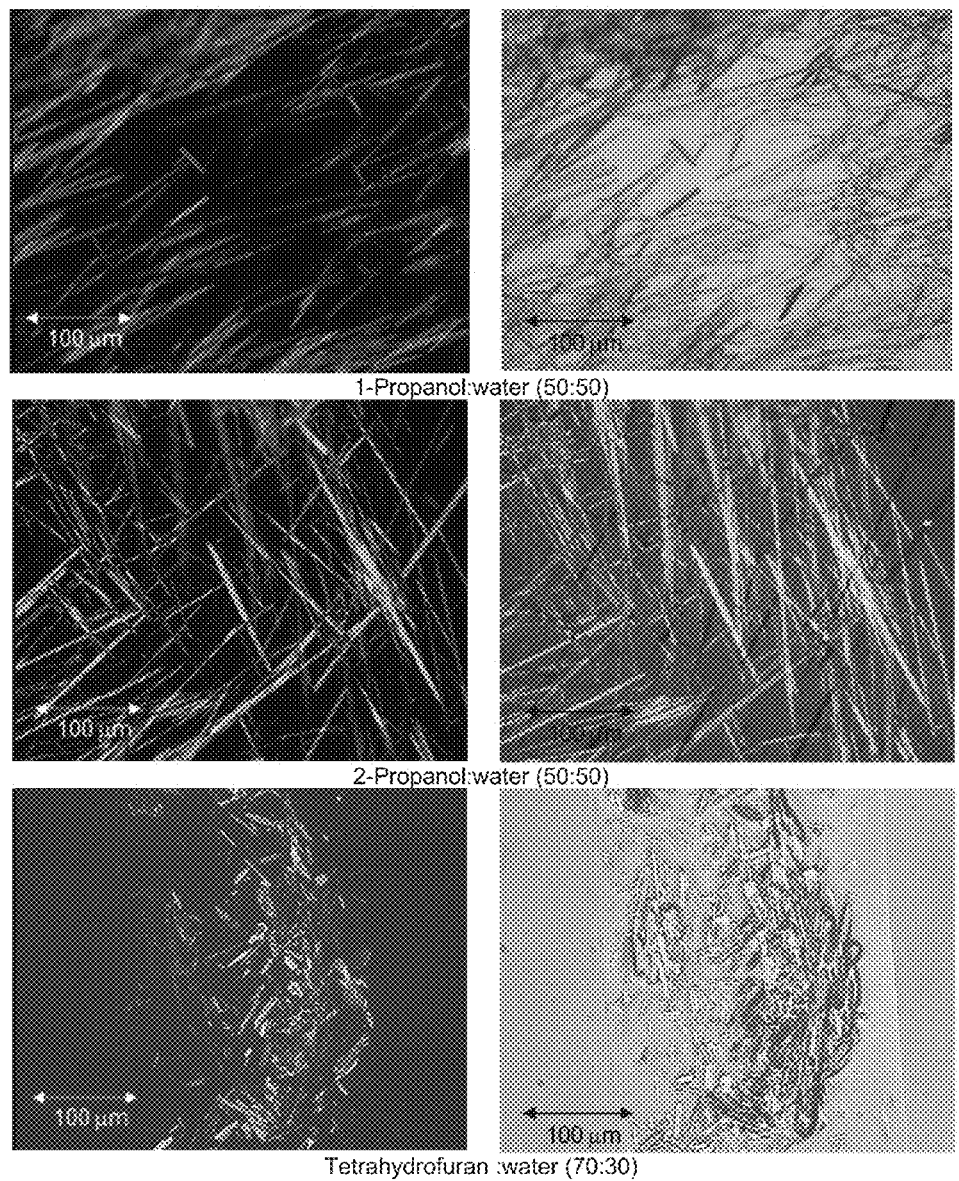
FIG. 160: Slow Cooling Experiments (from 60° C. to 5° C. at 0.3° C./min)—PLM Analysis of solid states of Compound A bis-mesylate—1-propanol:water (50:50), 2-propanol:water (50:50), and tetrahydrofuran:water (70:30)
Figure 161:
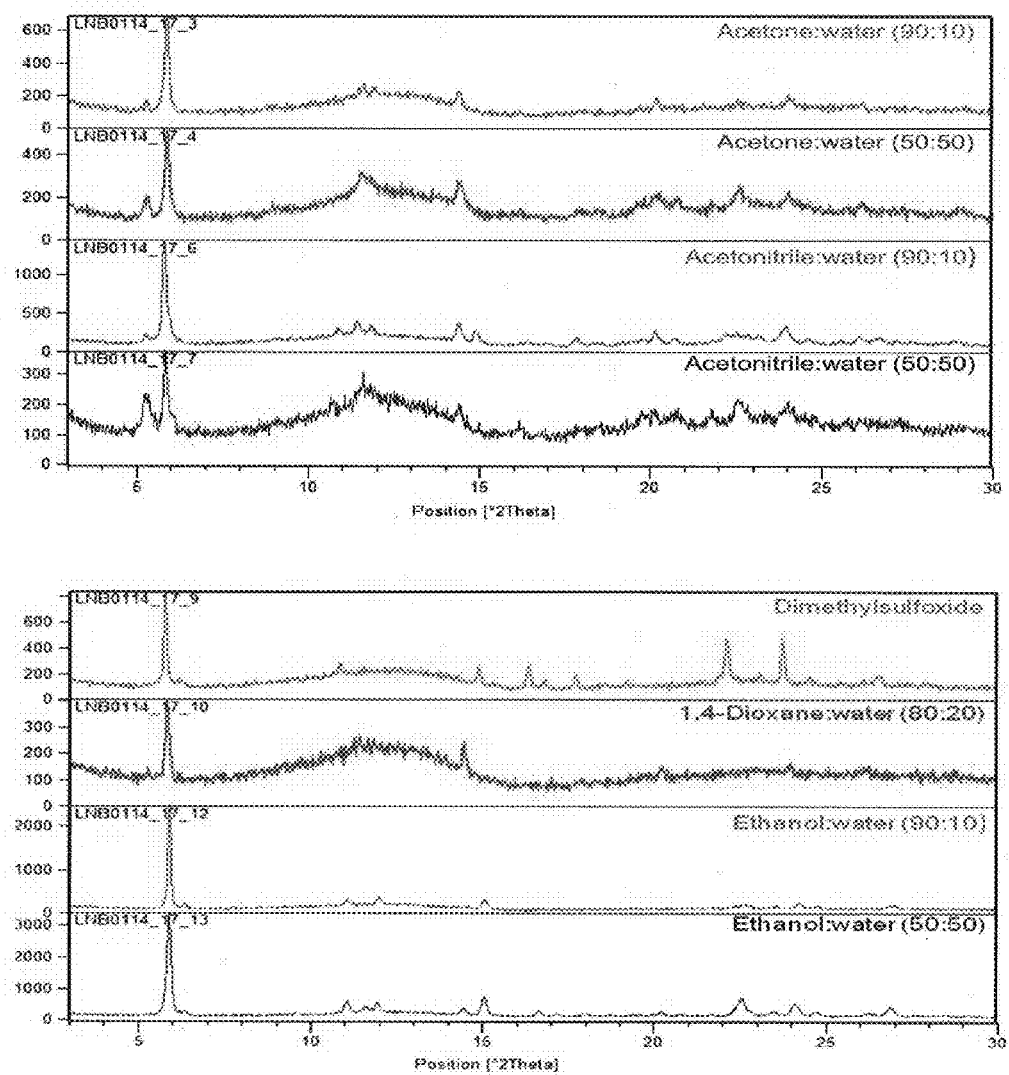
FIG. 161: Anti-Solvent (Acetone) Addition Experiments at Ambient Temperature in Various Solvents—XRPD Analysis of solid states of Compound A bis-mesylate
Figure 162:
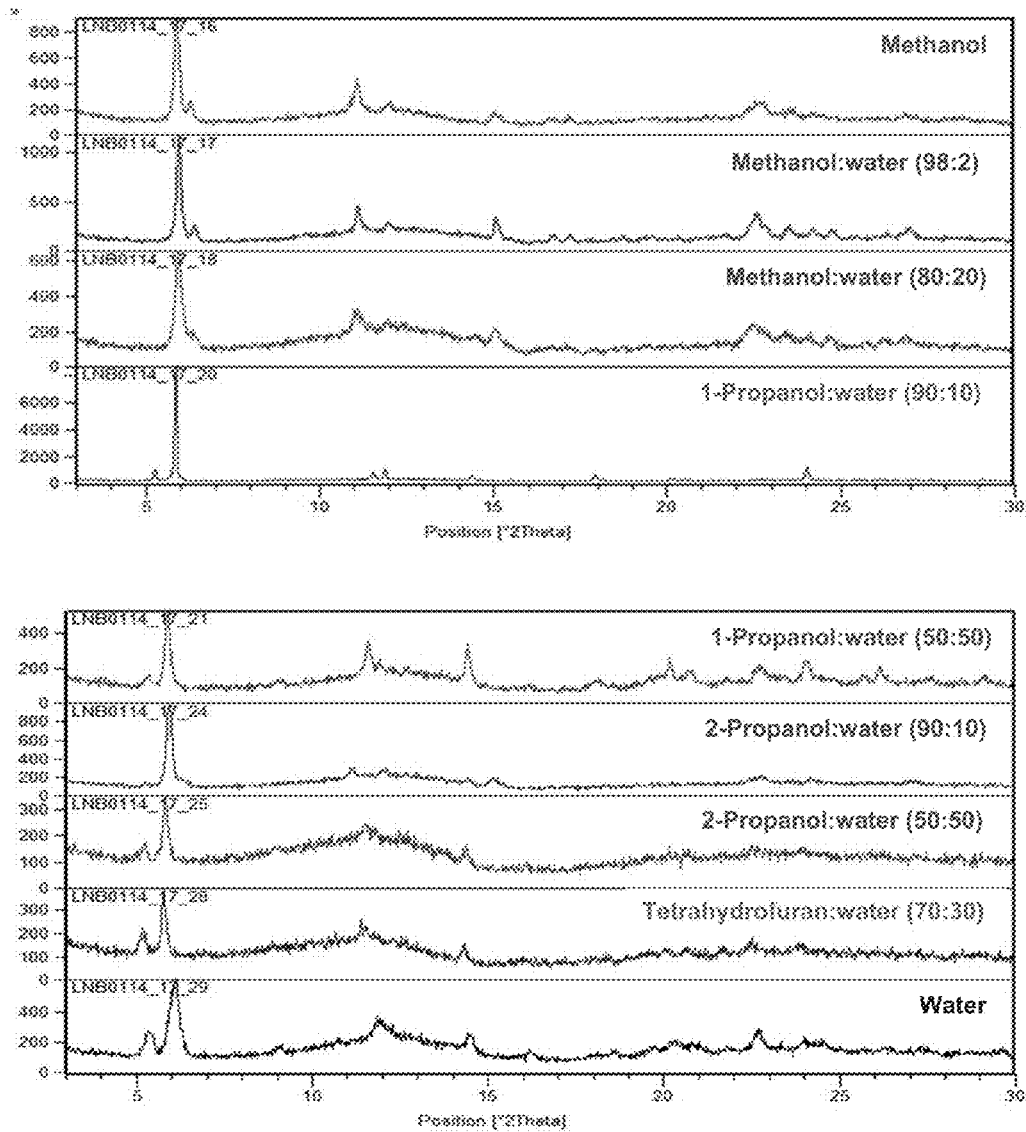
FIG. 162: Anti-Solvent (Acetone) Addition Experiments at Ambient Temperature in Various Solvents—XRPD Analysis of solid states of Compound A bis-mesylate
Figure 163:
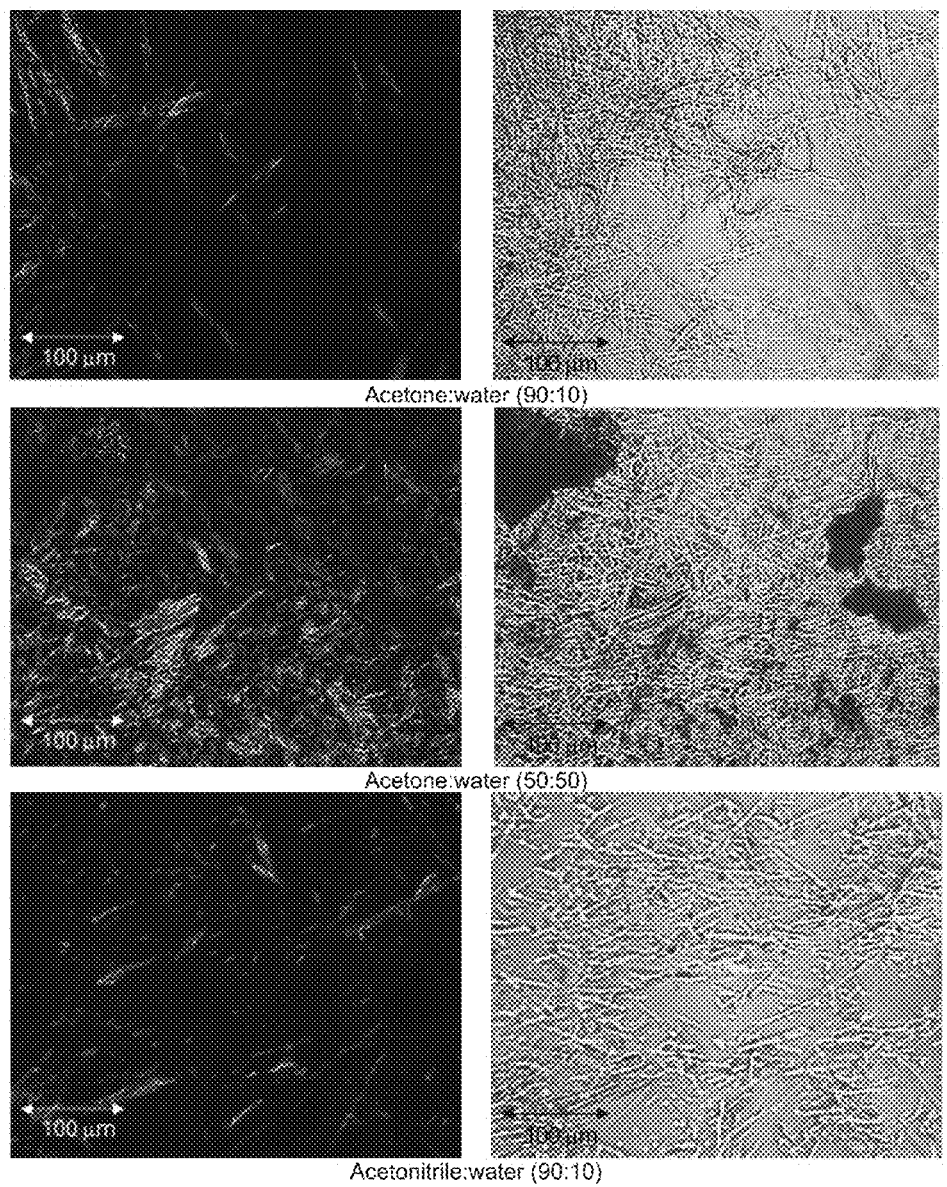
FIG. 163: Anti-Solvent (Acetone) Addition Experiments at Ambient Temperature in Various Solvents—PLM Analysis of solid states of Compound A bis-mesylate—Acetone:water (90:10), Acetone:water (50:50), and Acetonitrile:water (90:10)
Figure 164:
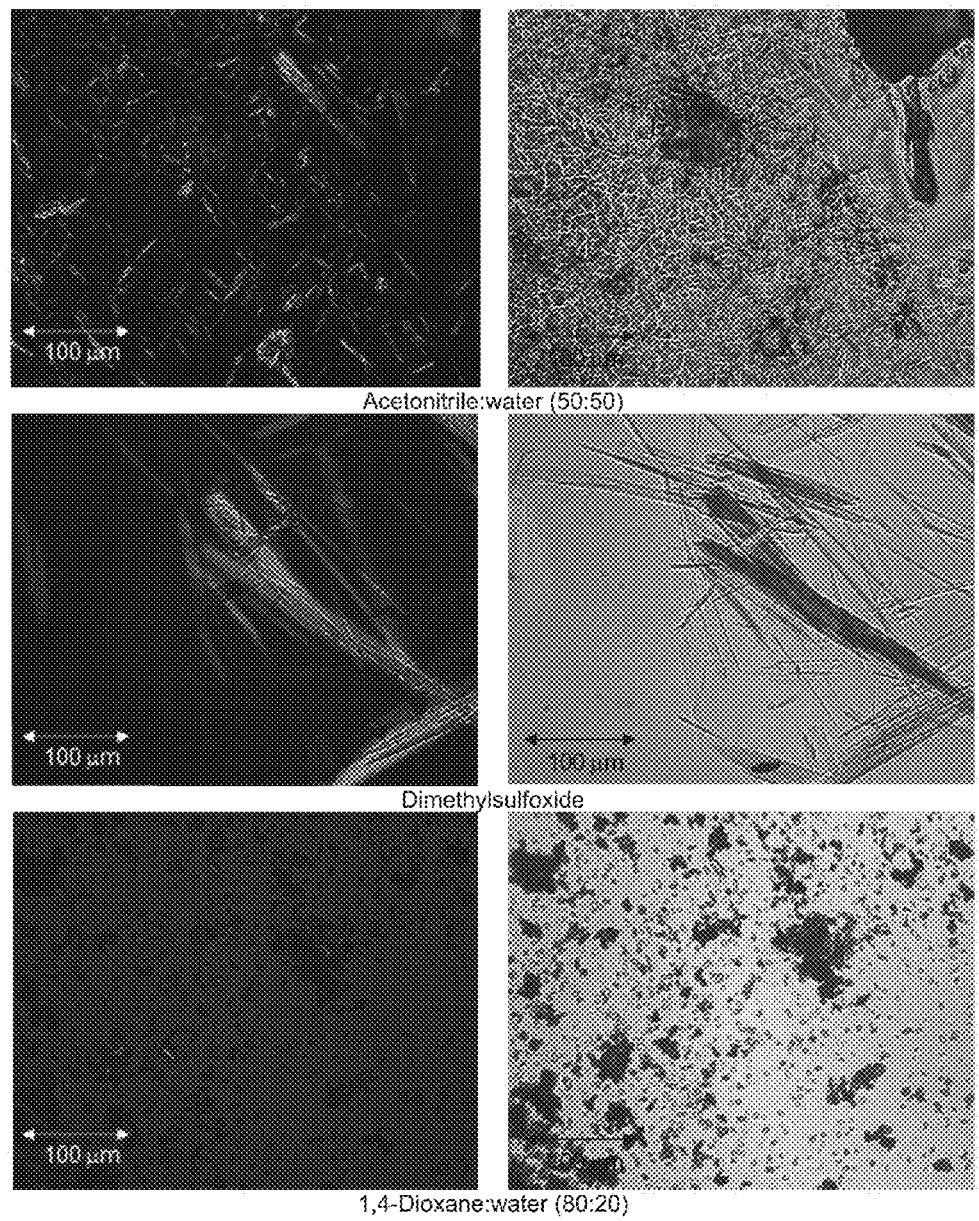
FIG. 164: Anti-Solvent (Acetone) Addition Experiments at Ambient Temperature in Various Solvents—PLM Analysis of solid states of Compound A bis-mesylate—Acetonitrile:water (50:50), Dimethylsulfoxide, and 1,4-Dioxane:water (80:20)
Figure 165:
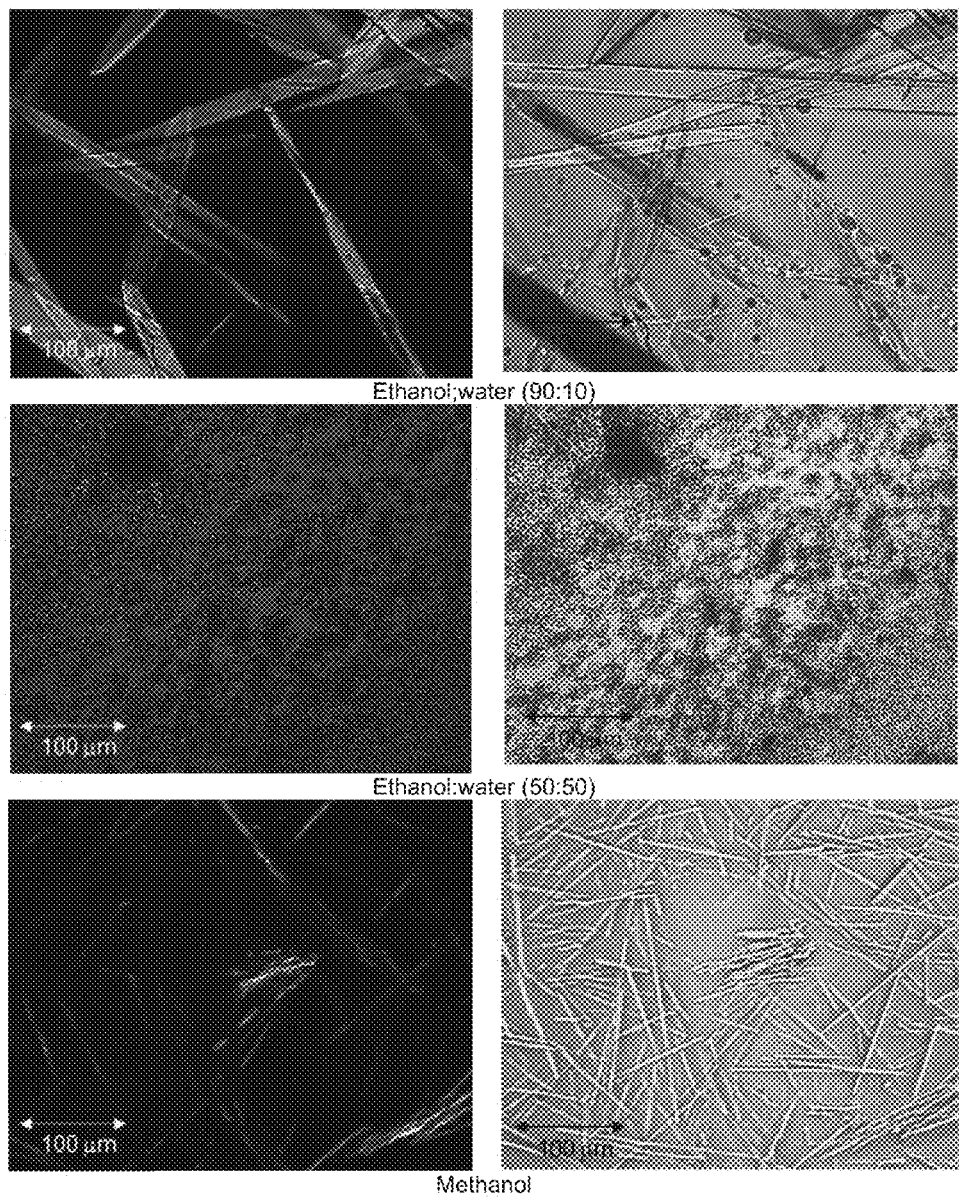
FIG. 165: Anti-Solvent (Acetone) Addition Experiments at Ambient Temperature in Various Solvents—PLM Analysis of solid states of Compound A bis-mesylate—Ethanol:water (90:10), Ethanol:water (50:50), and Methanol
Figure 166:
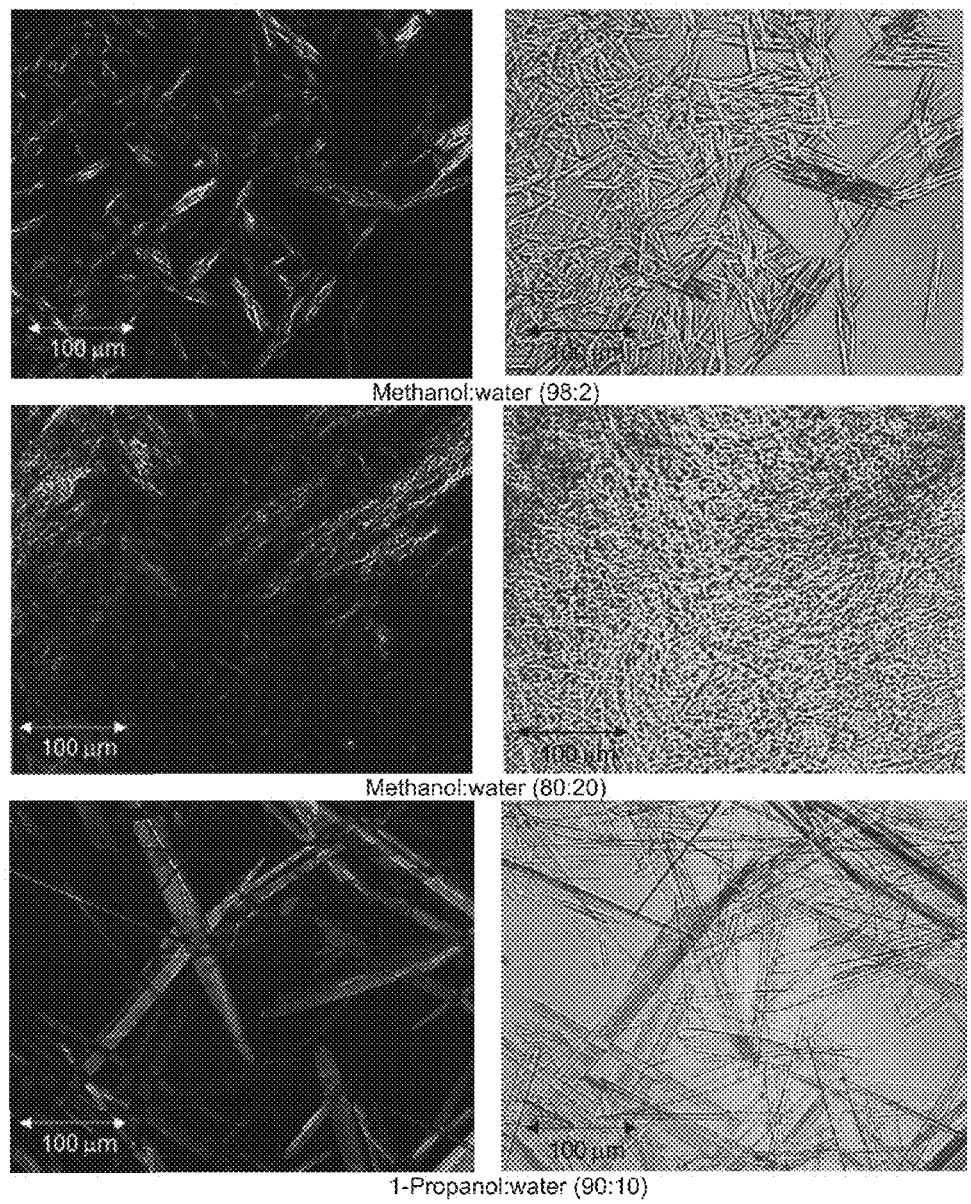
FIG. 166: Anti-Solvent (Acetone) Addition Experiments at Ambient Temperature in Various Solvents—PLM Analysis of solid states of Compound A bis-mesylate—Methanol:water (98:2), Methanol:water (80:20), and 1-propanol:water (90:10)
Figure 167:
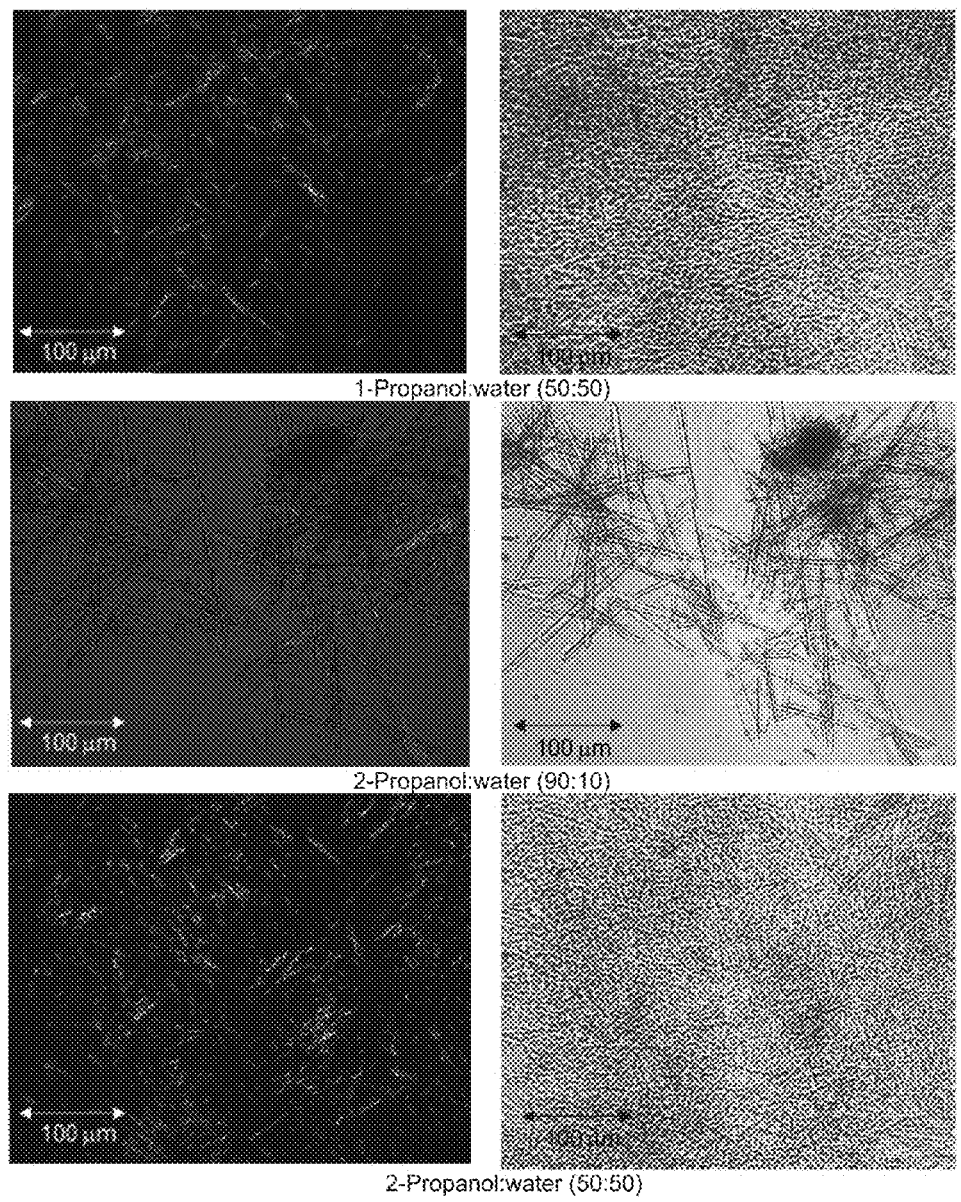
FIG. 167: Anti-Solvent (Acetone) Addition Experiments at Ambient Temperature in Various Solvents—PLM Analysis of solid states of Compound A bis-mesylate—1-propanol:water (50:50), 2-propanol:water (90:10), and 2-propanol:water (50:50)
Figure 168:
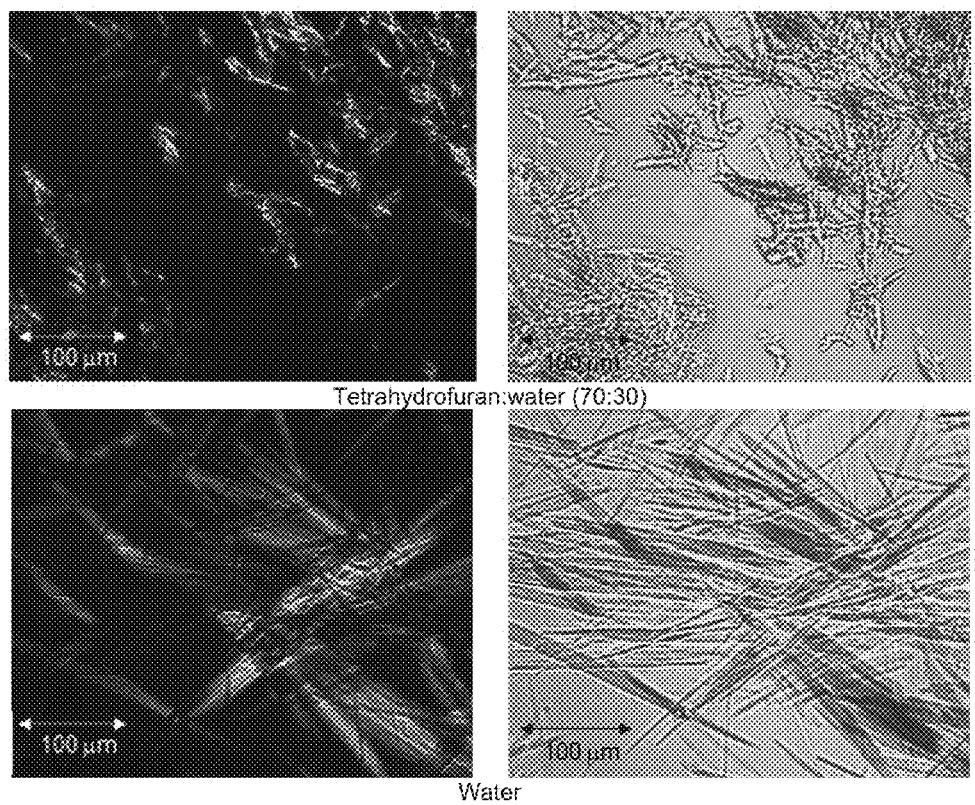
FIG. 168: Anti-Solvent (Acetone) Addition Experiments at Ambient Temperature in Various Solvents—PLM Analysis of solid states of Compound A bis-mesylate—Tetrahydrofuran:water (70:30) and water
Figure 169:
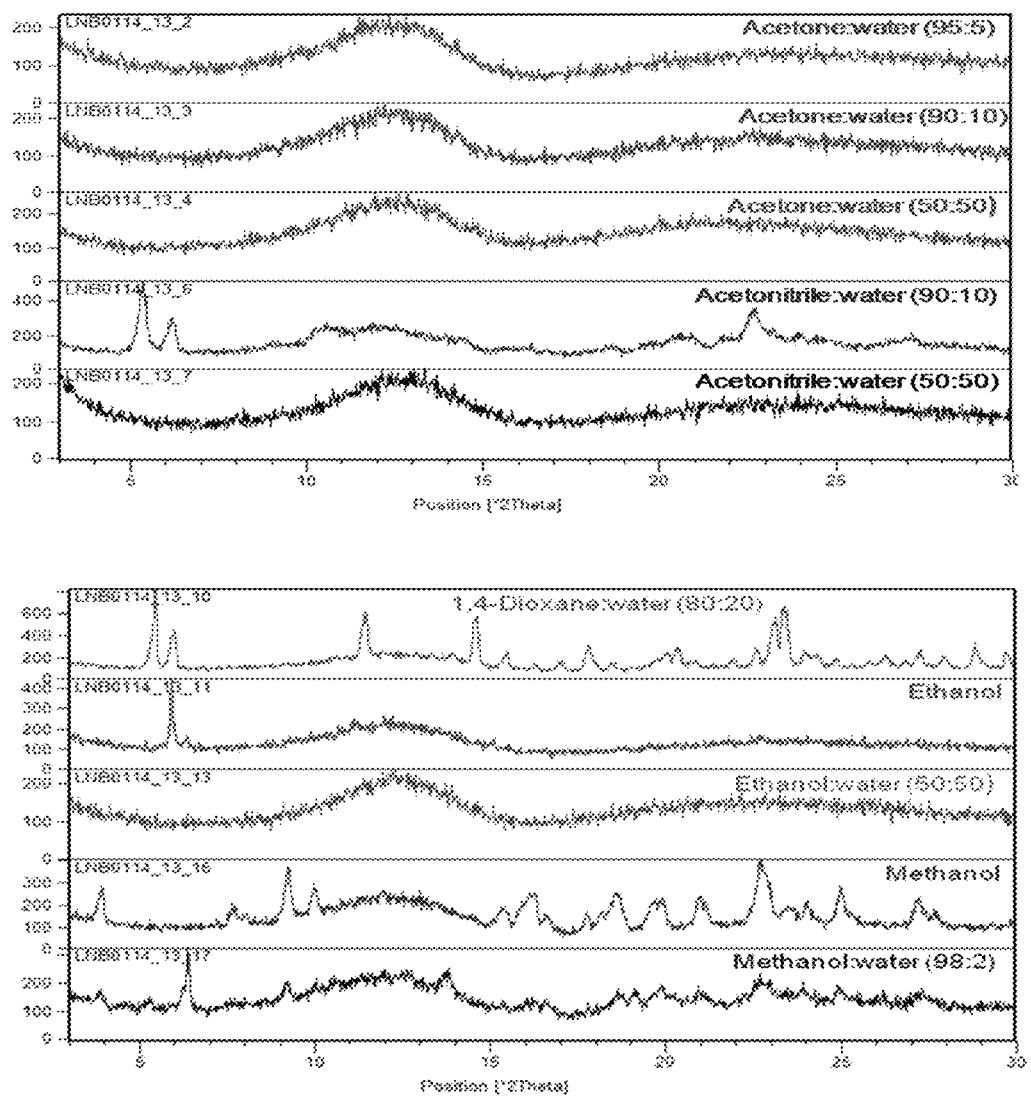
FIG. 169: Evaporation Experiments from Various Solvents—XRPD Analysis of solid states of Compound A bis-mesylate
Figure 170:
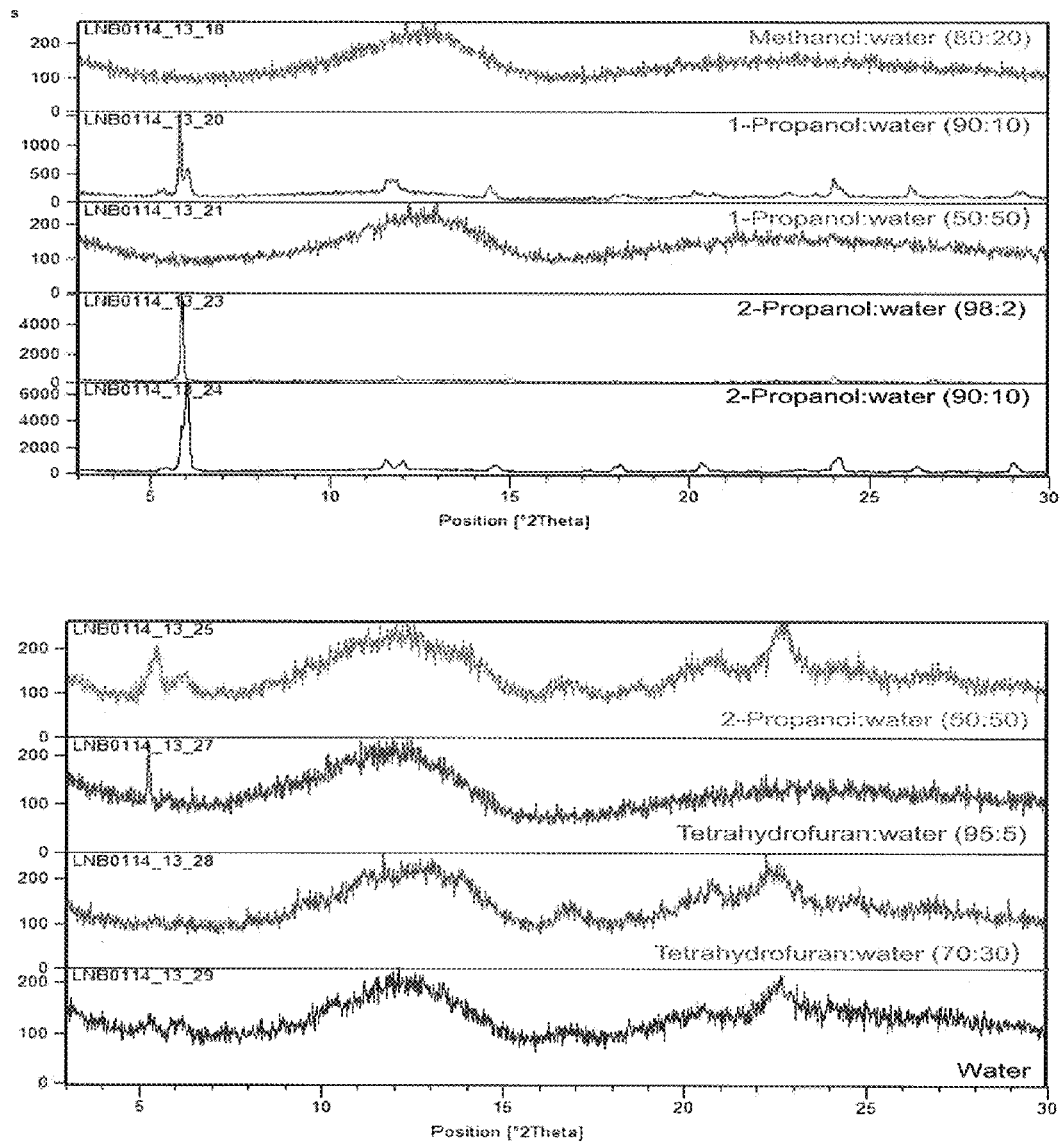
FIG. 170: Evaporation Experiments from Various Solvents—XRPD Analysis of solid states of Compound A bis-mesylate
Figure 171:
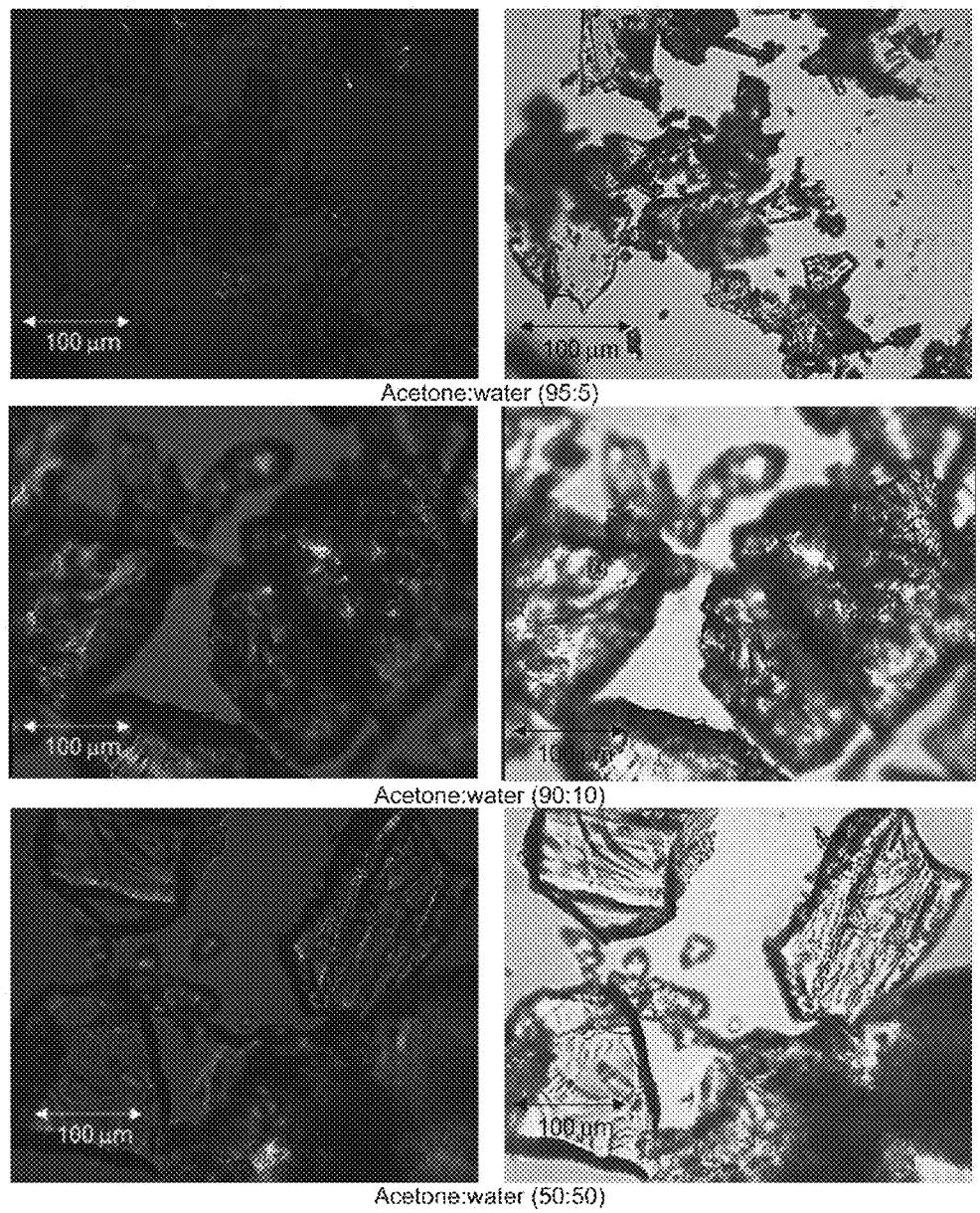
FIG. 171: Evaporation Experiments from Various Solvents—PLM Analysis of solid states of Compound A bis-mesylate—Acetone:water (95:5), Acetone:water (90:10), and Acetone:water (50:50)
Figure 172:
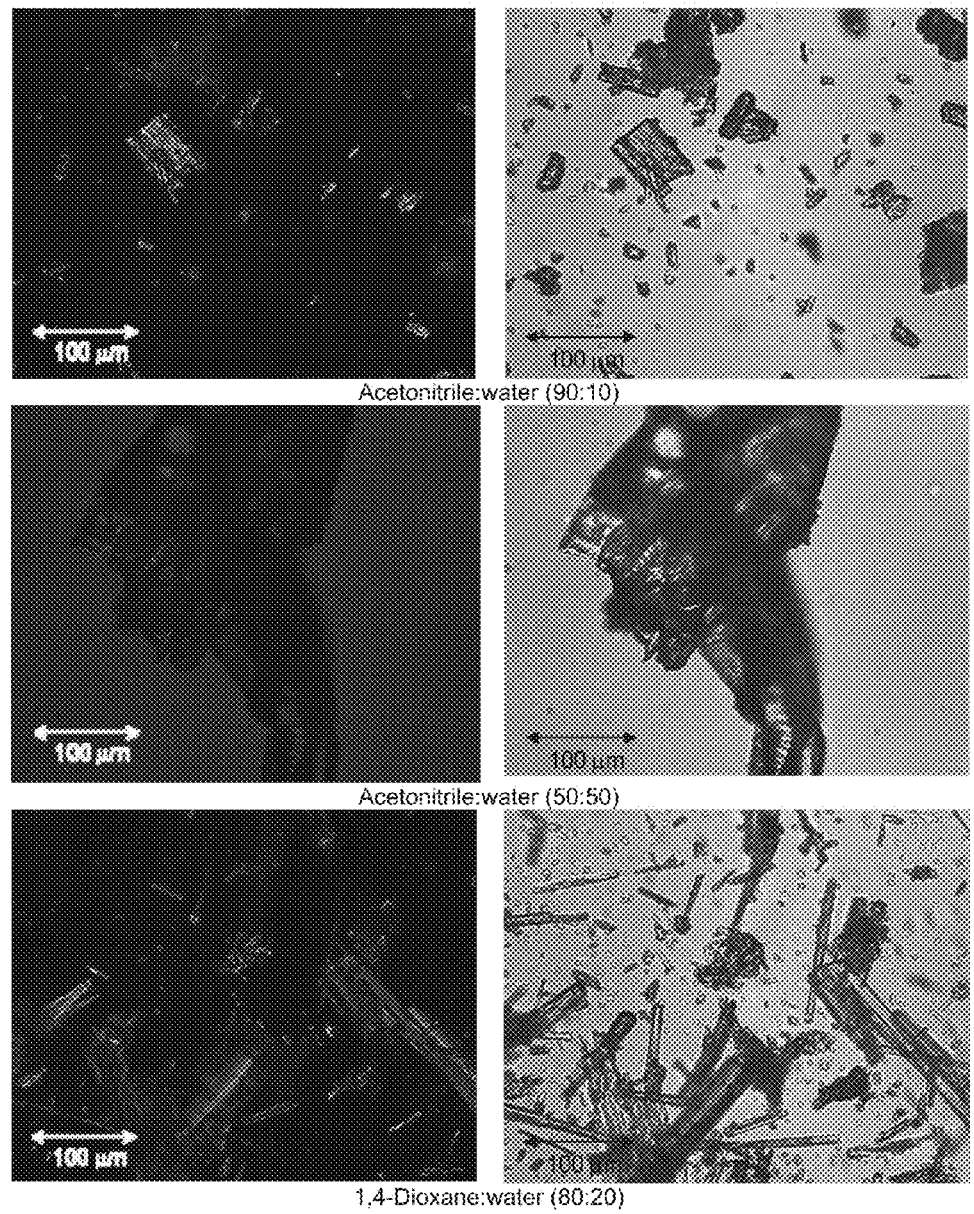
FIG. 172: Evaporation Experiments from Various Solvents—PLM Analysis of solid states of Compound A bis-mesylate—Acetonitrile:water (90:10), Acetonitrile:water (50:50), 1,4-Dioxane:Water (80:20)
Figure 173:
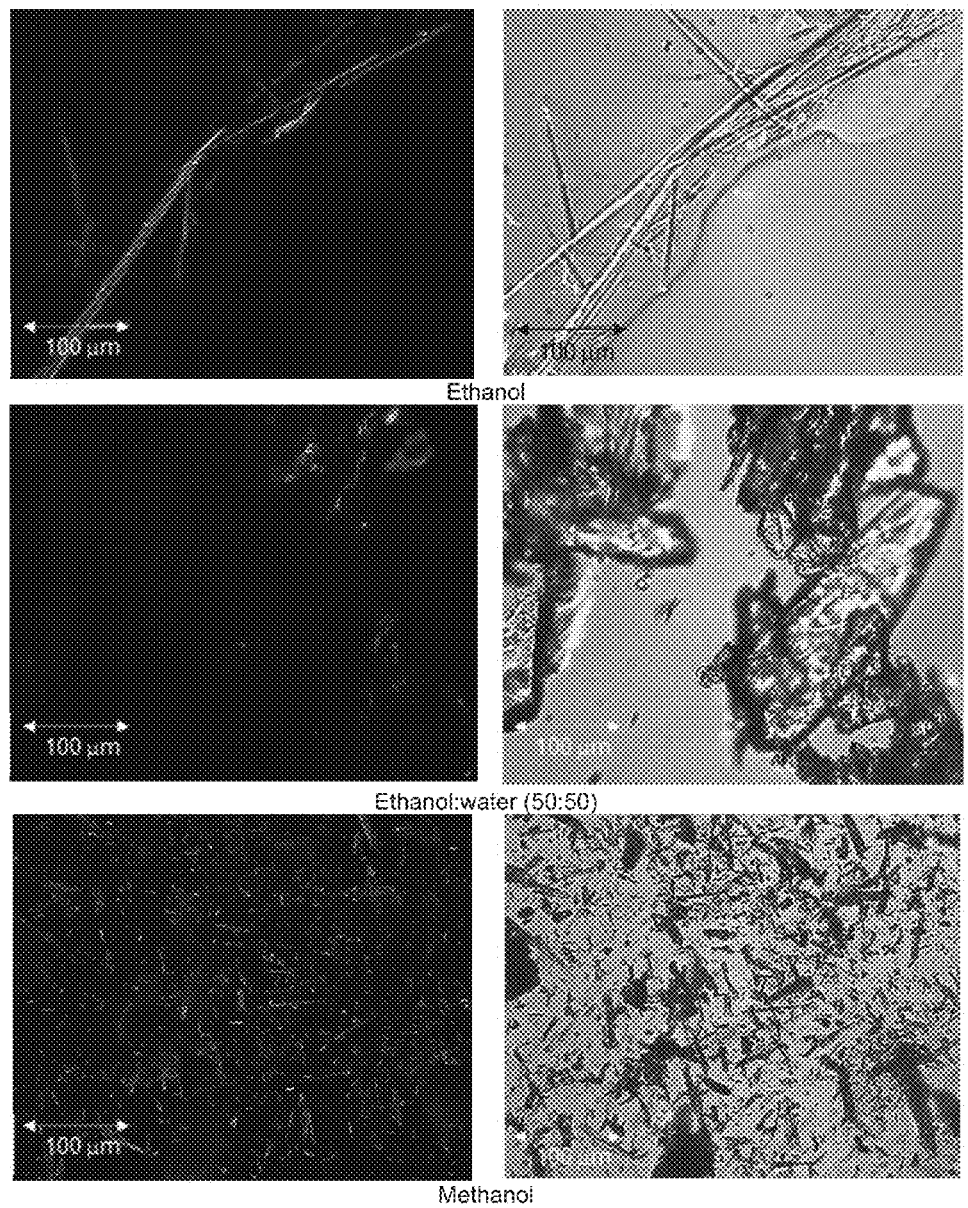
FIG. 173: Evaporation Experiments from Various Solvents—PLM Analysis of solid states of Compound A bis-mesylate—Ethanol, Ethanol:water (50:50), and Methanol
Figure 174:
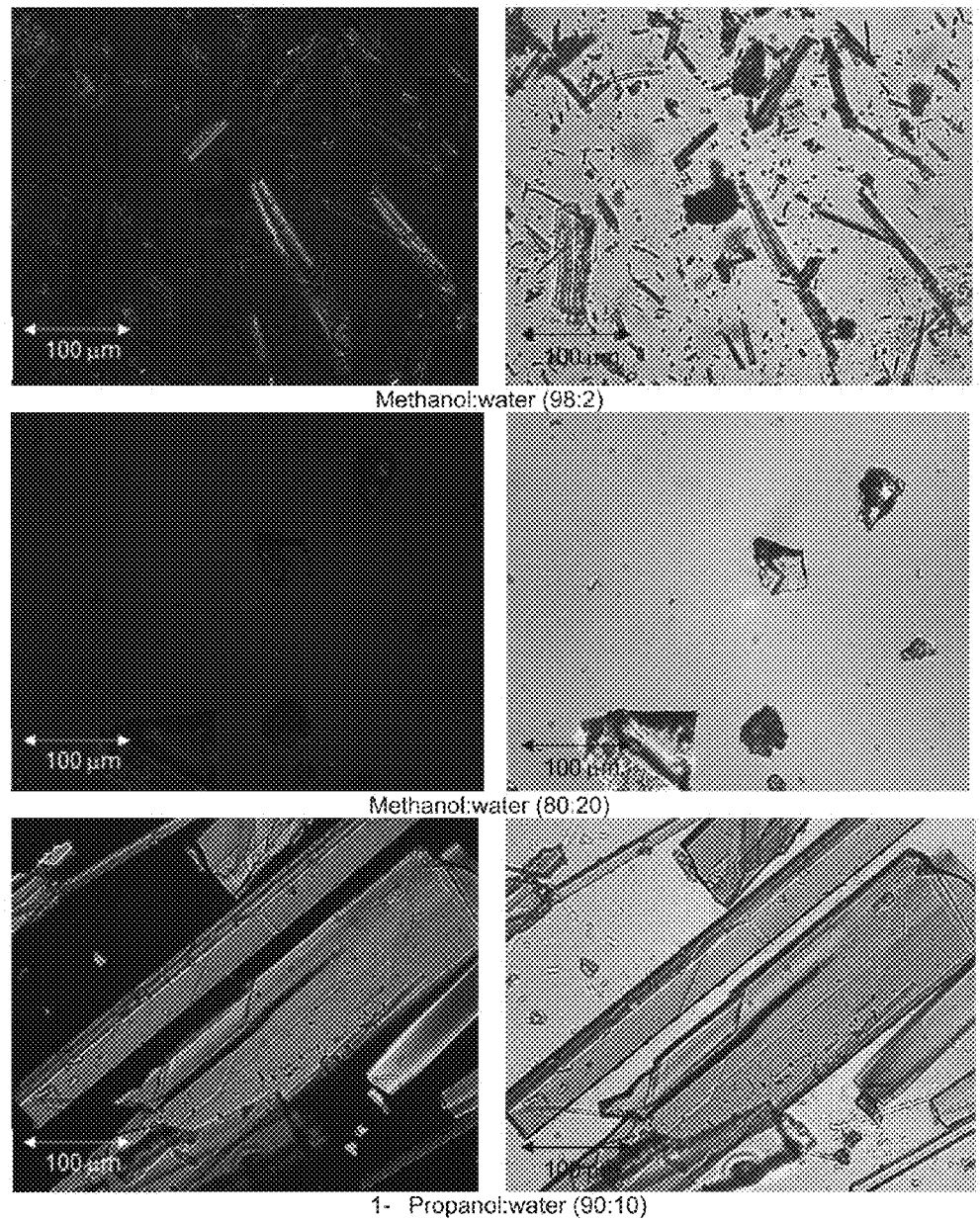
FIG. 174: Evaporation Experiments from Various Solvents—PLM Analysis of solid states of Compound A bis-mesylate—Methanol:water (98:2), Methanol:water (80:20), and 1-propanol:water (90:10)
Figure 175:
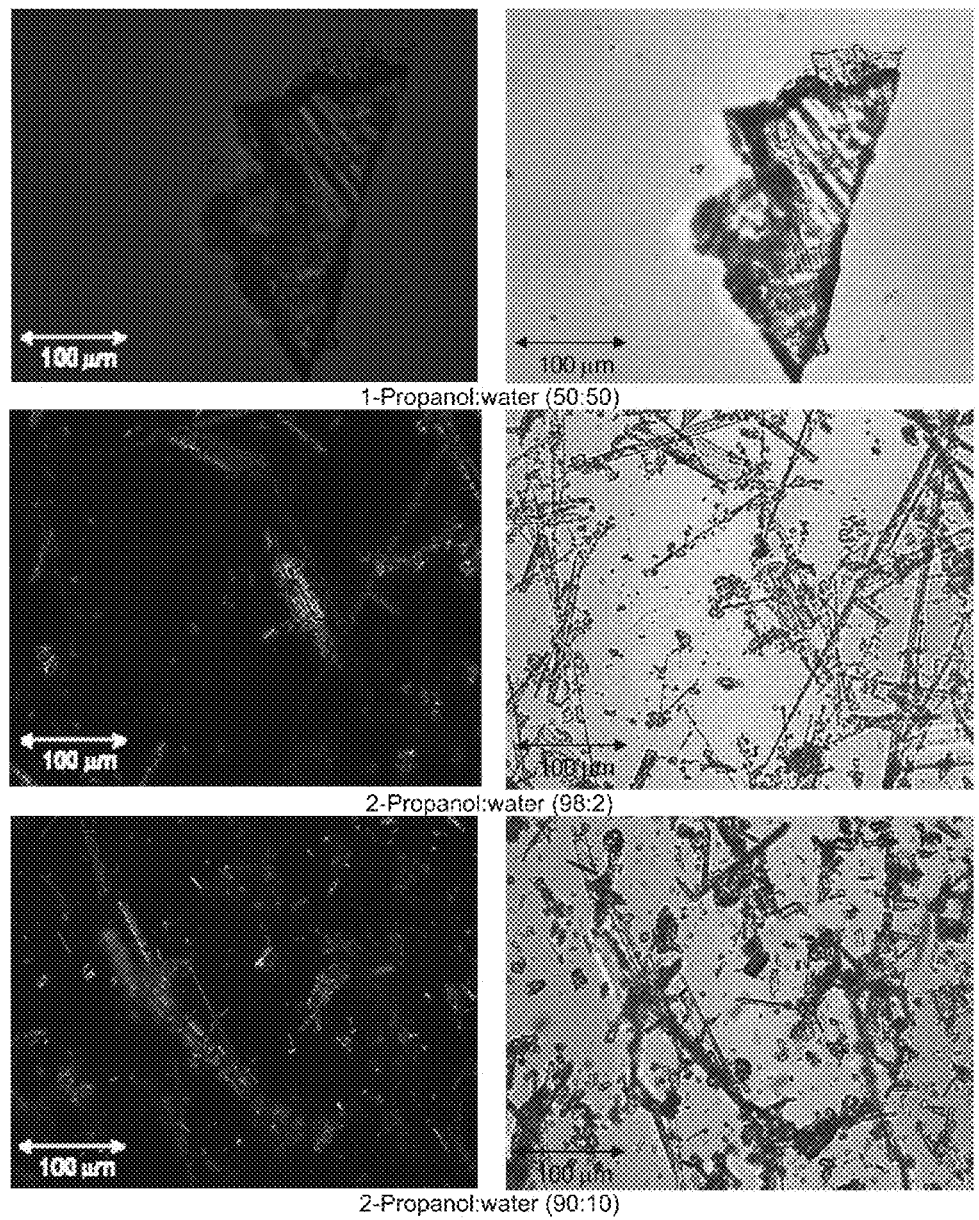
FIG. 175: Evaporation Experiments from Various Solvents—PLM Analysis of solid states of Compound A bis-mesylate—1-Propanol:water (50:50), 2-Propanol:water (98:2), and 2-Propanol:water (90:10)
Figure 176:
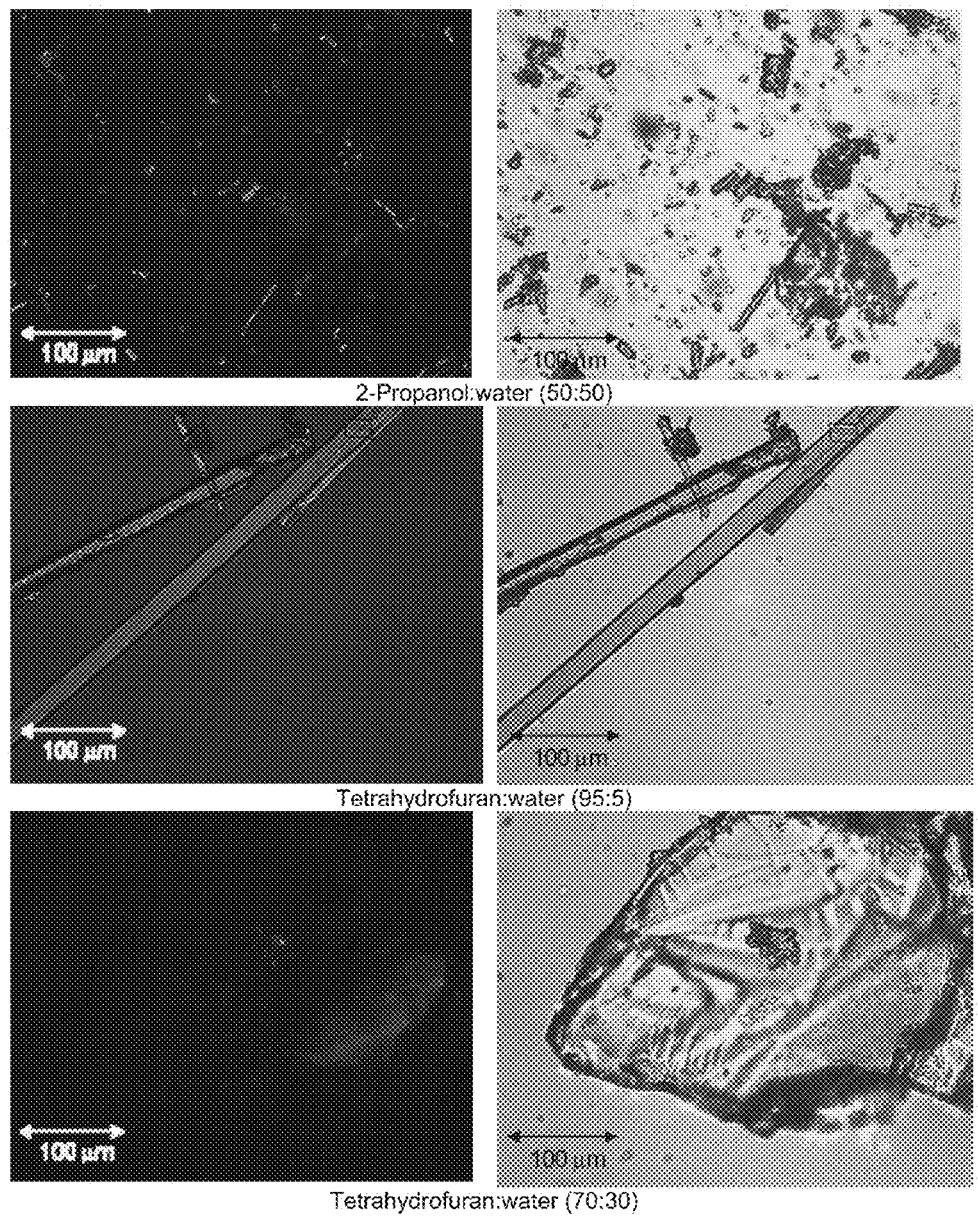
FIG. 176: Evaporation Experiments from Various Solvents—PLM Analysis of solid states of Compound A bis-mesylate—2-propanol:water (50:50), Tetrahydrofuran:water (95:5), and Tetrahydrofuran:water (70:30)
Figure 177:
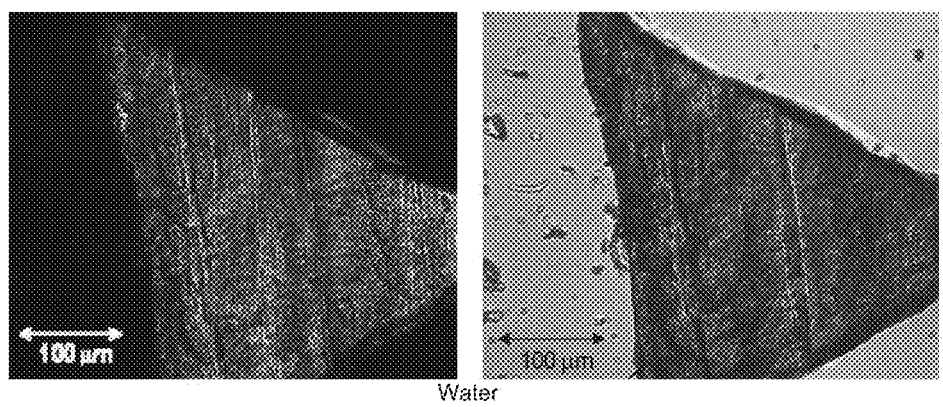
FIG. 177: Evaporation Experiments from Various Solvents—PLM Analysis of solid states of Compound A bis-mesylate—Water
Figure 178:
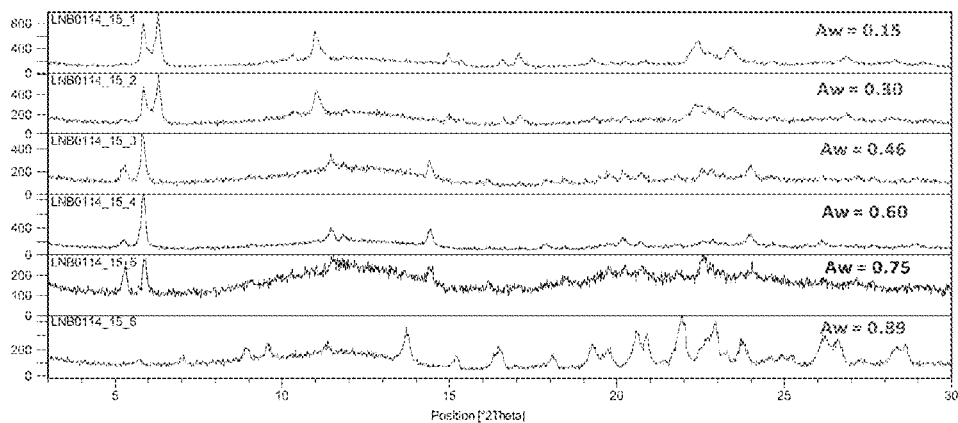
FIG. 178: Hydration Screen Experiments—XRPD Analysis of Low Concentration Slurry of solid states of Compound A bis-mesylate at 10° C. in Acetone and Acetonitrile
Figure 178:
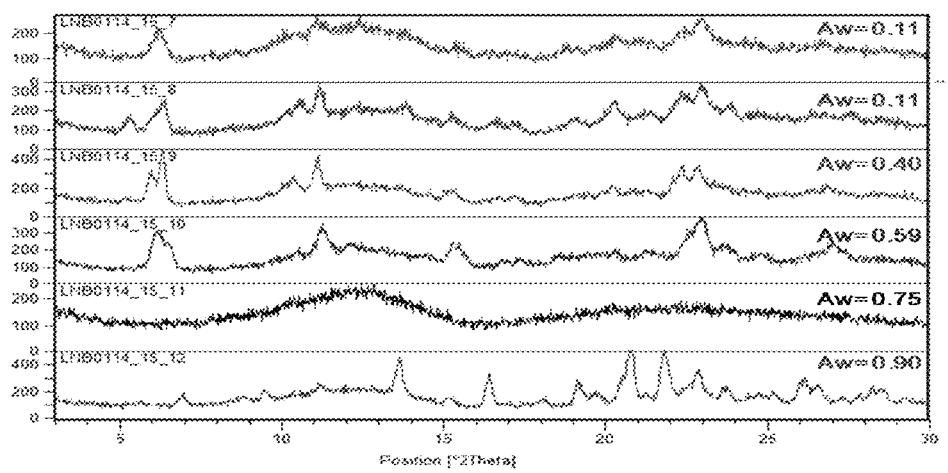
Figure 179:
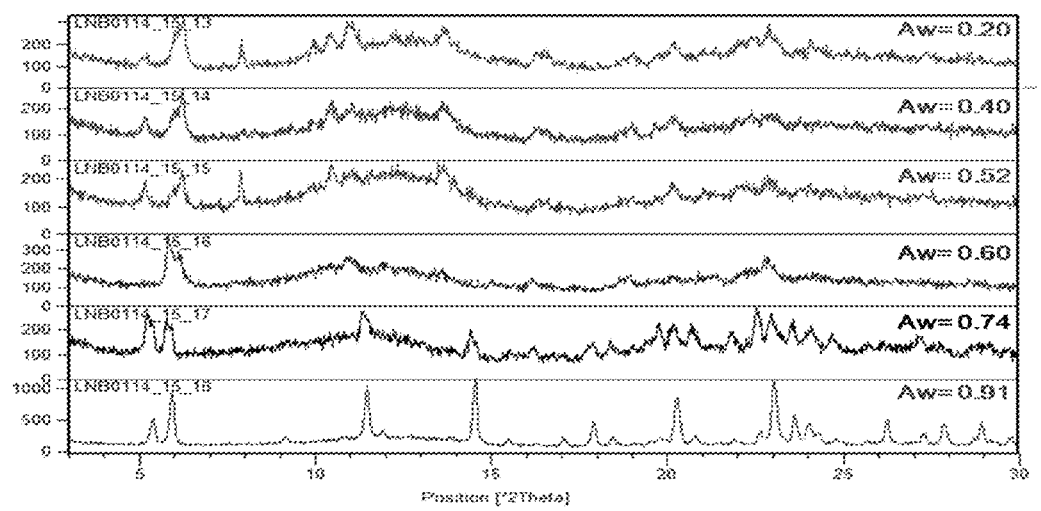
FIG. 179: Hydration Screen Experiments—XRPD Analysis of Low Concentration Slurry of solid states of Compound A bis-mesylate at 10° C. in 2-Propanol
Figure 180:
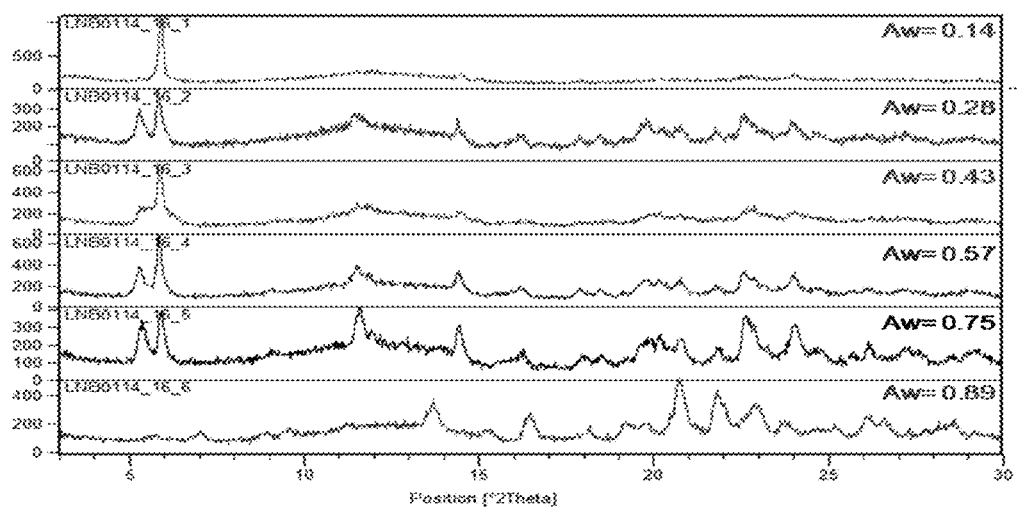
FIG. 180: Hydration Screen Experiments—XRPD Analysis of High Concentration Slurry of solid states of Compound A bis-mesylate at 10° C. in Acetone and Acetonitrile
Figure 180:
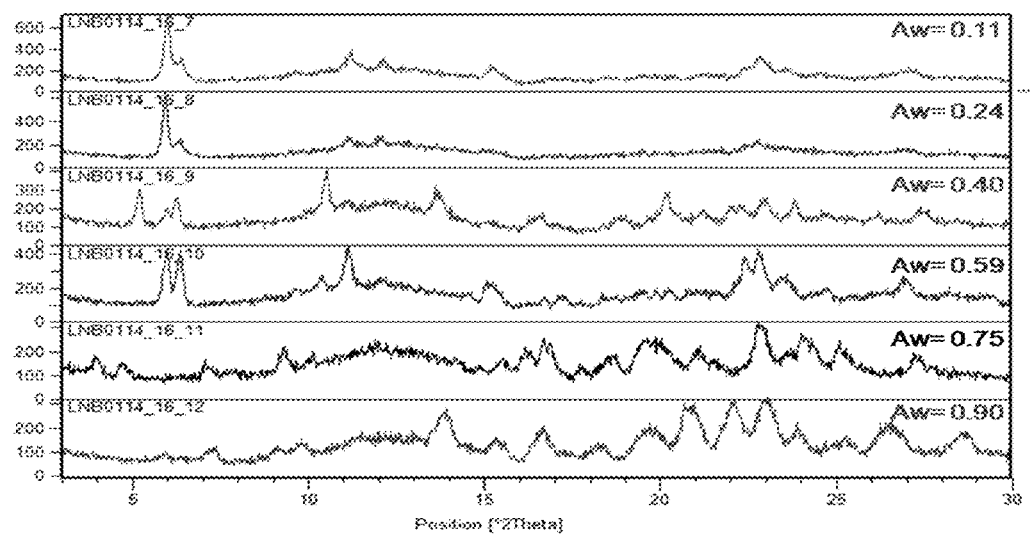
Figure 181:
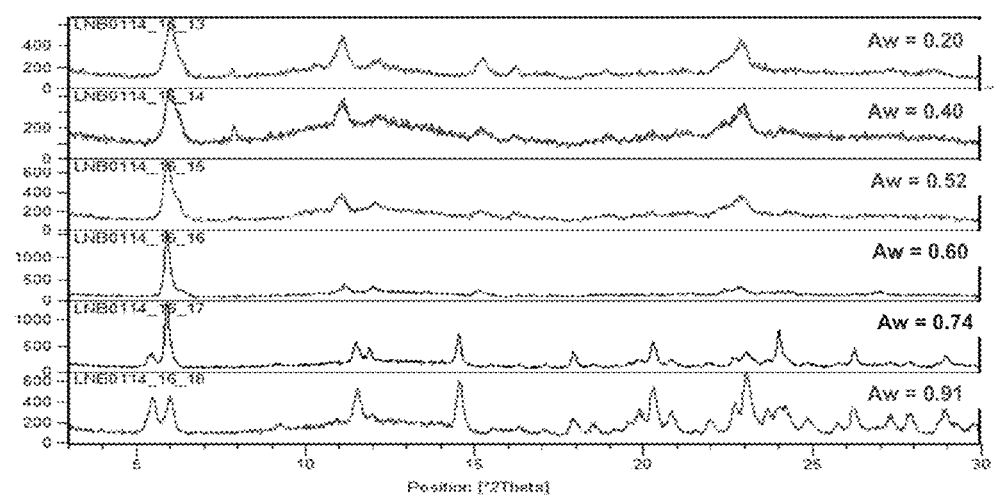
FIG. 181: Hydration Screen Experiments—XRPD Analysis of High Concentration Slurry of solid states of Compound A bis-mesylate at 10° C. in 2-Propanol
Figure 182:
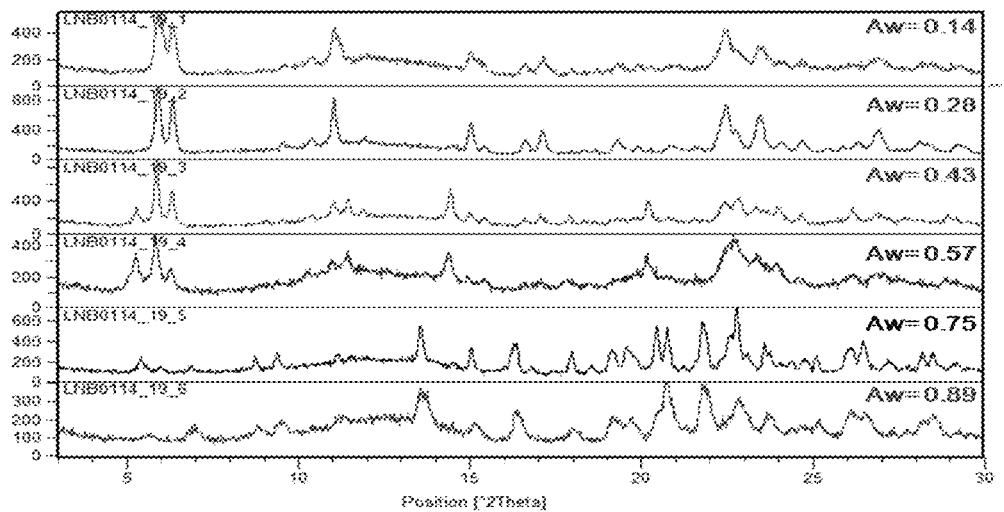
FIG. 182: Hydration Screen Experiments—XRPD Analysis of Low Concentration Slurry of solid states of Compound A bis-mesylate at 25° C. in Acetone and Acetonitrile
Figure 182:
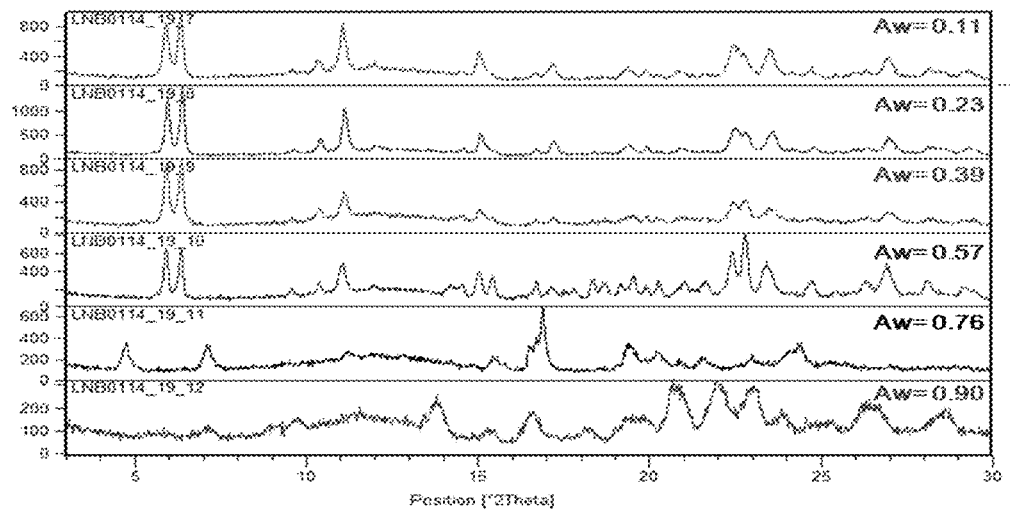
Figure 183:
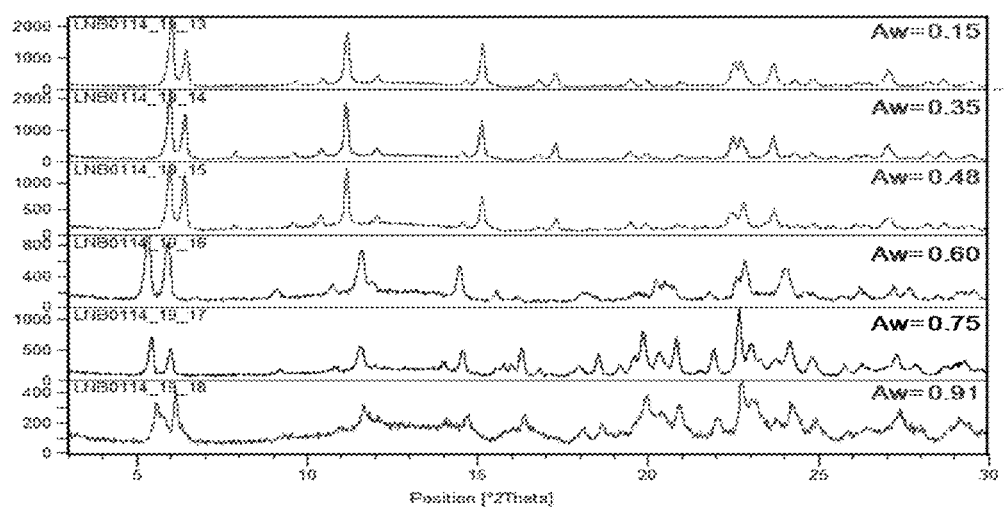
FIG. 183: Hydration Screen Experiments—XRPD Analysis of Low Concentration Slurry of solid states of Compound A bis-mesylate at 25° C. in 2-Propanol
Figure 184:
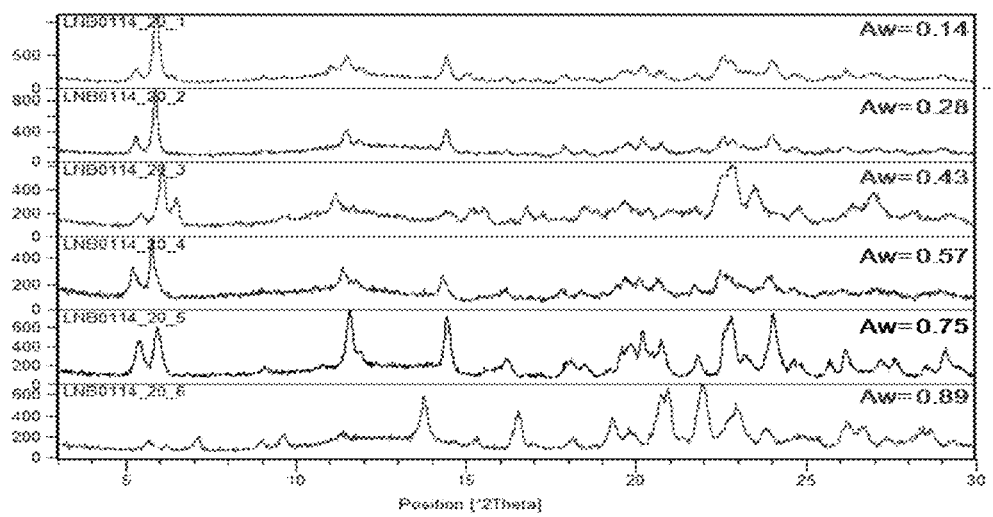
FIG. 184: Hydration Screen Experiments—XRPD Analysis of High Concentration Slurry of solid states of Compound A bis-mesylate at 25° C. in Acetone and Acetonitrile
Figure 184:
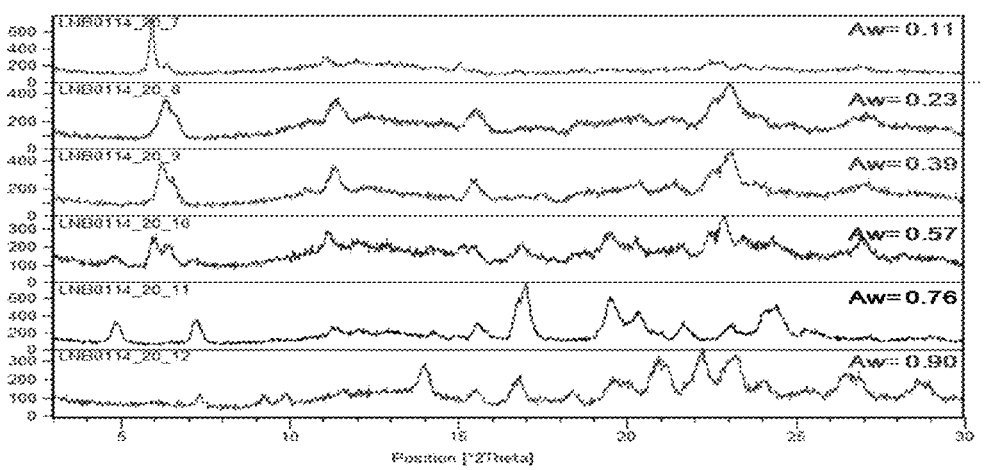
Figure 185:
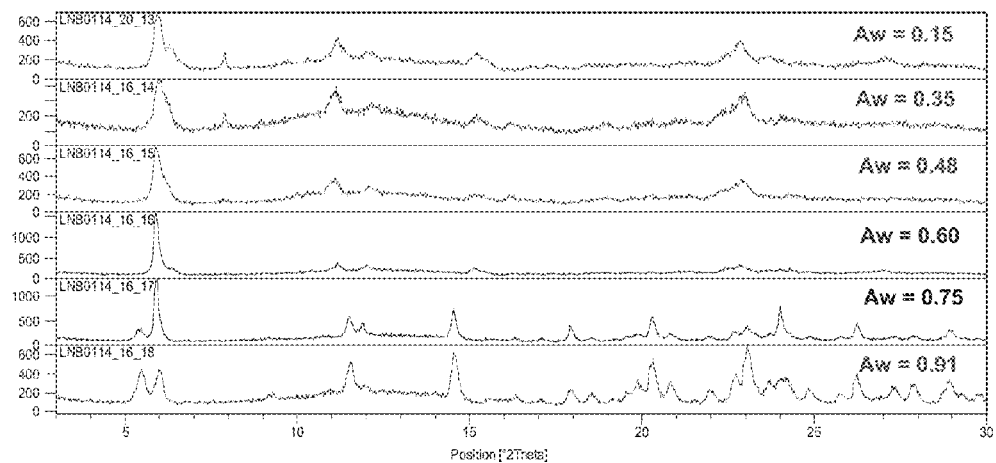
FIG. 185: Hydration Screen Experiments—XRPD Analysis of High Concentration Slurry of solid states of Compound A bis-mesylate at 25° C. in 2-Propanol
Figure 186:
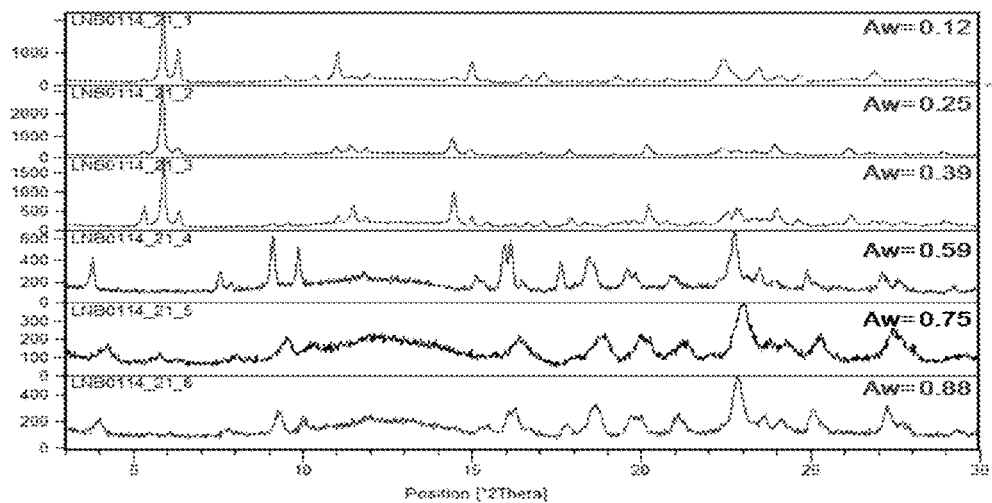
FIG. 186: Hydration Screen Experiments—XRPD Analysis of Low Concentration Slurry of solid states of Compound A bis-mesylate at 50° C. in Acetone and Acetonitrile
Figure 186:
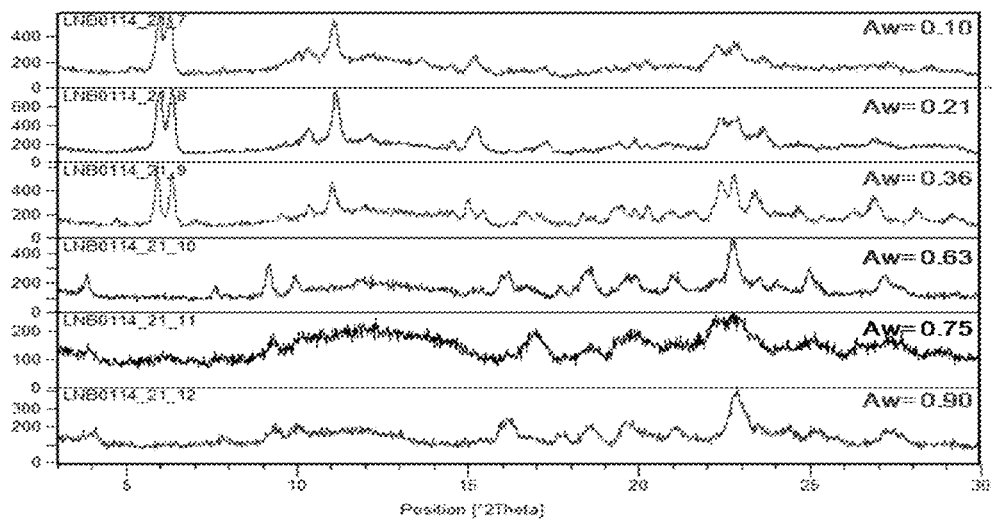
Figure 187:
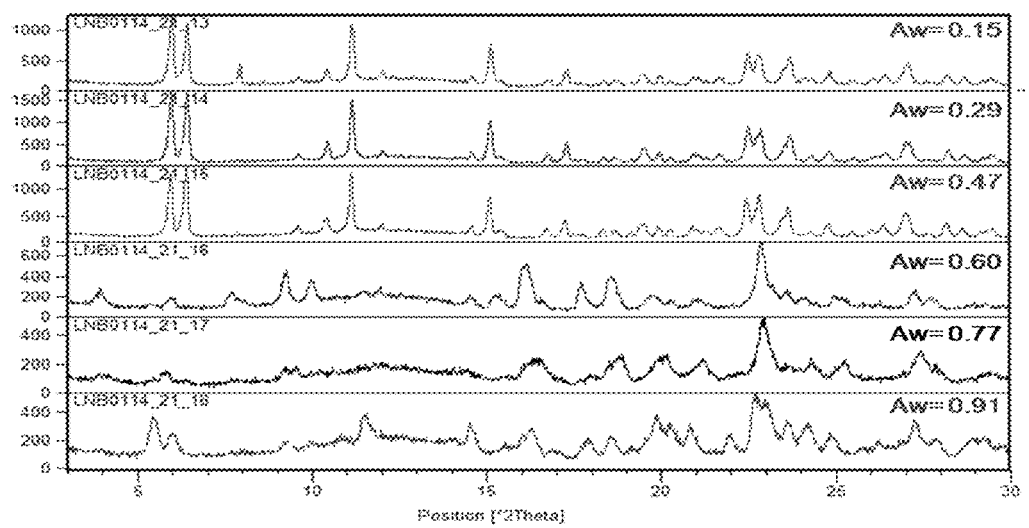
FIG. 187: Hydration Screen Experiments—XRPD Analysis of Low Concentration Slurry of solid states of Compound A bis-mesylate at 50° C. in 2-Propanol
Figure 188:
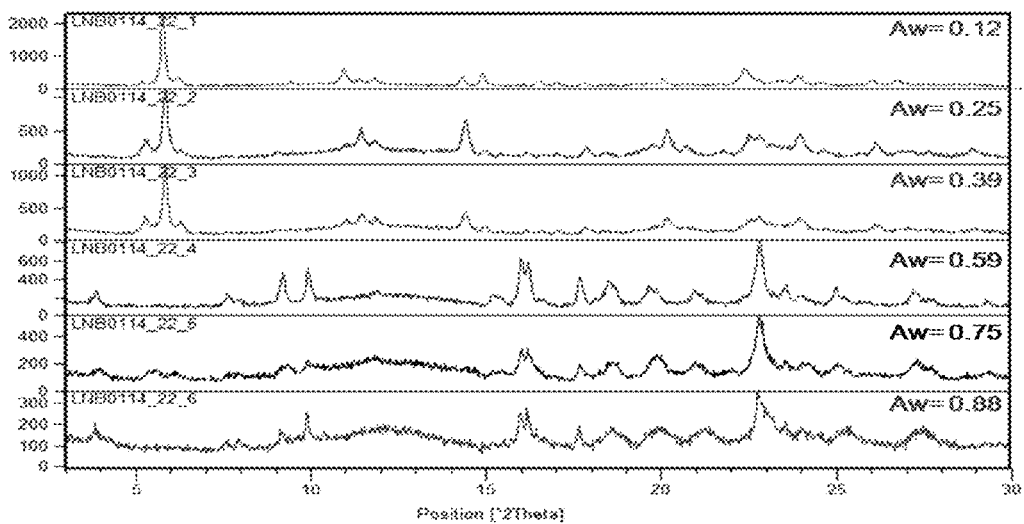
FIG. 188: Hydration Screen Experiments—XRPD Analysis of High Concentration Slurry of solid states of Compound A bis-mesylate at 50° C. in Acetone and Acetonitrile
Figure 188:
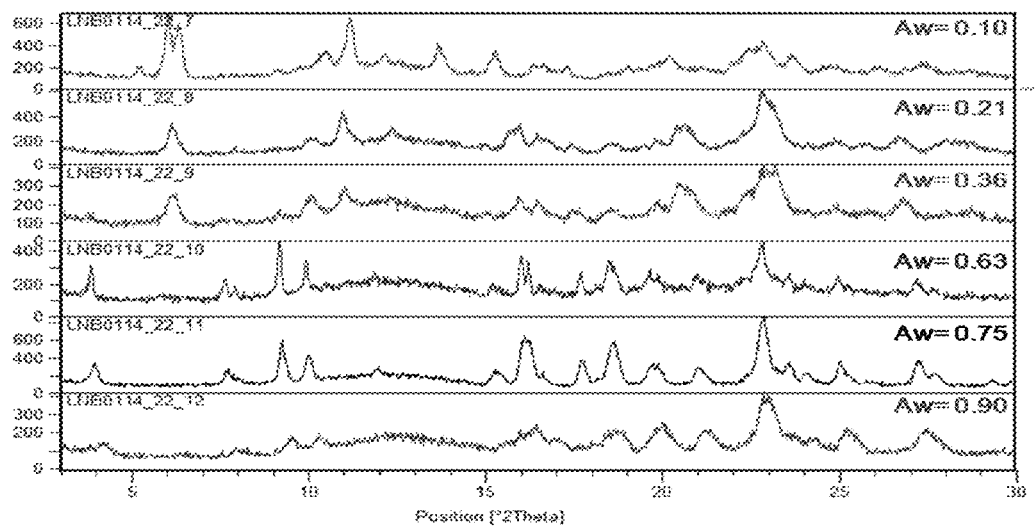
Figure 189:
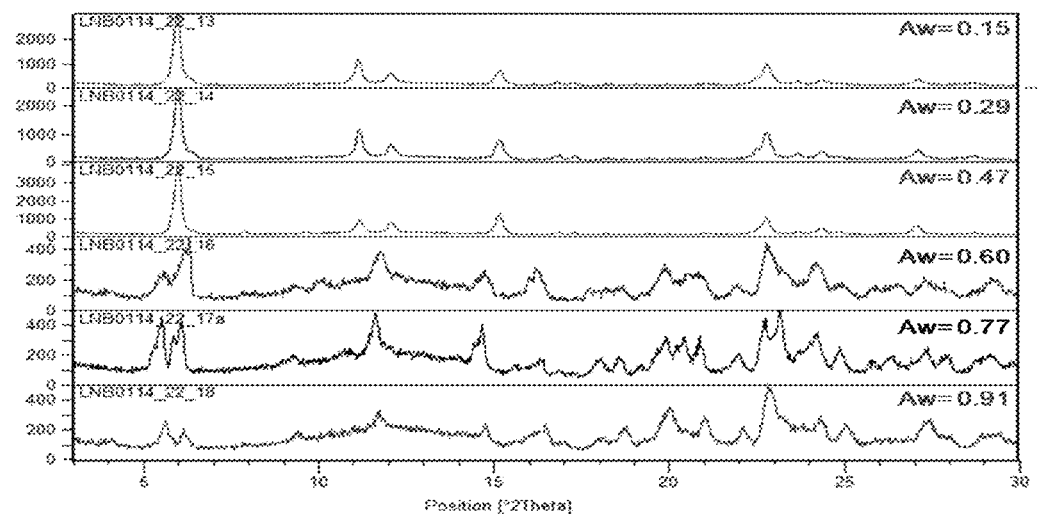
FIG. 189: Hydration Screen Experiments—XRPD Analysis of High Concentration Slurry of solid states of Compound A bis-mesylate at 50° C. in 2-Propanol

In one embodiment, Form C has X-ray powder diffraction peaks at approximately 20.1 and 22.6°2θ using Cu Kα radiation. In some embodiments, Form C has X-ray powder diffraction peaks at approximately 17.5, 18.2, 19.0, 19.6, 20.1, and 22.6°2θ using Cu Kα radiation. In some embodiments, Form C has X-ray powder diffraction peaks at approximately 12.5, 16.6, 17.5, 18.2, 19.0, 19.6, 20.1, 21.7, 22.6, 23.0, 23.6, 24.0, 26.6, and 27.2°2θ using Cu Kα radiation. In one embodiment, Form C has X-ray powder diffraction pattern substantially similar to that shown in FIG. 145. In one embodiment, Form C has X-ray powder diffraction peaks as shown in FIG. 147.

In one embodiment, the polymorph of Compound A mesylate is Form D. In some embodiments, Form D has X-ray powder diffraction peaks at approximately 14.5 and 23.0°2θ using Cu Kα radiation. In some embodiments, Form D has X-ray powder diffraction peaks at approximately 5.9, 11.5, 14.5, 20.3, and 23.0°2θ using Cu Kα radiation. In some embodiments, Form D has X-ray powder diffraction peaks at approximately 5.4, 5.9, 11.5, 14.5, 17.9, 20.3, 23.0, 23.6, 24.0, 26.2, 27.8, and 28.9°2θ using Cu Kα radiation. In one embodiment, Form D has X-ray powder diffraction peaks as shown in FIG. 241. In one embodiment, Form D has a X-ray powder diffraction pattern substantially similar to that shown in FIG. 239.

In one embodiment, Form D is Compound A bis-mesylate.

Figure 191:
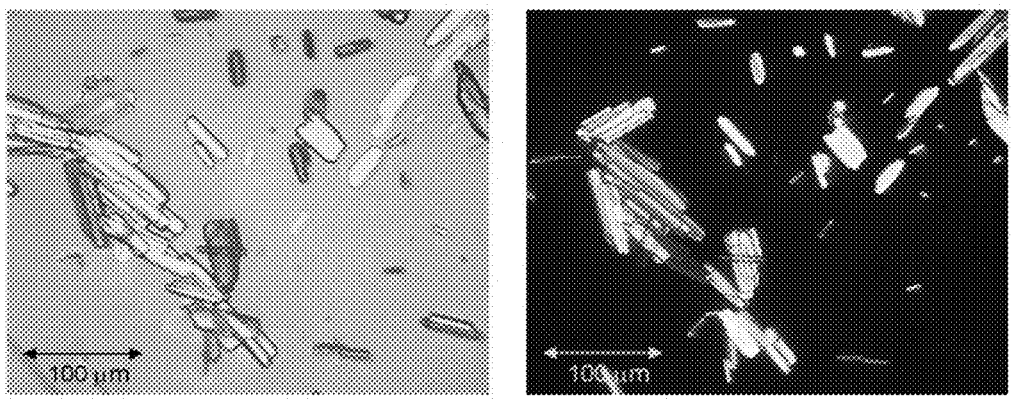
FIG. 191: Form D Compound A bis-mesylate—PLM Analysis

In one embodiment, Form D is birefringent with a flat rod/plate-like morphology as determined by PLM analysis as shown in FIG. 191.

Figure 194:
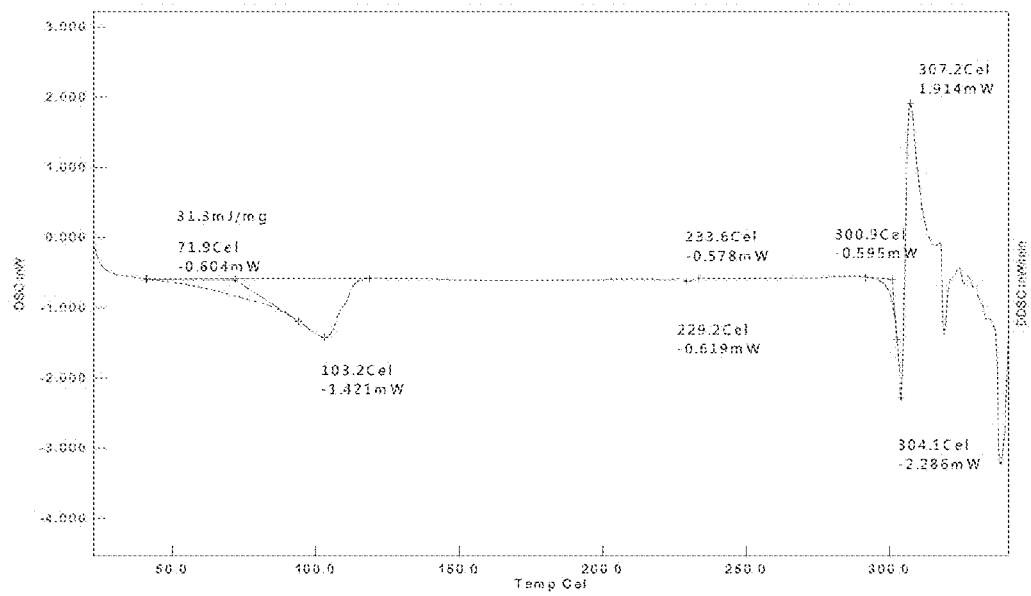
FIG. 194: Form D Compound A bis-mesylate—DSC Analysis

In one embodiment, Form D has an initial broad endotherm at onset about 50.3° C. (peak 103.2° C.). In one embodiment, Form D has a small endothermic/exothermic event between about 229° C. and 235° C. In one embodiment, Form D has a final endotherm at onset about 300.9° C. (peak 304.1° C.) (FIG. 194).

In one embodiment, Form D has a water content of about 3.8%, as measured by Karl-Fischer Titration.

Figure 199:
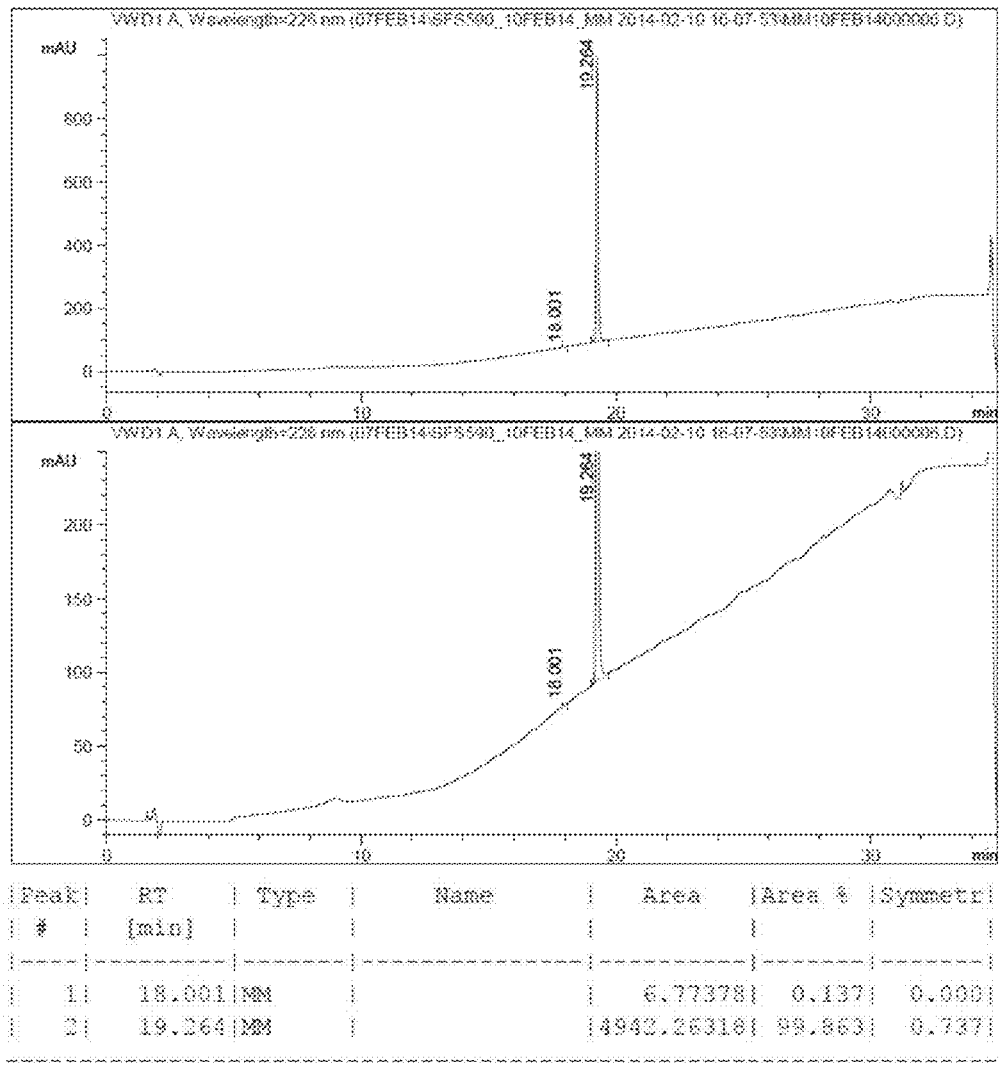
Figure 200:
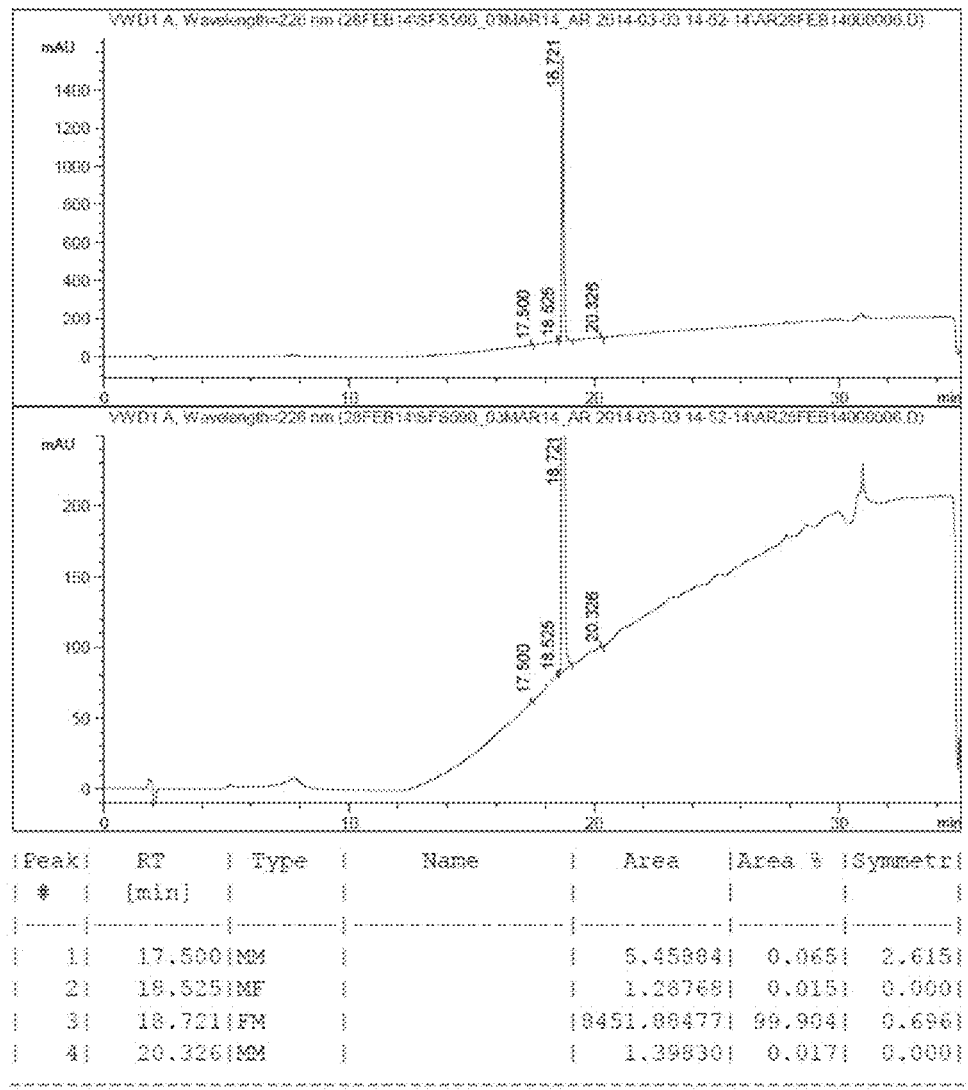

In one embodiment, Form D has an HPLC purity of 99.9% (FIG. 199).

In one embodiment, Form D is characterized by the $^1$H NMR spectrum in FIG. 204.

In one embodiment, Form D can be produced by: adding 2-propanol with 0.6 water activity to the amorphous form of Compound A bis-mesylate to form a slurry, stirring the slurry at about 22° C., and filtering and drying the slurry.

In one embodiment, the polymorph of Compound A mesylate is Form E. In some embodiments, Form E has X-ray powder diffraction peaks at approximately 20.9 and 21.9°2θ using Cu Kα radiation. In some embodiments, Form E has X-ray powder diffraction peaks at approximately 13.7, 20.6, 20.9, 21.9, and 23.0°2θ using Cu Kα radiation. In some embodiments, Form E has X-ray powder diffraction peaks at approximately 8.9, 11.3, 13.7, 16.5, 19.3, 20.6, 20.9, 21.9, 23.0, 23.8, and 26.2°2θ using Cu Kα radiation. In one embodiment, Form E has X-ray powder diffraction peaks as shown in FIG. 244. In one embodiment, Form E has a X-ray powder diffraction pattern substantially similar to that shown in FIG. 242.

In one embodiment, Form E is Compound A bis-mesylate.

Figure 206:
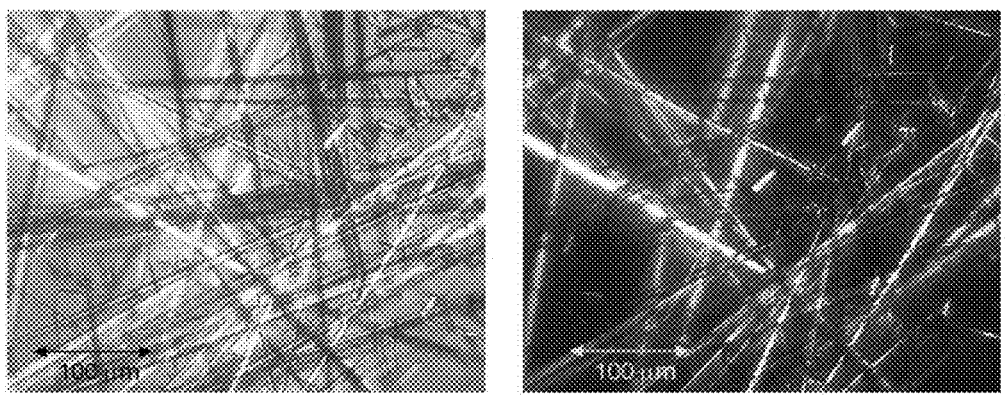

In one embodiment, Form E is birefringent with a long rod-like morphology as determined by PLM analysis as shown in FIG. 206.

In one embodiment, Form E has a broad endotherm at onset about 45.9° C. (peak 86.5° C.).

In one embodiment, Form E has an endothermic/exothermic event between about 189° C. and 215° C. In one embodiment, Form E has a final endothermic event at onset about 299.1° C. (peak 303.7° C.) (FIG. 210).

In one embodiment, Form E has a water content of about 6.2%, as measured by Karl-Fischer Titration.

Figure 215:
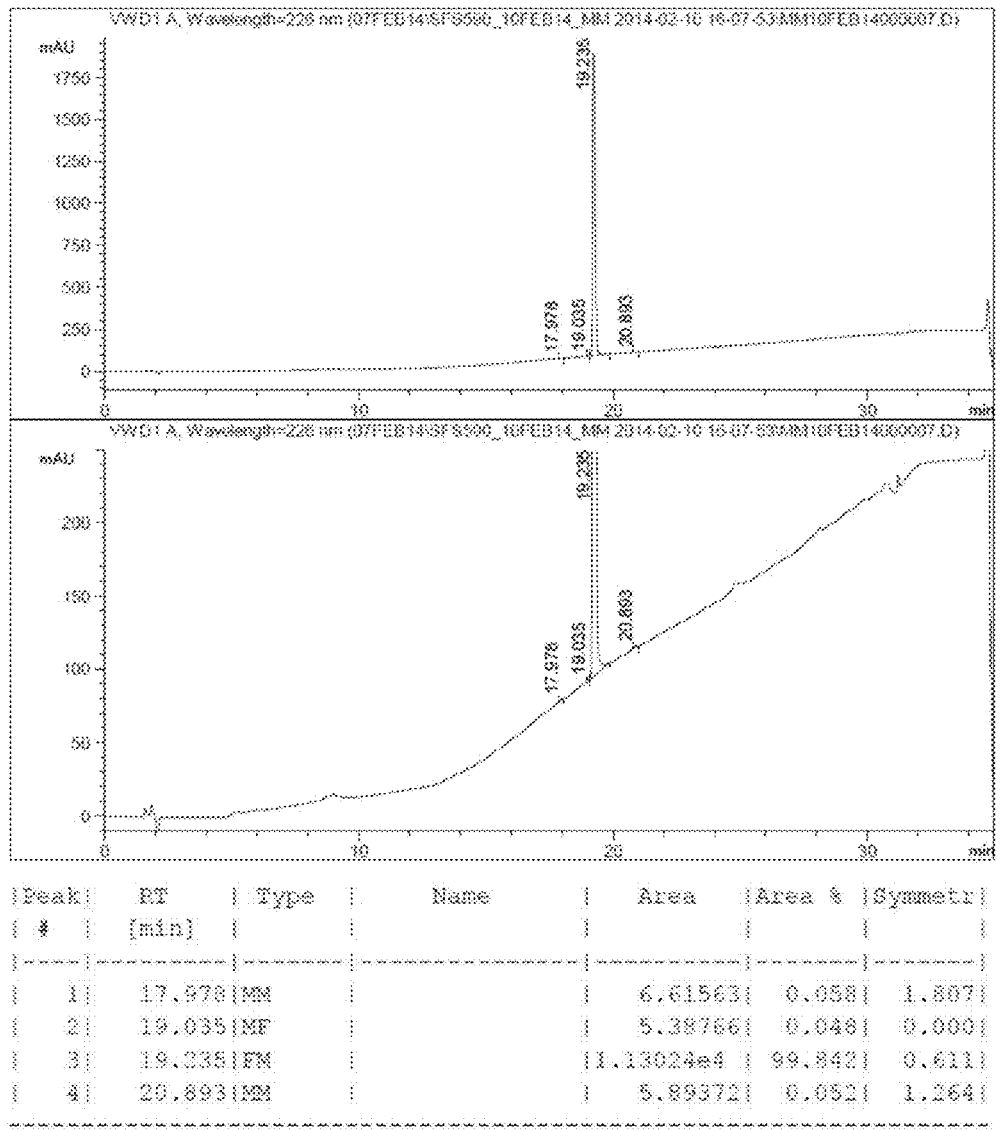
Figure 216:
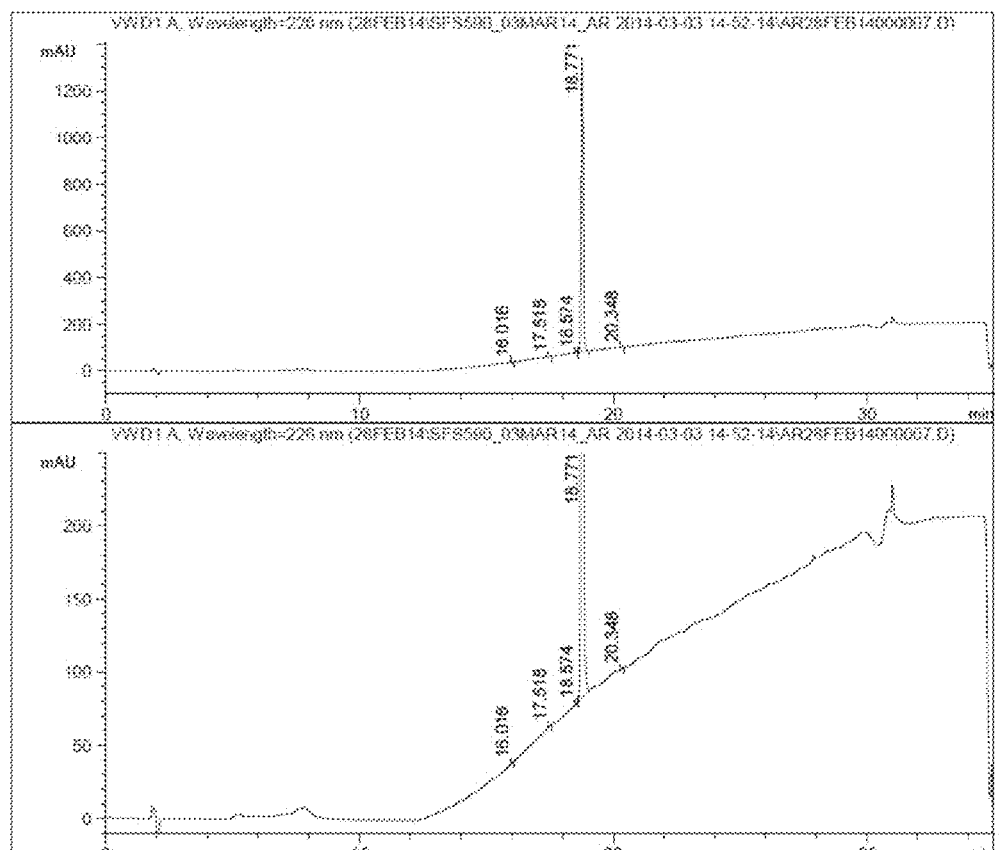

In one embodiment, Form E has an HPLC purity of 99.8% (FIG. 215).

In one embodiment, Form E is characterized by the $^1$H NMR spectrum in FIG. 220.

In one embodiment, Form E can be produced by: adding acetone with 0.89 water activity to the amorphous form of Compound A bis-mesylate salt to form a slurry, stirring the slurry at about 22° C., and filtering and drying the slurry.

In one embodiment, the polymorph of Compound A mesylate is Form F. In some embodiments, Form F has X-ray powder diffraction peaks at approximately 16.7 and 17.0°2θ using Cu Kα radiation. In some embodiments, Form F has X-ray powder diffraction peaks at approximately 16.7, 17.0, 19.5, 20.3, and 24.4°2θ using Cu Kα radiation. In some embodiments, Form F has X-ray powder diffraction peaks at approximately 4.8, 7.2, 15.6, 16.7, 17.0, 19.5, 20.3, 21.7, 24.0, and 24.4°2θ using Cu Kα radiation. In one embodiment, Form F has X-ray powder diffraction peaks as shown in FIG. 247. In one embodiment, Form F has a X-ray powder diffraction pattern substantially similar to that shown in FIG. 245.

In one embodiment, Form F is Compound A bis-mesylate.

In one embodiment, the polymorph of Compound A mesylate is Form G. In some embodiments, Form G has X-ray powder diffraction peaks at approximately 5.8 and 22.1°2θ using Cu Kα radiation. In some embodiments, Form G has X-ray powder diffraction peaks at approximately 5.8, 14.9, 16.3, 22.1, and 23.7°2θ using Cu Kα radiation. In some embodiments, Form G has X-ray powder diffraction peaks at approximately 5.8, 10.8, 14.9, 16.3, 17.7, 22.1, 23.1, 23.7, 24.5, and 26.5°2θ using Cu Kα radiation. In one embodiment, Form G has X-ray powder diffraction peaks as shown in FIG.

250. In one embodiment, Form G has a X-ray powder diffraction pattern substantially similar to that shown in FIG. 248.

In one embodiment, Form G is Compound A bis-mesylate.

In one embodiment, the polymorph of Compound A mesylate is Form H. In some embodiments, Form H has X-ray powder diffraction peaks at approximately 10.9 and 22.8°2θ using Cu Kα radiation. In some embodiments, Form H has X-ray powder diffraction peaks at approximately 6.1, 10.9, 12.4, 15.9, and 22.8°2θ using Cu Kα radiation. In some embodiments, Form H has X-ray powder diffraction peaks at approximately 6.1, 10.1, 10.9, 12.4, 15.7, 15.9, 16.4, 20.4, 20.8, and 22.8°2θ using Cu Kα radiation. In one embodiment, Form H has X-ray powder diffraction peaks as shown in FIG. 253. In one embodiment, Form H has a X-ray powder diffraction pattern substantially similar to that shown in FIG. 251.

In one embodiment, Form H is Compound A bis-mesylate.

In one embodiment, the polymorph of Compound A mesylate is Form I. In some embodiments, Form I has X-ray powder diffraction peaks at approximately 5.2 and 10.5°2θ using Cu Kα radiation. In some embodiments, Form I has X-ray powder diffraction peaks at approximately 5.2, 6.2, 10.5, 20.2, and 23.0°2θ using Cu Kα radiation. In some embodiments, Form I has X-ray powder diffraction peaks at approximately 5.2, 6.2, 10.5, 11.1, 13.6, 20.2, 22.0, 22.3, 23.0, and 23.8°2θ using Cu Kα radiation. In one embodiment, Form I has X-ray powder diffraction peaks as shown in FIG. 256. In one embodiment, Form I has a X-ray powder diffraction pattern substantially similar to that shown in FIG. 254.

In one embodiment, Form I is Compound A bis-mesylate.

Figure 225:
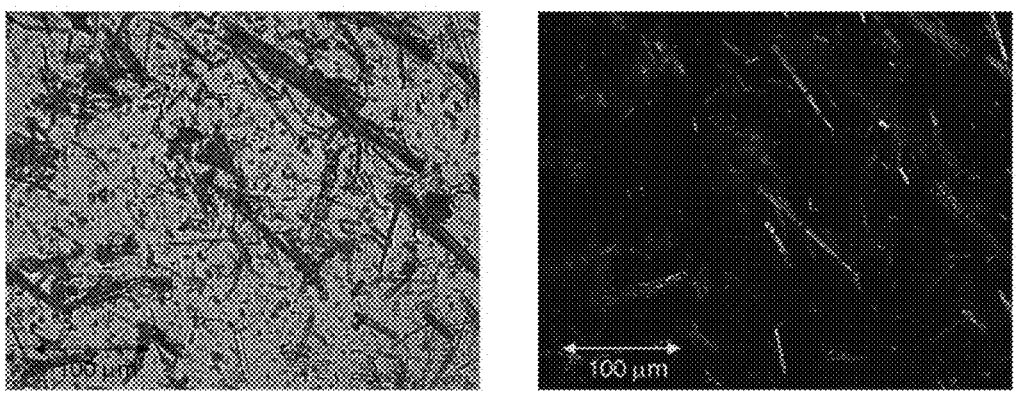

In one embodiment, Form I is birefringent with a rod-like morphology as determined by PLM analysis as shown in FIG. 225.

Figure 227:
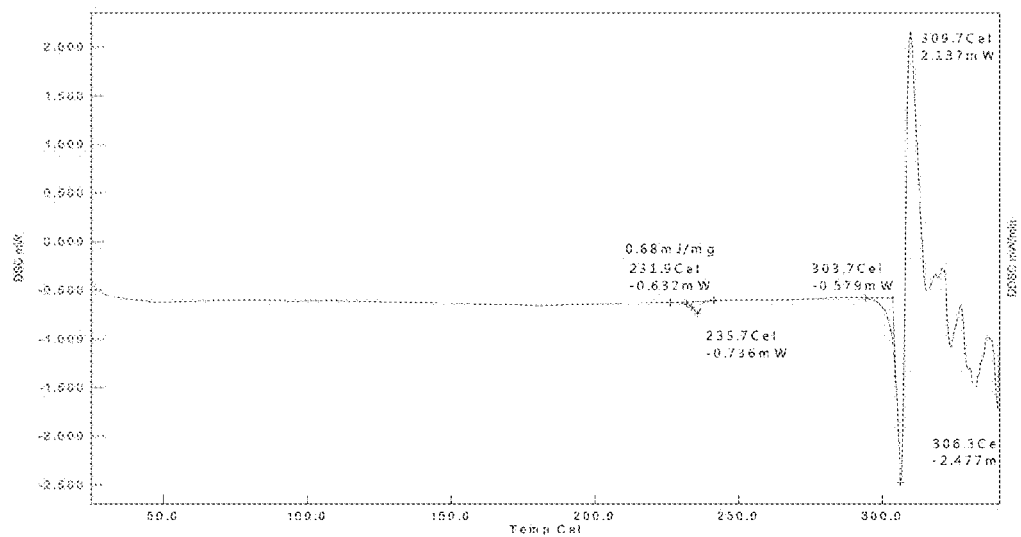

In one embodiment, Form I has a small endothermic event at onset about 231.9° C. (peak 235.7° C.). In one embodiment, Form I has a final endotherm at onset about 303.7° C. (peak 306.3° C.) (FIG. 227).

In one embodiment, Form I has a water content of about 0.8%, as measured by Karl-Fischer Titration.

Figure 231:
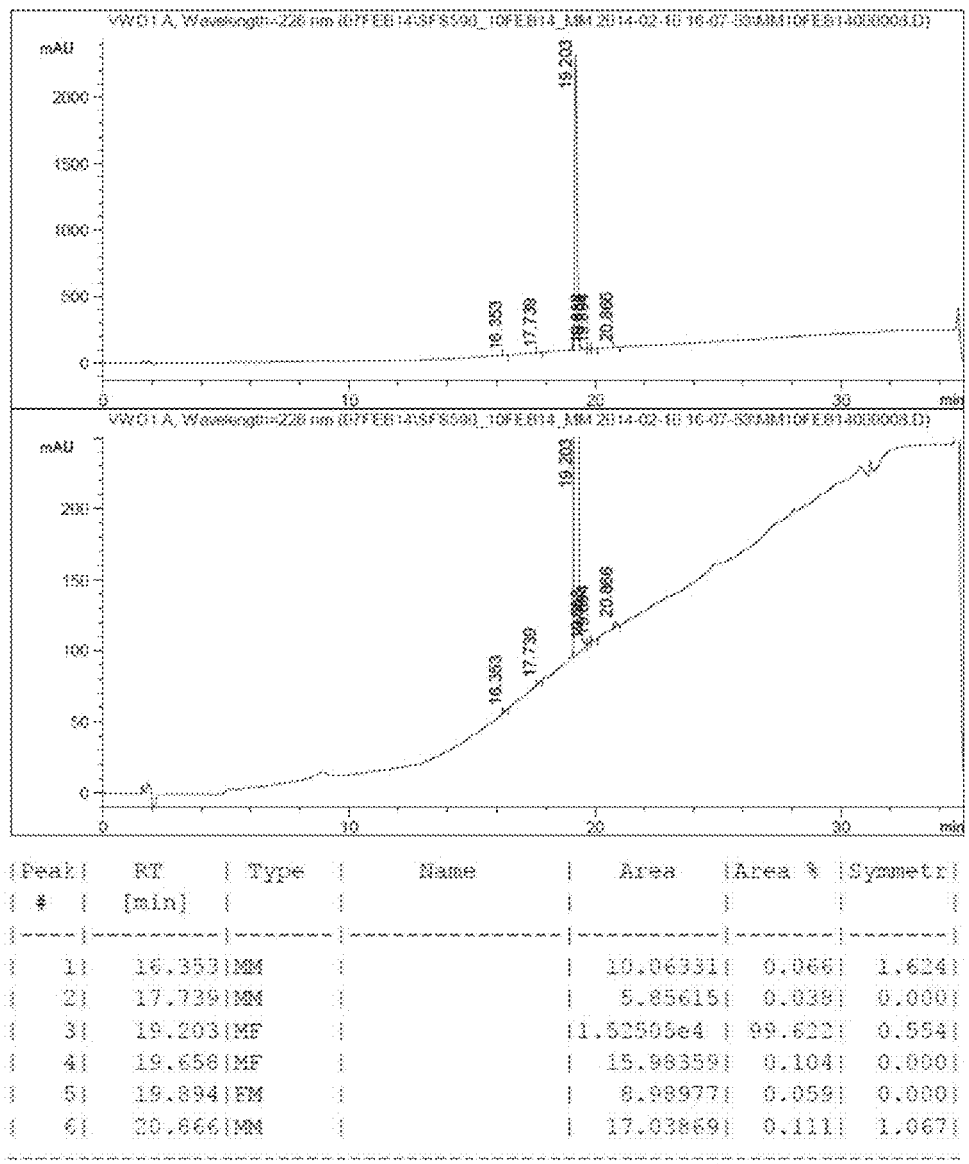
Figure 232:
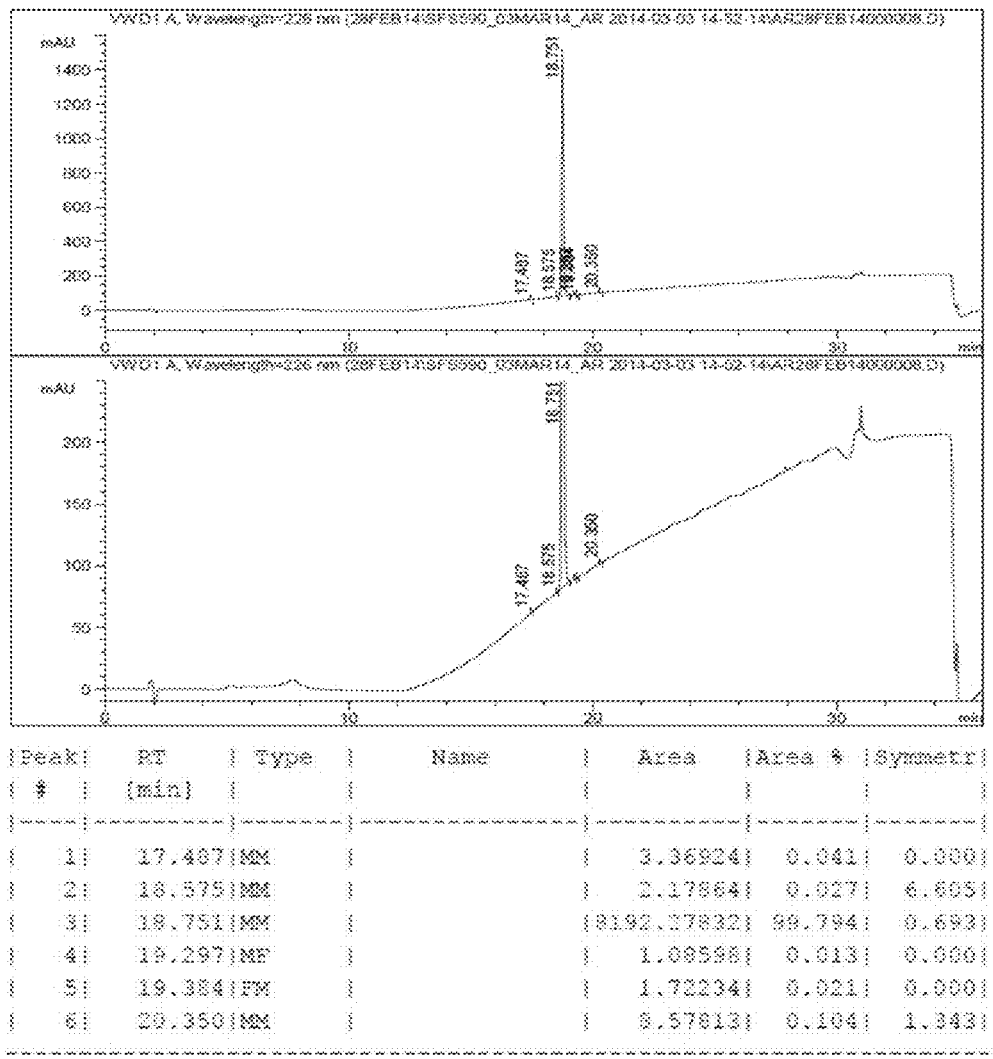

In one embodiment, Form I has an HPLC purity of 99.6% (FIG. 231).

In one embodiment, Form I is characterized by the $^1$H NMR spectrum in FIG. 236.

In one embodiment, Form I can be produced by: dissolving Form A of Compound A bis-mesylate salt in dry methanol. In one embodiment, the solution is evaporated at about 50° C. under vacuum.

In one embodiment, the polymorph of Compound A mesylate is Form J. In some embodiments, Form J has X-ray powder diffraction peaks at approximately 17.0 and 22.8°2θ using Cu Kα radiation. In some embodiments, Form J has X-ray powder diffraction peaks at approximately 14.6, 17.0, 21.9, 22.8, and 24.8°2θ using Cu Kα radiation. In some embodiments, Form J has X-ray powder diffraction peaks at approximately 14.6, 17.0, 19.7, 20.4, 21.9, 22.8, 24.8, 25.3, 26.7, and 27.7°2θ using Cu Kα radiation. In one embodiment, Form J has X-ray powder diffraction peaks as shown in FIG. 259. In one embodiment, Form J has a X-ray powder diffraction pattern substantially similar to that shown in FIG. 257.

In one embodiment, Form J is Compound A bis-mesylate.

In one embodiment, the polymorph of Compound A mesylate is Form K. In some embodiments, Form K has X-ray powder diffraction peaks at approximately 9.2 and 10.0°2θ using Cu Kα radiation. In some embodiments, Form K has X-ray powder diffraction peaks at approximately 9.2, 10.0, 15.7, 20.0, and 23.8°2θ using Cu Kα radiation. In some embodiments, Form K has X-ray powder diffraction peaks at approximately 4.1, 9.2, 10.0, 15.7, 17.5, 19.3, 20.0, 21.5, 23.2, and 23.8°2θ using Cu Kα radiation. In one embodiment, Form K has X-ray powder diffraction peaks as shown in FIG. 262. In one embodiment, Form K has a X-ray powder diffraction pattern substantially similar to that shown in FIG. 260.

In one embodiment, Form K is Compound A bis-mesylate.

All forms of the compounds (e.g., free base and salts, and amorphous forms, crystalline forms, polymorphs, and mesomorphs thereof) of the instant application are contemplated, either in admixture or in pure or substantially pure form, including racemic mixtures and mixtures of individual isomers. The racemic forms can be resolved by physical methods, such as, for example, separation or crystallization of diastereomeric derivatives, or separation by chiral column chromatography or by supercritical fluid chromatography. The individual optical isomers can be obtained from the racemates by conventional methods, such as, for example, salt formation with an optically active acid or base followed by crystallization. In addition, a crystal polymorphism may be present but is not limiting, and may be any a single crystal form or a crystal form mixture, or an anhydrous or solvated (e.g., DCM solvated, MEK solvated, THF solvated, and hydrated) crystal form.

The terms "crystalline polymorphs", "crystal polymorphs", "crystal forms", "polymorphs", or "polymorphic forms" means crystal structures in which a compound (e.g., free base, salts, or solvates thereof) can crystallize in different crystal packing arrangements, all of which have the same elemental composition. Different crystal forms usually have different X-ray diffraction patterns, infrared spectra, melting points, density, crystal shape, optical and electrical properties, stability and solubility. Crystallization solvent, rate of crystallization, storage temperature, and other factors may cause one crystal form to dominate. Crystal polymorphs of the compounds can be prepared by crystallization under different conditions.

Additionally, the compounds (e.g., free base and salts, and amorphous forms, crystalline forms, polymorphs, and mesomorphs thereof) of the present application, can exist in either hydrated or unhydrated (the anhydrous) form or as solvates with other solvent molecules or in an unsolvated form. Non-limiting examples of hydrates include monohydrates, dihydrates, etc. Nonlimiting examples of solvates include DCM solvates, MEK solvates, THF solvates, etc.

Some of the compounds (e.g., free base and salts, and amorphous forms, crystalline forms, polymorphs, and mesomorphs thereof) of the present application can exist in several tautomeric forms, and such tautomeric forms are included within the scope of the present application. "Tautomers" refers to compounds whose structures differ markedly in arrangement of atoms, but which exist in easy and rapid equilibrium. Tautomers may exist as mixtures of a tautomeric set in solution. In solid form, usually one tautomer predominates. It is to be understood that the compounds of the application may be depicted as different tautomers. It should also be understood that when compounds have tautomeric forms, all tautomeric forms are intended to be within the scope of the application, and the naming of the compounds does not exclude any tautomeric form. Even though one tautomer may be described, the present application includes all tautomers of the present compounds As used herein, the term "salt" is a pharmaceutically acceptable salt and can include acid addition salts including hydrochlorides, hydrobromides, phosphates, sulphates, hydrogen sulphates, alkylsulphonates, arylsulphonates, acetates, benzoates, citrates, maleates, fumarates, succinates, lactates, tartrates, mesylate, amino acid salt (e.g., L-glutamic acid salt), galactaric acid (mucic acid) salt, citric acid salt, glucuronic acid salt, hippuric acid salt, gluconic acid salt, and ascorbic acid salt; alkali metal cations such as Na$^+$, K$^+$, Li$^+$, alkali earth metal salts such as Mg$^{2+}$ or Ca$^{2+}$; and organic amine salts.

As used herein, the terms, "polymorphs", "polymorphic forms", "crystalline polymorphs", "crystal polymorphs" and "crystal forms" and related terms herein refer to crystalline forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in bioavailability). Differences in stability can also result from changes in chemical reactivity (e.g., differential oxidation, such that a dosage form discolors more rapidly when comprised of one polymorph than when comprised of another polymorph) or mechanical property (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph might be more likely to form solvates or might be difficult to filter and wash free of impurities (e.g., particle shape and size distribution might be different between polymorphs).

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion, and sublimation.

Techniques for characterizing polymorphs include, but are not limited to, differential scanning calorimetry (DSC), X-ray powder diffractometry (XRPD), single crystal X-ray diffractometry, vibrational spectroscopy (e.g., IR and Raman spectroscopy), TGA, DTA, DVS, solid state NMR, hot stage optical microscopy, scanning electron microscopy (SEM), electron crystallography and quantitative analysis, particle size analysis (PSA), surface area analysis, solubility studies, and dissolution studies.

As used herein, the term "amorphous form" refers to a noncrystalline solid state form of a substance.

As used herein, the term "mesomorph", "mesomorphous forms", or "mesomorphic forms" and related terms herein refer to substances that exist in states between a liquid state and a solid state (e.g., liquid crystal). In a mesomorphic form, the same molecules of the substance may be oriented in an organized way (e.g., crystalline), and the substance may flow like a liquid. Different types of mesomorphs exhibit distinct properties (e.g., optical properties (e.g., birefringence)) and may be distinguished by polarized light. Mesomorphs may or may not be identified by distinct XRPD peaks.

As used herein, the term "solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H$_2$O, such combination being able to form one or more hydrate. For example, the solvate may be a dichloromethane (DCM) solvate, a methyl ethyl ketone (MEK solvate), or a tetrahydrofuran (THF) solvate.

As used herein, the terms "unsolvated" or "desolvated" refer to a solid state form (e.g., crystalline forms, amorphous forms, and mesomorphs) of a substance which does not contain solvent.

As used herein, the term "pure" means about 90-100%, preferably 95-100%, more preferably 98-100% (wt./wt.), or 99-100% (wt./wt.) pure compound; e.g., less than about 10%, less than about 5%, less than about 2%, or less than about 1% impurity is present. Such impurities include, e.g., degradation products, oxidized products, solvents, and/or other undesirable impurities.

As used herein, a compound is "stable" where significant amounts of degradation products are not observed under constant conditions of humidity (e.g., 10%, 20%, 30%, 40%, 50%, 60%, 70%, 75%, 80%, 85%, 90%, and 95% RH), light exposure and temperatures (e.g., higher than 0° C., e.g., 20° C., 25° C., 30° C., 35° C., 40° C., 45° C., 50° C., 55° C., 60° C., 65° C., and 70° C.) over a certain period (e.g., one week, two weeks, three weeks, and four weeks). A compound is not considered to be stable at a certain condition when degradation impurities appear or an area percentage (e.g., AUC as characterized by HPLC) of existing impurities begins to grow. The amount of degradation growth as a function of time is important in determining compound stability.

As used herein, the term "mixing" means combining, blending, stirring, shaking, swirling, or agitating. The term "stirring" means mixing, shaking, agitating, or swirling. The term "agitating" means mixing, shaking, stirring, or swirling.

Unless explicitly indicated otherwise, the terms "approximately" and "about" are synonymous. In one embodiment, "approximately" and "about" refer to recited amount, value, or duration ±20%, ±15%, ±10%, ±8%, ±6%, ±5%, ±4%, ±2%, ±1%, or ±0.5%. In another embodiment, "approximately" and "about" refer to listed amount, value, or duration ±10%, ±8%, ±6%, ±5%, ±4%, or ±2%. In yet another embodiment, "approximately" and "about" refer to listed amount, value, or duration ±5%.

When the terms "approximately" and "about" are used when reciting XRPD peaks, these terms refer to the recited X-ray powder diffraction peak ±0.3°2θ, ±0.2°2θ, or ±0.1°2θ. In another embodiment, the terms "approximately" and "about" refer to the listed X-ray powder diffraction peak ±0.2°2θ. In another embodiment, the terms "approximately" and "about" refer to the listed X-ray powder diffraction peak ±0.1°2θ.

When the terms "approximately" and "about" are used when reciting temperature or temperature range, these terms refer to the recited temperature or temperature range ±5° C., ±2° C., or ±1° C. In another embodiment, the terms "approximately" and "about" refer to the recited temperature or temperature range ±2° C.

The compounds (e.g., free base and salts, and amorphous forms, crystalline forms, polymorphs, and mesomorphs thereof) of the present application can also be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) the compounds of the present application can be delivered in prodrug form. Thus, the present application is intended to cover prodrugs of the presently claimed compounds, methods of delivering the same and compositions containing the same. The term "prodrug" includes a compound of the present application covalently linked to one or more pro-moieties, such as an amino acid moiety or other water-solubilizing moiety. A compound of the present application may be released from the pro-moiety via hydrolytic, oxidative, and/or enzymatic release mechanisms. In an embodiment, a prodrug composition of the present application exhibits the added benefit of increased aqueous solubility, improved stability, and improved pharmacokinetic profiles. The pro-moiety may be selected to obtain desired prodrug characteristics. For example, the pro-moiety, e.g., an amino acid moiety or other water solubilizing moiety such as phosphate may be selected based on solubility, stability, bioavailability, and/or in vivo delivery or uptake. The term "prodrug" is also intended to include any covalently bonded carriers that release an active parent drug of the present application in vivo when such prodrug is administered to a subject. Prodrugs in the present application are prepared by modifying functional groups present in the compound in such a way that the modifications are cleaved, either in routine manipulation or in vivo, to the parent compound. Prodrugs include compounds of the present application wherein a hydroxyl, amino, sulfhydryl, carboxyl, or carbonyl group is bonded to any group that, may be cleaved in vivo to form a free hydroxyl, free amino, free sulfhydryl, free carboxyl or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxyl functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Pro-drugs" p 1-92, Elesevier, New York-Oxford (1985).

Synthesis of Compound A

Standard synthetic methods and procedures for the preparation of organic molecules and functional group transformations and manipulations, including the use of protective groups, can be obtained from the relevant scientific literature or from standard reference textbooks in the field. Although not limited to any one or several sources, recognized reference textbooks of organic synthesis include: Smith, M. B.; March, J. March's Advanced Organic Chemistry: Reactions, Mechanisms, and Structure, $5^{th}$ ed.; John Wiley & Sons: New York, 2001; and Greene, T. W.; Wuts, P. G. M. Protective Groups in Organic Synthesis, $3^{rh}$; John Wiley & Sons: New York, 1999.

Methods for preparing Compound A is described in US Patent Application Publication No. 20110172203, the entire contents of which are incorporated herein by reference.

Methods of Treatment

The present application provides methods for the treatment of a cell proliferative disorder in a subject in need thereof by administering to a subject in need of such treatment, a therapeutically effective amount of a compound (e.g., free base and salts, and amorphous forms, crystalline forms, polymorphs, and mesomorphs thereof) of the present application, or a pharmaceutically acceptable prodrug or metabolite thereof. The cell proliferative disorder can be cancer or a precancerous condition. The present application further provides the use of a compound of the present application, or a pharmaceutically acceptable prodrug or metabolite thereof, for the preparation of a medicament useful for the treatment of a cell proliferative disorder.

The present application also provides methods of protecting against a cell proliferative disorder in a subject in need thereof by administering a therapeutically effective amount of compound of the present application, or a pharmaceutically acceptable prodrug or metabolite thereof, to a subject in need of such treatment. The cell proliferative disorder can be cancer or a precancerous condition. The present application also provides the use of compound of the present application, or a pharmaceutically acceptable prodrug or metabolite thereof, for the preparation of a medicament useful for the prevention of a cell proliferative disorder.

As used herein, a "subject in need thereof" is a subject having a cell proliferative disorder, or a subject having an increased risk of developing a cell proliferative disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the application encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

As used herein, "treating" or "treat" describes the management and care of a patient for the purpose of combating a disease, condition, or disorder and includes the administration of a compound of the present application, or a pharmaceutically acceptable prodrug or metabolite thereof, to alleviate the symptoms or complications of a disease, condition or disorder, or to eliminate the disease, condition or disorder.

A compound of the present application, or a pharmaceutically acceptable prodrug or metabolite thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the application leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

Treating cancer can result in a reduction in size of a tumor. A reduction in size of a tumor may also be referred to as "tumor regression". Treating cancer can result in a reduction in tumor volume. Treating cancer results in a decrease in number of tumors. Treating cancer can result in a decrease in number of metastatic lesions in other tissues or organs distant from the primary tumor site. Treating cancer can result in an increase in average survival time of a population of treated subjects in comparison to a population receiving carrier alone. Treating cancer can result in an increase in average survival time of a population of treated subjects in comparison to a population of untreated subjects. Treating cancer can result in increase in average survival time of a population of treated subjects in comparison to a population receiving monotherapy with a drug that is not a compound of the present application, or a pharmaceutically acceptable salt, prodrug, metabolite, analog or derivative thereof. Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present application, or a pharmaceutically acceptable salt, prodrug, metabolite, analog or derivative thereof. Treating cancer can result in a decrease in tumor growth rate. Treating cancer can result in a decrease in tumor regrowth. Treating or preventing a cell proliferative disorder can result in a reduction in the rate of cellular proliferation. Treating or preventing a cell proliferative disorder can result in a reduction in the proportion of proliferating cells. Treating or preventing a cell proliferative disorder can result in a decrease in size of an area or zone of cellular proliferation. Treating or preventing a cell proliferative disorder can result in a decrease in the number or proportion of cells having an abnormal appearance or morphology.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present application, or a pharmaceutically acceptable prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present application, or a pharmaceutically acceptable prodrug or metabolite thereof, is more effective than combination therapy in inducing a desired biological effect.

As used herein, "combination therapy" or "co-therapy" includes the administration of a compound of the present application, or a pharmaceutically acceptable prodrug, metabolite, analog or derivative thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present application.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present application, or a pharmaceutically acceptable prodrug, metabolite, analog or derivative thereof, may be administered in combination with a second chemotherapeutic agent. The second chemotherapeutic agent (also referred to as an anti-neoplastic agent or anti-proliferative agent) can be an alkylating agent; an antibiotic; an antimetabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent.

Pharmaceutical Compositions

The present application also provides pharmaceutical compositions comprising salts of Compound A, solid state forms of Compound A free base or of salts of Compound A, amorphous forms of Compound A free base or of salts of Compound A, crystalline forms of Compound A free base or of salts of Compound A, polymorphs of Compound A free base or of salts of Compound A, and/or mesomorphs of Compound A free base or of salts of Compound A.

A "pharmaceutical composition" is a formulation containing the free base, salts and/or solid state forms thereof of the present application in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed free base, salts, and solid state forms thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, the active ingredient is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio0.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the application is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A pharmaceutical composition of the application can be administered to a subject in many of the well-known methods currently used for chemotherapeutic treatment. For example, for treatment of cancers, a compound of the application may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active ingredient or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing free base, salts, and/or solid state forms thereof of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active ingredient into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active ingredient can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the active ingredient is delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active ingredient is formulated into ointments, salves, gels, or creams as generally known in the art.

The active ingredient can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active ingredient calculated to produce the desired therapeutic effect in association with the required pharmaceutical carrier. The specification for the dosage unit forms of the application are dictated by and directly dependent on the unique characteristics of the active ingredient and the particular therapeutic effect to be achieved.

In therapeutic applications, the dosages of the pharmaceutical compositions used in accordance with the application vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active ingredient to produce the desired biological effect in a subject or cell.

The pharmaceutical compositions can be included in a container, pack, or dispenser together with instructions for administration.

The compounds of the present application are capable of further forming salts. All of these forms are also contemplated within the scope of the claimed application.

As used herein, "pharmaceutically acceptable salts" refer to derivatives of the compounds of the present application wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present application also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present application can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compounds of the present application can also be prepared as prodrugs, for example, pharmaceutically acceptable prodrugs. The terms "pro-drug" and "prodrug" are used interchangeably herein and refer to any compound which releases an active parent drug in vivo.

Since prodrugs are known to enhance numerous desirable qualities of pharmaceuticals (e.g., solubility, bioavailability, manufacturing, etc.), the compounds of the present application can be delivered in prodrug form. Thus, the present application is intended to cover prodrugs of the presently claimed compounds, methods of delivering the same and compositions containing the same. "Prodrugs" are intended to include any covalently bonded carriers that release an active parent drug of the present application in vivo when such prodrug is administered to a subject.

Prodrugs in the present application are prepared by modifying functional groups present in the compound in such a way that the modifications are cleaved, either in routine manipulation or in vivo, to the parent compound. Prodrugs include compounds of the present application wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the application, and the like, See Bundegaard, H., Design of Prodrugs, p 1-92, Elesevier, New York-Oxford (1985).

The pharmaceutical composition of the present application, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the application can be found in Remington: the Science and Practice of Pharmacy, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present application are apparent from the different examples. The provided examples illustrate different components and methodology useful in practicing the present application. The examples do not limit the claimed application. Based on the present disclosure the skilled artisan can identify and employ other components and methodology useful for practicing the present application.

EXAMPLES

Example 1

X-Ray Powder Diffraction (XRPD)

1.1. Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consisted of a single Gael multilayer mirror coupled with a pinhole collimator of 0.3 mm. A weekly performance check was carried out using a certified standard NIST 1976 Corundum (flat plate).

The beam divergence, i.e., the effective size of the X-ray beam on the sample, was approximately 4 mm. A θ-θ continuous scan mode was employed with a sample—detector distance of 20 cm which gave an effective 2θ range of 3.2°-29.7°. Typically the sample was exposed to the X-ray beam for 120 seconds. The software used for data collection was GADDS for WNT 4.1.16 and the data were analysed and presented using Diffrac Plus EVA v11.0.0.2 or v13.0.0.2.

Ambient Conditions

Samples run under ambient conditions were prepared as flat plate specimens using powder as received without grinding. Approximately 1-2 mg of the sample was lightly pressed on a glass slide to obtain a flat surface.

Non-Ambient Condition

Samples run under non-ambient conditions were mounted on a silicon wafer with heat-conducting compound. The sample was then heated to the appropriate temperature at 10° C./min and subsequently held isothermally for 1 minute before data collection was initiated.

1.2. Bruker AXS D8 Advance

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument was performance checked using a certified Corundum standard (NIST 1976). The software used for data collection was Diffrac Plus XRD Commander v2.5.0 and the data were analysed and presented using Diffrac Plus EVA v11.0.0.2 or v13.0.0.2. Samples were run under ambient conditions as flat plate specimens using powder as received The sample was gently packed into a cavity cut into polished, zero-background (510) silicon wafer. The sample was rotated in its own plane during analysis. The details of the data collection are:

Angular range: 2 to 42°2θ
Step size: 0.05°2θ
Collection time: 0.5 s/step 1.3. Bruker AXS D8 Advance Variable temperature XRPD analysis was carried out on a Bruker D8 ADVANCE in capillary mode, using an Oxford Cryosystems Cryostream at 23, 115, 150 and 200° C. Samples were scanned between 3.0 and 50.0°2-theta. The material was prepared in a capillary sample holder. The sample was then loaded into a Bruker D8 ADVANCE diffractometer and analyzed, using the following experimental conditions:

| | |
|---|---|
| Start Position [° 2Th.] | 3.0000 |
| End Position [° 2Th.] | 50.0000 |
| Step Size [° 2Th.] | 0.0500 |
| Scan Step Time [s] | 4 |
| Diffractometer Type | Bruker D8 ADVANCE |

1.4. Siemens D5000

XRPD analysis was carried out on a Siemens D5000, scanning the samples between 3.0 and 30.0 (or 50.0 for characterization of received material) ° 2-theta. The material was gently compressed on a glass disc inserted into a sample holder. The sample was then loaded into a Siemens D5000 diffractometer running in reflection mode and analyzed, using the following experimental conditions.

| | |
|---|---|
| Raw Data Origin | Siemens-binary V2 (.RAW) |
| Start Position [° 2Th.] | 3.0000 |
| End Position [° 2Th.] | 30.0000 or 50.0000 |
| Step Size [° 2Th.] | 0.0200 |
| Scan Step Time [s] | 1 |
| Scan Type | Continuous |
| Slit Types | Fixed |
| Divergence Slit Size [mm] | 2.0000 |
| Specimen Length [mm] | various |
| Receiving Slit Size [mm] | 2.0000 |
| Detector Slit Size [mm] | 0.2000 |
| Measurement Temperature [° C.] | 20.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 (nominal) |
| Generator Settings | 40 mA, 40 kV |
| Diffractometer Type | Siemens D5000 |
| Focussing Circle Diameter [mm] | 401.00 |
| Diffracted Beam Monochromator | Graphite |
| Spinning | No |

Example 2

$^1$H NMR

NMR spectra were collected on a Bruker 400 MHz instrument equipped with an autosampler and controlled by a DRX400 console. Automated experiments were acquired using ICON-NMR v4.0.4 running with Topspin v1.3 using the standard Bruker loaded experiments. For non-routine spectroscopy, data were acquired through the use of Topspin alone. Samples were prepared in DMSO-$d_6$, unless otherwise stated. Off-line analysis was carried out using ACD SpecManager v12.00.

$^1$H-NMR spectroscopic experiments were performed on a Bruker AV400 (frequency: 400 MHz). Experiments were performed in deuterium oxide and each sample was prepared to about 10 mM concentration.

Example 3

Differential Scanning Calorimetry (DSC)

3.1. Mettler DSC 823e

DSC data were collected on a Mettler DSC 823e equipped with a 34 position auto-sampler. The instrument was calibrated for energy and temperature using certified indium. Typically 0.5-3 mg of each sample, in a pin-holed aluminum pan, was heated at 10° C./min from 25° C. to 300° C. A nitrogen purge at 50 ml/min was maintained over the sample. The instrument control and data analysis software was STARe v9.20.

3.1. Seiko DSC6200

Approximately 5 mg of material was weighed into an aluminum DSC pan and sealed non-hermetically with a pierced aluminium lid. The sample pan was then loaded into a Seiko DSC6200 instrument (equipped with a cooler) and held at 25° C. Once a stable heat-flow response was obtained, the sample and reference were heated to about 360° C. at a scan rate of 10° C./min, and the resulting heat flow response monitored.

Example 4

Thermo-Gravimetric Analysis (TGA)

TGA data were collected on a Mettler TGA/SDTA 851e equipped with a 34 position autosampler. The instrument was temperature calibrated using certified indium. Typically 5-30 mg of each sample was loaded onto a pre-weighed aluminum crucible and was heated at 10° C./min from ambient temperature to 350° C. A nitrogen purge at 50 ml/min was maintained over the sample. The instrument control and data analysis software was STARe v9.20.

Approximately 5 mg of material was weighed into an open aluminium pan and loaded into a simultaneous thermogravimetric/differential thermal analyser (TG/DTA) and held at room temperature. The sample was then heated at a rate of 10° C./min from 25° C. to 300° C. during which time the change in sample weight was recorded along with any differential thermal events (DTA). Nitrogen was used as the purge gas, at a flow rate of 100 cm$^3$/min.

Example 5

Polarized Light Microscopy (PLM)

5.1. Leica LM/DM

Samples were studied on a Leica LM/DM polarized light microscope with a digital video camera for image capture. A small amount of each sample was placed on a glass slide, mounted in immersion oil and covered with a glass slip, the individual particles being separated as well as possible. The sample was viewed with appropriate magnification and partially polarized light, coupled to a λ false-color filter.

5.1. Olympus BX50

The presence of birefringence was determined using an Olympus BX50 polarising microscope, equipped with a Motic camera and image capture software (Motic Images Plus 2.0). All images were recorded using a 20× objective, unless otherwise stated.

Example 6

Chemical Purity Determination by HPLC

Purity analysis was performed on an Agilent HP1100 series system equipped with a diode array detector and using ChemStation software vB.02.01-SR1 using the method detailed below:

TABLE 1

HPLC Method Parameters for Chemical Purity Determination

| | |
|---|---|
| Sample Preparation | 1 mg/ml in acetonitrile:water 1:1 |
| Column | Supelco Ascentis Express C18, 100 × 4.6 mm, 2.7 μm |
| Column Temperature (° C.) | 25 |
| Injection (μl) | 2 |
| Detection (Wavelength, Bandwidth) (nm) | 255, 90 nm |
| Flow Rate (ml/min) | 2.0 |
| Phase A | 0.1% TFA in water |
| Phase B | 0.085% TFA in acetonitrile |

| Timetable | Time (min) | % Phase A | % Phase B |
|---|---|---|---|
| | 0 | 95 | 5 |
| | 6 | 5 | 95 |
| | 6.2 | 95 | 5 |
| | 8 | 95 | 5 |

Example 7

Gravimetric Vapor Sorption (GVS)

7.1. SMS DVS Intrinsic

Sorption isotherms were obtained using a SMS DVS Intrinsic moisture sorption analyzer, controlled by DVS Intrinsic Control software v1.0.0.30. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg).

Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (4 scans giving 2 complete cycles). The standard isotherm was performed at 25° C. at 10% RH intervals over a 0-90% RH range. Data analysis was undertaken in Microsoft Excel using DVS Analysis Suite v6.0.0.7.

TABLE 2

Method Parameters for SMS DVS Intrinsic Experiments

| Parameters | Values |
|---|---|
| Adsorption - Scan 1 | 40-90 |
| Desorption/Adsorption - Scan 2 | 90-0, 0-40 |
| Intervals (% RH) | 10 |
| Number of Scans | 4 |
| Flow Rate (ml/min) | 200 |
| Temperature (° C.) | 25 |
| Stability (° C./min) | 0.2 |
| Sorption Time (hours) | 6 hour time out |

The sample was recovered after completion of the isotherm and re-analysed by XRPD.

7.2. Dynamic Vapour Sorption (DVS)

Approximately 10 mg of sample was placed into a mesh vapour sorption balance pan and loaded into a DVS-1 dynamic vapour sorption balance by Surface Measurement Systems. The sample was subjected to a ramping profile of 0-90%, 90-0% relative humidity (RH) at 10% increments for anhydrous samples and 30-90%, 90-0%, 0-90%, 90-0% for hydrated samples, maintaining the sample at each step until a stable weight had been achieved (99.5% step completion). The weight changes during the sorption/desorption cycles were plotted, allowing the hygroscopic nature of the sample to be determined.

Example 8

Water Determination by Karl Fischer Titration (KF)

8.1. Mettler Toledo DL39 Coulometer

The water content of each sample was measured on a Mettler Toledo DL39 Coulometer using Hydranal Coulomat AG reagent and an argon purge. Weighed solid samples were dissolved in a solvent and a volume introduced into the vessel equivalent to approx 10 mg of sample per titration. Duplicate determinations were made.

8.2. Mettler Toledo C30 Compact Titrator

Initially, a blank sample containing only methanol was analysed by KF (Mettler Toledo C30 Compact Titrator) to determine the blank water content before sample analysis. Approximately 10-15 mg of solid material was accurately weighed into a vial. The material was then dissolved in methanol and the amount added was recorded. The resultant solution was then manually introduced into the titration cell of a Mettler Toledo C30 Compact Titrator. The water content was calculated as a percentage and the data printed.

Example 9

Thermodynamic Aqueous Solubility 9.1. Solubility

Aqueous solubility was determined by suspending sufficient compound in water to give a maximum final concentration of ≥10 mg/ml of the parent free-form of the compound. The suspension was equilibrated at 25° C. for 24 hours then the pH was measured. The suspension was then filtered through a glass fiber C filter. The filtrate was then diluted by an appropriate factor e.g., 101. Quantitation was by HPLC with reference to a standard solution of approximately 0.25 mg/ml in DMSO. Different volumes of the standard, diluted and undiluted sample solutions were injected. The solubility was calculated using the peak areas determined by integration of the peak found at the same retention time as the principal peak in the standard injection.

TABLE 3

HPLC Method Parameters for Solubility Measurements

| | |
|---|---|
| Type of Method | Reverse phase with gradient elution |
| Column | Phenomenex Luna, C18 (2) 5 μm 100 × 4.6 mm |
| Column Temperature (° C.) | 25 |
| Standard Injections (μl) | 1, 2, 3, 5, 7, 10 |
| Test Injections (μl) | 1, 2, 3, 10, 20, 50 |
| Detection (Wavelength, Bandwidth) (nm) | 260, 80 |
| Flow Rate (ml/min) | 2 |
| Phase A | 0.1% TFA in water |
| Phase B | 0.085% TFA in acetonitrile |

| Timetable | Time (min) | % Phase A | % Phase B |
|---|---|---|---|
| | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Analysis was performed on an Agilent HP1100 series system equipped with a diode array detector and using ChemStation software vB.02.01-SR1.

9.2. High Performance Liquid Chromatography-Ultraviolet Detection (HPLC-UV)

Purity and concentration analyses were carried out using the following method:

Instrument Parameters:

Column: Waters Xbridge Shield RP18, 4.6×150 mm, 3.5 µm, Pan Number 186003045

Column Temperature: 25° C.

Autosampler Temperature: 5° C.

Detection: 226 nm

Mobile Phase A: 95:5:0.1% Water:Methanol:TFA

Mobile Phase B: 95:5:0.1% Methanol:Water:TFA

Gradient: See table below for conditions

Flow Rate: 1.0 mL/minute

Injection Volume: 10 µl

Analysis Time: 36 minutes

Re-equilibration Time: 4 minutes

Data Collection time: 36 minutes

Needle Wash: 100% Methanol

Gradient Conditions

| Time (minutes) | % A | % B |
| --- | --- | --- |
| 0.0 | 100 | 0 |
| 2.0 | 100 | 0 |
| 28.0 | 0 | 100 |
| 32.0 | 0 | 100 |
| 32.1 | 100 | 0 |
| 36.0 | 100 | 0 |

Example 10

Ion Chromatography (IC)

Data were collected on a Metrohm 761 Compact IC (for cations)/a Metrohm 861 Advanced Compact IC (for anions) using IC Net software v2.3. Accurately weighed samples were prepared as stock solutions in an appropriate dissolving solution and diluted appropriately prior to testing. Quantification was achieved by comparison with standard solutions of known concentration of the ion being analysed.

TABLE 4

IC Method Parameters for Anion Chromatography

| Type of Method | Anion exchange |
| --- | --- |
| Column | Metrosep A Supp 5-250 (4.0 × 250 mm) |
| Column Temperature (° C.) | Ambient |
| Injection (µl) | 20 |
| Detection | Conductivity detector |
| Flow Rate (ml/min) | 0.7 |
| Eluent | 3.2 mM sodium carbonate |
|  | 1.0 mM sodium hydrogen carbonate in 5% aqueous acetone |

Example 11

Hot Stage Microscopy

Samples were analyzed by Polarised Light Microscopy (PLM) with a 10× magnification lens using hot stage apparatus. The temperature was ramped at 10° C./min from 25° C. to 325° C.

Example 12

Polymorphs of Compound a Free Base

Multiple polymorphs were prepared for Compound A free base.

Figure 1:
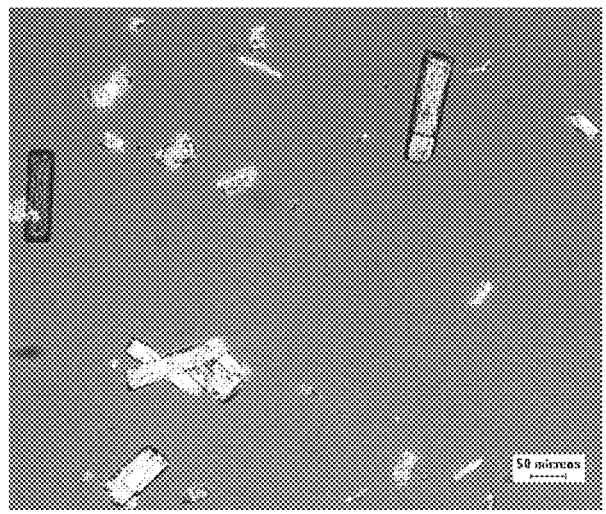
FIG. 1: Images of crystals of Compound A free base
Figure 6:
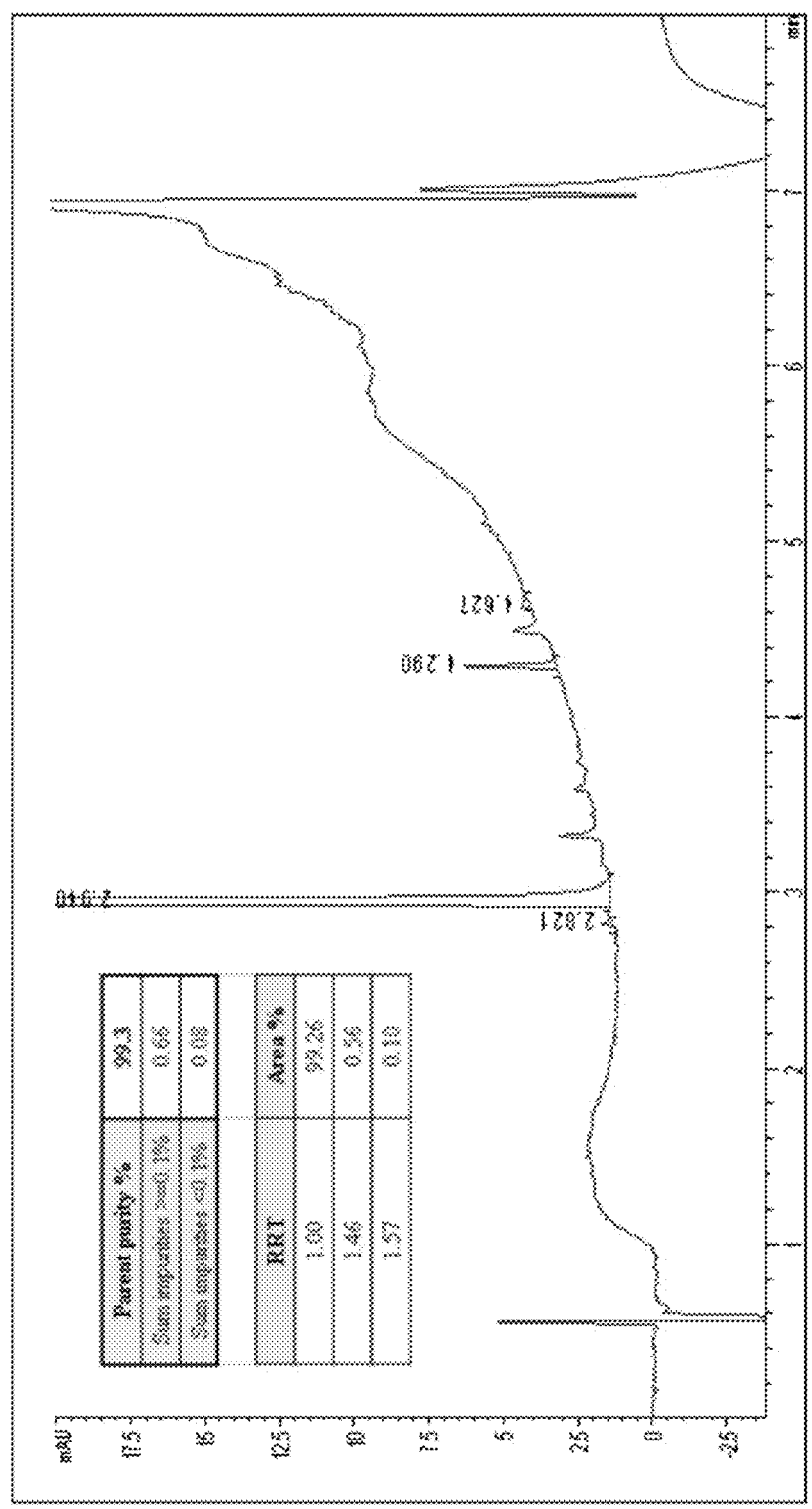
FIG. 6: HPLC of Form 1 of Compound A free base

Form 1 was formed by isolation of Compound A free base from isopropanol (IPA), methyl ethyl ketone (MEK) or acetone. Form 1 constituted rod-shaped birefringent particles (FIG. 1). It is 99.3% chemically pure (FIG. 6) with 0.01 eq. of residue dioxane. The crystalline Compound A free base was insoluble in water.

Figure 4:
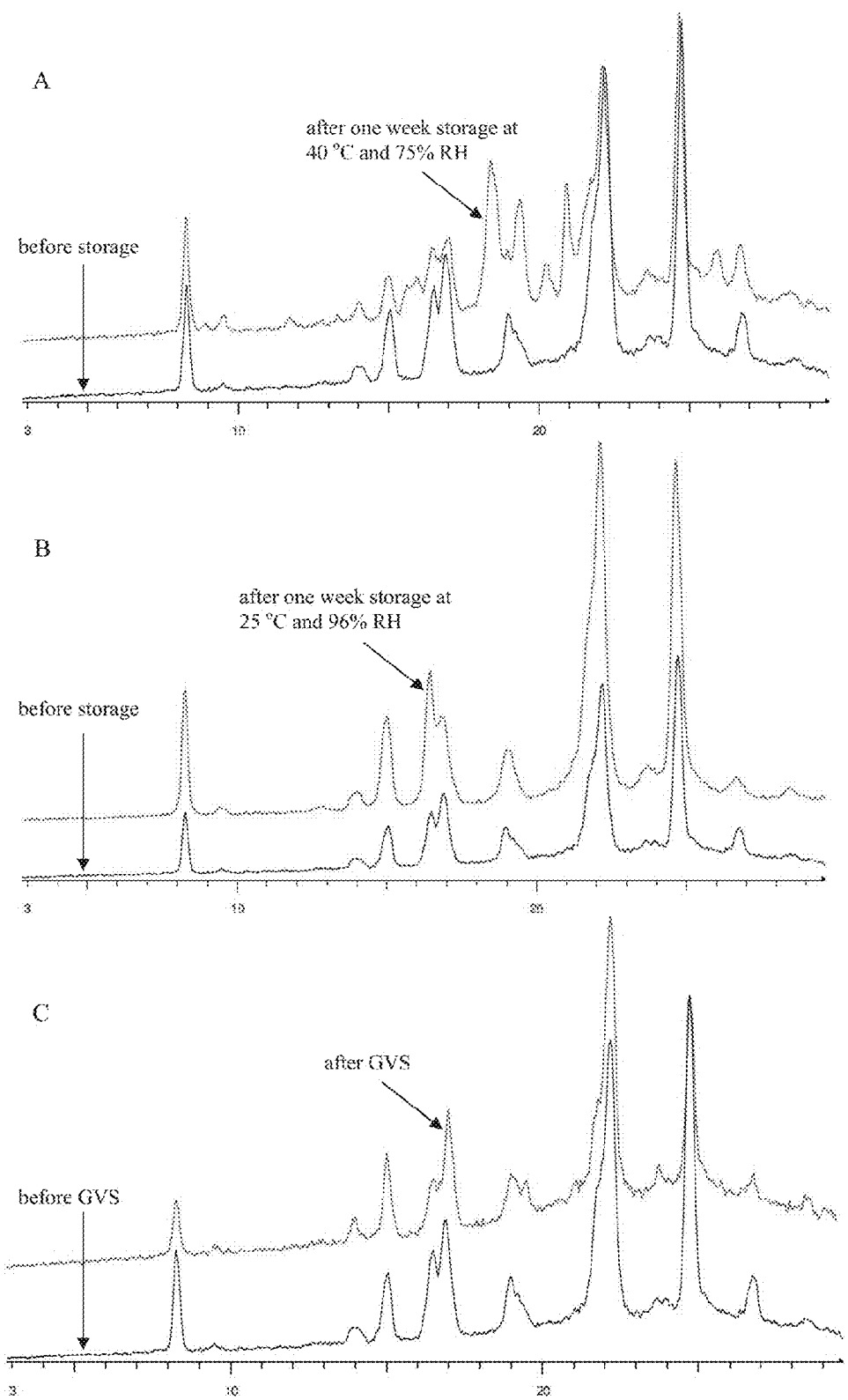
FIG. 4: XRPD of Form 1 of Compound A free base. (A) XRPD comparison of Form 1 of Compound A free base before and after one week storage at 40° C. and 75% RH; (B) XRPD comparison of Form 1 of Compound A free base before and after one week storage at 25° C. and 96% RH; (C) XRPD comparison of Form 1 of Compound A free base before and after GVS
Figure 5:
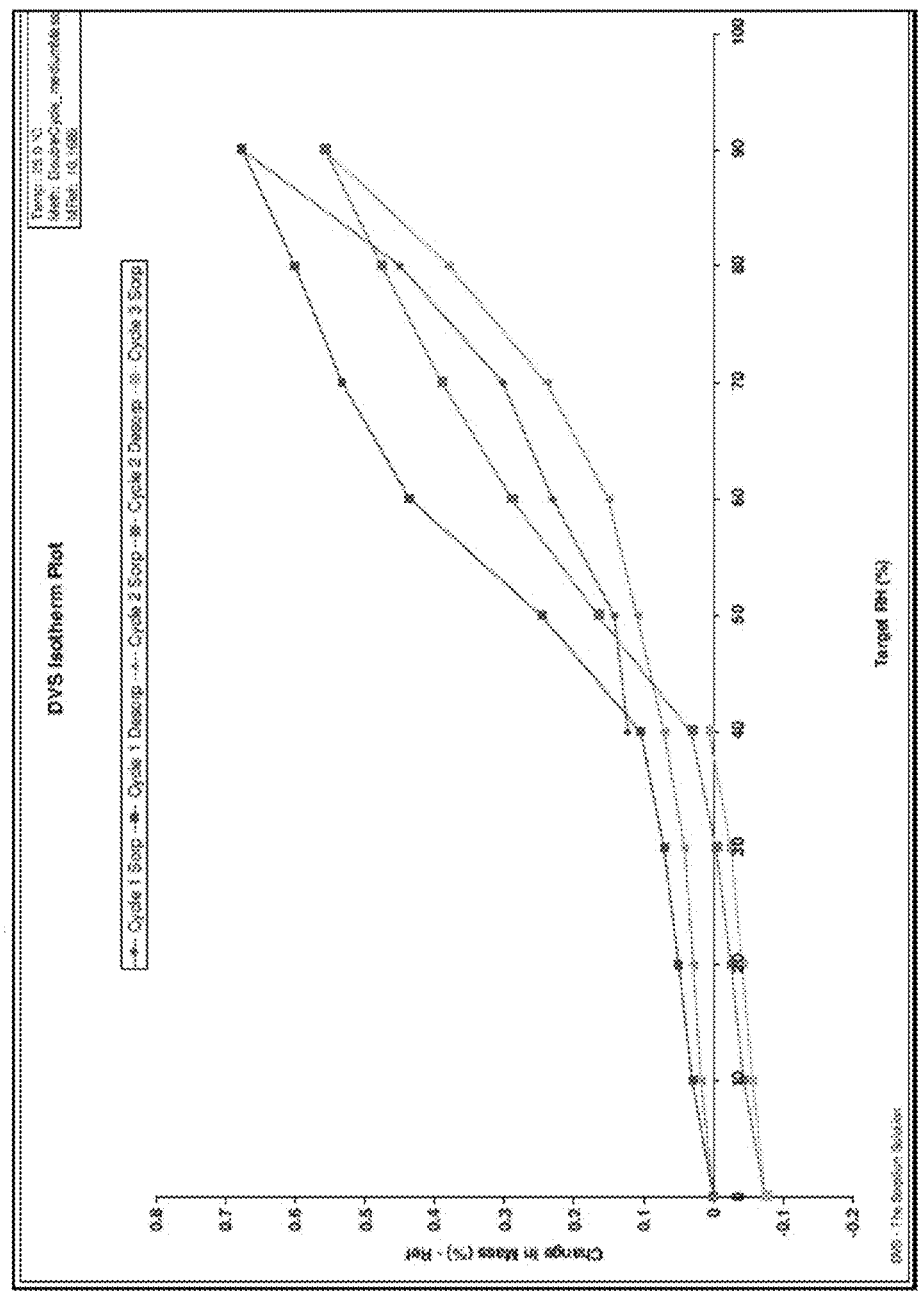
FIG. 5: GVS isotherm of Form 1 of Compound A free base
Figure 7A:
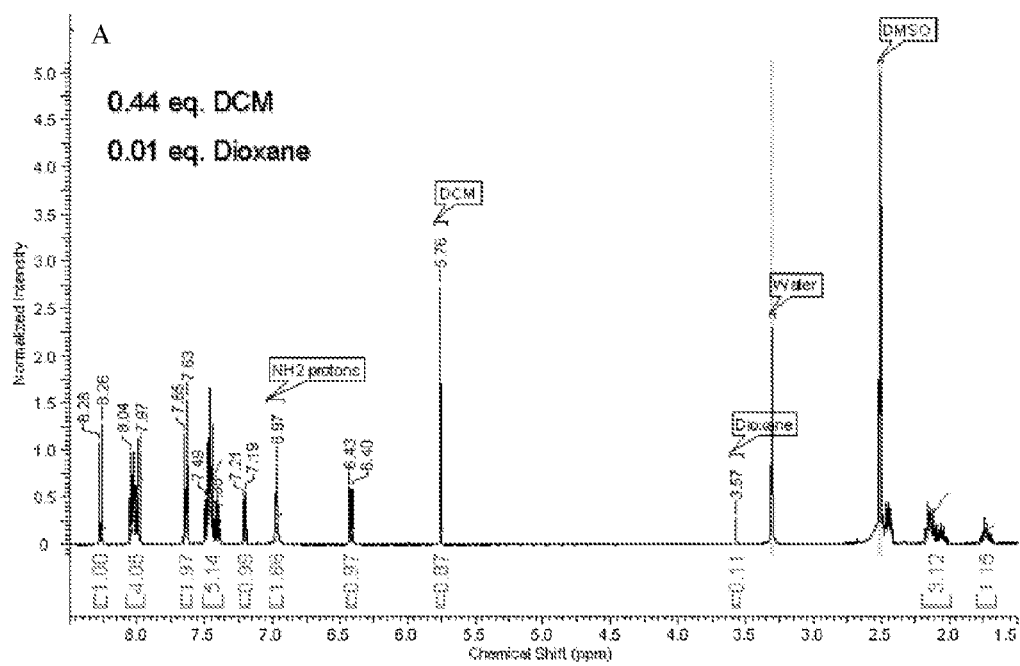
FIGS. 7A-7C: $^1$H NMR of Compound A free base: Form 1 DCM solvate (FIG. 7A), Form 2 (FIG. 7B), and Form 1 MEK solvate (FIG. 7C)
Figure 7B:
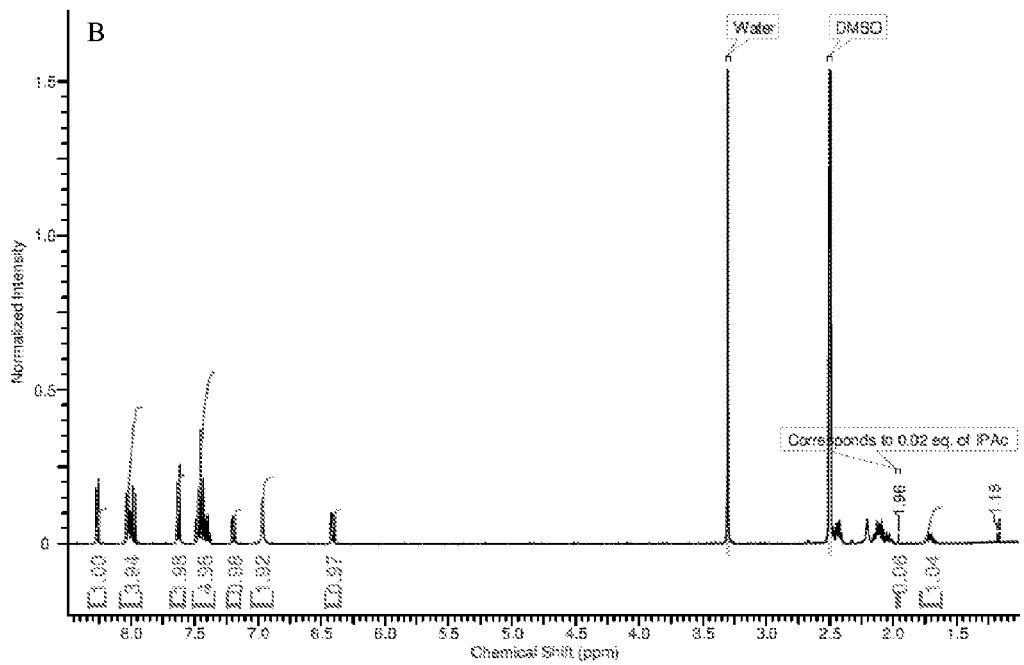
Figure 7C:
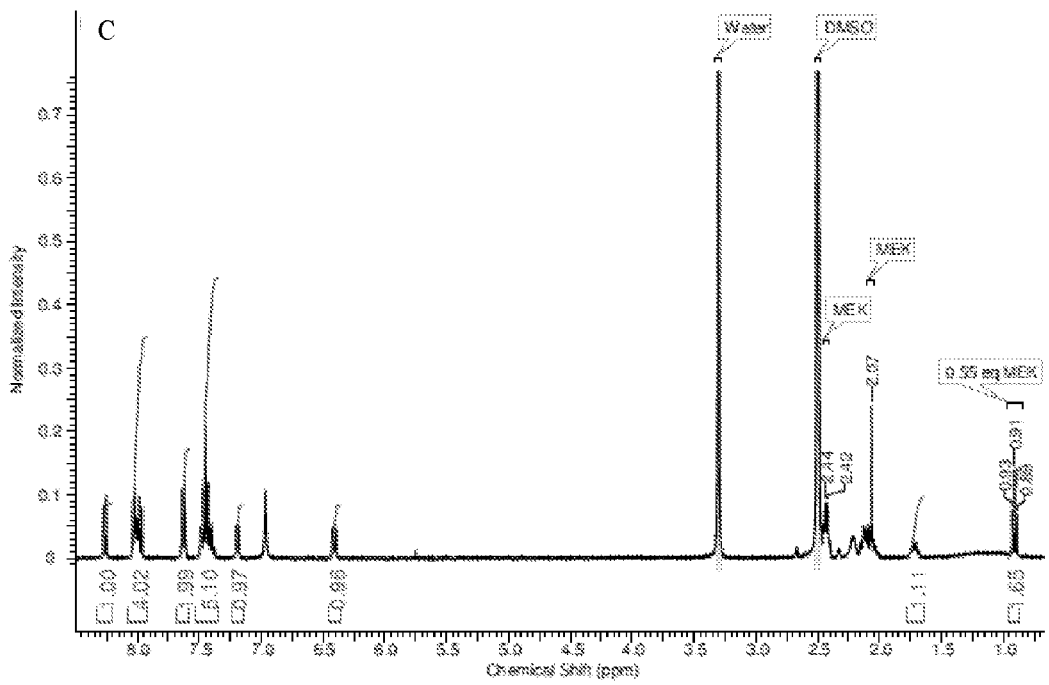

Form 1 can be dichloromethane (DCM) solvate, which contained 0.4~0.6 equivalent of DCM (FIG. 7A), or a MEK solvate, which contained 0.4~0.6 equivalent of MEK (FIG. 7C). Form 1 was stable under a storage condition of 25° C. and 0-96% RH (FIGS. 4B and C), and exhibited minimal water uptake (<0.8%, w/w) 0-90% RH (FIG. 5).

Figure 8:
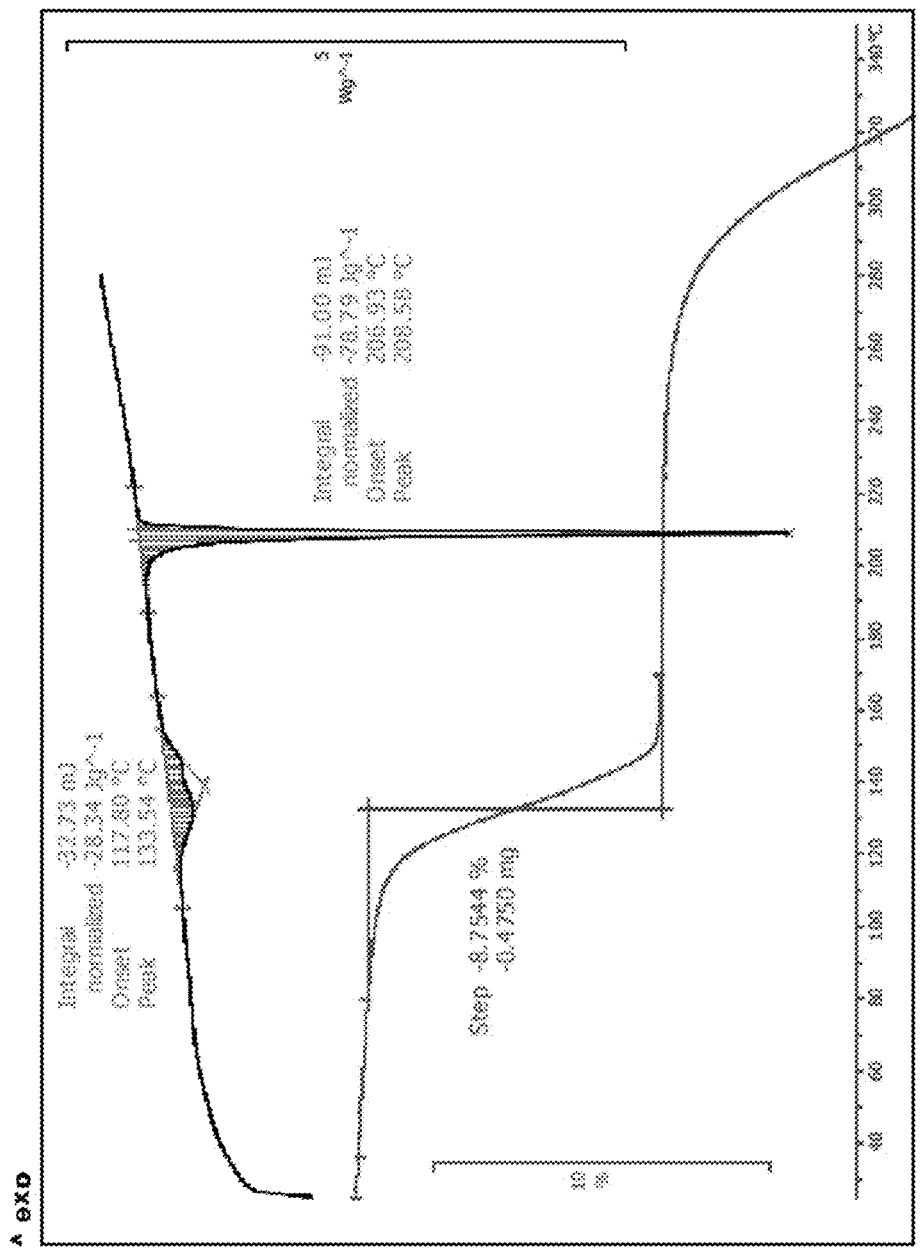
FIG. 8: DSC and TGA thermogram of Form 1 of Compound A free base
Figure 9:
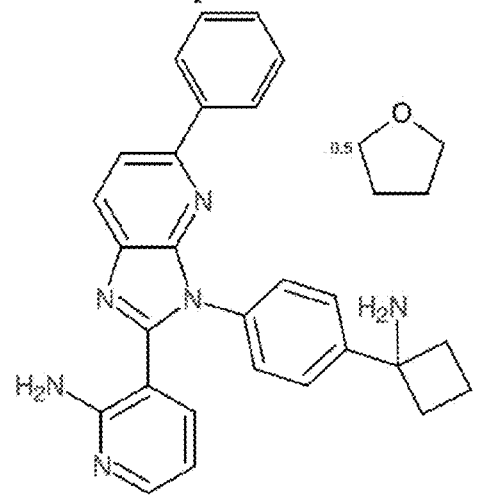
FIG. 9: Structural representation of Compound A free base hemi THF solvate
Figure 9:
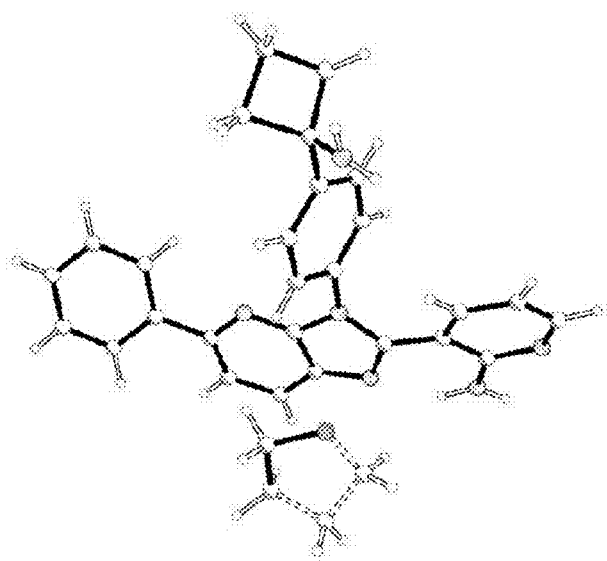

Form 1 exhibited a broad endotherm with an onset temperature of ~118° C., and melted at ~207° C. (FIG. 8). Form 1 lost 8.8% (w/w) weight in the temperature range 110-150° C., which corresponds to 0.49 equivalent DCM (FIG. 8). Minimal water absorption was observed for Form 1 upon storage (FIG. 5).

Figure 3:
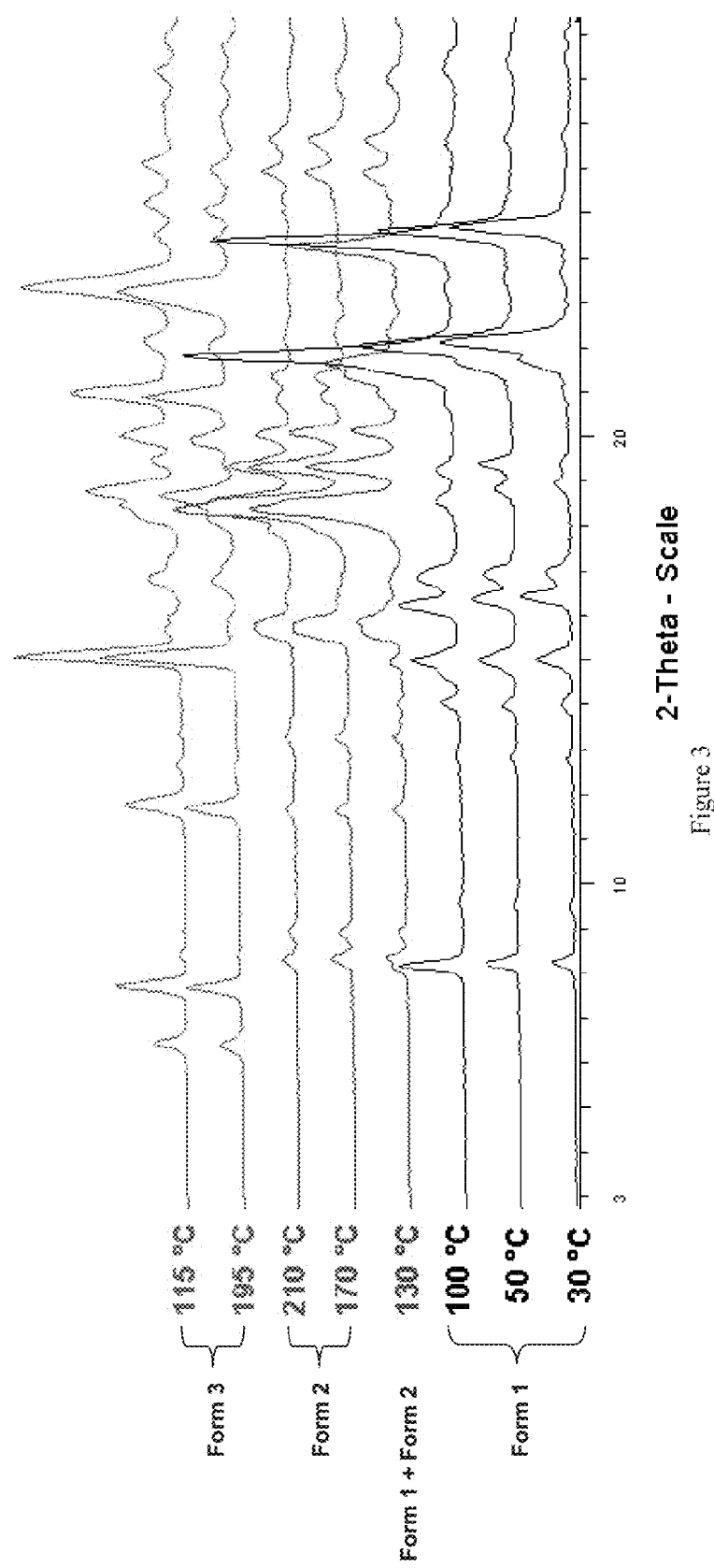
FIG. 3: XRPD of Forms 1, 2 and 3 of Compound A free base

Form 1 released DCM at ~110° C. and transformed into an unsolvated Form 2 (FIG. 3). Form 1 also transformed to Form 2 when stored under 40° C. and 75% RH (FIG. 4A).

Form 2 was also formed by isolation of Compound A free base from isopropyl acetate (IPAc) or acetonitrile. Form 2 did not contain any significant amount of solvent (FIG. 7B). Form 2 melted at ~210° C., and when cooled, converted to Form 3 (FIG. 3).

Figure 10:
FIG. 10: Images of crystals of Compound A free base hemi THF solvate

Form 4 was grown by slow evaporation of a free-base solution containing a mixture of 5% $H_2O$ in THF (FIG. 10). Form 4 is a hemi THF solvate, and has asymmetric unit which contains an independent molecule of Compound A free base displaying minor disorder and half a molecule of THF. The disorder in Compound A free base is located on the amine group substituted on the cyclobutyl ring and was observed as the elongated nitrogen ellipsoid. This type of disorder can be observed when an amine group is not conjugated by an aromatic ring. The final $R_1$ [$I>2\sigma(I)$]=4.74%. A calculated least-squares plane through the 6 atoms of the pyridinyl ring (C1-05) gave an RMSD from planarity of 0.0267 with C5 showing the greatest deviation from planarity −0.0463 (9) Å. A calculated least-squares plane through the 9 atom fused rings (C6-C11, N3, N4, N5) gave an RMSD from planarity of 0.0083 with C7 showing the greatest deviation from planarity 0.016 (1) Å. The dihedral angle between this and previous plane is 20.27 (5°). A calculated least-squares plane through the 6 atoms of the phenyl ring (C12-C17) gave an RMSD from planarity of 0.0015 with C16 showing the greatest deviation from planarity 0.0025 (9) Å. The dihedral angle between this and previous plane is 27.53 (2) °. A calculated least-squares plane through the 6 atoms of the second phenyl ring (C18-C23) gave an RMSD from planarity of 0.0125 with C23 showing the greatest deviation from planarity −0.0187 (8). The dihedral angle between this and previous plane is 61.64

(4)°. The cyclobutyl ring (C24-C27) adopts a typical puckered (butterfly-like) structure to minimize ring strain.

Figure 11:
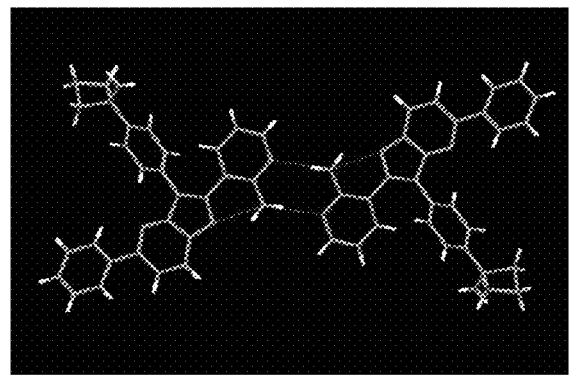
FIG. 11: Hydrogen bonded dimer of Compound A free base hemi THF solvate
Figure 12:
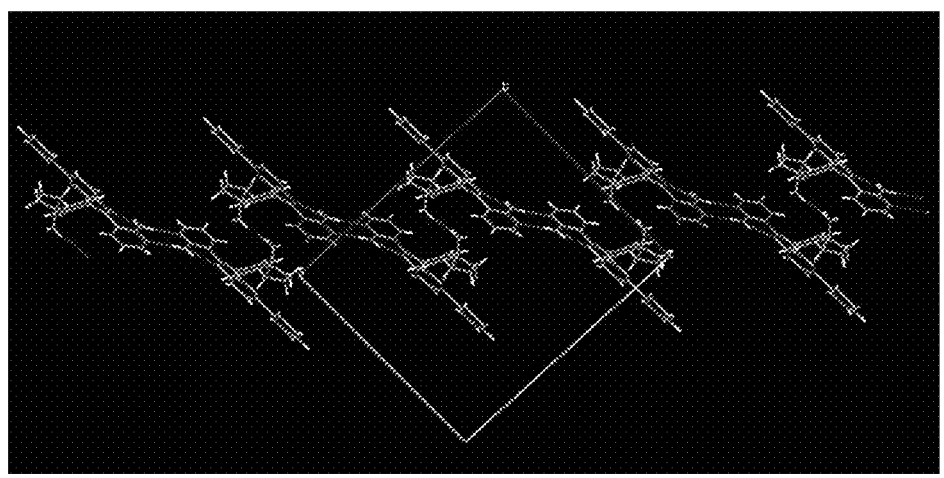
FIG. 12: Hydrogen bonded chains of dimers of Compound A free base hemi THF solvate
Figure 13:
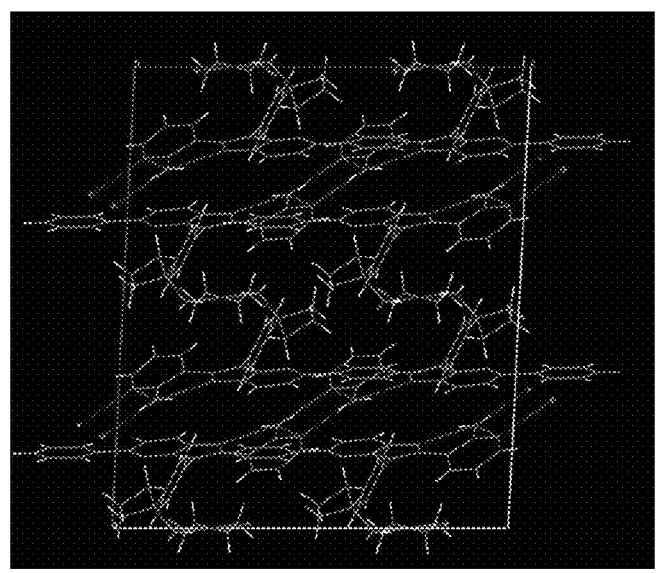
FIG. 13: Packing of Compound A free base hemi THF solvate within the unit cell viewed down the b-crystallographic axis
Figure 14:
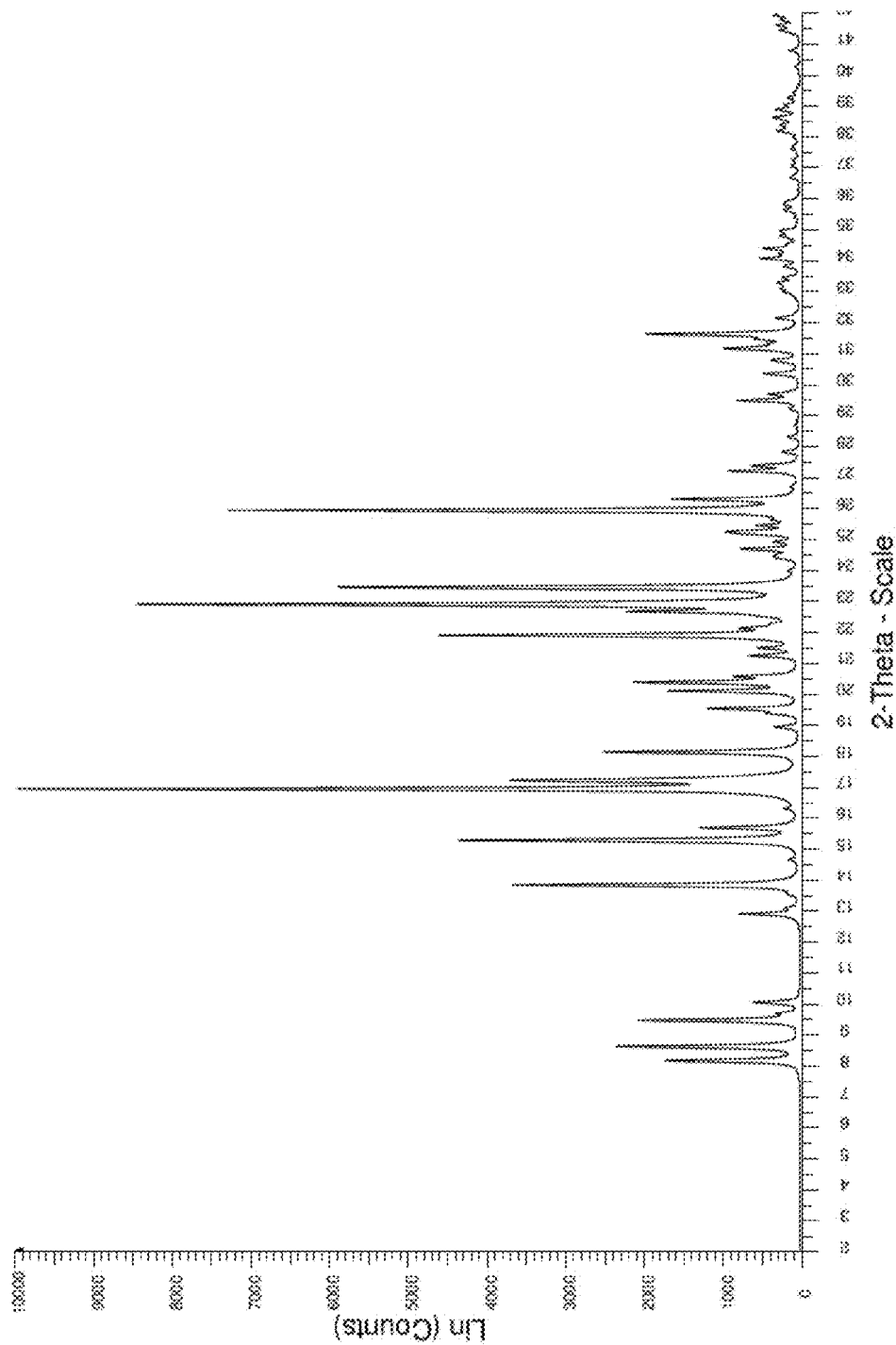
FIG. 14: Simulated XRPD of Compound A free base hemi THF solvate
Figure 15:
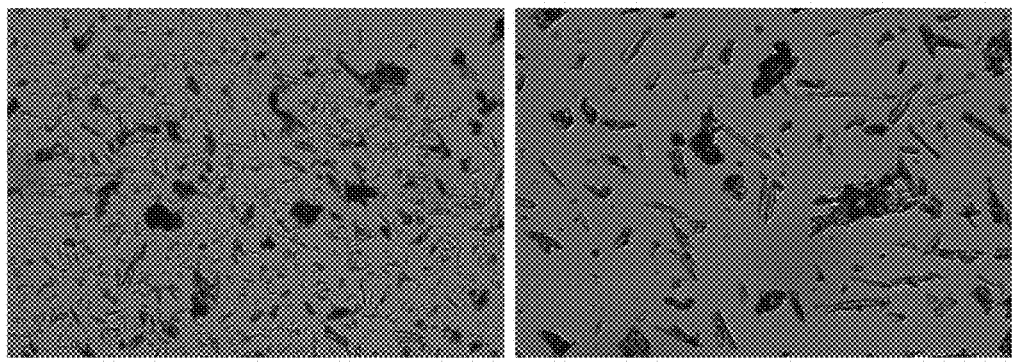
FIG. 15: Images of crystals of Compound A HCl salt

In Form 4, Compound A free base formed a dimer via a hydrogen bond with the nitrogen of the amine group on the pyridinyl ring, N1, acting as donor and the nitrogen, N2, of the pyridinyl ring on a symmetry related molecule acting as an acceptor, N1-H1AB - - - N2 [D . . . A=3.051 (2) A] (FIG. 11). The dimer units of Compound A free base are linked together by hydrogen bonds between the amine substituent of the cyclobutyl ring, N6, and the same group in a symmetry related molecule resulting in chains of Compound A dimer units, N6-H6B - - - N2 [D . . . A=3.284 (4)Å] (FIG. 12). An internal hydrogen bond was also observed within the structure between the nitrogen of the amine group on the pyridinyl ring, N1, and the nitrogen, N4, of the nine atom ring system, N1-H1AA - - - N4 [D . . . A=2.696 (2) A] (FIG. 11). An image of the packing of Compound A free base hemi THF solvate within the unit cell is given in FIG. 13. There are no other unusual structural features, and the Fourier difference map is featureless, showing maximal and minimal electron densities of 0.372 and −0.285eÅ-3, respectively. A simulated XRPD pattern has been generated as a reference pattern for this material (FIG. 14). Features of Form 4 are provided in Tables 5-13.

TABLE 5

Crystal data

| | |
|---|---|
| Empirical formula | $C_{29}H_{28}N_6O_{0.5}$ |
| Formula weight | 468.57 |
| Temperature | 100(2) K |
| Wavelength | 1.5418 Å |
| Crystal size | 0.20 × 0.12 × 0.06 mm |
| Crystal habit | Colorless, plate |
| Crystal system | monoclinic |
| Space group | C2/c |
| Unit cell dimensions | a = 20.6321(3) Å, α = 90° |
| | b = 12.8184(2) Å, β = 92.7870(10)° |
| | c = 17.6964(3) Å, γ = 90° |
| Volume | 4674.64 Å$^3$ |
| Z | 8 |
| Density (calculated) | 1.332 mg/m$^3$ |
| Absorption coefficient | 0.653 mm$^{-1}$ |
| F (000) | 1984 |

TABLE 6

| | |
|---|---|
| Diffractometer | SuperNova, Dual, Cu at zero, Atlas |
| Radiation source | SuperNova (Cu) X-ray Source, Cu Kα |
| Data collection method | phi and omega scans |
| Theta range for data collection | 9.06 to 74.29° |
| Index ranges | −25 ≤ h ≤ 25, −15 ≤ k ≤ 15, −18 ≤ l ≤ 22 |
| Reflections collected | 16885 |
| Independent reflections | 4679 [R(int) = 0.0375] |
| Coverage of independent reflections | 98.3% |
| Variation in check reflections | N/A |
| Absorption correction | Semi-empirical from equivalents |
| Max. and min. transmission | 1.00000 and 0.73960 |
| Structure solution technique | direct |
| Structure solution program | Bruker SHELXTL |
| Refinement technique | Full-matrix least-squares on F$^2$ |
| Refinement program | Bruker SHELXTL |
| Function minimized | $\Sigma w(F_a^2 - F_c^2)^2$ |
| Data/restraints/parameters | 4679/1/335 |
| Goodness-of-fit on F$^2$ | 1.010 |
| Δ/σ$_{max}$ | 0.000 |
| Final R indices | |
| 4292 data; I > 2σ(I) | R1 = 0.0474, wR2 = 0.1307 |
| all data | R1 = 0.0505, wR2 = 0.1348 |

TABLE 6-continued

| | |
|---|---|
| Weighting scheme | calc w = 1/[σ$^2$(F$_o^2$) + (0.0900P)$^2$ + 2.4199] where P = {F$_o^2$ + 2F$_c^2$}/3 |
| Largest diff. peak and hole | 0372 and −0.285 eÅ$^{-3}$ |

Refinement summary:
Ordered Non-H atoms, XYZ Freely refining
Ordered Non-H atoms, U Anisotropic
H atoms (on carbon), XYZ Idealized positions riding on attached atoms
H atoms (on carbon), U Appropriate multiple of U(eq) for bonded atom
H atoms (on heteroatoms), XYZ Freely refining except H6B DFIX N6
H atoms (on heteroatoms), U Isotropic
Disordered atoms, OCC Disorder in N6, not modelled
Disordered atoms, XYZ Disorder in N6, not modelled
Disordered atoms, U Disorder in N6, not modelled

TABLE 7

Atomic coordinates and equivalent isotropic atomic displacement parameters (Å$^2$)

| | x/a | y/b | z/c | U(eq) |
|---|---|---|---|---|
| N1 | 0.27740(6) | 0.79080(10) | 0.40372(6) | 0.0325(3) |
| N2 | 0.30169(5) | 0.63762(9) | 0.46458(6) | 0.0273(3) |
| N3 | 0.34971(5) | 0.68020(9) | 0.19566(6) | 0.0245(2) |
| N4 | 0.31784(5) | 0.81882(9) | 0.26258(6) | 0.0259(2) |
| N5 | 0.34595(5) | 0.75775(8) | 0.07075(6) | 0.0258(2) |
| N6 | 0.50896(9) | 0.26635(17) | 0.15831(10) | 0.0731(7) |
| C1 | 0.30604(6) | 0.69711(11) | 0.40167(7) | 0.0259(3) |
| C2 | 0.33276(6) | 0.54672(11) | 0.46842(7) | 0.0270(3) |
| C3 | 0.37159(6) | 0.50988(11) | 0.41254(7) | 0.0267(3) |
| C4 | 0.37461(6) | 0.56811(10) | 0.34684(7) | 0.0260(3) |
| C5 | 0.33963(6) | 0.66051(10) | 0.33746(7) | 0.0243(3) |
| C6 | 0.33607(6) | 0.71993(10) | 0.26636(7) | 0.0243(3) |
| C7 | 0.33986(6) | 0.76195(10) | 0.14492(7) | 0.0246(3) |
| C8 | 0.33218(6) | 0.84830(10) | 0.03471(7) | 0.0259(3) |
| C9 | 0.31311(6) | 0.93923(10) | 0.07203(7) | 0.0272(3) |
| C10 | 0.30593(6) | 0.93977(10) | 0.14955(7) | 0.0276(3) |
| C11 | 0.32007(6) | 0.84698(10) | 0.18768(7) | 0.0253(3) |
| C12 | 0.33507(6) | 0.84614(10) | −0.04899(7) | 0.0261(3) |
| C13 | 0.34686(7) | 0.93633(11) | −0.09043(7) | 0.0304(3) |
| C14 | 0.34803(7) | 0.93237(11) | −0.16896(8) | 0.0321(3) |
| C15 | 0.33758(7) | 0.83853(12) | −0.20679(7) | 0.0306(3) |
| C16 | 0.32606(6) | 0.74873(11) | −0.16593(7) | 0.0291(3) |
| C17 | 0.32458(6) | 0.75269(10) | −0.08769(7) | 0.0272(3) |
| C18 | 0.37356(6) | 0.58038(10) | 0.17300(6) | 0.0244(3) |
| C19 | 0.43397(6) | 0.57700(11) | 0.14130(8) | 0.0300(3) |
| C20 | 0.45798(6) | 0.48233(11) | 0.11795(8) | 0.0319(3) |
| C21 | 0.42421(6) | 0.38968(11) | 0.12756(7) | 0.0271(3) |
| C22 | 0.36384(6) | 0.39489(10) | 0.15924(6) | 0.0262(3) |
| C23 | 0.33766(6) | 0.49021(10) | 0.18053(6) | 0.0251(3) |
| C24 | 0.45487(6) | 0.28831(11) | 0.10425(7) | 0.0302(3) |
| C25 | 0.41072(8) | 0.19250(11) | 0.08758(9) | 0.0367(3) |
| C26 | 0.45043(8) | 0.16767(12) | 0.01798(9) | 0.0398(3) |
| C27 | 0.47629(5) | 0.28025(7) | 0.02107(6) | 0.0336(3) |
| O1B | 0.50000(5) | 0.78748(7) | 0.25000(6) | 0.0565(5) |
| C1B | 0.50835(5) | 0.85180(7) | 0.18548(6) | 0.0488(4) |
| C2B | 0.49038(8) | 0.96104(14) | 0.20819(13) | 0.0570(5) |

TABLE 8

Selected bond lengths (Å)

| | | | |
|---|---|---|---|
| N1—C1 | 1.3398(18) | N1—H1AA | 0.93(2) |
| N1—H1AB | 0.93(2) | N2—C2 | 1.3301(18) |
| N2—C1 | 1.3560(16) | N3—C7 | 1.3885(16) |
| N3—C6 | 1.3922(16) | N3—C18 | 1.4351(16) |
| N4—C6 | 1.3231(17) | N4—C11 | 1.3767(16) |
| N5—C7 | 1.3257(16) | N5—C8 | 1.3481(17) |
| N6—C24 | 1.4615(19) | N6—H6A | 0.84(3) |
| N6—H6B | 0.819(17) | C1—C5 | 1.4381(17) |
| C2—C3 | 1.3855(18) | C3—C4 | 1.3856(17) |
| C4—C5 | 1.3927(18) | C5—C6 | 1.4695(17) |
| C7—C11 | 1.3990(18) | C8—C9 | 1.4053(18) |
| C8—C12 | 1.4854(17) | C9—C10 | 1.3869(18) |

TABLE 8-continued

Selected bond lengths (Å)

| | | | |
|---|---|---|---|
| C10—C11 | 1.3913(19) | C12—C17 | 1.3916(19) |
| C12—C13 | 1.3968(18) | C13—C14 | 1.3919(18) |
| C14—C15 | 1.388(2) | C15—C16 | 1.3861(19) |
| C16—C17 | 1.3873(18) | C18—C23 | 1.3827(18) |
| C18—C19 | 1.3920(18) | C19—C20 | 1.3815(19) |
| C20—C21 | 1.3916(19) | C21—C22 | 1.3922(18) |
| C21—C24 | 1.5113(18) | C22—C23 | 1.3952(18) |
| C24—C25 | 1.549(2) | C24—C27 | 1.5608(16) |
| C25—C26 | 1.5453(19) | C26—C27 | 1.5387(18) |
| C1B—C2B | 1.508(2) | | |

TABLE 9

Selected bond angles (°)

| | | | |
|---|---|---|---|
| C1—N1—H1AA | 119.4(12) | C1—N1—H1AB | 121.4(13) |
| H1AA—N1—H1AB | 119.2(17) | C2—N2—C1 | 118.92(11) |
| C7—N3—C6 | 105.99(10) | C7—N3—C18 | 122.25(10) |
| C6—N3—C18 | 131.63(10) | C6—N4—C11 | 106.09(10) |
| C7—N5—C8 | 113.92(11) | C24—N6—H6A | 106(2) |
| C24—N6—H6B | 126(2) | H6A—N6—H6B | 120(3) |
| N1—C1—N2 | 115.78(11) | N1—C1—C5 | 122.95(12) |
| N2—C1—C5 | 121.26(12) | N2—C2—C3 | 123.79(12) |

TABLE 9-continued

Selected bond angles (°)

| | | | |
|---|---|---|---|
| C2—C3—C4 | 117.81(12) | C3—C4—C5 | 120.92(11) |
| C4—C5—C1 | 116.75(11) | C4—C5—C6 | 123.15(11) |
| C1—C5—C6 | 120.10(11) | N4—C6—N3 | 111.99(11) |
| N4—C6—C5 | 122.83(11) | N3—C6—C5 | 125.17(11) |
| N5—C7—N3 | 126.27(12) | N5—C7—C11 | 127.69(12) |
| N3—C7—C11 | 106.00(11) | N5—C8—C9 | 123.31(11) |
| N5—C8—C12 | 115.97(11) | C9—C8—C12 | 120.65(11) |
| C10—C9—C8 | 120.99(12) | C9—C10—C11 | 116.45(12) |
| N4—C11—C10 | 132.46(12) | N4—C11—C7 | 109.93(11) |
| C10—C11—C7 | 117.61(11) | C17—C12—C13 | 118.75(12) |
| C17—C12—C8 | 119.60(11) | C13—C12—C8 | 121.64(12) |
| C14—C13—C12 | 120.39(13) | C15—C14—C13 | 120.21(12) |
| C16—C15—C14 | 119.64(12) | C15—C16—C17 | 120.19(12) |
| C16—C17—C12 | 120.81(12) | C23—C18—C19 | 120.48(12) |
| C23—C18—N3 | 121.72(11) | C19—C18—N3 | 117.79(11) |
| C20—C19—C18 | 119.27(12) | C19—C20—C21 | 121.61(12) |
| C20—C21—C22 | 118.12(12) | C20—C21—C24 | 118.79(11) |
| C22—C21—C24 | 123.08(12) | C21—C22—C23 | 121.09(12) |
| C18—C23—C22 | 119.33(11) | N6—C24—C21 | 107.66(12) |
| N6—C24—C25 | 113.28(15) | C21—C24—C25 | 118.92(11) |
| N6—C24—C27 | 111.25(12) | C21—C24—C27 | 117.12(10) |
| C25—C24—C27 | 87.64(9) | C26—C25—C24 | 89.17(11) |
| C27—C26—C25 | 88.56(10) | C26—C27—C24 | 88.97(9) |
| O1B—C1B—C2B | 106.42(9) | | |

TABLE 10

Selected torsion angles (°)

| | | | |
|---|---|---|---|
| C2—N2—C1—N1 | −175.49(11) | C2—N2—C1—C5 | 4.40(18) |
| C1—N2—C2—C3 | 2.24(19) | N2—C2—C3—C4 | −4.45(19) |
| C2—C3—C4—C5 | −0.07(18) | C3—C4—C5—C1 | 6.09(18) |
| C3—C4—C5—C6 | −173.93(11) | N1—C1—C5—C4 | 171.45(12) |
| N2—C1—C5—C4 | −8.42(18) | N1—C1—C5—C6 | −8.53(19) |
| N2—C1—C5—C6 | 171.60(11) | C11—N4—C6—N3 | −0.82(14) |
| C11—N4—C6—C5 | −179.57(11) | C7—N3—C6—N4 | 0.89(14) |
| C18—N3—C6—N4 | 176.72(12) | C7—N3—C6—C5 | 179.61(11) |
| C18—N3—C6—C5 | −4.6(2) | C4—C5—C6—N4 | −161.93(12) |
| C1—C5—C6—N4 | 18.05(18) | C4—C5—C6—N3 | 19.48(19) |
| C1—C5—C6—N3 | −160.54(12) | C8—N5—C7—N3 | 178.72(11) |
| C8—N5—C7—C11 | 1.39(18) | C6—N3—C7—N5 | −178.37(12) |
| C18—N3—C7—N5 | 5.31(19) | C6—N3—C7—C11 | −0.56(13) |
| C18—N3—C7—C11 | −176.89(11) | C7—N5—C8—C9 | 0.02(18) |
| C7—N5—C8—C12 | −177.03(10) | N5—C8—C9—C10 | −1.45(19) |
| C12—C8—C9—C10 | 175.47(11) | C8—C9—C10—C11 | 1.47(18) |
| C6—N4—C11—C10 | 179.45(13) | C6—N4—C11—C7 | 0.43(14) |
| C9—C10—C11—N4 | −179.18(13) | C9—C10—C11—C7 | −0.22(18) |
| N5—C7—C11—N4 | 177.87(12) | N3—C7—C11—N4 | 0.10(14) |
| N5—C7—C11—C10 | −1.3(2) | N3—C7—C11—C10 | −179.08(11) |
| N5—C8—C12—C17 | 26.33(17) | C9—C8—C12—C17 | −150.81(12) |
| N5—C8—C12—C13 | −154.94(12) | C9—C8—C12—C13 | 27.92(19) |
| C17—C12—C13—C14 | 0.0(2) | C8—C12—C13—C14 | −178.72(12) |
| C12—C13—C14—C15 | −0.1(2) | C13—C14—C15—C16 | −0.1(2) |
| C14—C15—C16—C17 | 0.4(2) | C15—C16—C17—C12 | −0.5(2) |
| C13—C12—C17—C16 | 0.30(19) | C8—C12—C17—C16 | 179.07(1.2) |
| C7—N3—C18—C23 | −119.15(13) | C6—N3—C18—C23 | 65.58(18) |
| C7—N3—C18—C19 | 59.46(16) | C6—N3—C18—C19 | −115.81(14) |
| C23—C18—C19—C20 | −0.52(19) | N3—C18—C19—C20 | −179.15(11) |
| C18—C19—C20—C21 | −2.1(2) | C19—C20—C21—C22 | 2.23(19) |
| C19—C20—C21—C24 | −176.99(12) | C20—C21—C22—C23 | 0.25(18) |
| C24—C21—C22—C23 | 179.43(11) | C19—C18—C23—C22 | 2.92(18) |
| N3—C18—C23—C22 | −178.50(11) | C21—C22—C23—C18 | −2.80(18) |
| C20—C21—C24—N6 | 70.95(18) | C22—C21—C24—N6 | −108.22(17) |
| C20—C21—C24—C25 | −158.53(12) | C22—C21—C24—C25 | 22.30(18) |
| C20—C21—C24—C27 | −55.24(16) | C22—C21—C24—C27 | 125.59(13) |
| N6—C24—C25—C26 | −94.39(14) | C21—C24—C25—C26 | 137.66(12) |
| C27—C24—C25—C26 | 17.76(10) | C24—C25—C26—C27 | −18.02(10) |
| C25—C26—C27—C24 | 17.88(10) | N6—C24—C27—C26 | 96.26(15) |
| C21—C24—C27—C26 | −139.35(12) | C25—C24—C27—C26 | −17.84(10) |

TABLE 11

Anisotropic atomic displacement parameters (Å²)

| | $U_{11}$ | $U_{22}$ | $U_{33}$ | $U_{23}$ | $U_{13}$ | $U_{12}$ |
|---|---|---|---|---|---|---|
| N1 | 0.0394(6) | 0.0382(6) | 0.0205(5) | 0.0021(5) | 0.0091(4) | 0.0088(5) |
| N2 | 0.0280(5) | 0.0370(6) | 0.0171(5) | 0.0005(4) | 0.0022(4) | 0.0004(4) |
| N3 | 0.0283(5) | 0.0291(5) | 0.0163(5) | 0.0003(4) | 0.0019(4) | 0.0001(4) |
| N4 | 0.0287(5) | 0.0320(6) | 0.0171(5) | −0.0011(4) | 0.0012(4) | 0.0002(4) |
| N5 | 0.0282(5) | 0.0313(6) | 0.0180(5) | 0.0006(4) | 0.0017(4) | −0.0015(4) |
| N6 | 0.0696(11) | 0.1018(15) | 0.0449(9) | −0.0357(9) | −0.0272(8) | 0.0586(11) |
| C1 | 0.0247(6) | 0.0357(7) | 0.0173(5) | −0.0003(5) | 0.0007(4) | −0.0007(5) |
| C2 | 0.0279(6) | 0.0365(7) | 0.0166(5) | 0.0016(5) | 0.0000(4) | −0.0020(5) |
| C3 | 0.0262(6) | 0.0341(7) | 0.0196(6) | 0.0000(5) | −0.0012(4) | 0.0013(5) |
| C4 | 0.0255(6) | 0.0353(7) | 0.0172(5) | −0.0027(5) | 0.0006(4) | −0.0009(5) |
| C5 | 0.0246(6) | 0.0325(6) | 0.0159(5) | −0.0016(5) | 0.0009(4) | −0.0013(5) |
| C6 | 0.0240(5) | 0.0320(6) | 0.0168(5) | −0.0015(5) | 0.0020(4) | −0.0008(5) |
| C7 | 0.0251(6) | 0.0300(6) | 0.0186(6) | 0.0006(4) | 0.0009(4) | −0.0016(5) |
| C8 | 0.0259(6) | 0.0319(7) | 0.0198(6) | 0.0010(5) | 0.0001(4) | −0.0032(5) |
| C9 | 0.0288(6) | 0.0306(7) | 0.0221(6) | 0.0017(5) | −0.0007(5) | 0.0003(5) |
| C10 | 0.0291(6) | 0.0310(7) | 0.0227(6) | −0.0023(5) | 0.0002(5) | 0.0008(5) |
| C11 | 0.0253(6) | 0.0320(6) | 0.0185(6) | −0.0016(5) | 0.0013(4) | −0.0012(5) |
| C12 | 0.0253(6) | 0.0335(7) | 0.0195(6) | 0.0012(5) | 0.0008(4) | −0.0009(5) |
| C13 | 0.0365(7) | 0.0322(7) | 0.0224(6) | 0.0009(5) | −0.0002(5) | −0.0033(5) |
| C14 | 0.0383(7) | 0.0360(7) | 0.0222(6) | 0.0066(5) | 0.0014(5) | −0.0022(5) |
| C15 | 0.0338(6) | 0.0408(7) | 0.0173(6) | 0.0023(5) | 0.0013(5) | 0.0005(5) |
| C16 | 0.0299(6) | 0.0356(7) | 0.0220(6) | −0.0021(5) | 0.0014(5) | −0.0021(5) |
| C17 | 0.0285(6) | 0.0325(7) | 0.0209(6) | 0.0023(5) | 0.0034(4) | −0.0024(5) |
| C18 | 0.0282(6) | 0.0310(6) | 0.0139(5) | −0.0003(4) | 0.0004(4) | 0.0017(5) |
| C19 | 0.0286(6) | 0.0334(7) | 0.0284(6) | 0.0002(5) | 0.0046(5) | −0.0031(5) |
| C20 | 0.0267(6) | 0.0402(7) | 0.0294(7) | −0.0014(5) | 0.0063(5) | 0.0019(5) |
| C21 | 0.0291(6) | 0.0347(7) | 0.0172(5) | −0.0008(5) | −0.0018(4) | 0.0040(5) |
| C22 | 0.0309(6) | 0.0310(6) | 0.0165(5) | 0.0002(4) | 0.0006(4) | −0.0006(5) |
| C23 | 0.0265(6) | 0.0339(7) | 0.0151(5) | −0.0002(4) | 0.0024(4) | −0.0008(5) |
| C24 | 0.0329(7) | 0.0373(7) | 0.0204(6) | −0.0013(5) | 0.0011(5) | 0.0072(5) |
| C25 | 0.0439(8) | 0.0311(7) | 0.0358(7) | 0.0011(6) | 0.0098(6) | 0.0044(6) |
| C26 | 0.0483(8) | 0.0396(8) | 0.0319(7) | −0.0085(6) | 0.0072(6) | 0.0017(6) |
| C27 | 0.0387(7) | 0.0378(7) | 0.0247(6) | −0.0049(5) | 0.0061(5) | 0.0013(6) |
| O1B | 0.0890(14) | 0.0358(9) | 0.0446(10) | 0.000 | −0.0004(9) | 0.000 |
| C1B | 0.0455(9) | 0.0514(10) | 0.0486(10) | 0.0075(7) | −0.0083(7) | −0.0058(7) |
| C2B | 0.0347(8) | 0.0440(9) | 0.0914(15) | 0.0218(9) | −0.0064(8) | −0.0036(7) |

TABLE 12

Hydrogen atom coordinates and isotropic atomic displacement parameters (Å²)

| | x/a | y/b | z/c | U |
|---|---|---|---|---|
| H1AA | 0.2796(9) | 0.8352(16) | 0.3626(12) | 0.044(5) |
| H1AB | 0.2555(10) | 0.8123(16) | 0.4455(12) | 0.047(5) |
| H6A | 0.5262(15) | 0.211(2) | 0.1433(17) | 0.088 |
| H6B | 0.5102(14) | 0.281(2) | 0.2035(10) | 0.088 |
| H2A | 0.3281 | 0.5046 | 0.5120 | 0.032 |
| H3A | 0.3954 | 0.4468 | 0.4191 | 0.032 |
| H4A | 0.4009 | 0.5447 | 0.3076 | 0.031 |
| H9A | 0.3050 | 1.0012 | 0.0437 | 0.033 |
| H10A | 0.2921 | 1.0003 | 0.1752 | 0.033 |
| H13A | 0.3541 | 1.0008 | −0.0649 | 0.037 |
| H14A | 0.3560 | 0.9941 | −0.1968 | 0.039 |
| H15A | 0.3383 | 0.8359 | −0.2604 | 0.037 |
| H16A | 0.3192 | 0.6843 | −0.1916 | 0.035 |
| H17A | 0.3163 | 0.6908 | −0.0602 | 0.033 |
| H19A | 0.4584 | 0.6391 | 0.1358 | 0.036 |
| H20A | 0.4985 | 0.4804 | 0.0948 | 0.038 |
| H22A | 0.3401 | 0.3325 | 0.1665 | 0.031 |
| H23A | 0.2956 | 0.4931 | 0.2000 | 0.030 |
| H25A | 0.4139 | 0.1383 | 0.1274 | 0.044 |
| H25B | 0.3649 | 0.2107 | 0.0747 | 0.044 |
| H26A | 0.4843 | 0.1140 | 0.0275 | 0.048 |
| H26B | 0.4235 | 0.1516 | −0.0284 | 0.048 |
| H27A | 0.4528 | 0.3284 | −0.0144 | 0.040 |
| H27B | 0.5238 | 0.2855 | 0.0162 | 0.040 |
| H1BA | 0.4799 | 0.8279 | 0.1423 | 0.067(7) |
| H1BB | 0.5540 | 0.8494 | 0.1705 | 0.046(5) |
| H2BA | 0.4433 | 0.9740 | 0.1992 | 0.061(6) |
| H2BB | 0.5150 | 1.0139 | 0.1806 | 0.074(7) |

TABLE 13

Selected hydrogen bond information (Å and °)

| D-H...A | d(D-H) | d(H...A) | d(D...A) | <(DHA) |
|---|---|---|---|---|
| N1—H1AA...N4 | 0.93(2) | 1.98(2) | 2.6956(15) | 132.2(16) |
| N1—H1AB...N2#1 | 0.93(2) | 2.13(2) | 3.0505(15) | 175.4(18) |
| N6—H6B...N6#2 | 0.819(17) | 2.504(19) | 3.284(4) | 160(3) |

1 −x + 1/2, −y + 3/2, −z + 1
2 −x + 1, y, −z + 1/2

Example 13

Preparation of Compound A salts and polymorphs

Approximately 40 to 45 mg of Compound A free base was weighed accurately and 50 volumes of the appropriate solvent were added. The solvents included dioxane, ethyl acetate, isopropyl acetate (IPAc), isopropanol (IPA), tetrahydrofuran (THF), methyl ethyl ketone (MEK), acetone, ethanol, acetonitrile, and nitromethane. The samples were warmed to 50° C. for an hour and various acid stock solutions (e.g., HCl, sulfuric acid, methane sulfonic acid, maleic acid, phosphoric acid, L-glutamic acid, L-tartaric acid, galactaric acid (mucic acid), citric acid, D-glucuronic acid, hippuric acid, D-gluconic acid, L-lactic acid, L-ascorbic acid, succinic acid, acetic acid) were added. For formation of mono-salts, 1.1 equivalents of the acid were added; and for formation of bis-salts, 2.1 equivalents of the acid were added. The samples were left at 50° C. for additional 2 to 3 hours and cooled to 0° C. at 0.1° C./min and left at 0° C. overnight.

Example 14

Polymorphs of Salts of Compound A

Various salts of Compound A prepared according to Example 12 formed polymorphs with distinct XRPD patterns (FIGS. 49-64). The polymorphs of salts of Compound A were stable under storage (FIGS. 65-79).

Example 15

Preparation of Compound a HCl Salts and Polymorphs

Approximately 10 mg of Compound A free base was weighed accurately and 50 volumes of the appropriate solvent were added. The solvents included dioxane, ethyl acetate, IPAc, IPA, THF, MEK, acetone, ethanol, acetonitrile, and nitromethane. The samples were warmed to 50° C. for an hour and the various HCl acid stock solutions (e.g., in THF, ethyl acetate, or ethanol) were added. For formation of mono-salts, 1.1 equivalents of the acid were added; and for formation of bis-salts, 2.1 equivalents of the acid were added. The samples were left at 50° C. for additional 4 hours and cooled to 0° C. at 0.1° C./min and left at 0° C. overnight.

Example 16

Preparation of Compound A HCl salts and polymorphs

HCl (1 M in THF) (3.4 ml, 3.4 mmol, 3.3 equiv.) was added to a stirred suspension of Compound A free base (450.3 mg, 1.04 mmol, 1 equiv.) and ethanol (22.5 ml, 50 relative volumes) at 50° C. over a period of 1 min. The mixture became a solution upon addition of ~3 ml of acid, and remained in solution after complete addition. The mixture was stirred at 50° C. for 1 h then cooled to 0° C. at 0.1° C./min and stirred for a further 5 h. An aliquot was taken, the solid was isolated by vacuum filtration, dried under suction and analysed by XRPD to confirm formation of the desired material. The remaining mixture was stirred at 0° C. for a further 4 h. The solid was isolated by vacuum filtration, dried under suction and at 30° C./5 mbar to yield the desired material as a yellow solid. Table 14 shows analysis of one of the polymorphs of the Compound A HCl salt.

TABLE 14

Figure 18:
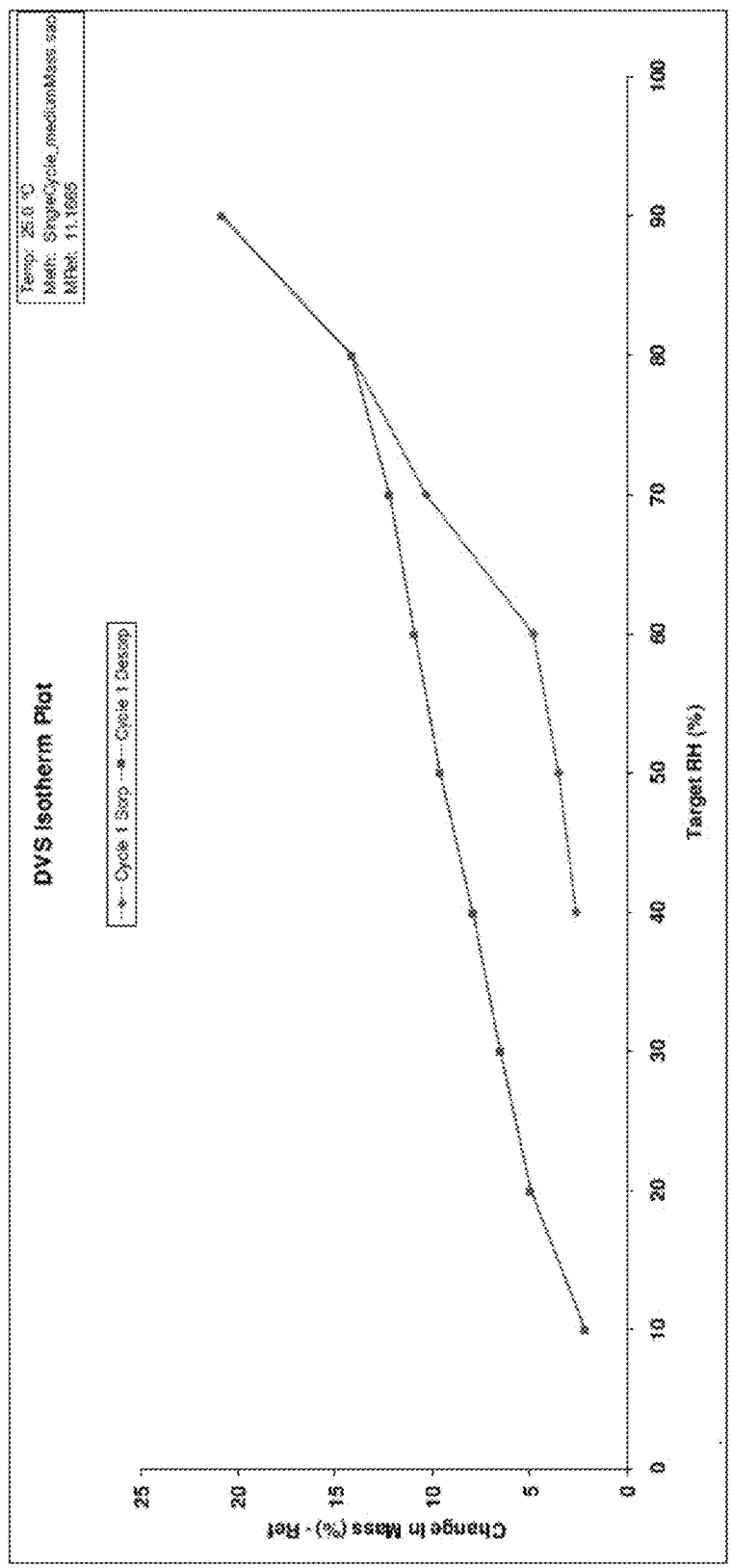
FIG. 18: GVS isotherm of Compound A HCl salt
Figure 19:
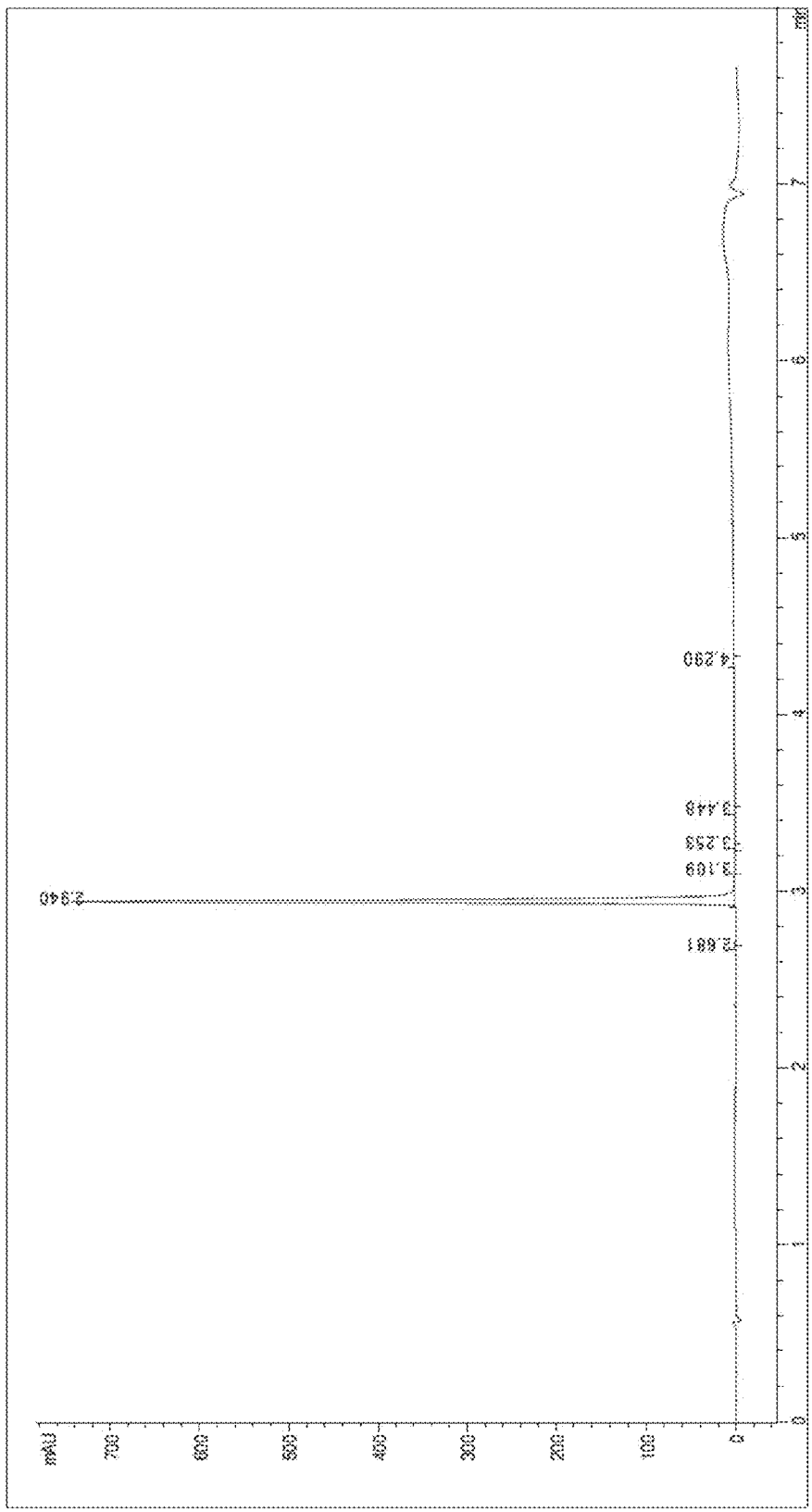
FIG. 19: HPLC of Compound A HCl salt
Figure 20A:
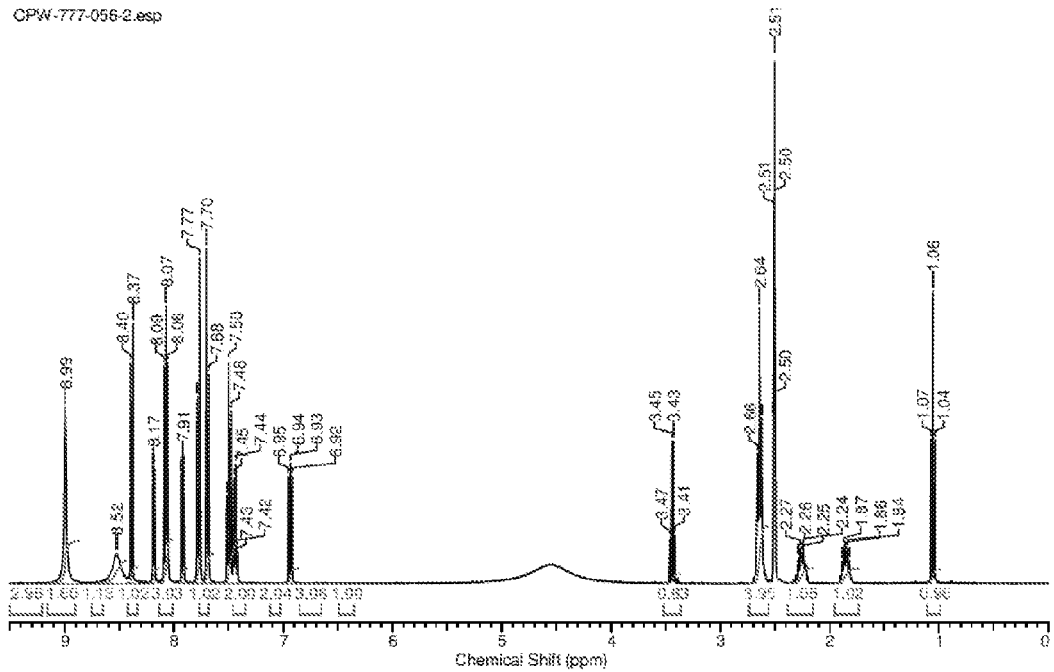
FIGS. 20A-20B: $^1$H NMR of Compound A HCl salt before drying (FIG. 20A) and after drying (FIG. 20B).
Figure 20B:
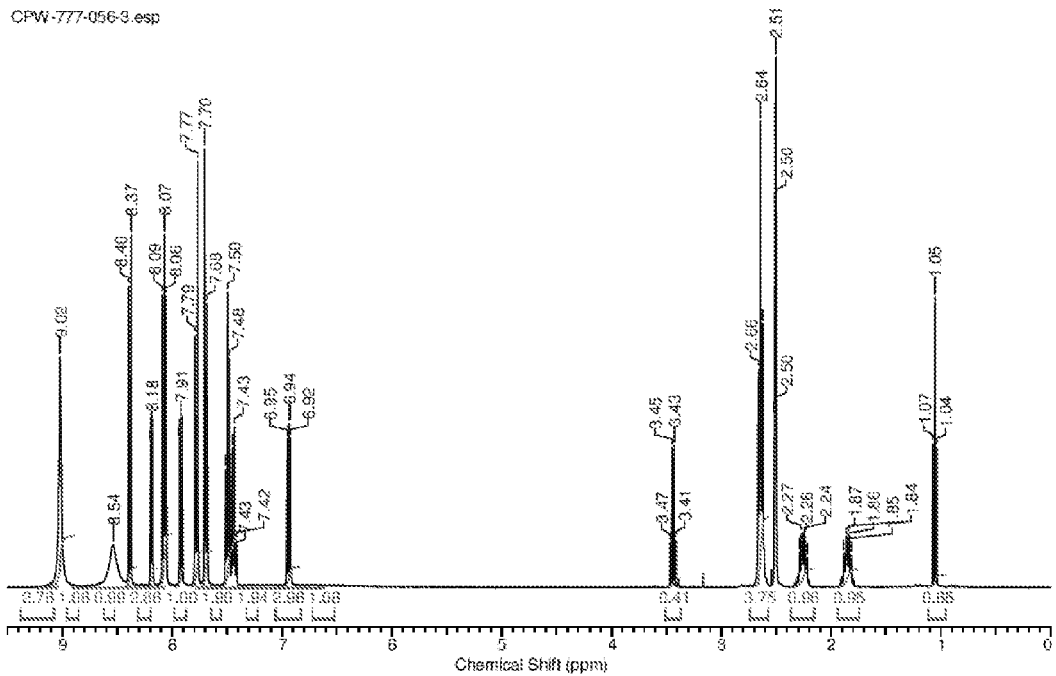
Figure 21:
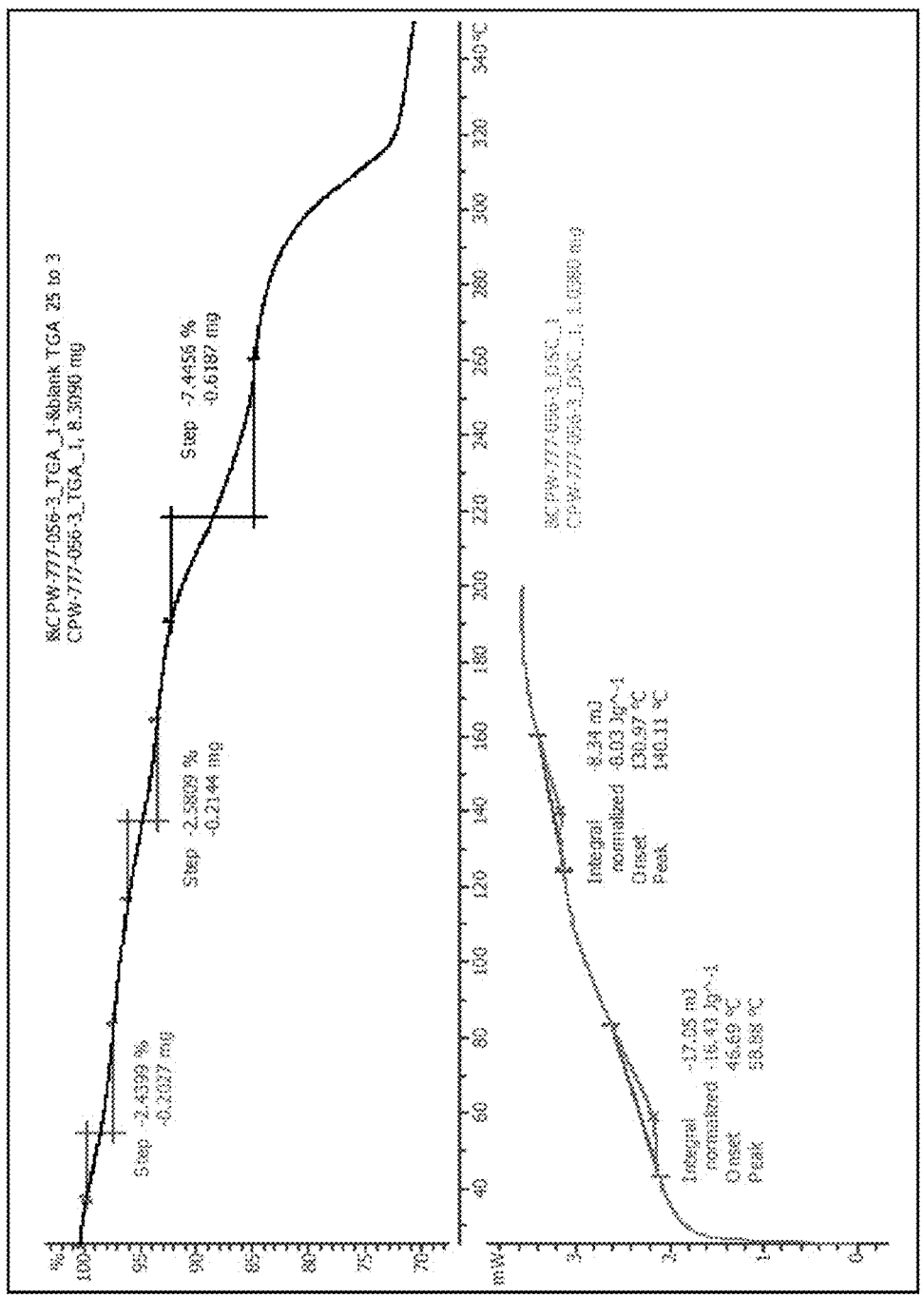
FIG. 21: DSC and TGA thermogram of Compound A HCl salt

| | | |
|---|---|---|
| $^1$H NMR | 1.8% residual EtOH | (FIG. 20) |
| DSC | Two minor broad endotherms 46.7 and 131.0° C. (ΔH 16 and 8 J/g) | (FIG. 21) |
| TGA | 2.4% wt loss 37 to 85° C. 2.6% wt loss 116 to 165° C. decomposition >190° C. (7.4% wt loss 192 to 262° C.) | (FIG. 21) |
| IC | 2.2 equi. HCl | |
| Aqueous solubility | 8.3 mg/ml (pH 1.2) (max conc. 50 mg/ml) | |
| GVS | partial run: ~18 wt % water uptake from 40-90% RH | (FIG. 18) |
| PLM | Birefringent laths (5 to 50 μm) and irregular shaped particles and agglomerates to >100 μm | |
| HPLC | 99.7% (largest % impurity: 0.3% at 1.46 RRT) | (FIG. 19) |
| Storage under 40° C. and 75% RH, 7 days | IC converted to 1.6 equi. HCl | |

Example 17

Polymorphs of Compound A HCl Salts

Figure 17:
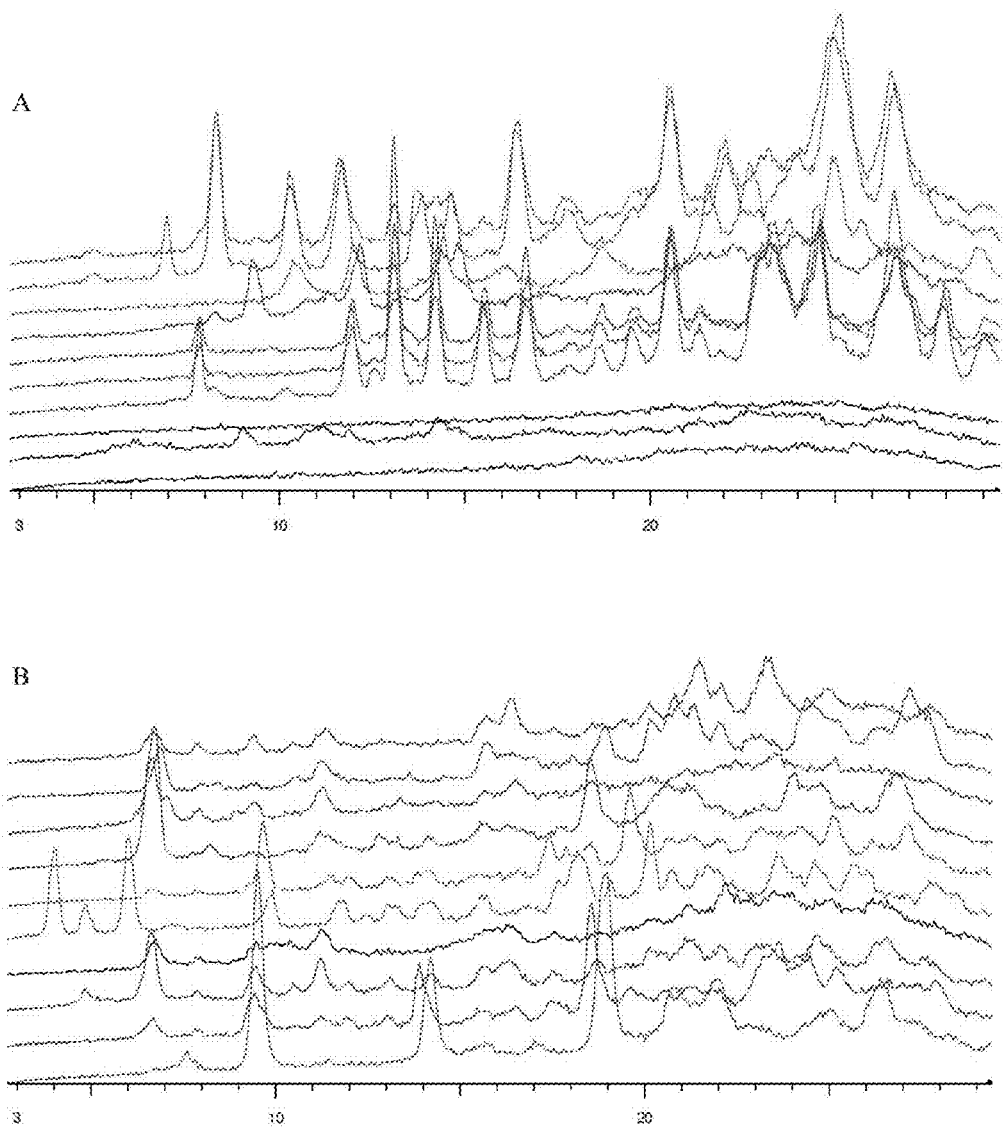
FIG. 17: XRPD of polymorphs of Compound A mono-HCl salt (A) and bis-HCl salt (B)

Compound A formed mono-HCl salt in all the solvents used. The mono-HCl salt of Compound A exhibited four distinct crystalline XRPD patterns (FIG. 17A).

Compound A also formed bis-HCl salt in all the solvents used. The bis-HCl salt of Compound A exhibited four distinct crystalline XRPD patterns (FIG. 17B).

Figure 16:
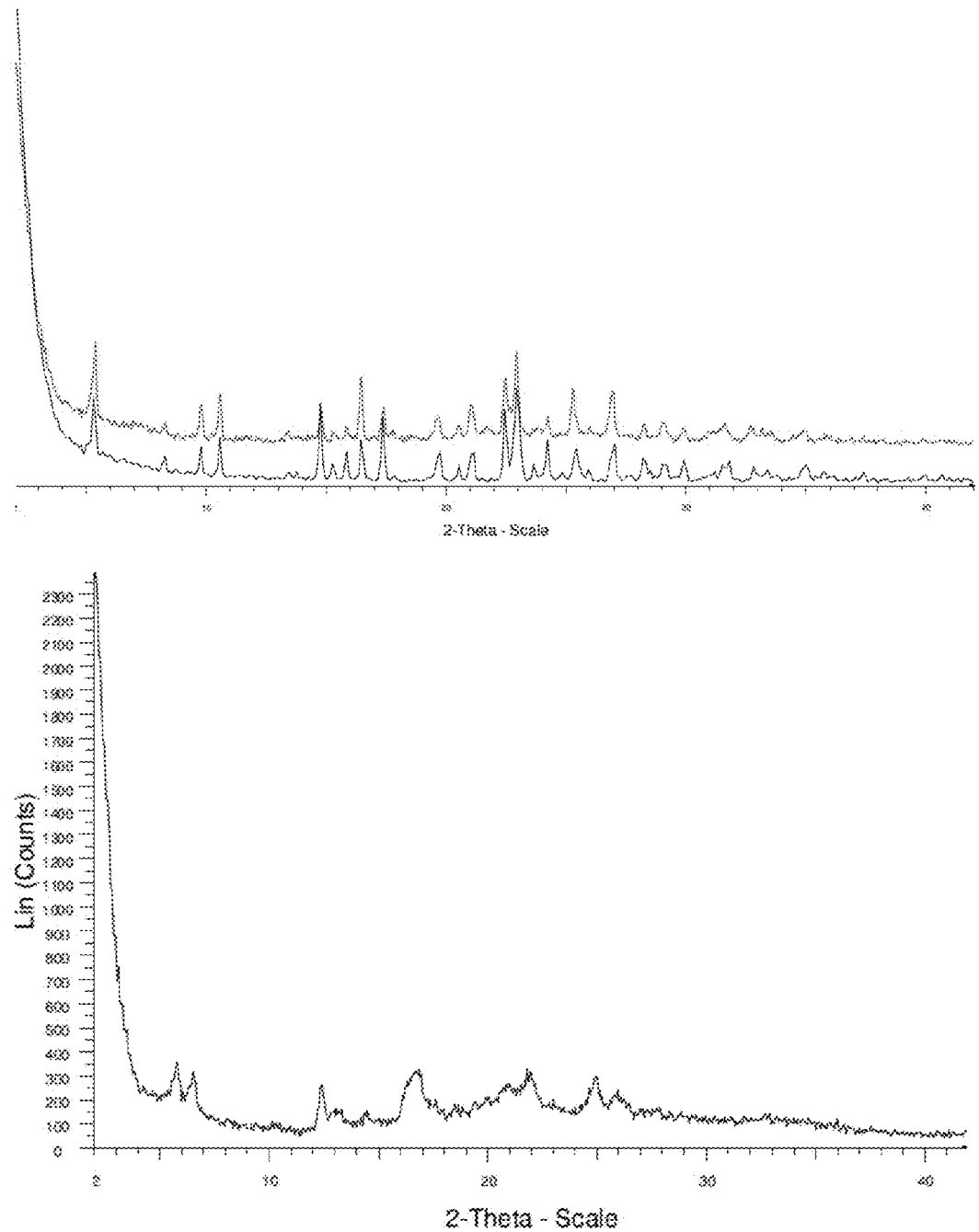
FIG. 16: XRPD of Compound A HCl salt
Figure 22:
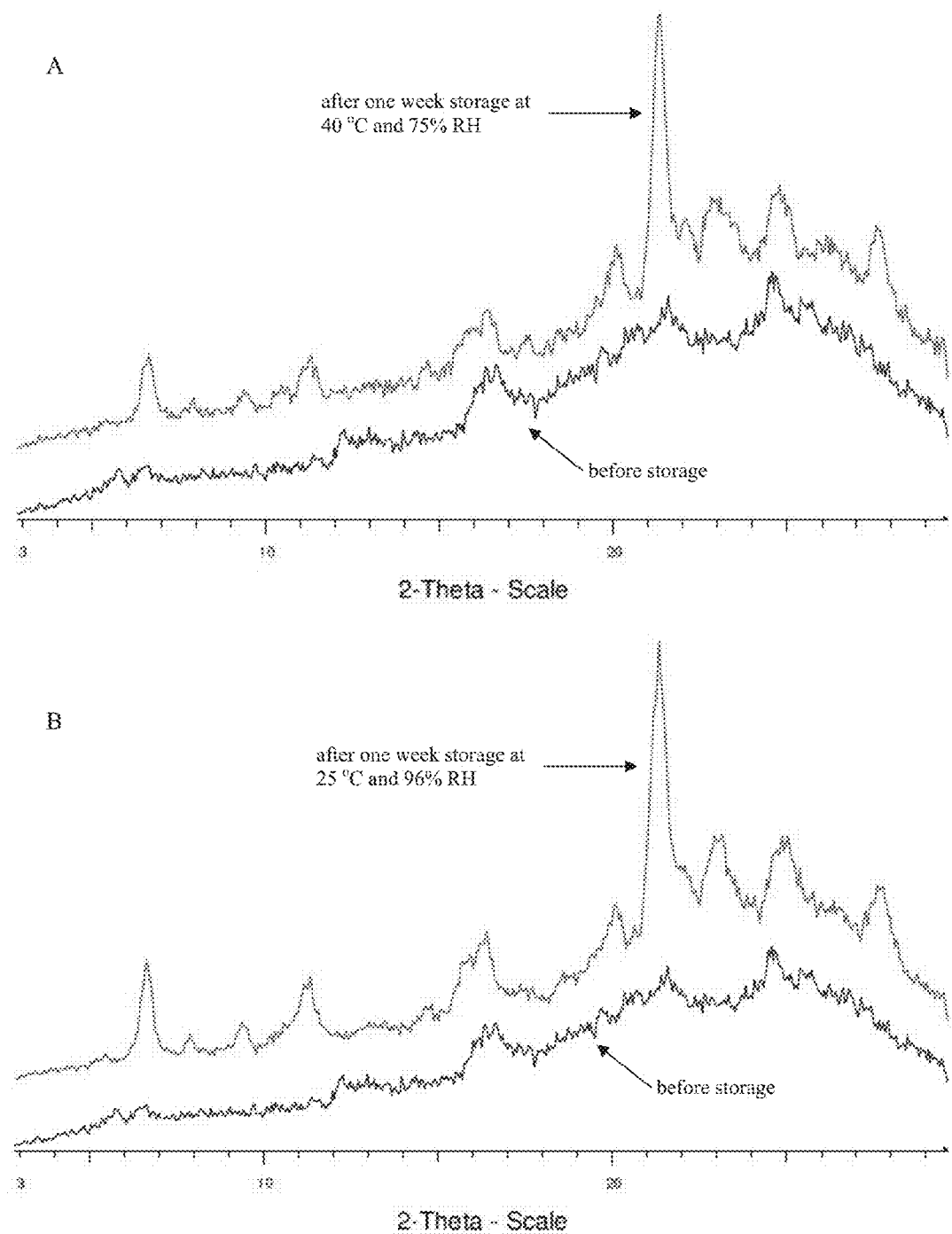
FIG. 22: XRPD of Compound A tris-HCl salt after storage
Figure 23:
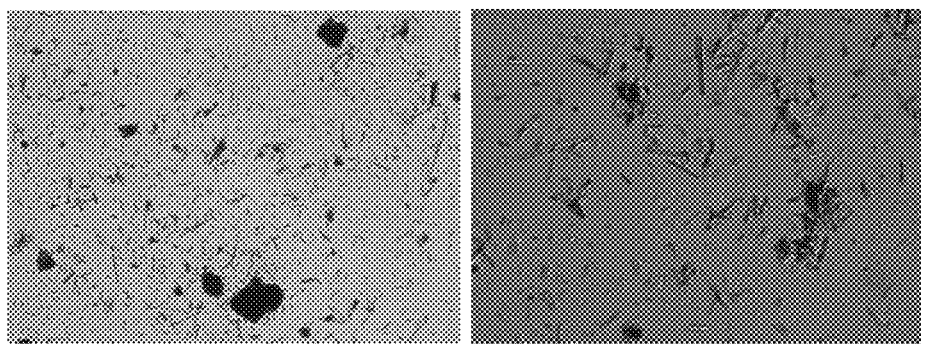
FIG. 23: Images of crystals of Compound A methane sulfonic acid salt
Figure 24:
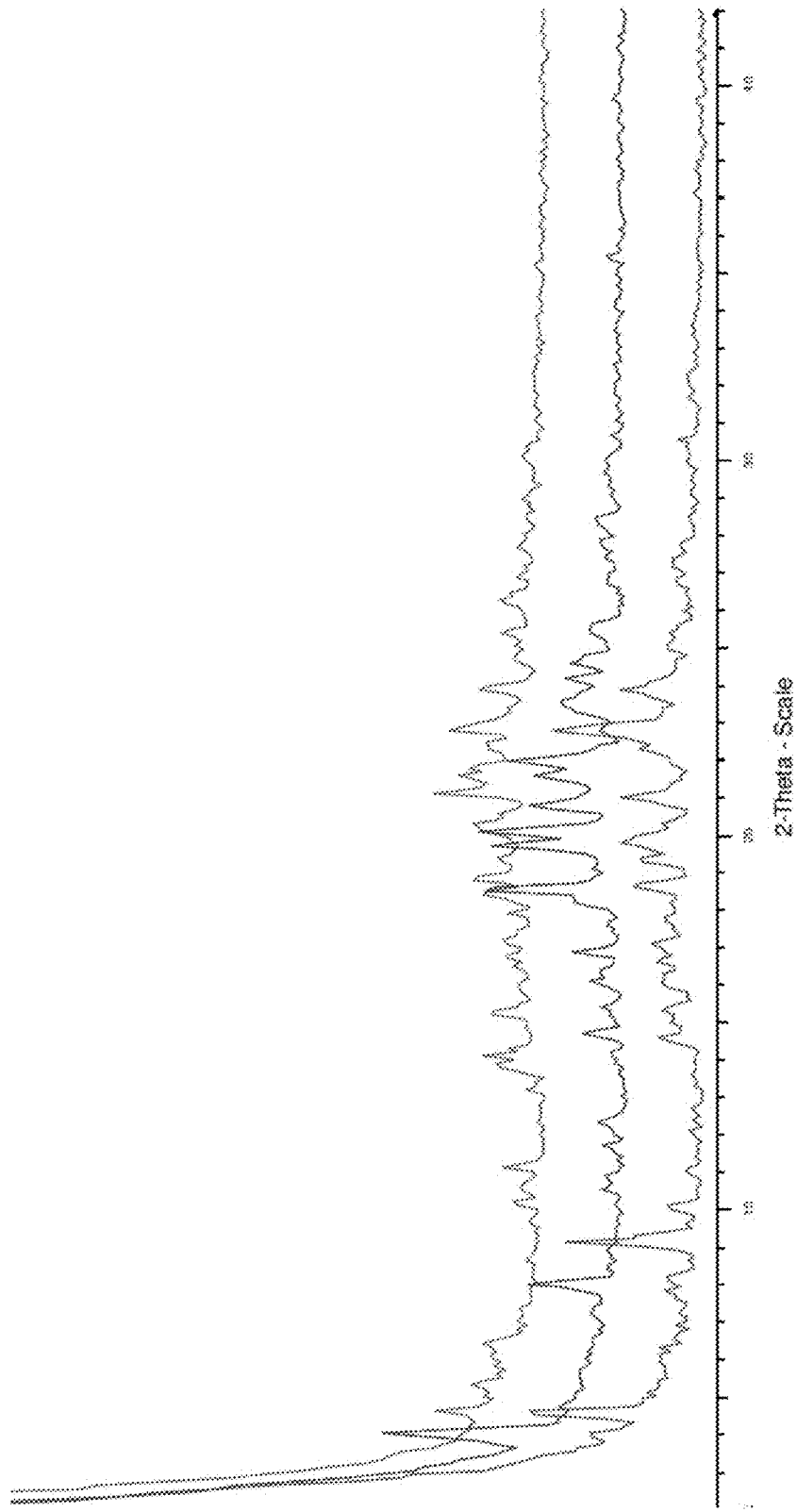
FIG. 24: XRPD of Compound A methane sulfonic acid salt
Figure 25A:
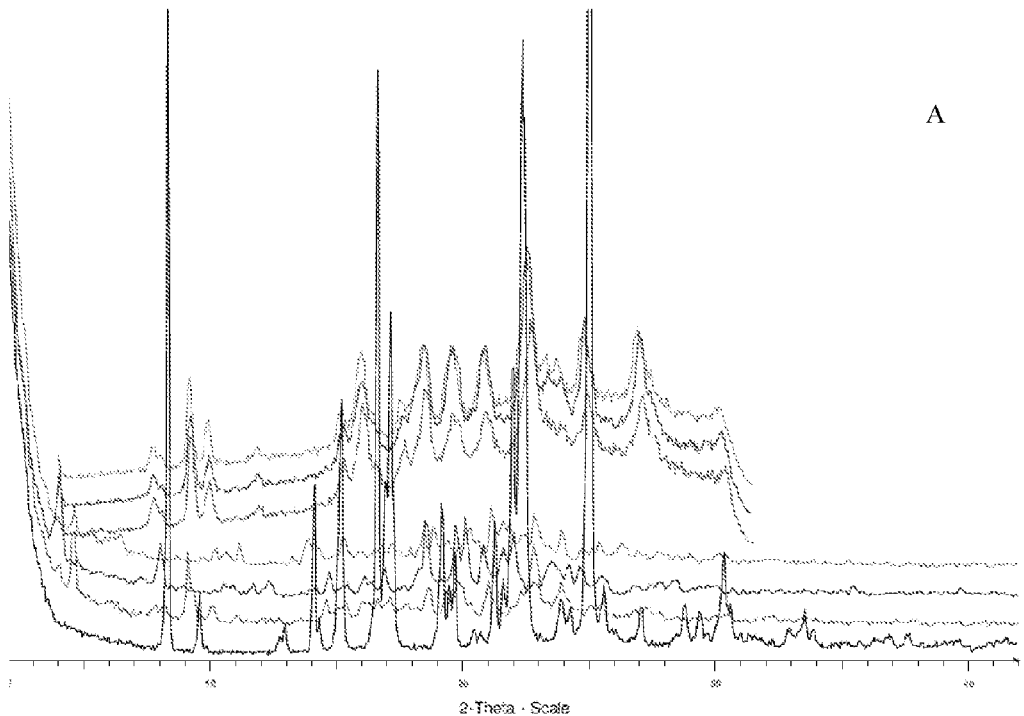
FIGS. 25A-25C: XRPD of Compound A methane sulfonic acid salt: pre- and post-storage at 40° C. and 75% RH (the top three curves showing post-storage XRPD; the middle three curves showing pre-storage XRPD; and the bottom curve showing the XRPD of Compound A free base) (FIG. 25A), pre- and post-GVS (the bottom curve showing pre-GVS XRPD) (FIG. 25B), and pre- and post-storage at 40° C. and 75% RH (the bottom curve showing pre-storage XRPD) (FIG. 25C)
Figure 25B:
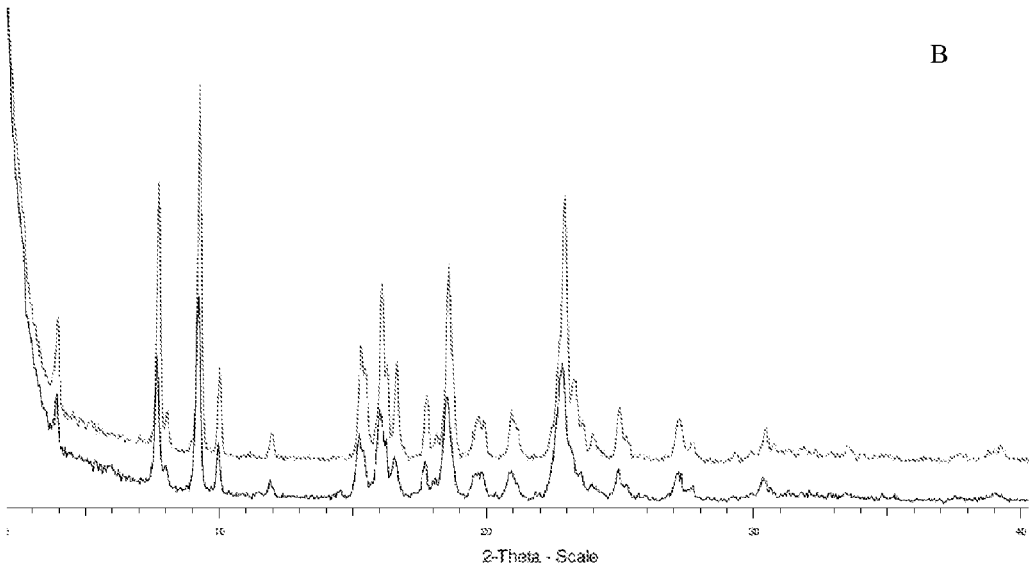
Figure 25C:
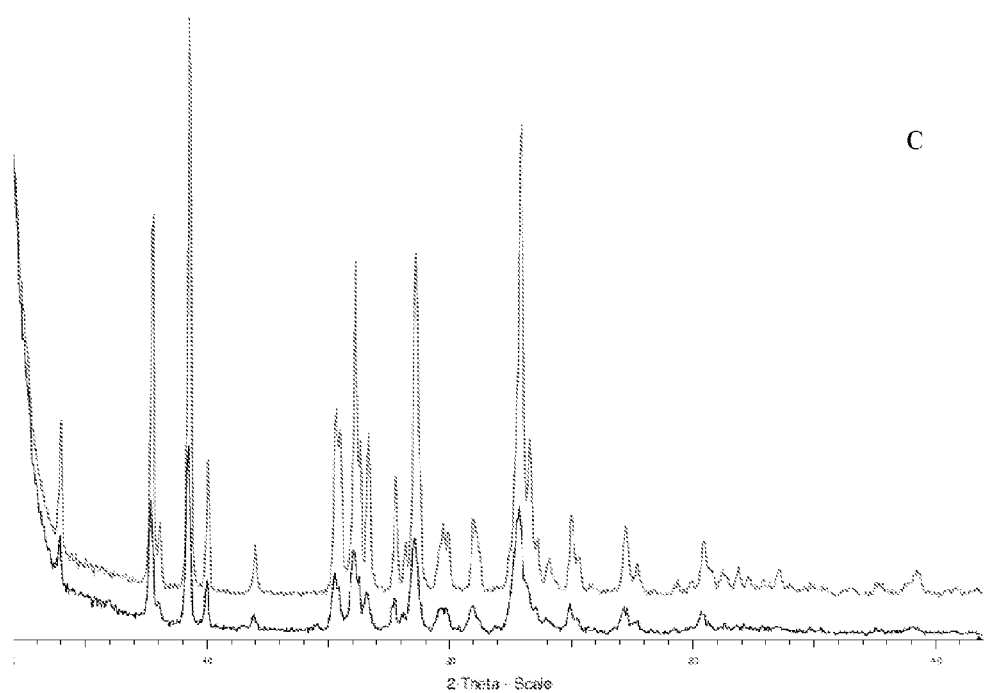

Compound A also formed tris-HCl salt. The XRPD showed that the tris-HCl was amorphous (FIG. 16). Compound A tris-HCl salt was highly soluble in water. Stability study showed that under storage, Compound A tris-HCl salt partially transformed to bis-HCl salt and/or mono-HCl salt and exhibited distinct XRPD pattern (FIG. 22).

Example 18

Preparation of Compound A mesylate and polymorphs

Approximately 10 mg of Compound A free base was weighed accurately and added to 50 volumes of the appropriate solvent were added. The solvents included dioxane, ethyl acetate, IPAc, IPA, THF, MEK, acetone, ethanol, acetonitrile, and nitromethane. The samples were warmed to 50° C. for an hour and the various methane sulfonic acid stock solutions (e.g., in THF, ethyl acetate, or ethanol) were added. For formation of mono-salts, 1.1 equivalents of the acid were added; and for formation of bis-salts, 2.1 equivalents of the acid were added. The samples were left at 50° C. for additional 4 hours and cooled to 0° C. at 0.1° C./min and left at 0° C. overnight.

Polymorphs of Compound A mesylate salt were isolated from various solvents, including, for example, THF, ethyl acetate, and ethanol. Polymorphs of Compound A mesylate salt are highly soluble in water and stable under storage. No change in the XRPD of polymorphs of Compound A mesylate salt was observed pre- and post-storage under 40° C. and 75% RH. Neither was any loss of methane sulfonic acid observed.

Example 19

Preparation of Compound A methane sulfonic acid salts and polymorphs

Methane sulfonic acid (1 M solution in THF) (3.4 ml, 3.4 mmol, 3.3 equiv.) was added to a stirred solution of Compound A free base (450.1 mg, 1.04 mmol, 1 equiv.) in THF (22.5 ml, 50 relative volumes) at 50° C. over a period of 1 min. A very thick precipitate formed and the stirring rate was increased to obtain a mobile suspension. The mixture was stirred at 50° C. for 1 h then cooled to 0° C. at 0.1° C./min and stirred for a further 6 h. An aliquot was taken, the solid was isolated by vacuum filtration, dried under suction and analysed by XRPD to confirm formation of the desired material. The remaining mixture was stirred at 0° C. for a further 1 h. The solid was isolated by vacuum filtration and dried under suction to yield the desired material as a yellow solid. Table 15 shows analysis of one of the polymorphs of the Compound A mesylate salt.

TABLE 15

Figure 26:
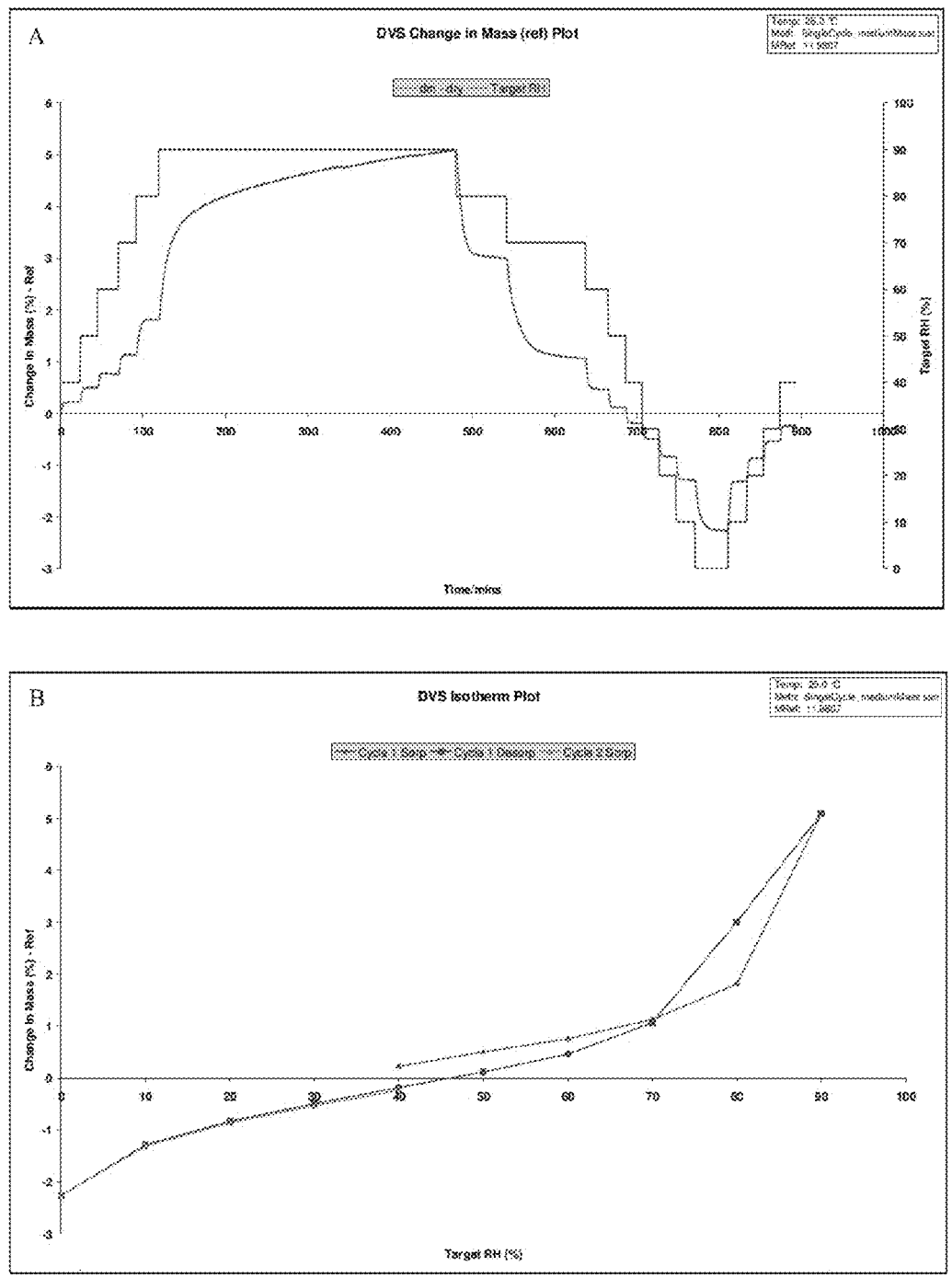
FIG. 26: GVS of Compound A methane sulfonic acid salt. (A) kinetic plot, (B) isotherm plot.
Figure 27:
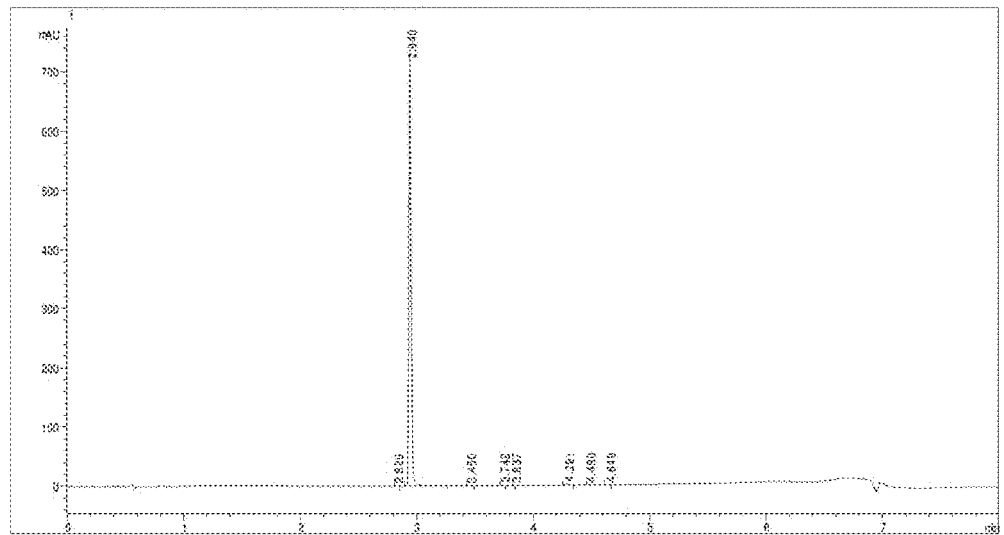
FIG. 27: HPLC of Compound A methane sulfonic acid salt
Figure 28:
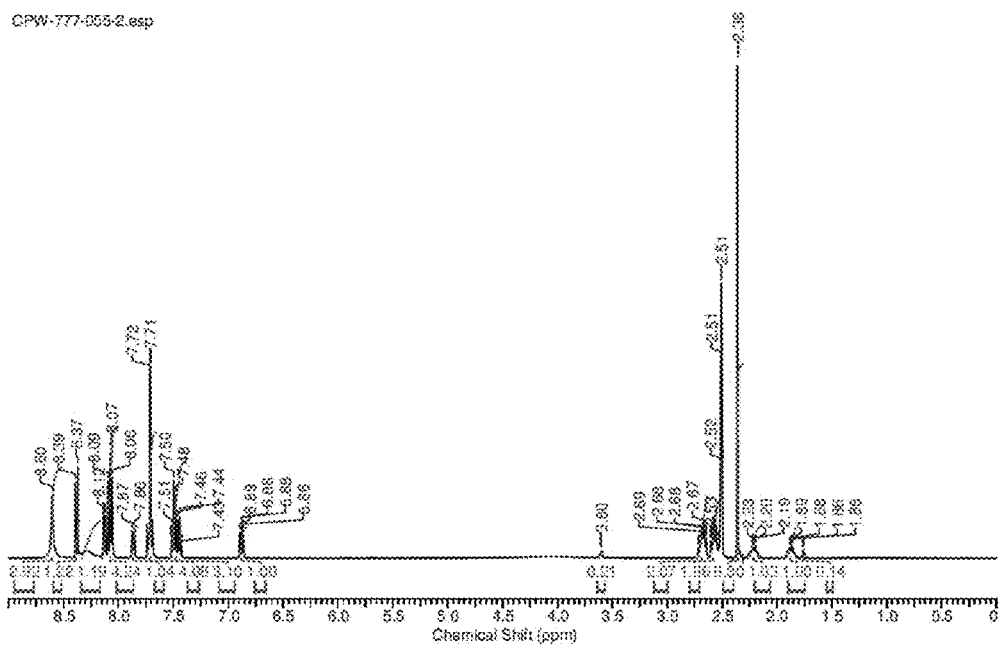
FIG. 28: $^1$H NMR of Compound A methane sulfonic acid salt
Figure 29:
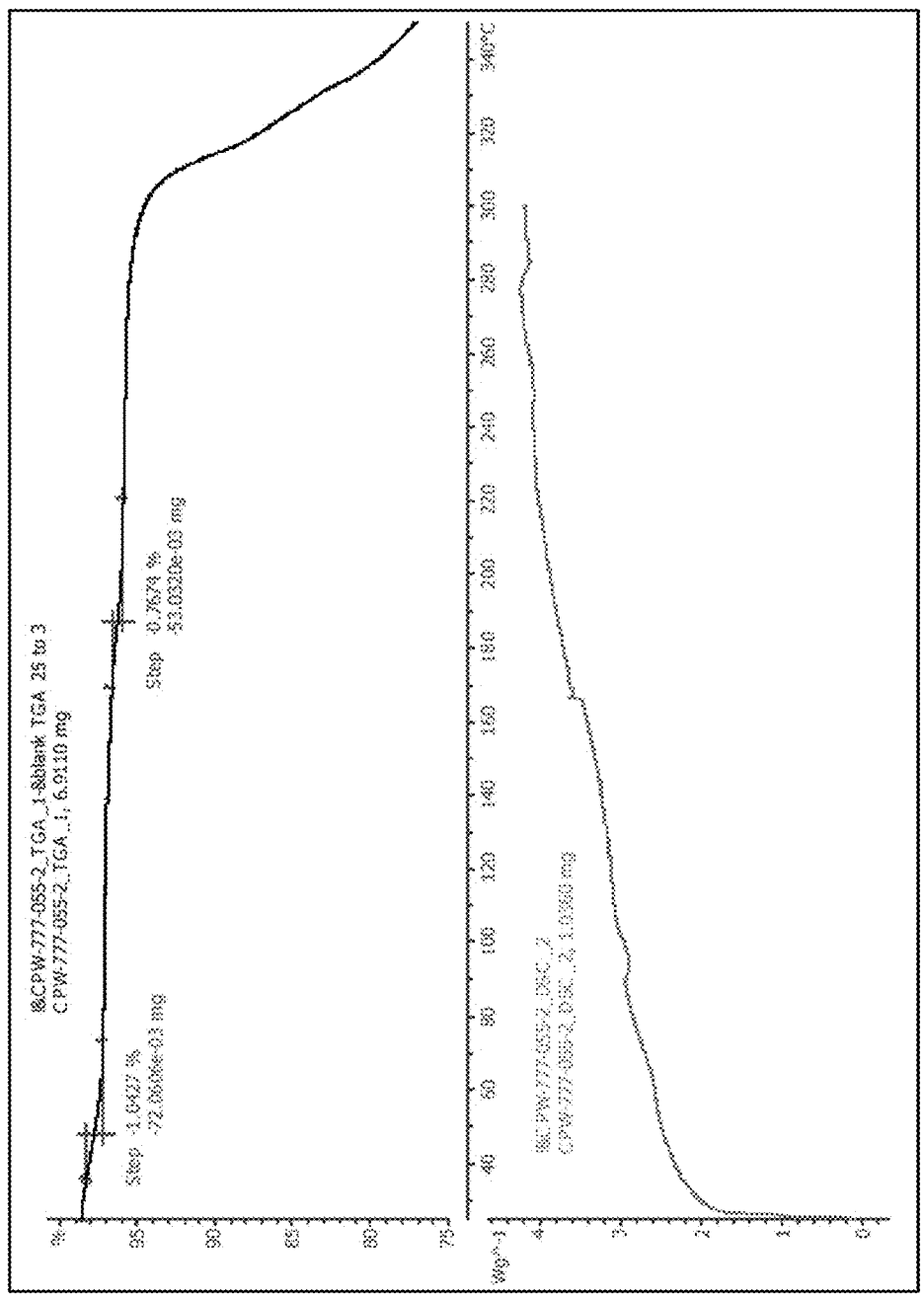
FIG. 29: DSC and TGA thermogram of Compound A methane sulfonic acid salt

| | | |
|---|---|---|
| ¹H NMR | 2.1 equi. methane sulfonic acid 0.5% residual THF | (FIG. 28) |
| DSC | No significant events before 300° C. | (FIG. 29) |
| TGA | 1.0% wt loss 36 to 74° C. (0.4 equi. water) 0.8% wt loss 170 to 220° C. decomposition >300° C. | (FIG. 29) |
| IC | 1.9 equi. methane sulfonic acid | |
| Aqueous solubility | >50 mg/ml in 5 min (pH 2.1) | |
| GVS | Reversible uptake of ~5 wt % water from 40-90% RH Reversible loss of ~2% water from 40 to 0% RH No change in XRPD after GVS | (FIG. 26) |
| PLM | Birefringent laths (5 to 75 μm) and irregular shaped particles and agglomerates to >100 μm | |
| HPLC | 99.6% (largest % impurity: 0.3% at 1.46 RRT) | (FIG. 27) |
| Storage under 40° C. and 75% RH, 7 days | No change in XRPD or ¹H NMR | |

Example 20

Polymorphs of Compound A bis-mesylate

Figure 30:
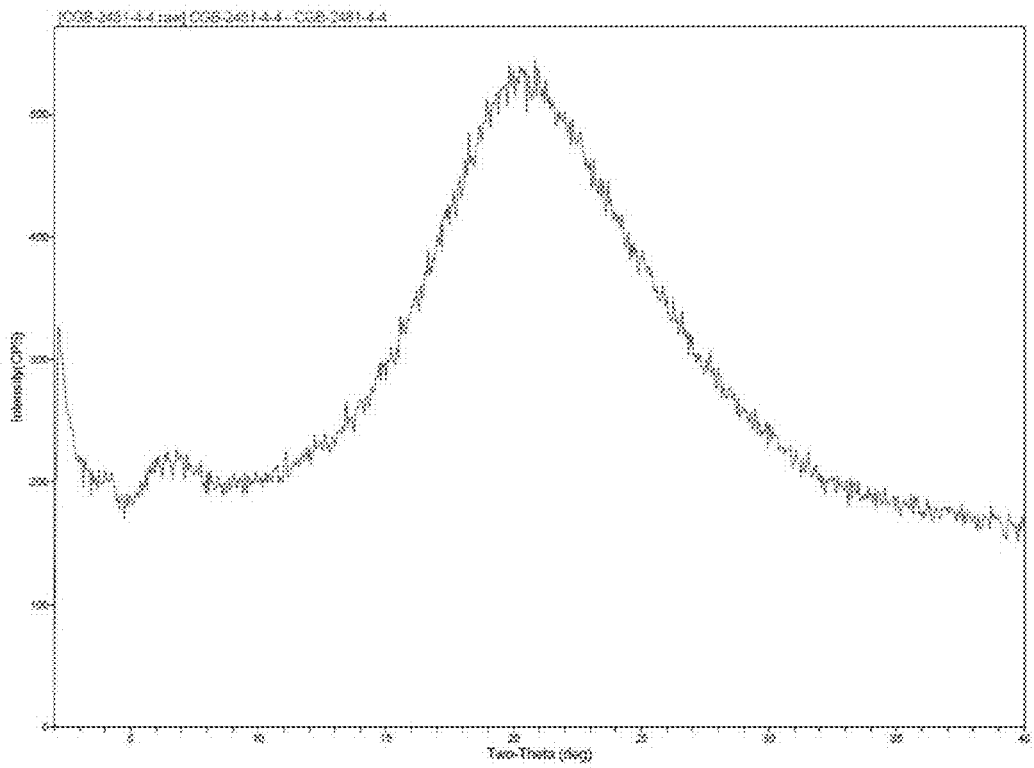
FIG. 30: XRPD of lyophilized Compound A bis-methane sulfonic acid salt
Figure 31:
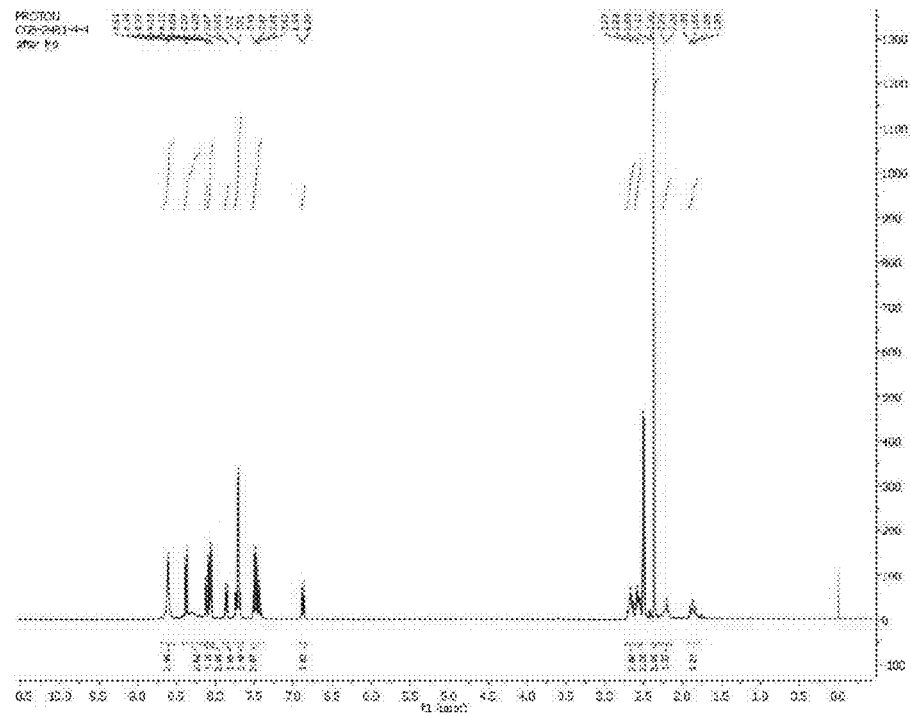
FIG. 31: $^1$H NMR of lyophilized Compound A bis-methane sulfonic acid salt

Compound A bis-mesylate was lyophilized to generate an amorphous salt (FIG. 30). Maturation of Compound A bis-mesylate was conducted with various solvent under different conditions. 250 mg of amorphous mesylate salt was slurried in 5 mL of the appropriate solvent.

The temperature was cycled between 55° C. and 0° C. with a 4 hour hold at each temperature. Between cycles, the temperature was adjusted over one hour to the next set temperature. The temperature cycle was repeated 4 times. Once the cycle was complete, the slurries were filtered and each isolated solid was analyzed by XRPD. Twenty-three solvents tested afforded filterable solids. XRPD patterns are summarized in Table 16. Two distinct polymorphs of Compound A bis-mesylate were identified.

TABLE 16

| Solvent | Polymorph |
|---|---|
| MeOH | Form A + Form B (minor) |
| EtOH | Form A |
| i-PrOH | Form B |
| EtOAc | Form B |
| i-PrOAc | Form A |
| PrOAc | Form A |
| BuOAc | Form A |
| THF | Form A |
| 2-MeTHF | Form A (high amorphous content) |
| Toluene | Solvate |
| Acetonitrile | Form B |
| Benzonitrile | Form A |
| Chloroform | Form B |
| 1,2-Dichloroethane | Form B |
| Hexafluoro benzene | Amorphous |
| n-Heptane | Amorphous |
| Isopropylether | Amorphous |
| 1,2-Dimethoxy ethane | Form B |
| Nitromethane | Form B |
| Isobutanol | Form B |

TABLE 16-continued

| Solvent | Polymorph |
|---|---|
| Acetone | Form B |
| Methyl Ethyl Ketone | Form B |
| Methyl Isobutyl Ketone | Form A (minor) + Form B |

Example 21

Polymorphs of Compound a Bis-Mesylate Form a

A solution of Compound A free-base (41.06 g, 94.93 mmol, 1.0 equiv.) in THF (2.0 L, 50 vol.) at 50° C. was treated with a 1 M solution of methanesulfonic acid (208 mL, 208 mmol, 2.2 equiv.) in THF over the course of 3 minutes. The resulting thick slurry was stirred at 50° C. for an additional hour before being cooled to 20° C. and stirred at 20° C. for 17 hours. The resulting slurry was then filtered and the solids were washed with THF (2×300 mL) and dried under vacuum at 50° C. for 22 hours and 20° C. 48 hours. This yielded Compound A bis-mesylate as a light yellow, crystalline solid (58.1 g, 98% isolated yield). Alternatively, Form A may be further slurried in dry methanol at about 22° C. for about 48 hours to improve crystallinity.

The XRPD, ¹H NMR, DSC, TGA and IR data for Compound A bis-mesylate Form A are provided as FIGS. 32-36. The XRPD pattern (FIG. 32) for Form A is distinguished by the observed single peaks at 4.1, 7.8, 9.4, 10.1, 12.1, 15.5, 16.2, 18.8, 19.9, 21.1, 23.0, 25.1 and 27.4 of ° 2θ. ¹H NMR of the Form A salt shows the presence of the mesylate counter-ion at 2.41 ppm corresponding to 1.87 equivalents. Ion chromatography measured 30.1% (wt) of methanesulfonic acid which corresponds to 1.94 equivalents (anhydrous basis). Residual THF was also observed in the ¹H NMR which corresponds to the OVI analysis by GC measured at 2918 ppm of THF. The DSC (FIG. 34) shows a sharp endotherm with an onset temperature of 305.9° C. and a melt at 307.6° C. There was no significant weight loss events observed in the TGA (FIG. 35) until the melting event observed in the DSC experiment. The IR spectrum which is representative of Form A is given as FIG. 36.

Additional characterization of Form A is described below.

PLM analysis indicated that Form A is birefringent with a needle-like morphology.

TGA showed a weight loss of about 1.47% below about 60° C., likely due to unbound solvent/water. No further weight losses were observed prior to degradation above about 300° C. The DTA indicated a small endotherm at onset about 92.2° C. (peak 96.1° C.), and a final sharp endotherm at onset about 302.6° C. (peak 312.8° C.).

DSC analysis showed a small endothermic event at onset about 107.1° C. (peak 115.4° C.), and a final endotherm at onset about 305.1° C. (peak 308.2° C.).

A sample of Form A was heated to about 150° C. and post-heating XRPD analysis was carried out, giving a diffractogram consistent with Form A. Further TG/DTA analysis was carried out after heating to about 150° C. and then allowing the sample to cool to ambient temperature. The analysis was consistent with the initial TG/DTA, again showing the endotherm at about 92.2° C. These heating experiments indicated that the endothermic event at about 92.2° C. likely corresponds to a solid to solid transition, where Form A converts to a higher melting form above this temperature i.e. an enantiotropic relationship between Form A and a high temperature form.

Further confirmation of this transition was sought through variable temperature XRPD analysis (VT-XRPD), where a sample of Form A was placed into a capillary and XRPD analysis carried out at 23, 115, 150 and 200° C. At 23° C., the diffractogram was consistent with Form A. At 150 and 200° C., diffraction patterns different from Form A were observed indicating conversion to a different polymorphic form. This different form was assigned as Form K. At 115° C. (transition temperature), a mixture of Form A and Form K was observed. The VT-XRPD analysis confirmed the solid-to-solid transition at about 107.1° C. (peak 115.4° C.) and a likely enantiotropic relationship between the two forms.

A water content of about 1.1% was measured by Karl-Fischer Titration.

An HPLC purity of 99.8% was observed.

HPLC concentration analysis indicated an aqueous solubility of about 383.4 mg/mL. XRPD analysis after slurrying Form A in deionised water for about 24 hours indicated that Form A converted to Form E.

DVS analysis showed a water uptake of about 2.4% up to 70% RH, indicating moderate hygroscopicity. No significant hysteresis was observed. XRPD analysis carried out after DVS analysis gave a diffractogram consistent with Form A, although some loss in crystallinity was observed.

No change in the polymorphic form was observed after stability tests at 40° C./75% RH, 80° C. and at ambient temperature. HPLC analysis indicated a purity of about 99.8% for 40° C./75% RH, about 99.8% for 80° C. and about 99.7% at ambient temperature.

Form B

A slurry of Compound A free-base (5.0 g, 11.56 mmol, 1.0 equiv.) in 2% H$_2$O/MeOH (50 mL, 10 vol.) at 55° C. was treated with neat methanesulfonic acid (1.51 mL, 23.35 mmol, 2.02 equiv.). The resulting solution was stirred at 55° C. for 5 minutes. Addition of i-PrOAc (95 mL) over a period of 80 minutes resulted in the formation of a thick slurry which was cooled to 20° C. and stirred for 18 hours. The slurry was filtered and the wet cake washed with i-PrOAc (50 mL) prior to drying the filter cake under vacuum at 55° C. for 22 hours. The resulting solids were white solid (7.07 g, 98% yield). Form B may be scaled up by slurrying amorphous Compound A bis-mesylate salt in 2-propanol with A$_w$=0.35 at about 22° C. for about 72 hours.

The XRPD, $^1$H NMR, DSC, TGA and IR data for Compound A bis-mesylate Form B are provided as FIGS. 37-41. The XRPD pattern (FIG. 37) for Form B is distinguished by the observed doublet peak at 6.2 and 6.6° of N. $^1$H NMR of the Form B salt (FIG. 38) shows the presence of the mesylate counter ion at 2.39 ppm corresponding to 1.91 equivalents. Ion chromatography measured 29.9% methanesulfonic acid which corresponds to 1.92 equivalents of mesylate (anhydrous basis). Residual i-PrOAc is observed by $^1$H NMR which corresponds to the OVI analysis by GC which measured 32,783 ppm of i-PrOAc. The DSC (FIG. 39) shows a broad endotherm with an onset temperature of 182.6° C. and a melt at 194.1° C. The endotherm is immediately followed by an exotherm at an onset temperature of 199.3° C. with a peak at 204.5° C. A second endotherm was observed with an onset temperature of 299.9° C. and a second melt at 302.3° C. There were 3 separate weight loss events observed in the TGA (FIG. 40). One event precedes the melt/recrystallization event observed in the DSC (<150° C.), one corresponds with the melt/recrystallization event (~250° C.) and the third occurs during the second endothermic event (~300° C.). The representative IR spectrum for Form B is given as FIG. 41.

Additional characterization of Form B is described below.

PLM analysis indicated that Form B is birefringent with small rod/needle-like crystals.

After air drying at ambient temperature for 2-3 days, TGA showed a 1.90% weight loss below about 50° C., followed by a 4.26% weight loss between about 50 and 130° C., with a further weight loss of 2.35% between about 130 and 190° C. The DTA trace showed an initial endothermic event at onset about 189.8° C. (peak 195.6° C.), followed by an exothermic event at peak 205.7° C. A sharp endotherm was then observed at onset about 303.6° C. (peak 306.8° C.). After drying under vacuum at ambient temperature for a further 1 day, TGA showed a 2.37% weight loss below about 60° C., followed by a 2.61% weight loss between about 60° C. and 140° C., with a further weight loss of 2.43% between about 140° C. and 200° C. The DTA trace showed an initial endothermic event at onset about 187.3° C. (peak 193.6° C.), followed by an exothermic event at peak 205.7° C. A sharp endotherm was then observed at onset about 300.0° C. (peak 304.9° C.). After drying at 50° C. for a further day, TGA showed a 0.81% weight loss below about 60° C., followed by a 1.54% weight loss between about 60° C. and 140° C., with a further weight loss of 2.39% between about 140° C. and 200° C. The DTA trace showed an initial endothermic event at onset about 189.3° C. (peak 195.0° C.), followed by an exothermic event at peak 205.8° C. A sharp endotherm was then observed at onset about 302.1° C. (peak 305.9° C.).

To assess the thermal transition which occurs between about 190° C. and 210° C. (after dehydration/desolvation), a sample of Form B was heated to about 250° C. and post-heating XRPD analysis was carried out on the resulting solid. The diffractogram obtained was consistent with Form A.

DSC analysis showed a broad endotherm at peak about 108.6° C. A further endotherm was observed at onset about 172.6° C. (peak 186.4° C.), followed by an exotherm at peak 201.4° C. A final endotherm was observed at onset about 298.1° C. (peak 302.2° C.).

A water content of about 2.3% was measured by Karl-Fischer Titration.

An HPLC purity of 99.7% was observed.

HPLC concentration analysis indicated an aqueous solubility of about 359 mg/mL.

XRPD analysis after slurrying Form B in deionised water for about 24 hours indicated that Form B converted to Form E.

DVS analysis indicated that some of the solvent present in Form B may have been forced out of the sample during the initial sorption cycle. The desorption cycles indicated a gradual loss from 90% down to 0% RH. XRPD analysis carried out after DVS analysis gave a diffractogram different from Form B and all other forms previously identified. This form was assigned as Form J.

During stability studies, Form B remained unchanged in terms of polymorphic form at ambient temperature but converted to Form J at 40° C./75% RH and Form I at 80° C. HPLC analysis indicated a purity of about 99.8% at 40° C./75% RH, about 99.8% at 80° C. and about 99.7% at ambient temperature.

Form C

A slurry of Compound A free-base (40.0 g, 92.48 mmol, 1.0 equiv.) in 2% H$_2$O/MeOH (480 mL, 12 vol.) at 55° C. was treated with neat methanesulfonic acid (12.1 mL, 185.9 mmol, 2.01 equiv.) and the resulting solution was seeded with Compound A bis-mesylate Form C. The resulting thin slurry was cooled to 50° C. over a period of 30 minutes and held for 1 hour before cooling the mixture to 40° C. over a period of 45 minutes. The slurry was stirred at 40° C. for 1 hour and the heat source was removed to slowly cool the slurry to ambient temperature. After stirring at 20° C. for 19 hours, the slurry was filtered. The solids were dried under vacuum at 60° C. for 24 hours to afford an off-white solid (41.52 g, 72% yield). Form C may be scaled up by slurrying Compound A bis-mesylate salt in aqueous methanol (2% water) at 60° C.

The XRPD, $^1$H NMR, DSC, TGA data for Compound A bis-mesylate Form C are provided as FIGS. 42-46. The XRPD pattern (FIG. 42) for Form C is distinguished by a single, shallow peak observed 6.2° of 2θ followed by additional peaks starting at 8.9°, 9.8° and 10.1° of N. $^1$H NMR analysis of Form C (FIG. 43) shows the presence of the mesylate counter ion at 2.41 ppm corresponding to 1.92 equivalents. Ion chromatography measured 30.7% methanesulfonic acid which corresponds to 1.99 equivalents of mesylate (anhydrous basis). A minor amount of residual MeOH is observed in the $^1$H NMR spectrum which corresponds to the OVI analysis by GC which measured 552 ppm MeOH. The DSC (FIG. 44) shows a sharp endotherm with an onset temperature of 286.1° C. and a melt at 288.5° C. There was no significant weight loss events observed in the TGA (FIG. 45) until the melting event observed in the DSC experiment, consistent with decomposition of the sample. The IR spectrum of Form C is provided as FIG. 46.

Figure 47A:
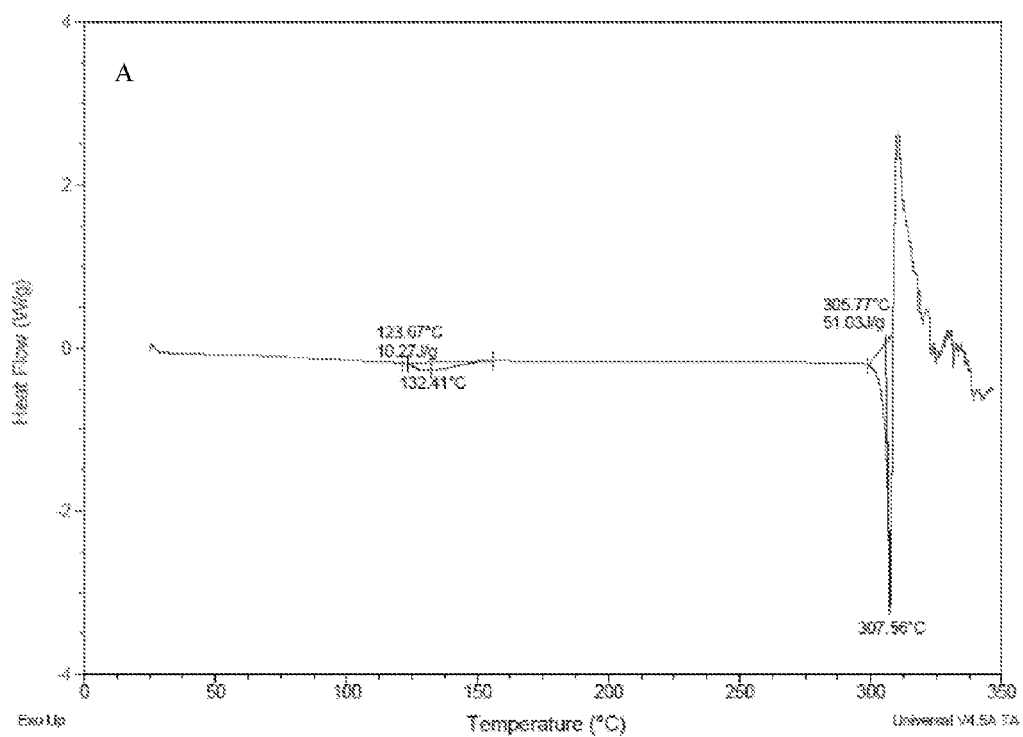
FIGS. 47A-47C: DSC of Form A (FIG. 47A) and Form B (FIG. 47B) of Compound A methane sulfonic acid salt, and overlay of DSC of Form A and Form B (FIG. 47C)
Figure 47B:
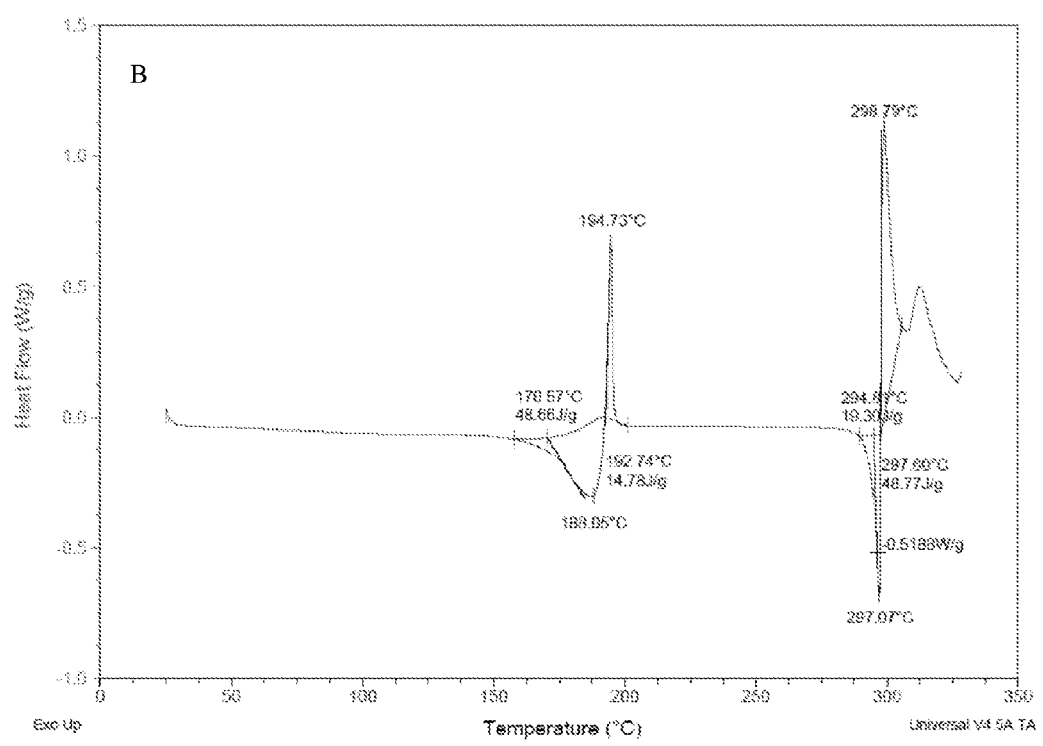
Figure 47C:
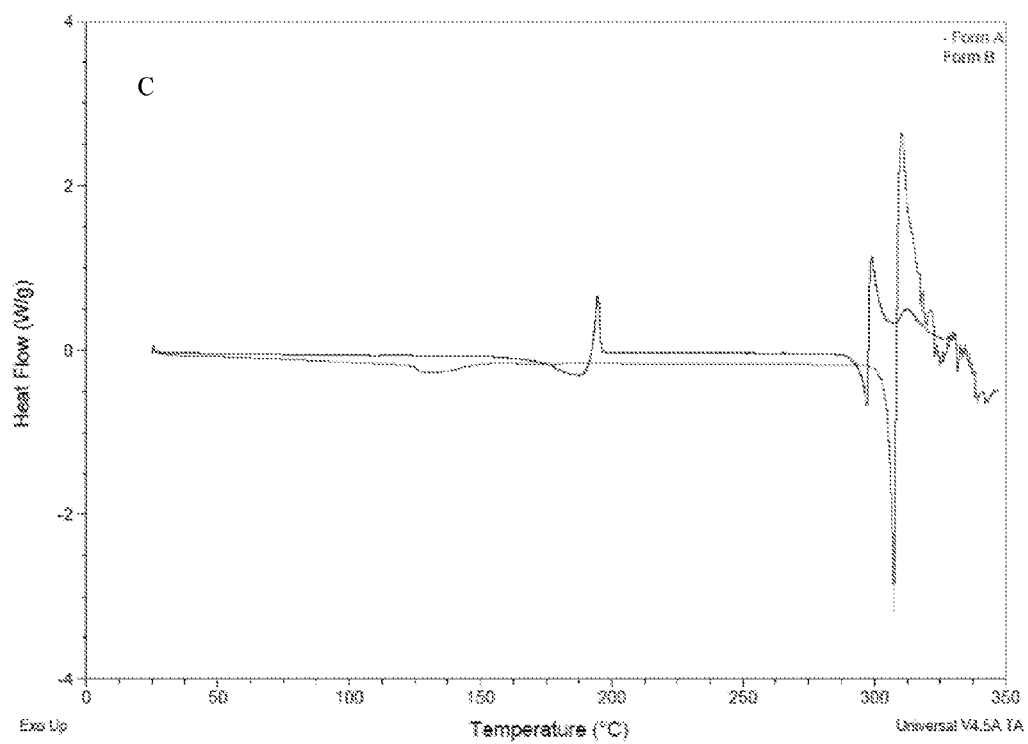

The DSC of Form A (FIG. 47A) and Form B (FIG. 47B) were measured and shown in overlay (FIG. 47C). A broad endotherm was observed in Form B that occurs around 190° C. followed by a sharp exotherm at 195° C. indicative of a potential change in form. A second endotherm occurs at 297° C. and this is similar to the endotherm observed in Form A.

Figure 48:
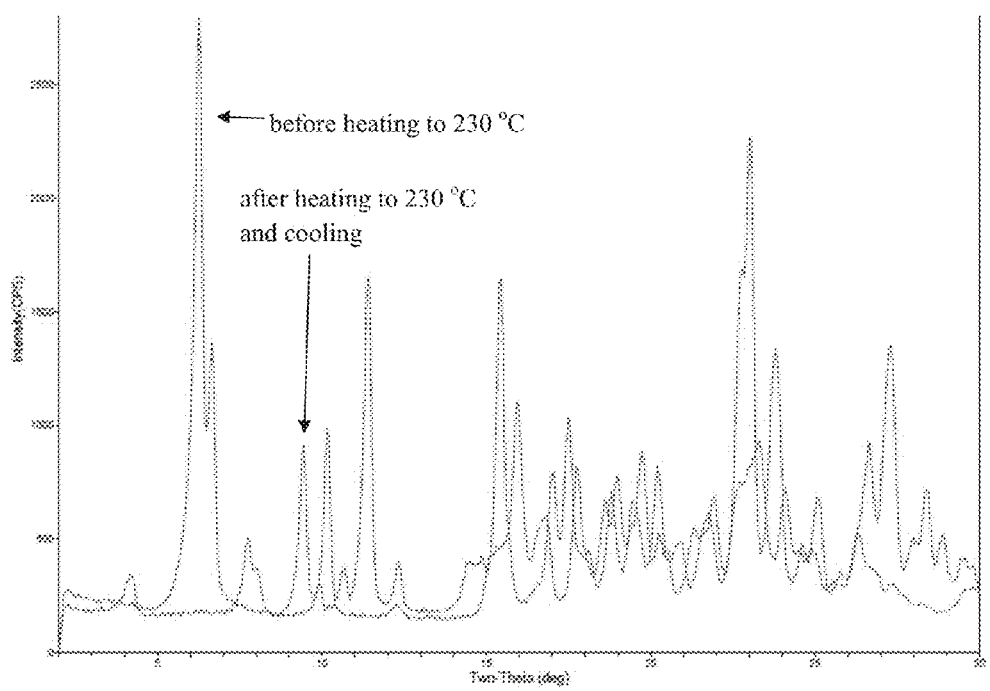
FIG. 48: XRPD of Form B of Compound A methane sulfonic acid salt before and after heating
Figure 50:
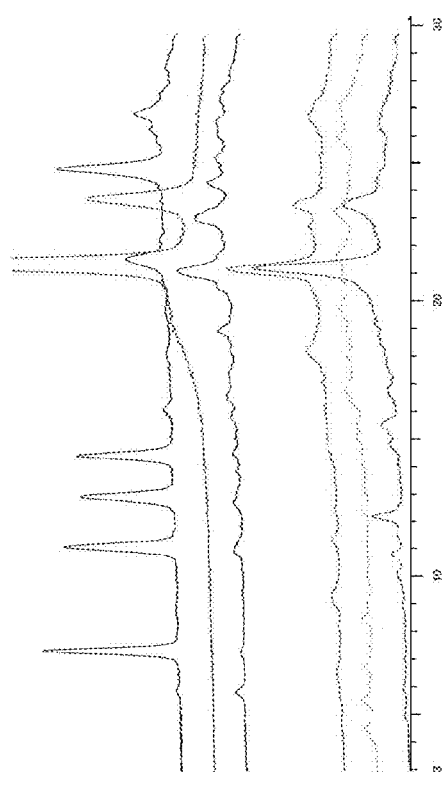
FIG. 50: XRPD of Compound A sulfuric acid salts
Figure 52:
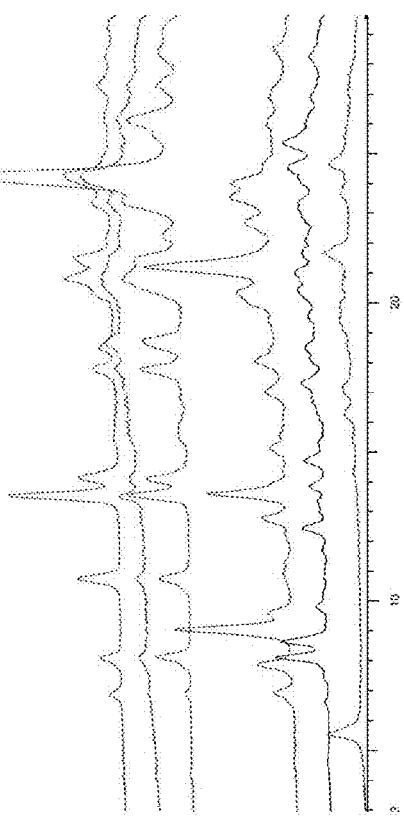
FIG. 52: XRPD of Compound A maleic acid salts
Figure 49:
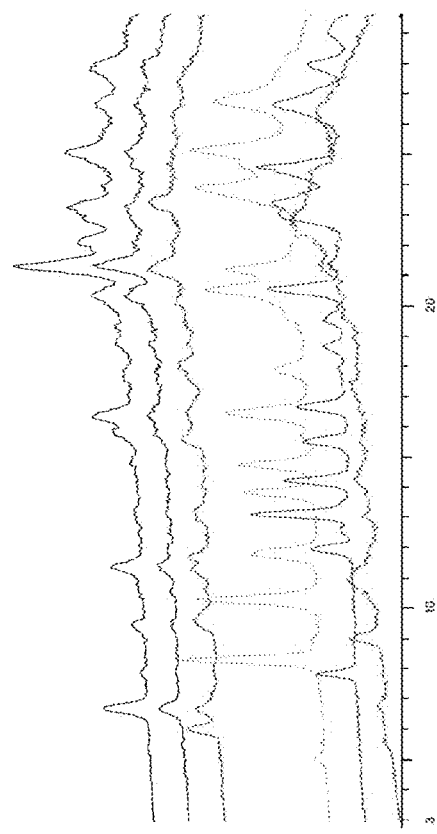
FIG. 49: XRPD of Compound A HCl salts
Figure 51:
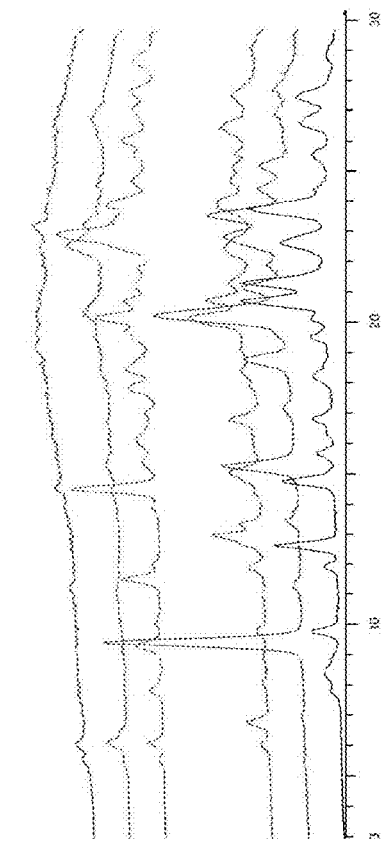
FIG. 51: XRPD of Compound A methane sulfonic acid salts
Figure 61:
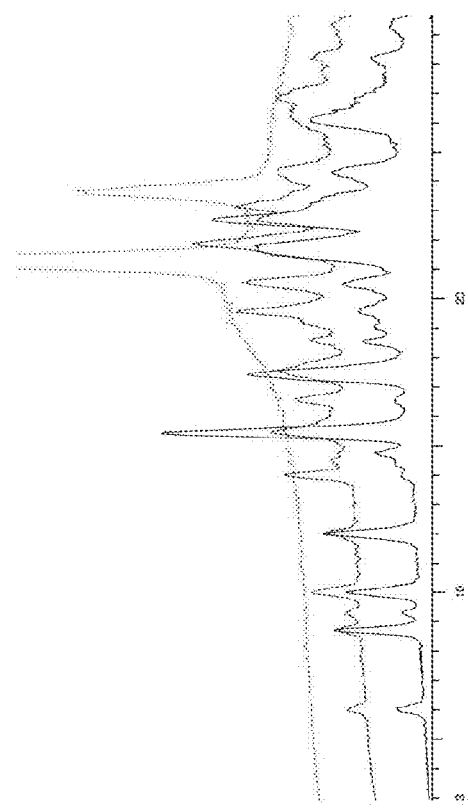
FIG. 61: XRPD of Compound A L-lactic acid salts
Figure 62:
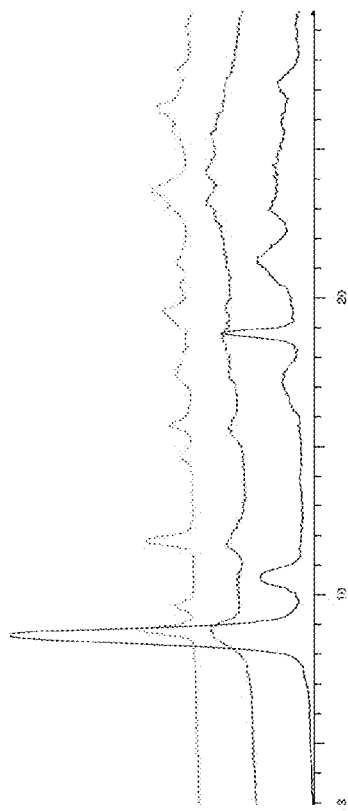
FIG. 62: XRPD of Compound A L-ascorbic acid salts
Figure 63:
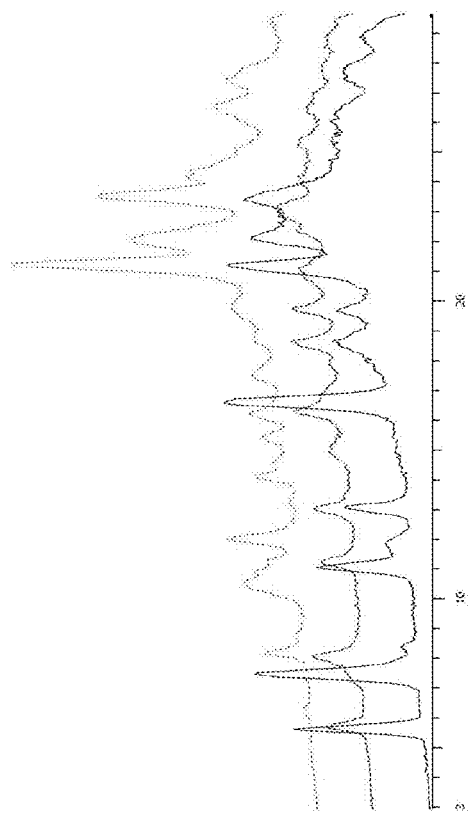
FIG. 63: XRPD of Compound A succinic acid salts
Figure 64:
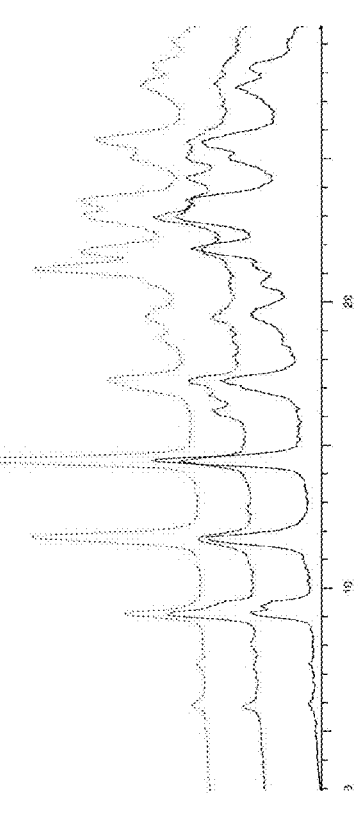
FIG. 64: XRPD of Compound A acetic acid salts
Figure 74:
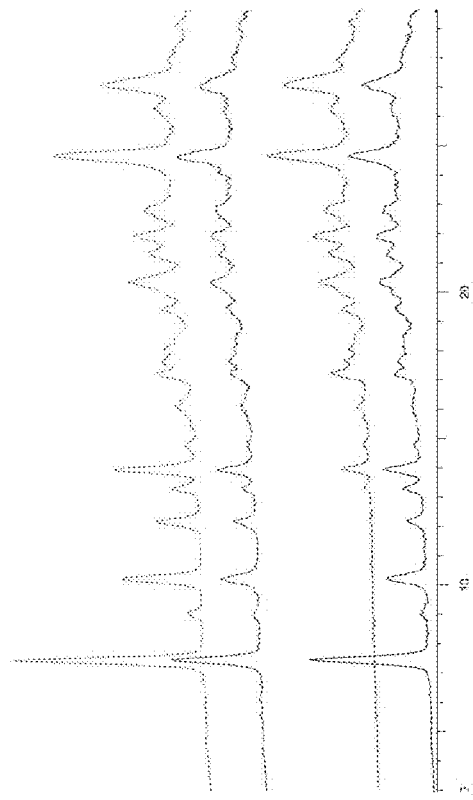
FIG. 74: XRPD of Compound A hippuric acid salts pre- and post-storage at 40° C. and 75% RH (2 pairs of curves shown, with the lower curve of each curve pair showing pre-storage XRPD)
Figure 76:
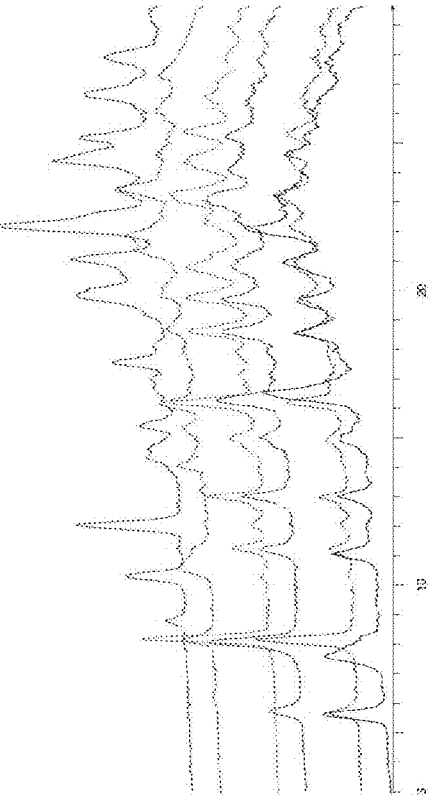
FIG. 76: XRPD of Compound A L-lactic acid salts pre- and post-storage at 40° C. and 75% RH (3 pairs of curves shown, with the lower curve of each curve pair showing pre-storage XRPD)
Figure 73:
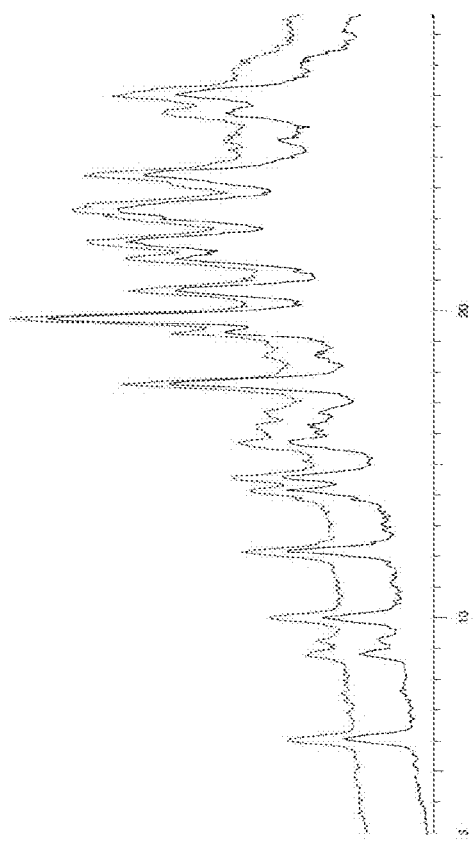
FIG. 73: XRPD of Compound A D-glucuronic acid salts pre- and post-storage at 40° C. and 75% RH (the lower curve showing pre-storage XRPD)
Figure 75:
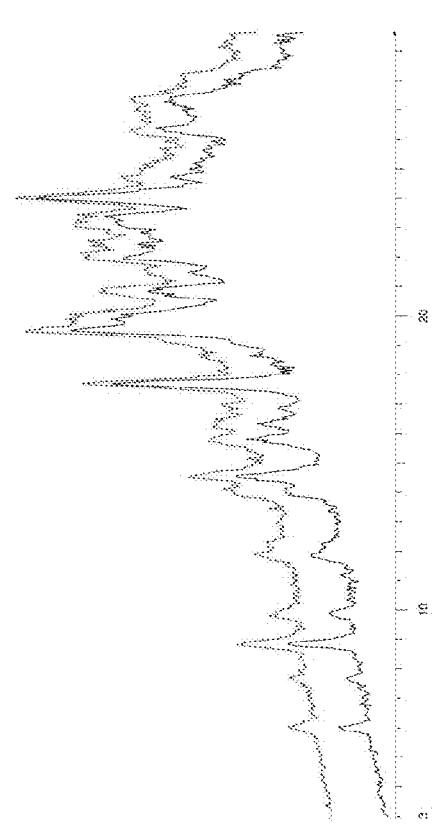
FIG. 75: XRPD of Compound A D-gluconic acid salts pre- and post-storage at 40° C. and 75% RH (the lower curve showing pre-storage XRPD)
Figure 78:
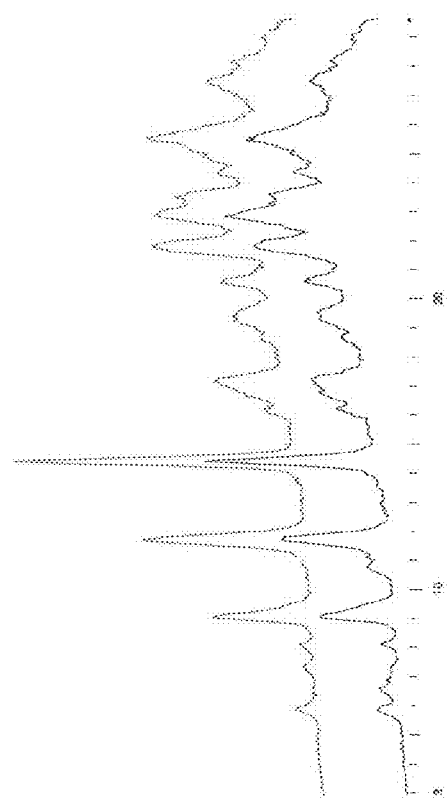
FIG. 78: XRPD of Compound A succinic acid salts pre- and post-storage at 40° C. and 75% RH (the lower curve showing pre-storage XRPD)
Figure 77:
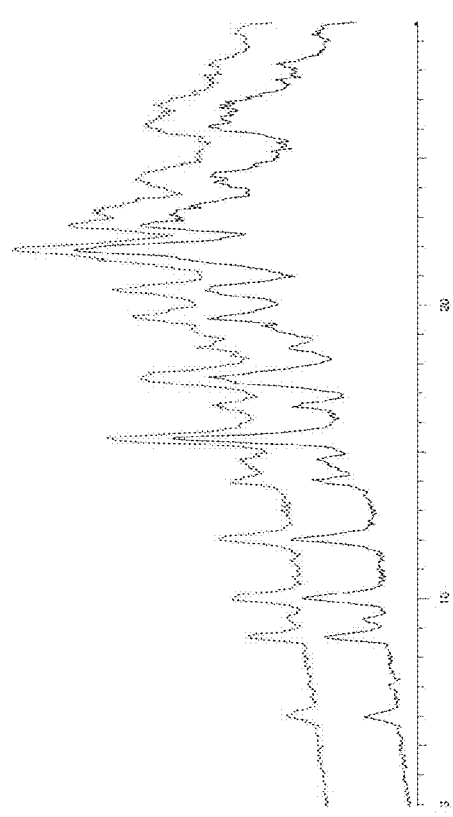
FIG. 77: XRPD of Compound A L-ascorbic acid salts pre- and post-storage at 40° C. and 75% RH (the lower curve showing pre-storage XRPD)
Figure 79:
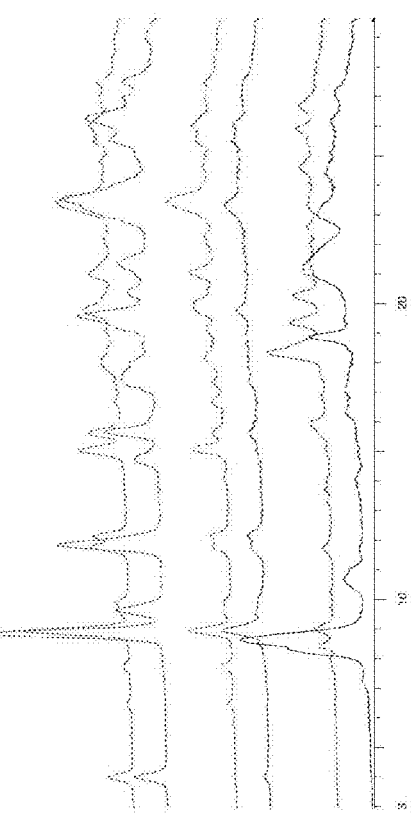
FIG. 79: XRPD of Compound A acetic acid salts pre- and post-storage at 40° C. and 75% RH (3 pairs of curves shown, with the lower curve of each curve pair showing pre-storage XRPD)
Figure 80A:
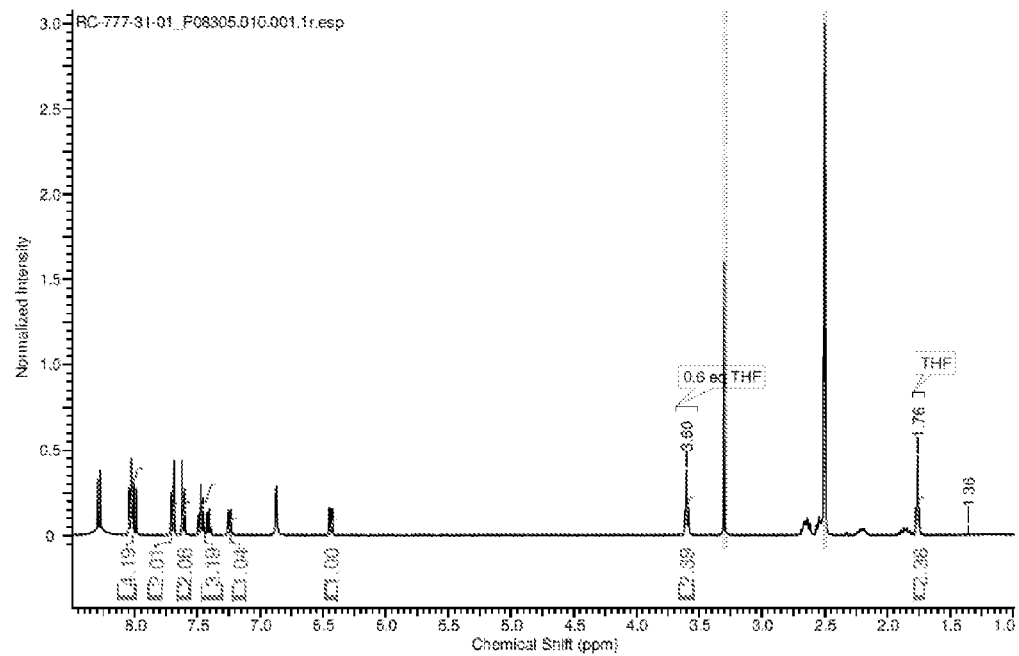
FIGS. 80A-80D: $^1$H NMR of Compound A mono-HCl salt from THF (FIG. 80A), ethyl acetate (FIG. 80B), and ethanol (FIG. 80C), and Compound A bis-HCl salt from ethanol (FIG. 80D)
Figure 80B:
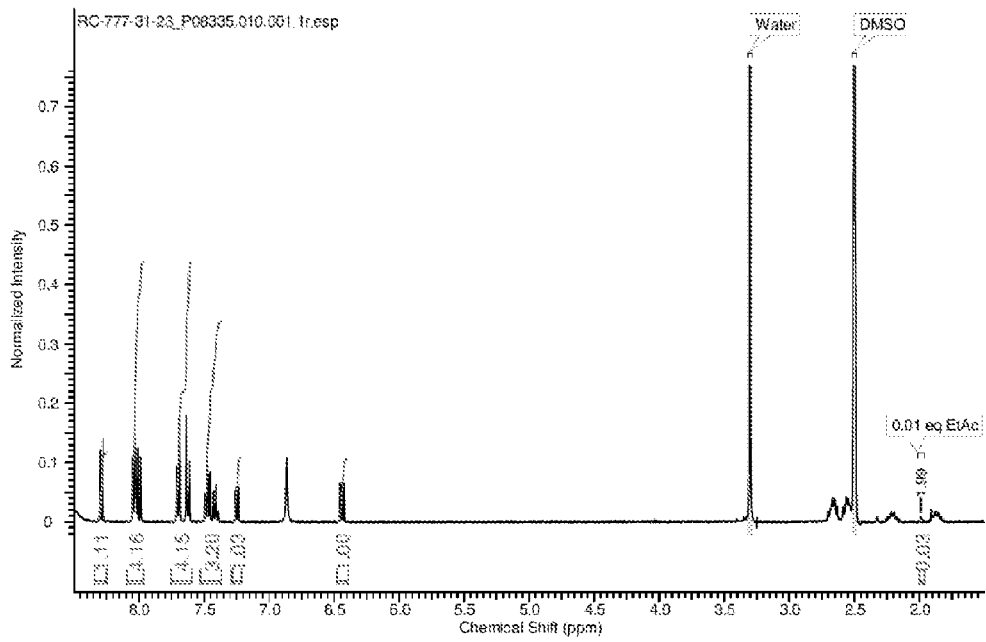
Figure 80C:
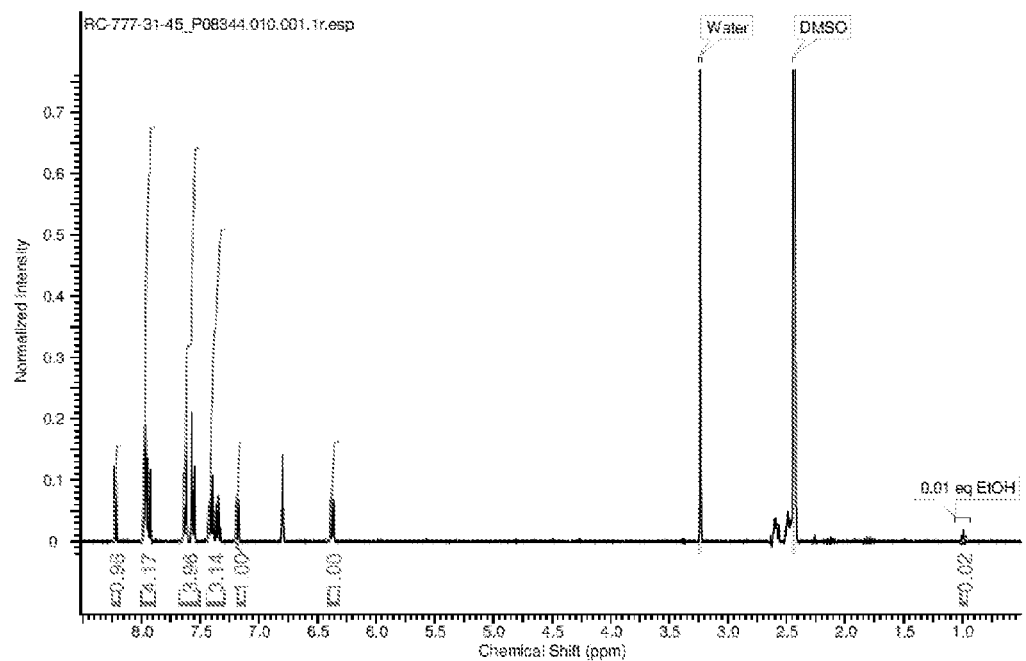
Figure 80D:
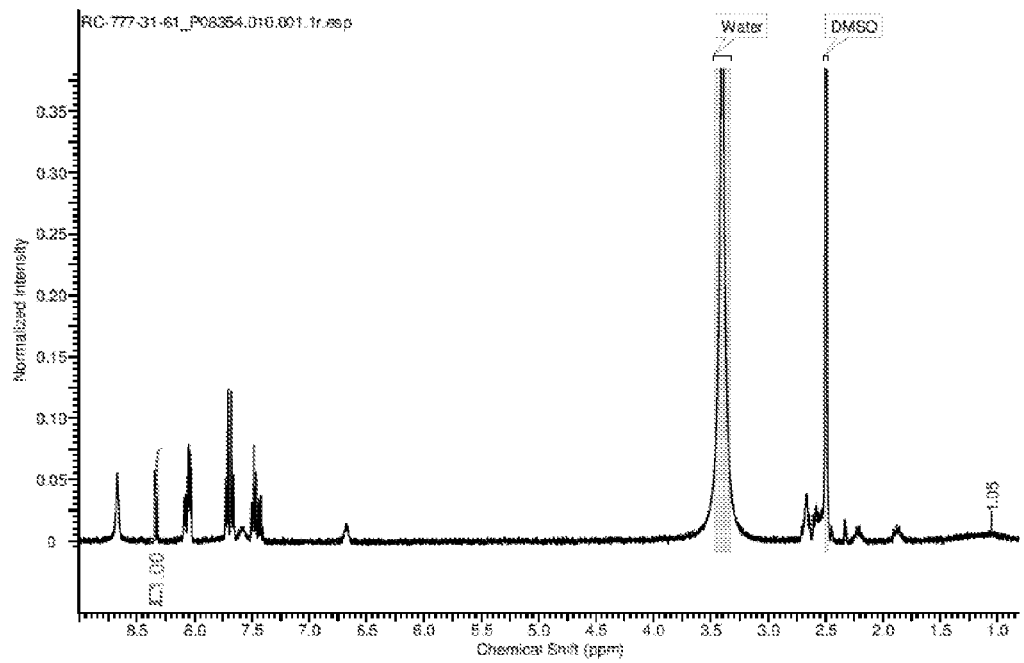
Figure 81:
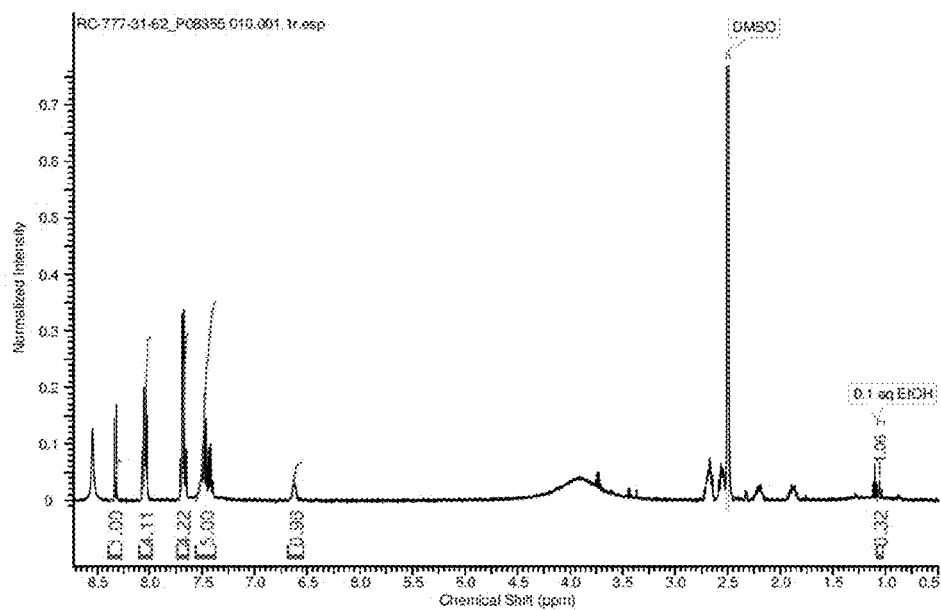
FIG. 81: $^1$H NMR of Compound A bis-sulfuric acid salt from ethanol
Figure 82A:
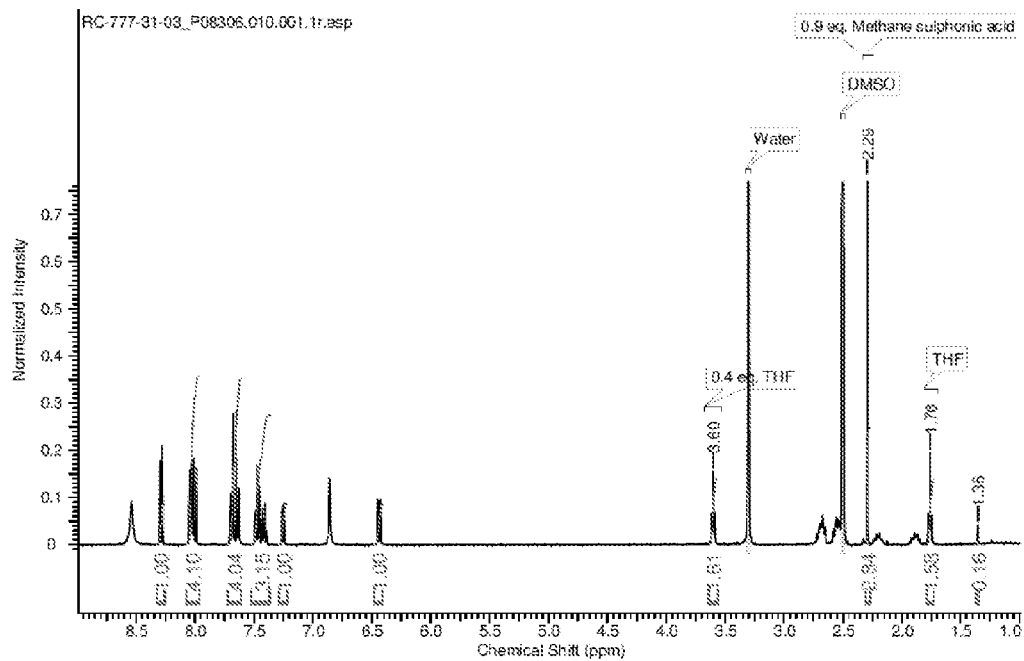
FIGS. 82A-82D: $^1$H NMR of Compound A mono-methane sulfonic acid salt from THF (FIG. 82A), ethyl acetate (FIG. 82B), and ethanol (FIG. 82C), and Compound A bis-methane sulfonic acid salt from THF (FIG. 82D)
Figure 82B:
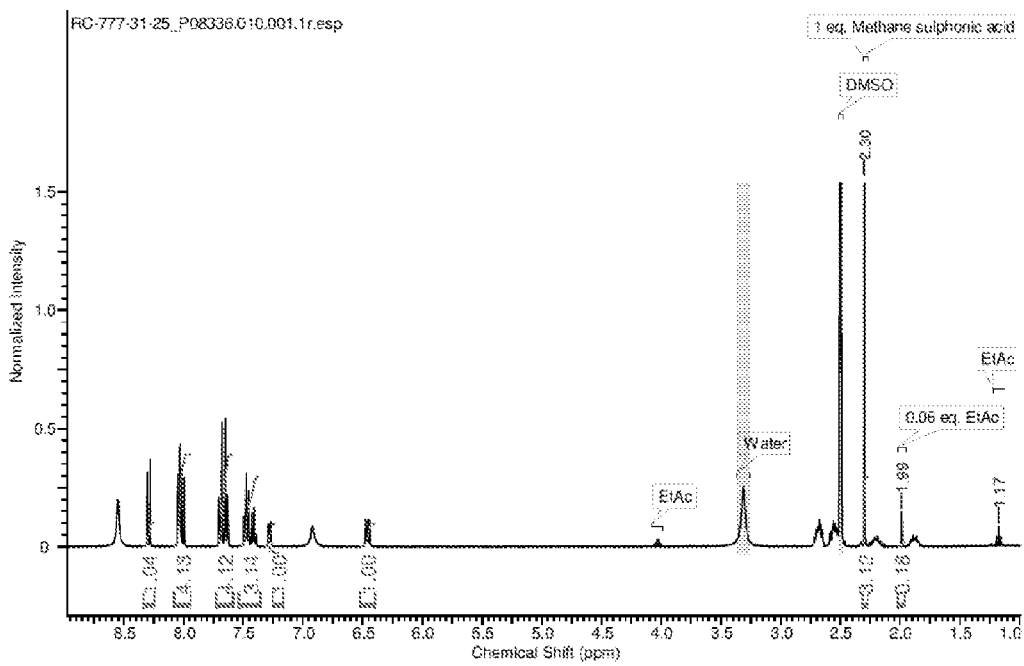
Figure 82C:
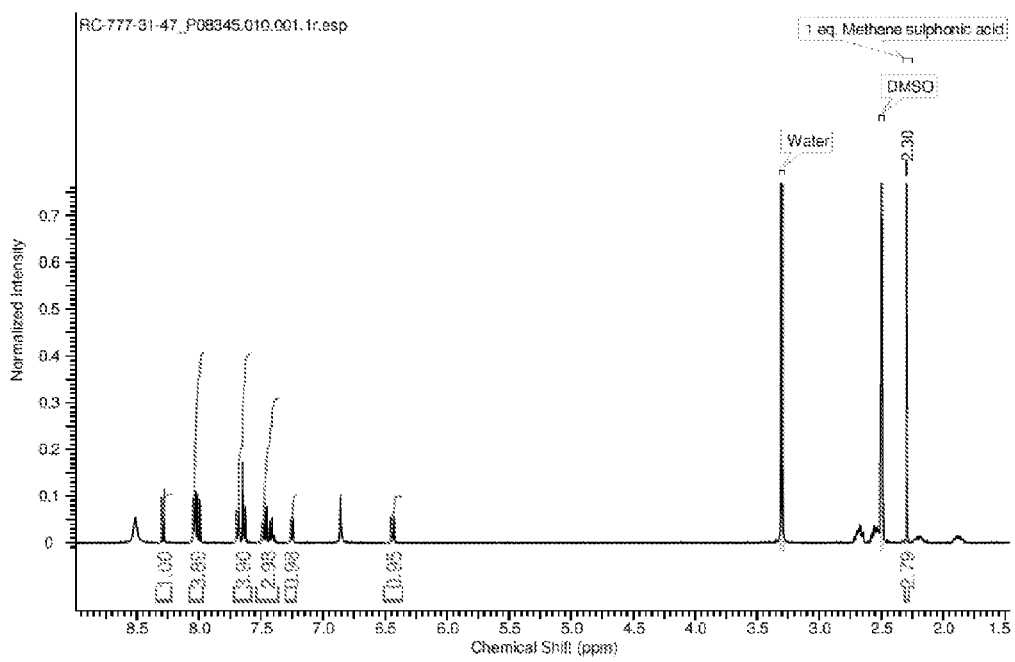
Figure 82D:
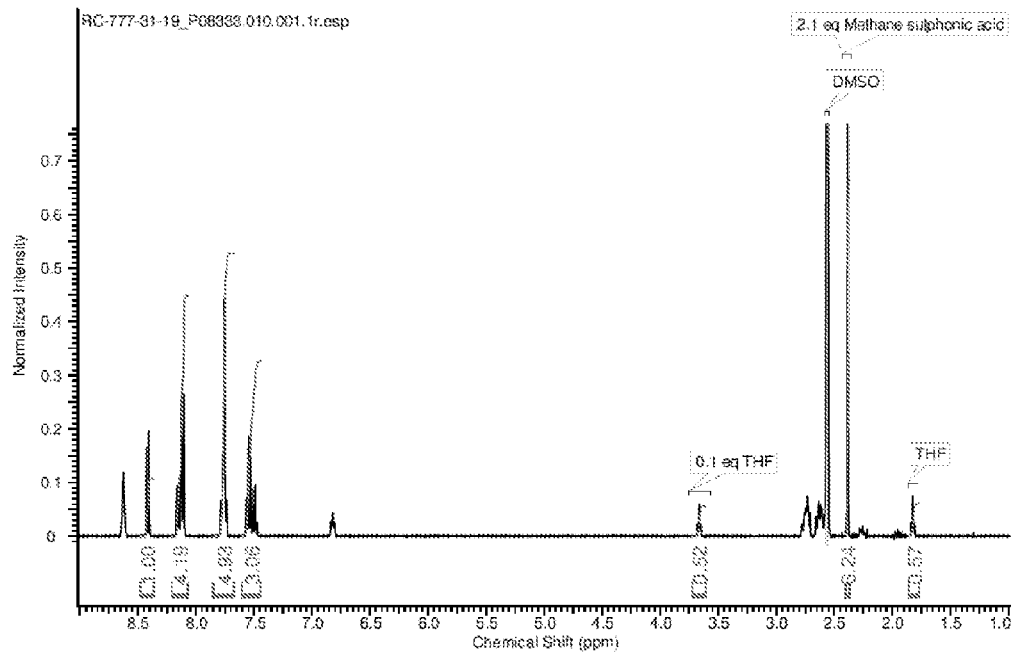
Figure 83A:
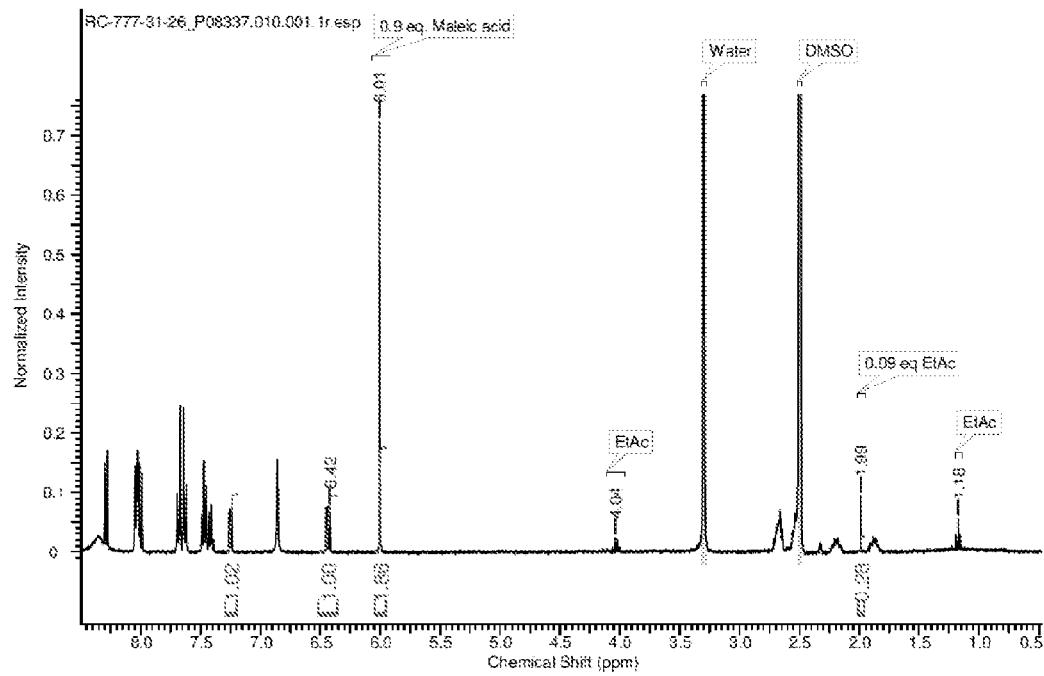
FIGS. 83A-83C: $^1$H NMR of Compound A mono-maleic acid salt from ethyl acetate (FIG. 83A) and ethanol (FIG. 83B), and Compound A bis-maleic acid salt from THF (FIG. 83C)
Figure 83B:
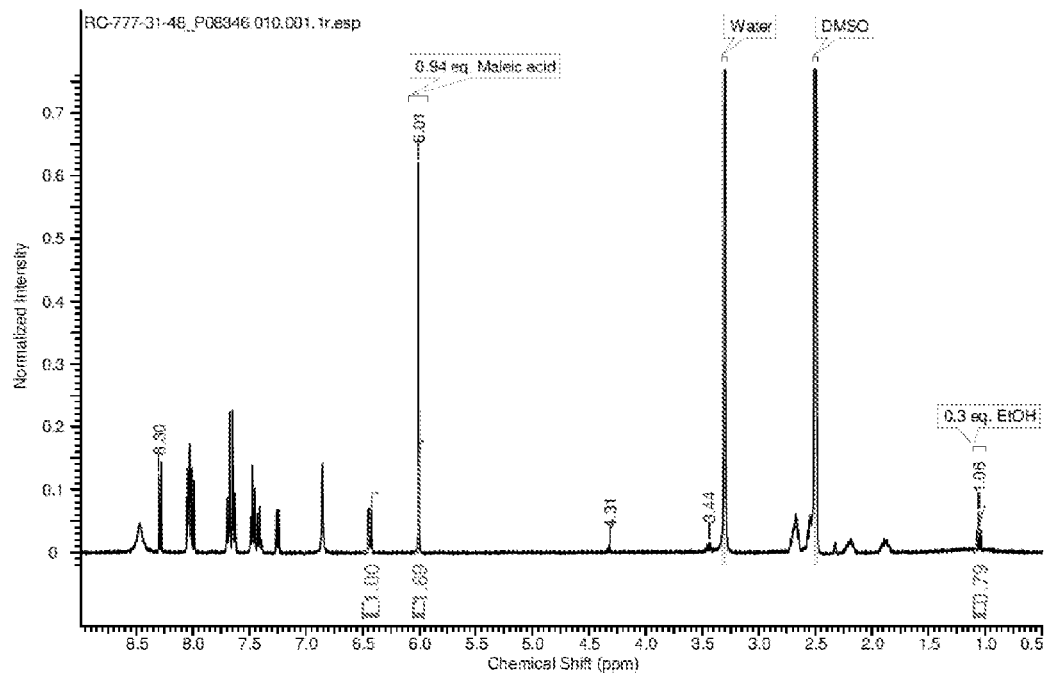
Figure 83C:
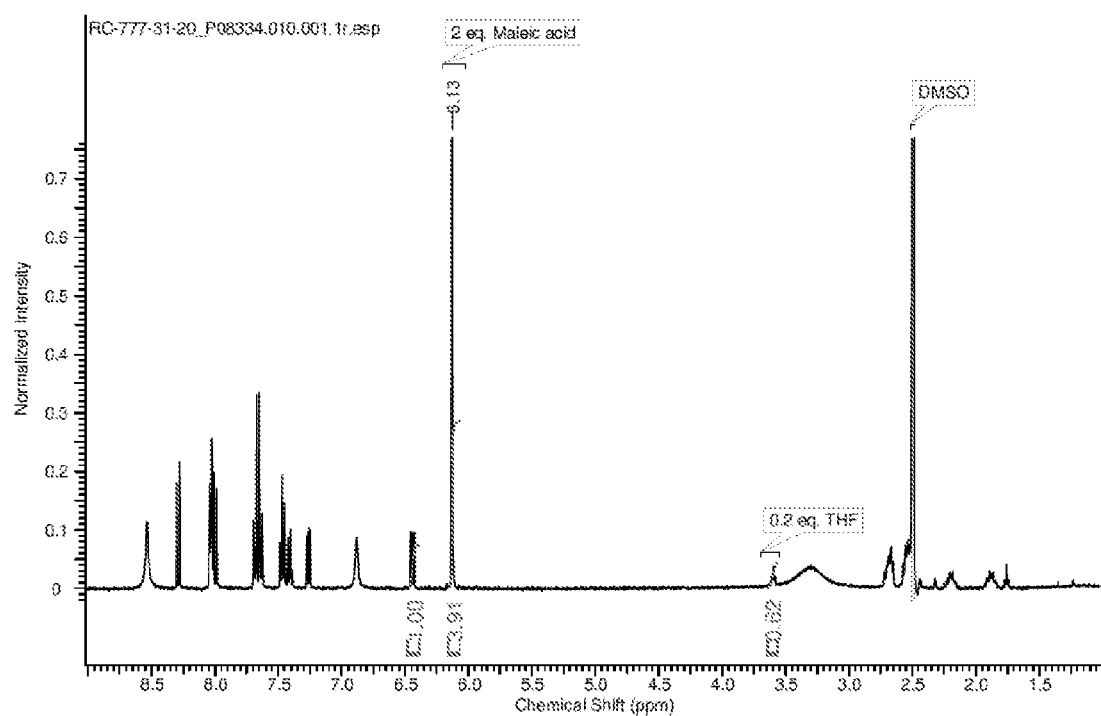
Figure 84A:
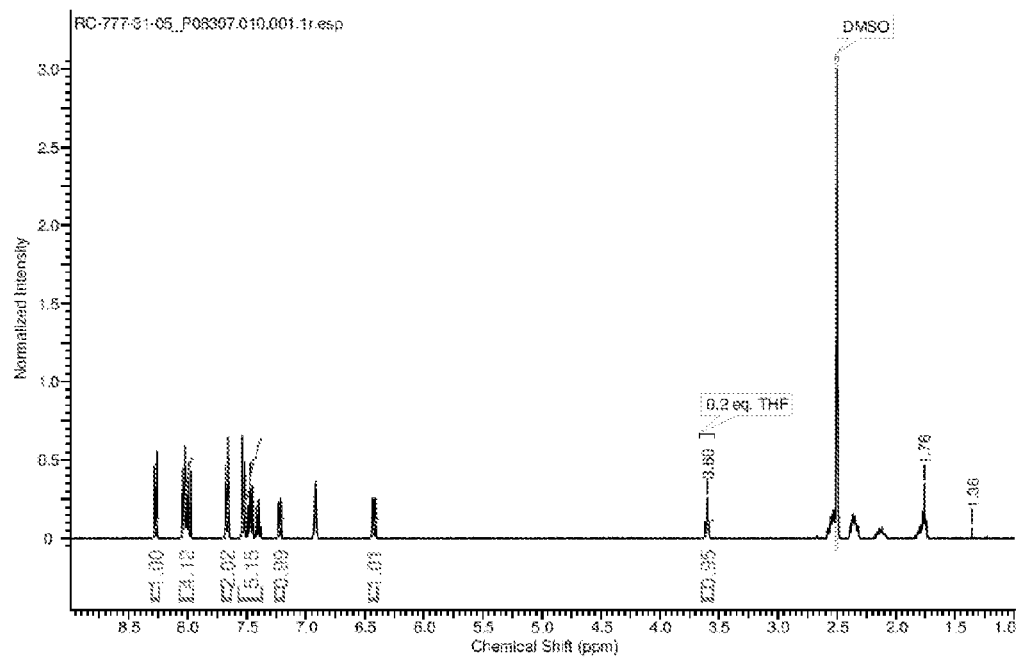
FIGS. 84A-84E: $^1$H NMR of Compound A mono-phosphoric acid salt from THF (FIG. 84A), ethyl acetate (FIG. 84B), and ethanol (FIG. 84C), and Compound A bis-phosphoric acid salt from ethyl acetate (FIG. 84D) and ethanol (FIG. 84E)
Figure 84B:
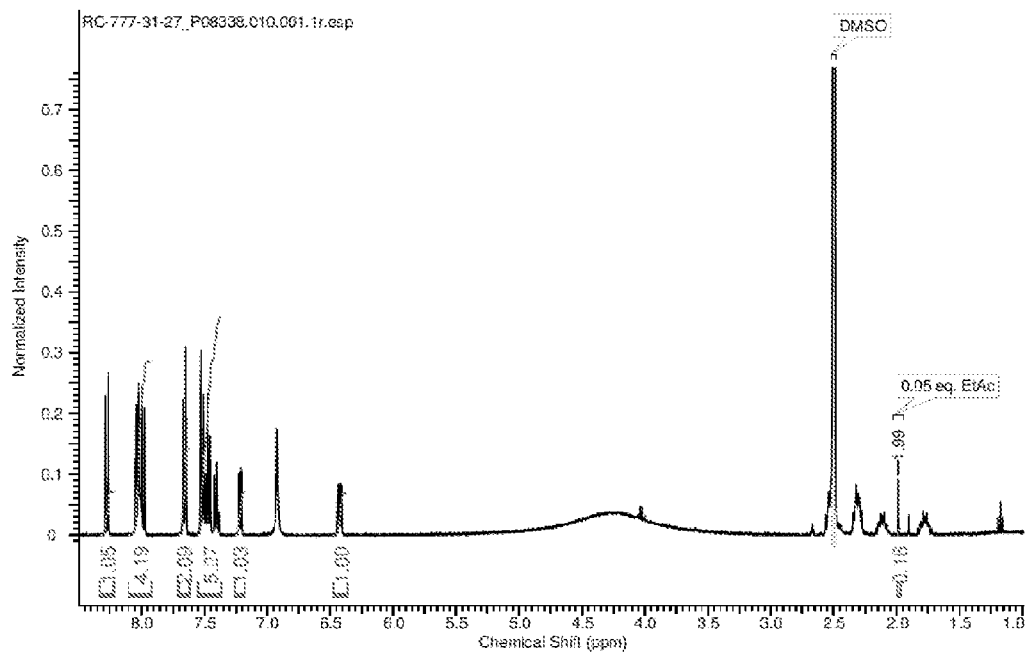
Figure 84C:
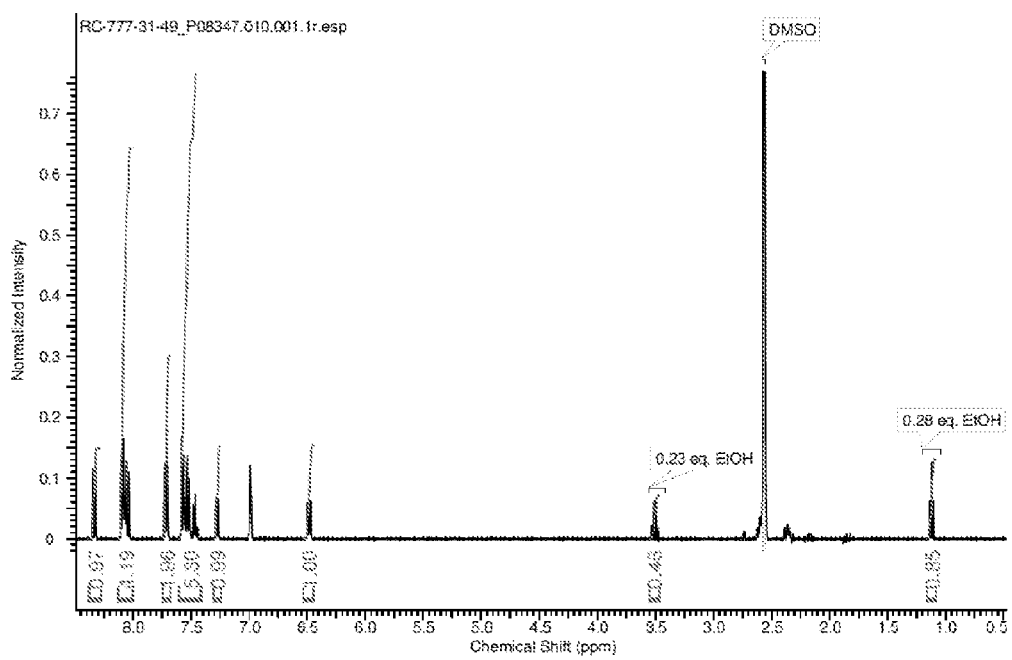
Figure 84D:
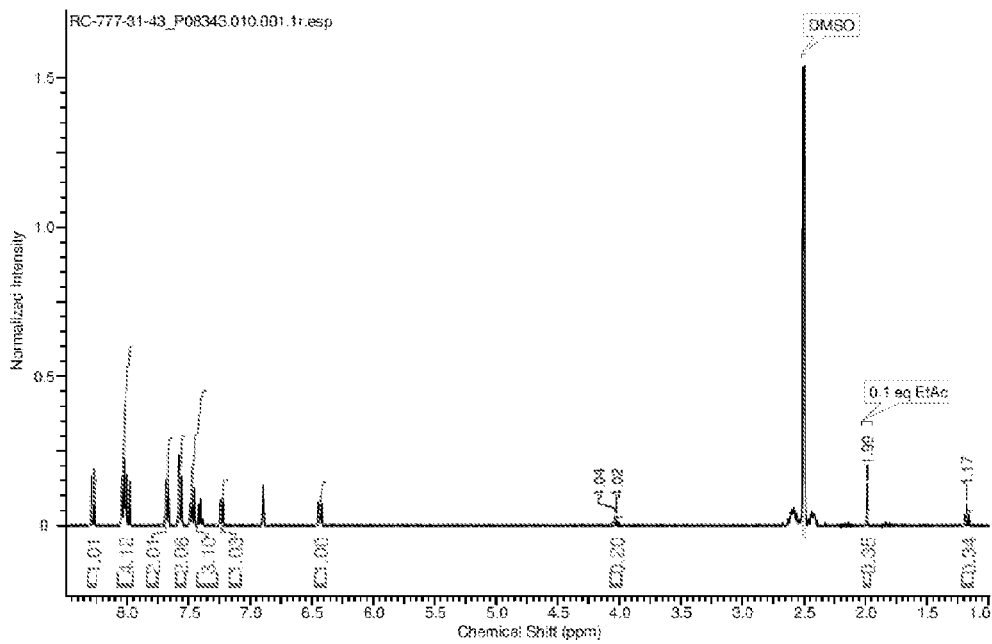
Figure 84E:
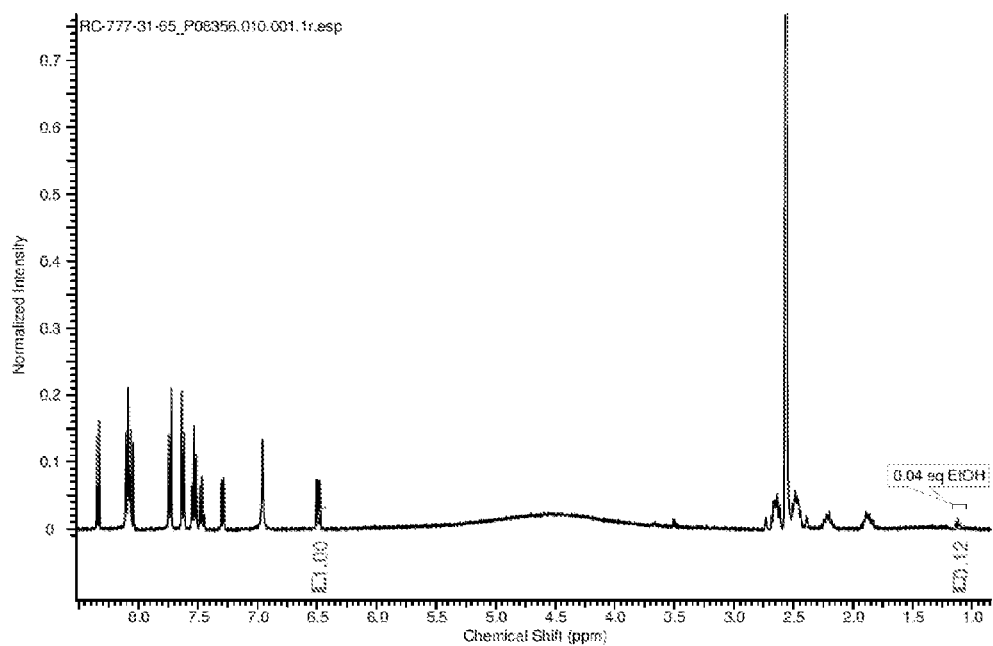
Figure 85:
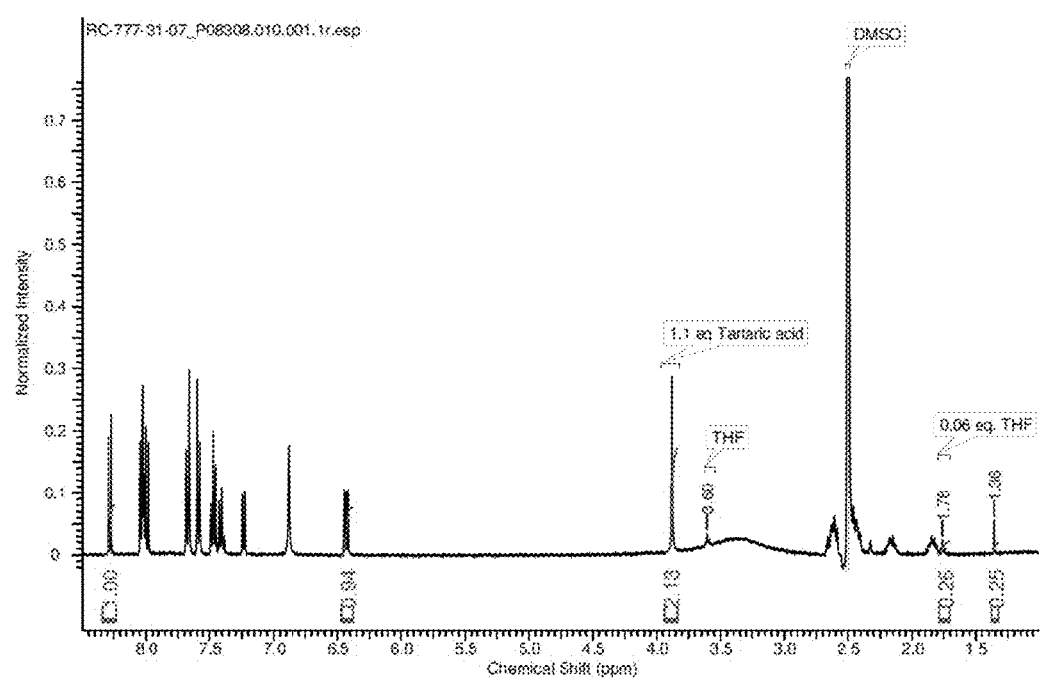
FIG. 85: $^1$H NMR of Compound A mono-tartaric acid salt from THF
Figure 86A:
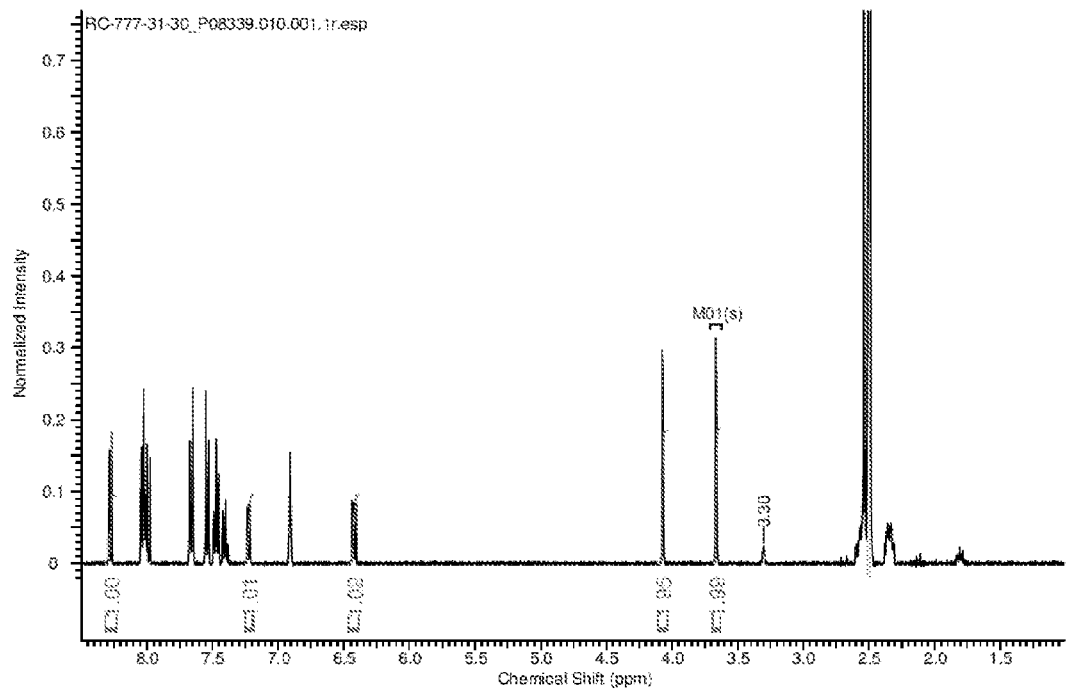
FIGS. 86A-86B: $^1$H NMR of Compound A mono-mucic acid salt from ethyl acetate (FIG. 86A) and ethanol (FIG. 86B)
Figure 86B:
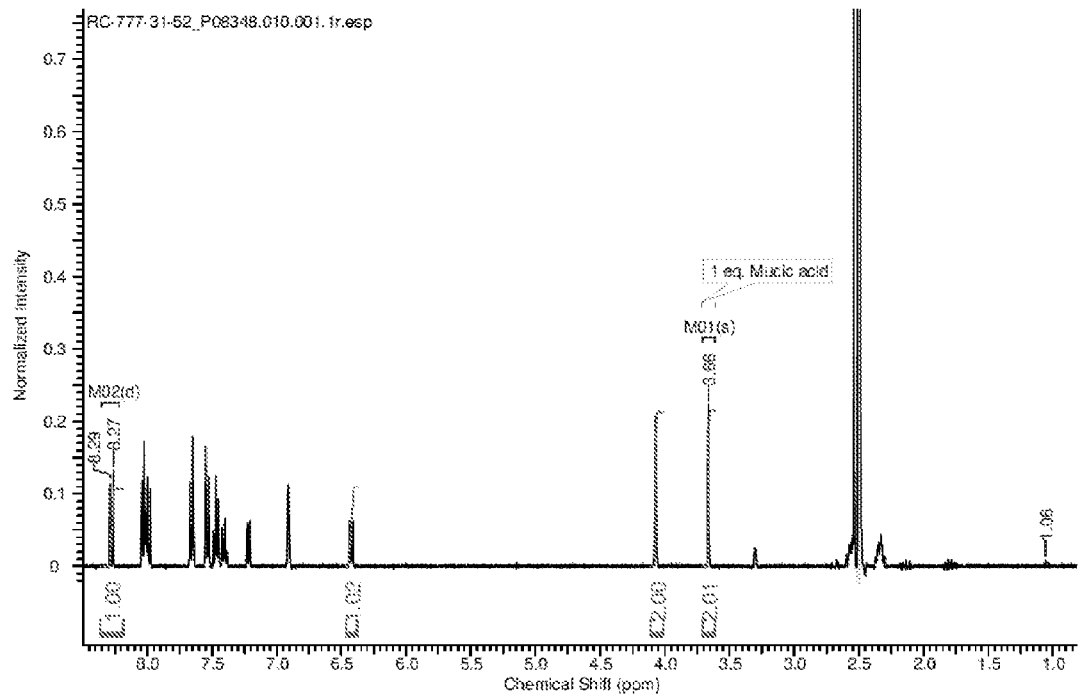
Figure 87:
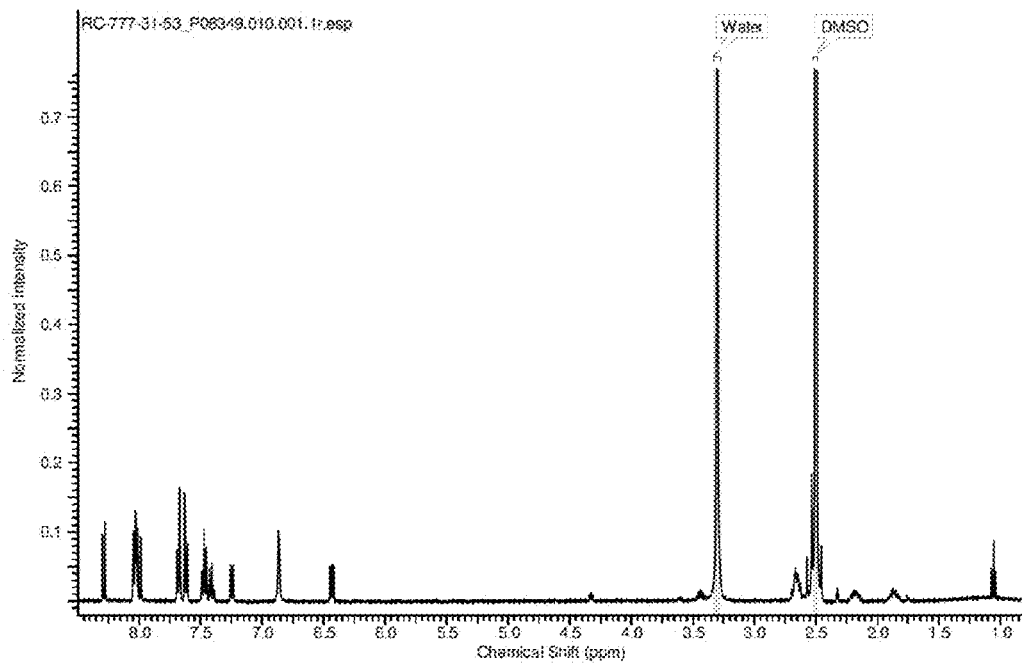
FIG. 87: $^1$H NMR of Compound A mono-citric acid salt from ethanol
Figure 88:
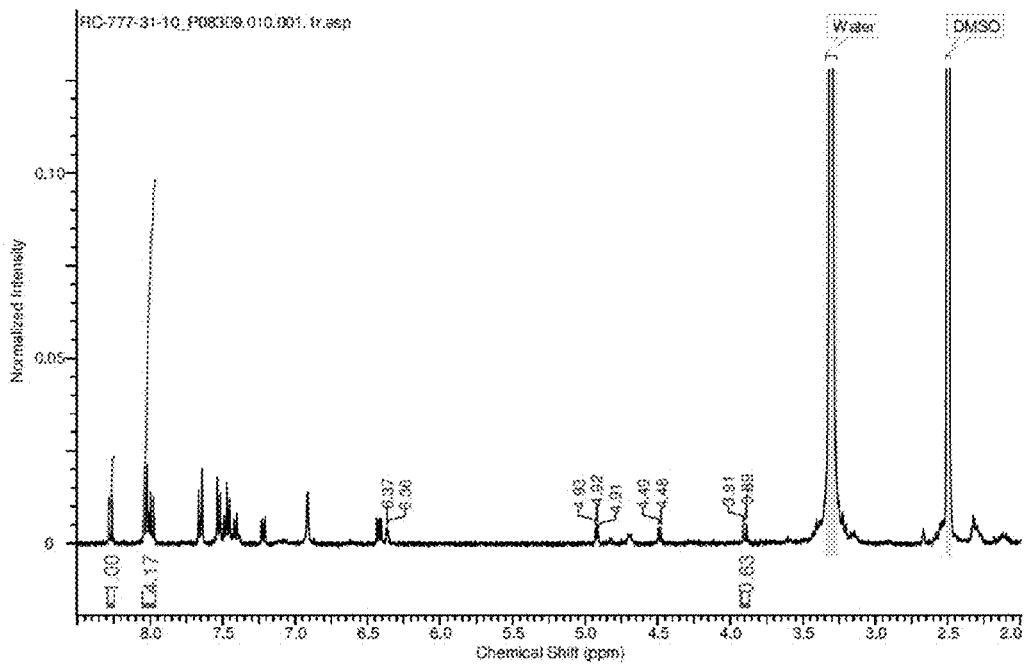
FIG. 88: $^1$H NMR of Compound A D-glucuronic acid salt from THF
Figure 89A:
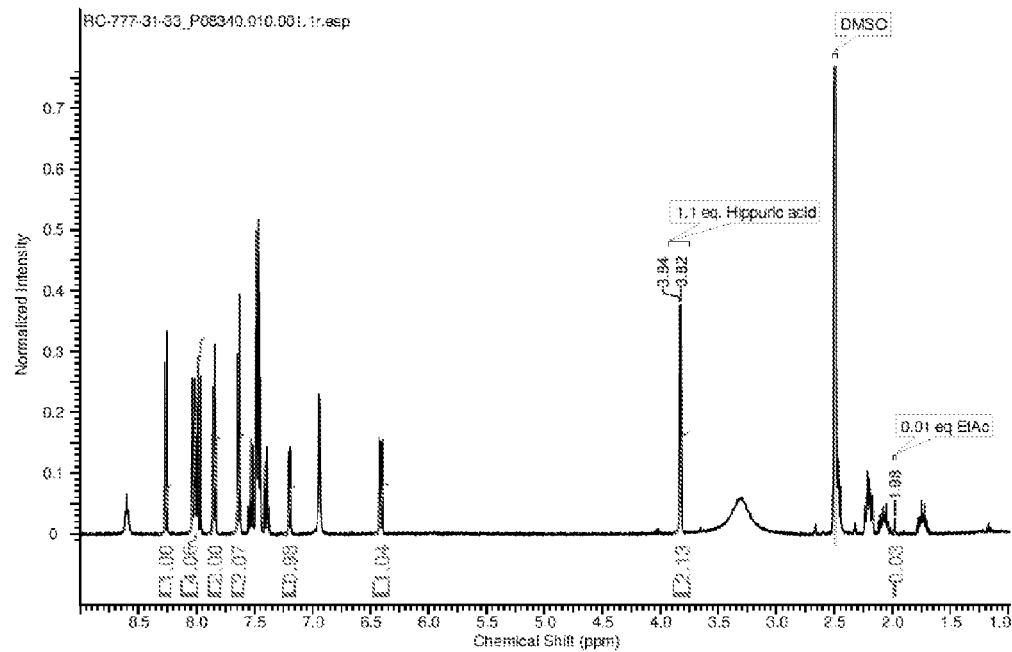
FIGS. 89A-89B: $^1$H NMR of Compound A mono-hippuric acid salt from ethyl acetate (FIG. 89A) and ethanol (FIG. 89B)
Figure 89B:
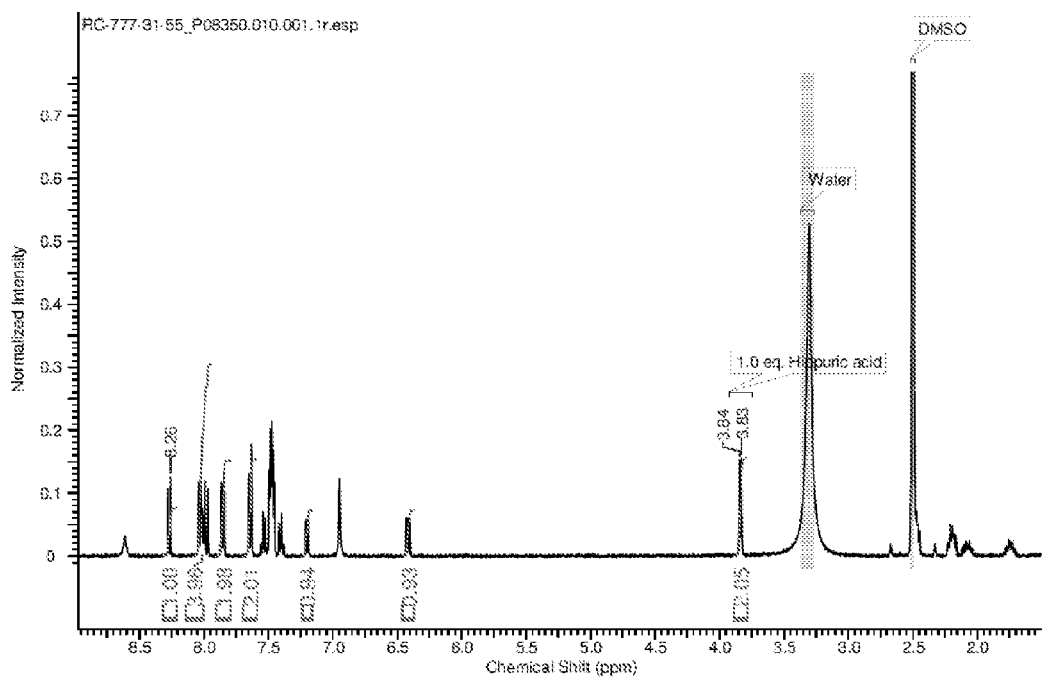
Figure 90:
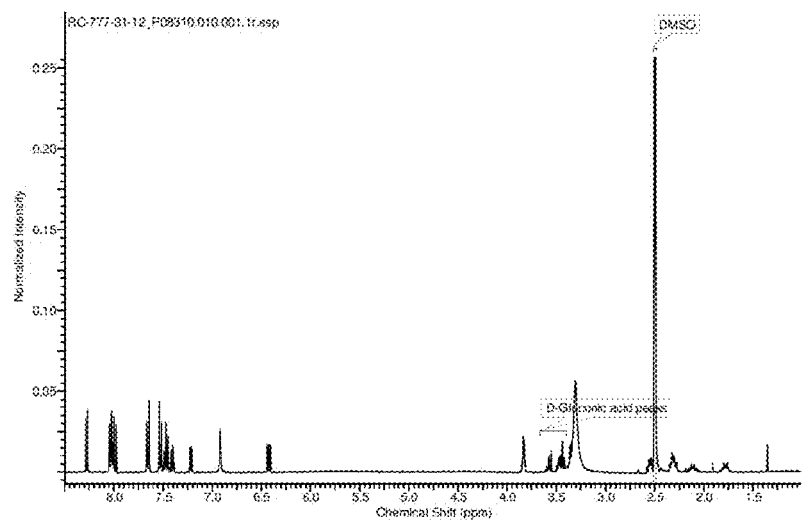
FIG. 90: $^1$H NMR of Compound A D-gluconic acid salt from THF
Figure 91:
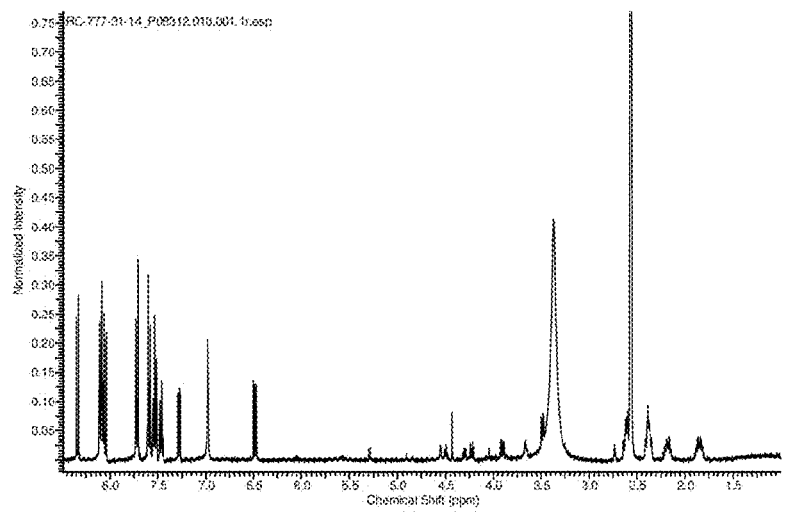
FIG. 91: $^1$H NMR of Compound A L-ascorbic acid salt from THF
Figure 92:
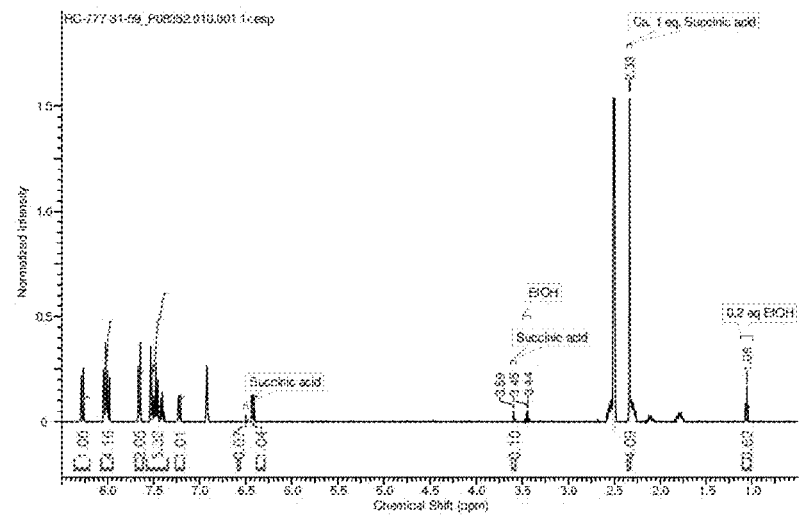
FIG. 92: $^1$H NMR of Compound A succinic acid salt from ethanol
Figure 93A:
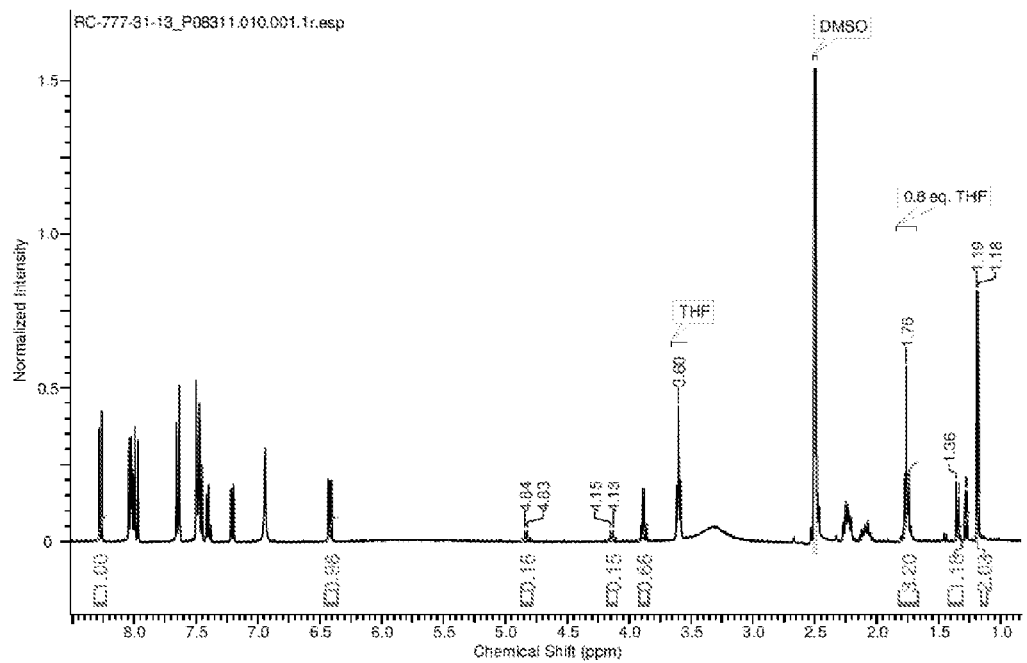
FIGS. 93A-93C: $^1$H NMR of Compound A mono-L-lactic acid salt from THF (FIG. 93A), ethyl acetate (FIG. 93B), and ethanol (FIG. 93C)
Figure 93B:
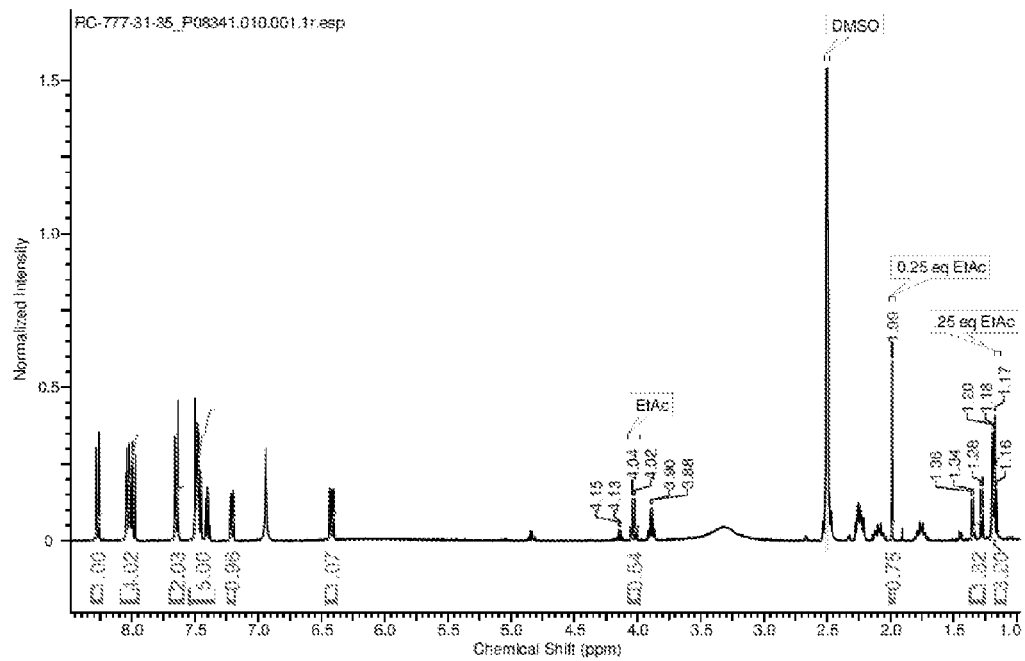
Figure 93C:
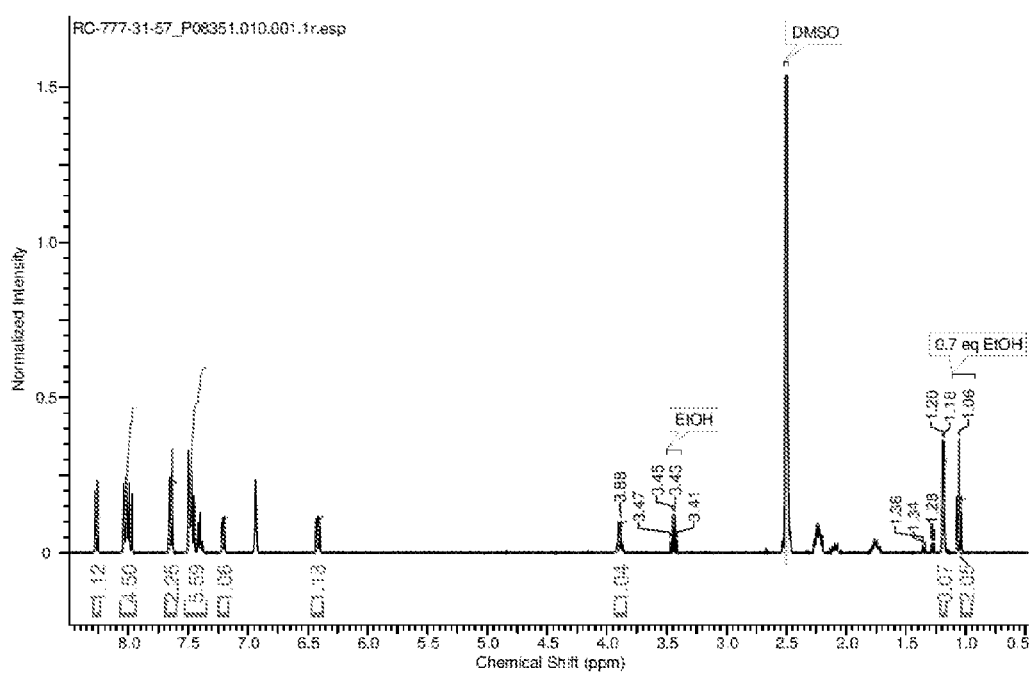
Figure 94A:
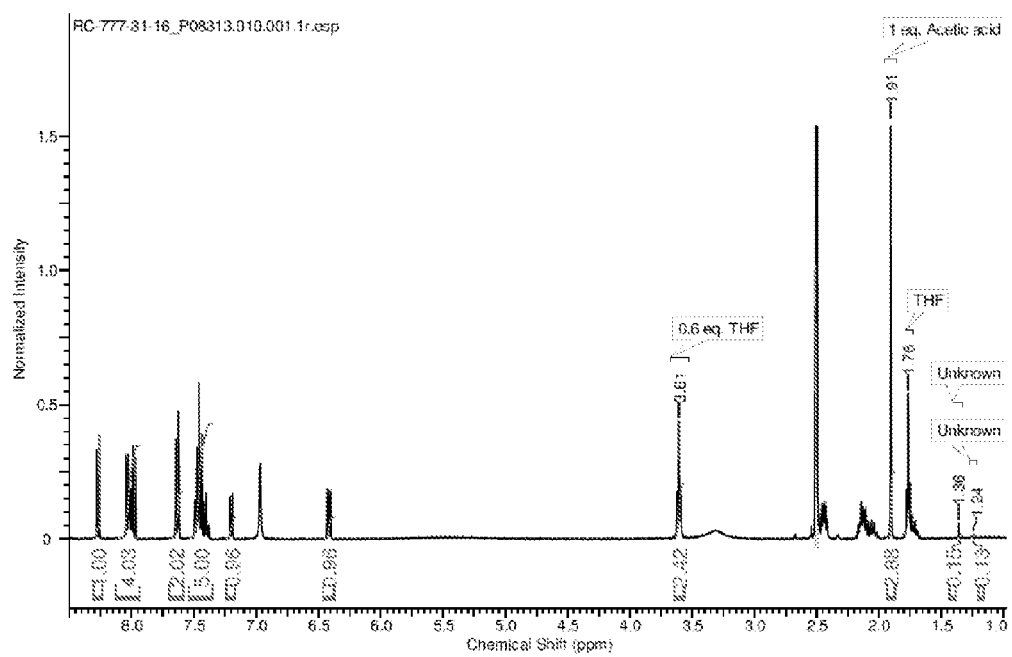
FIGS. 94A-94C: $^1$H NMR of Compound A mono-acetic acid salt from THF (FIG. 94A), ethyl acetate (FIG. 94B), and ethanol (FIG. 94C)
Figure 94B:
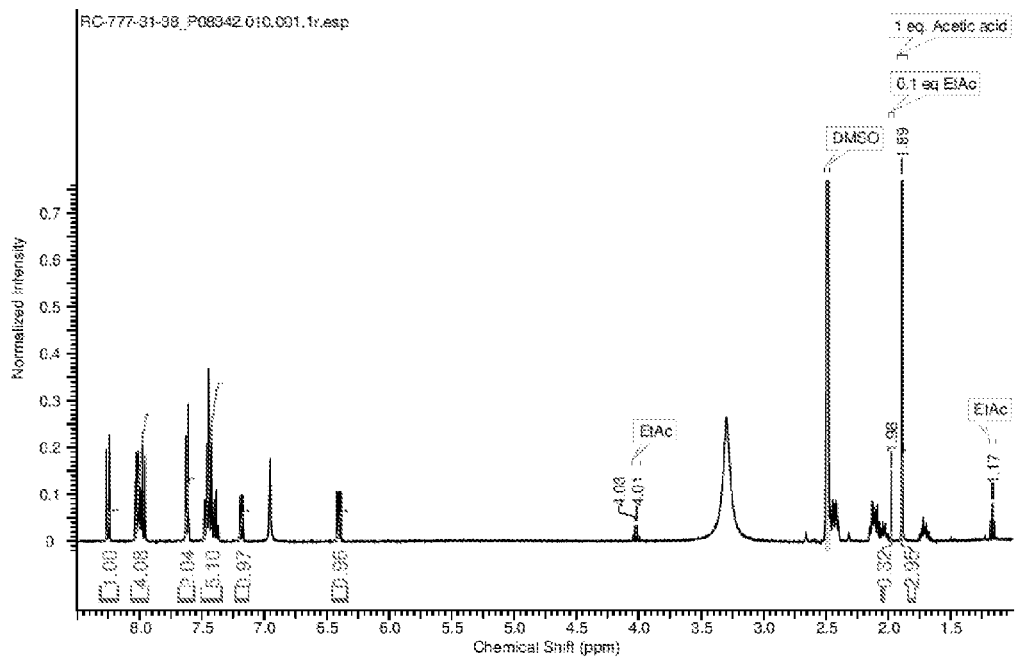
Figure 94C:
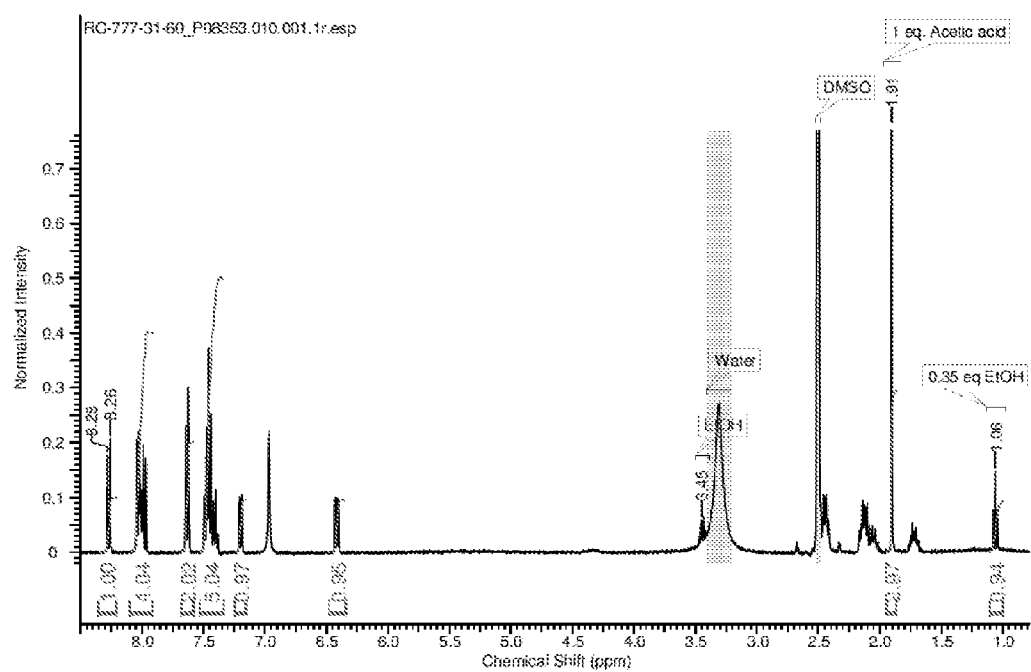
Figure 95:
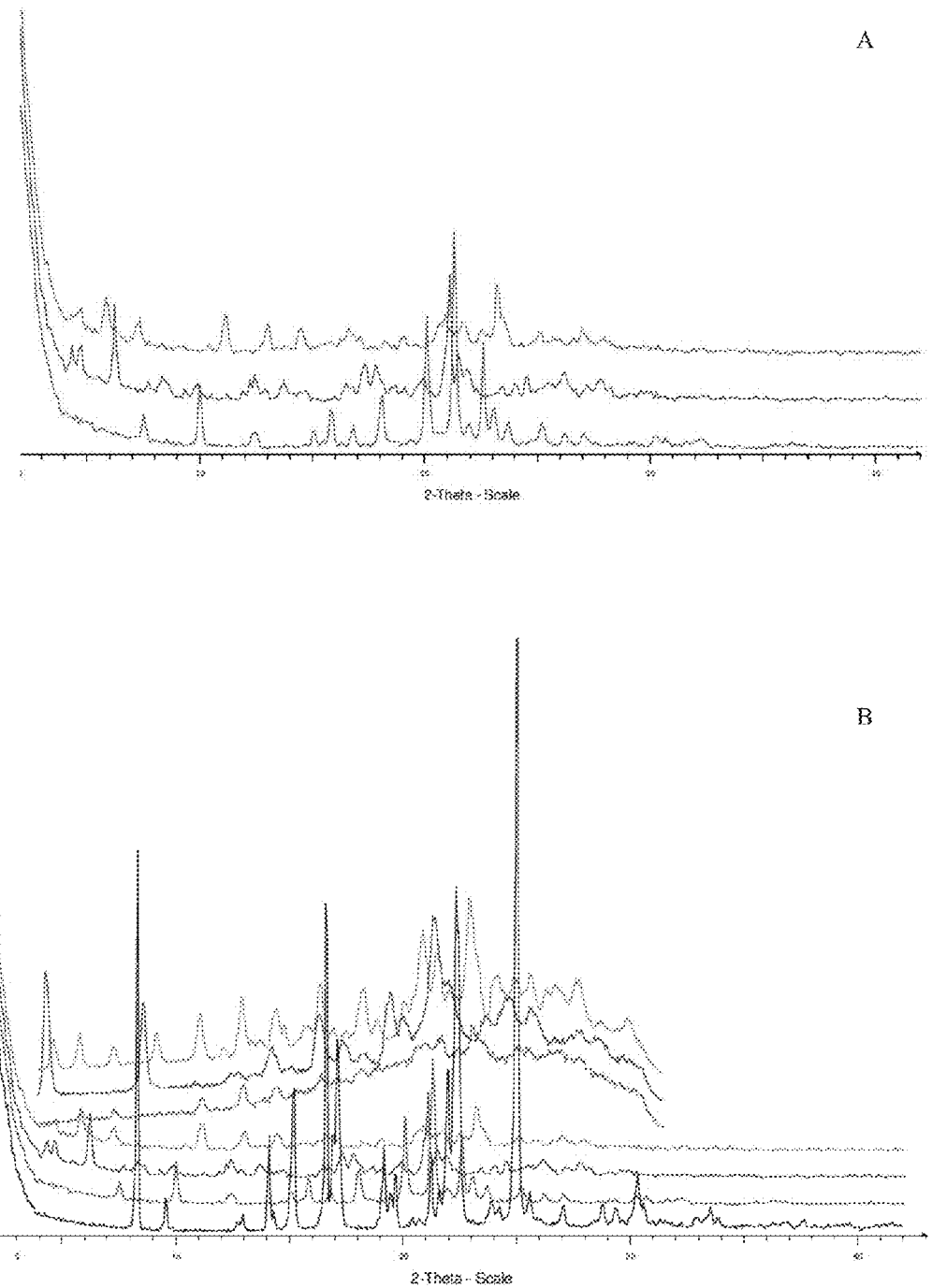
FIG. 95: (A) XRPD of Compound A sulfuric acid salt, and (B) Compound A sulfuric acid salt pre- and post-storage at 40° C. and 75% RH (the top three curves showing post-storage XRPD; the middle three curves showing pre-storage XRPD; and the bottom curve showing the XRPD of Compound A free base)
Figure 96:
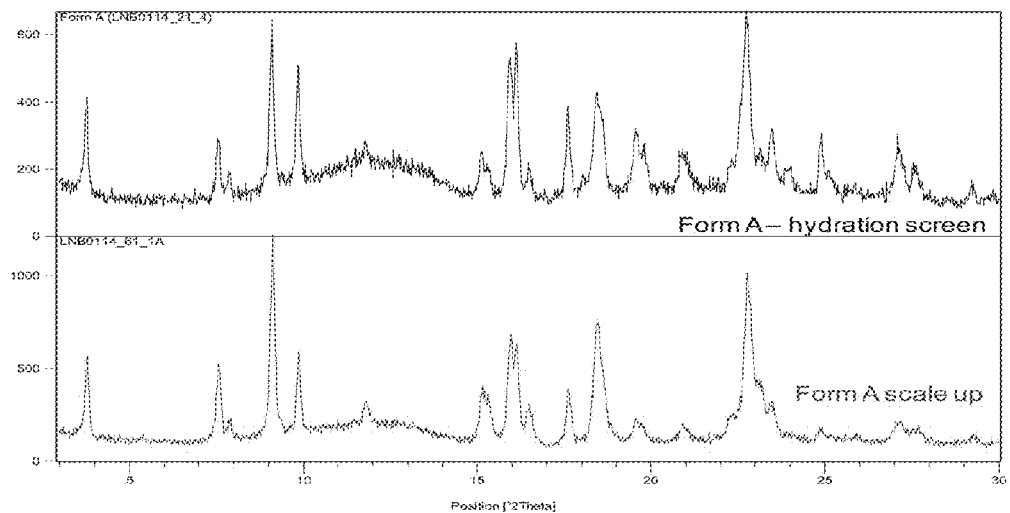
FIG. 96: Form A Compound A bis-mesylate—XRPD Analysis: Hydration Screen and Scale-Up
Figure 97:
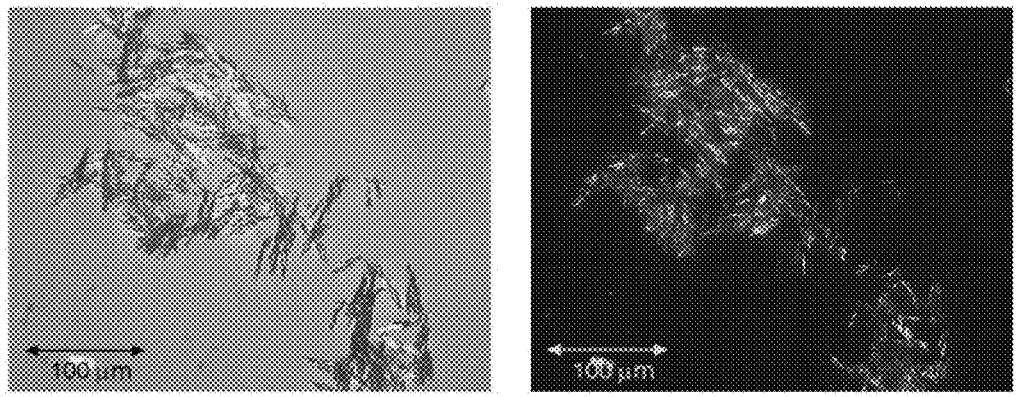
FIG. 97: Form A Compound A bis-mesylate—PLM Analysis
Figure 98:
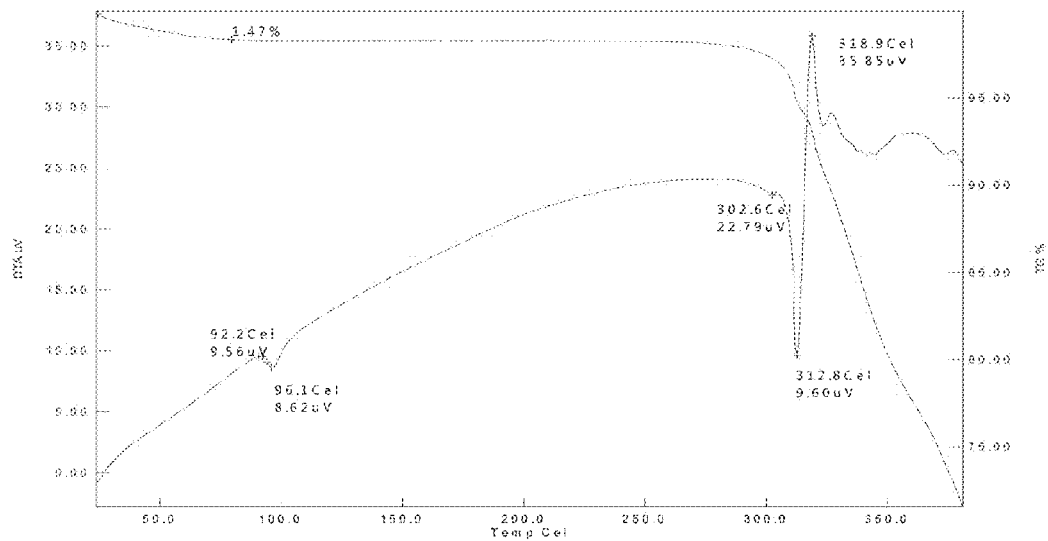
FIG. 98: Form A Compound A bis-mesylate—TG/DTA Analysis
Figure 99:
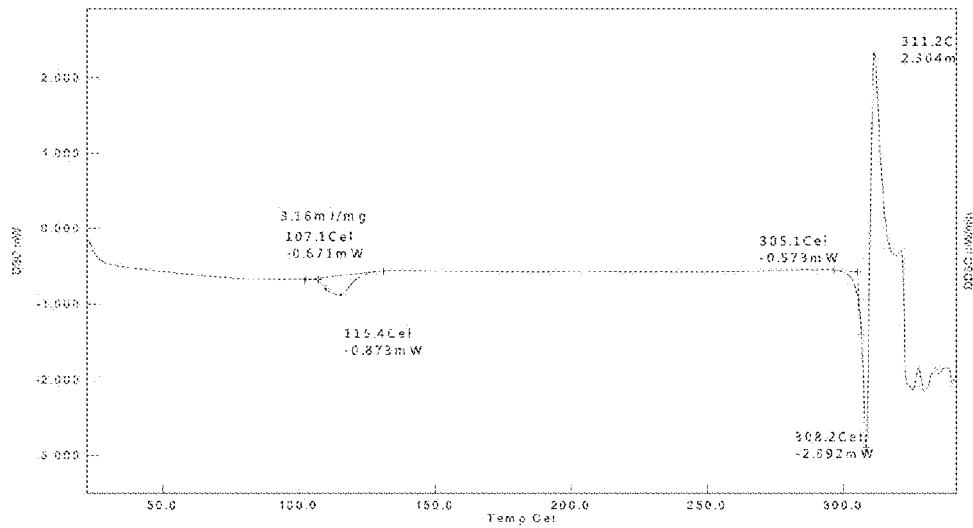
FIG. 99: Form A Compound A bis-mesylate—DSC Analysis
Figure 100:
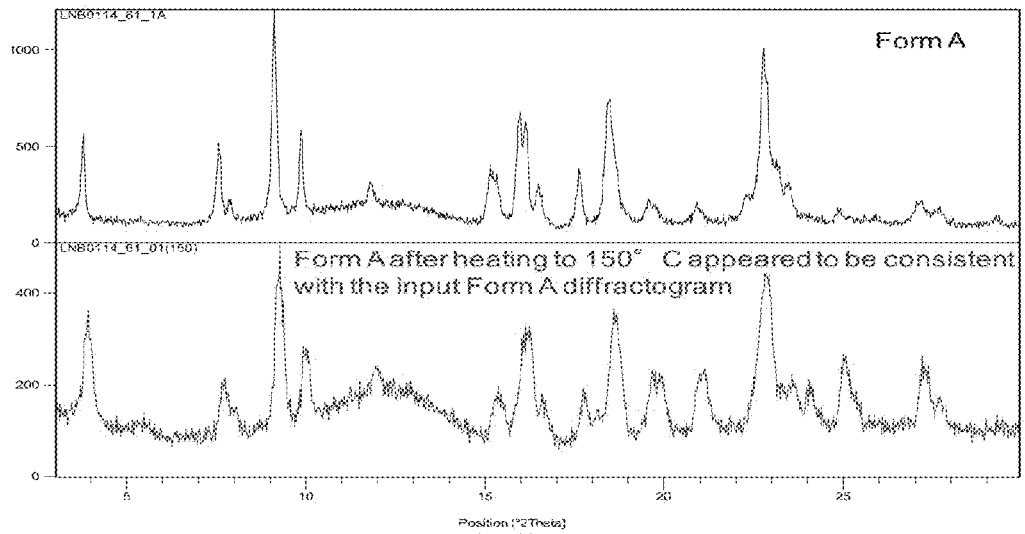
FIG. 100: Form A Compound A bis-mesylate—XRPD Analysis: Form A Compared to Form A after heating to 150° C.
Figure 101:
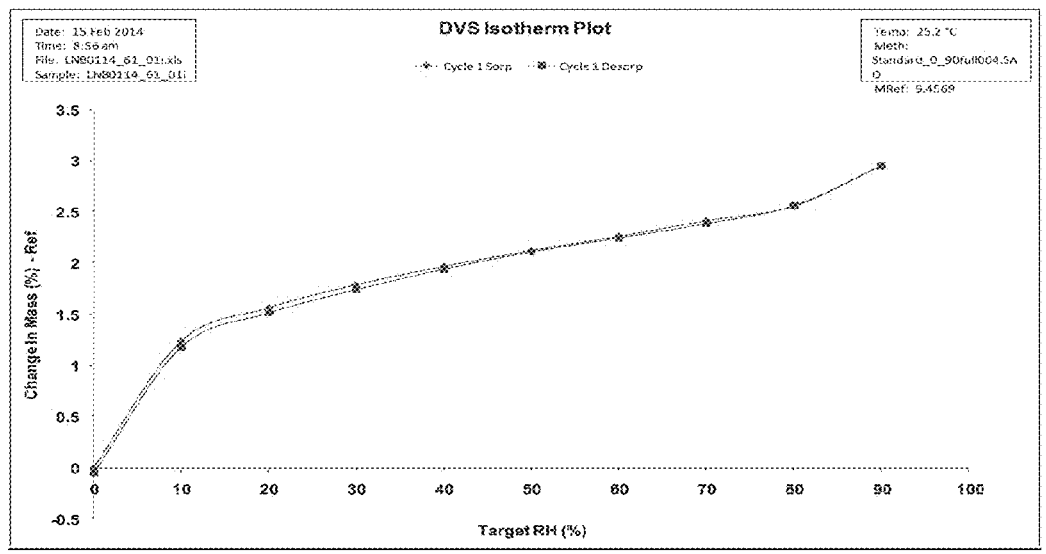
FIG. 101: Form A Compound A bis-mesylate—DVS Analysis
Figure 102:
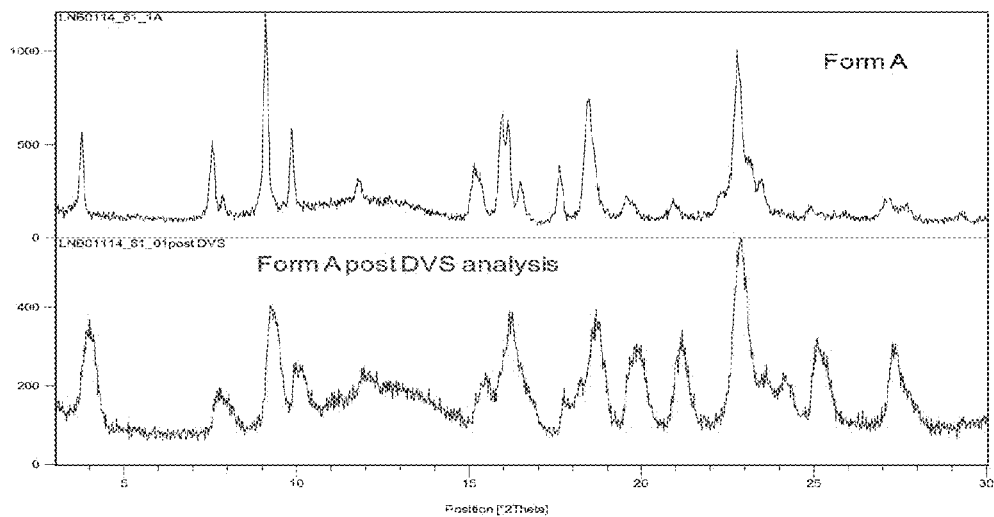
FIG. 102: Form A Compound A bis-mesylate—XRPD Analysis: Post-DVS Analysis
Figure 103:
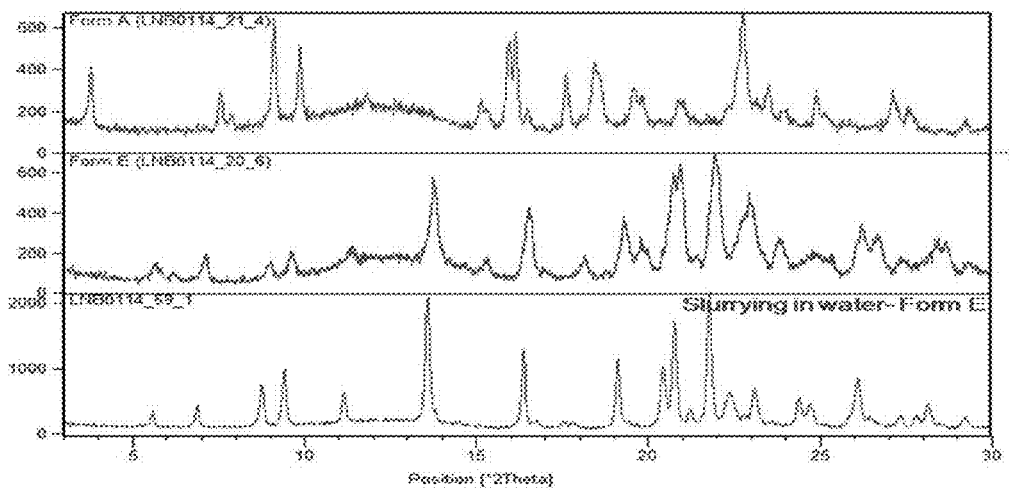
FIG. 103: Form A Compound A bis-mesylate—XRPD Analysis: Slurry in Deionized Water
Figure 104:
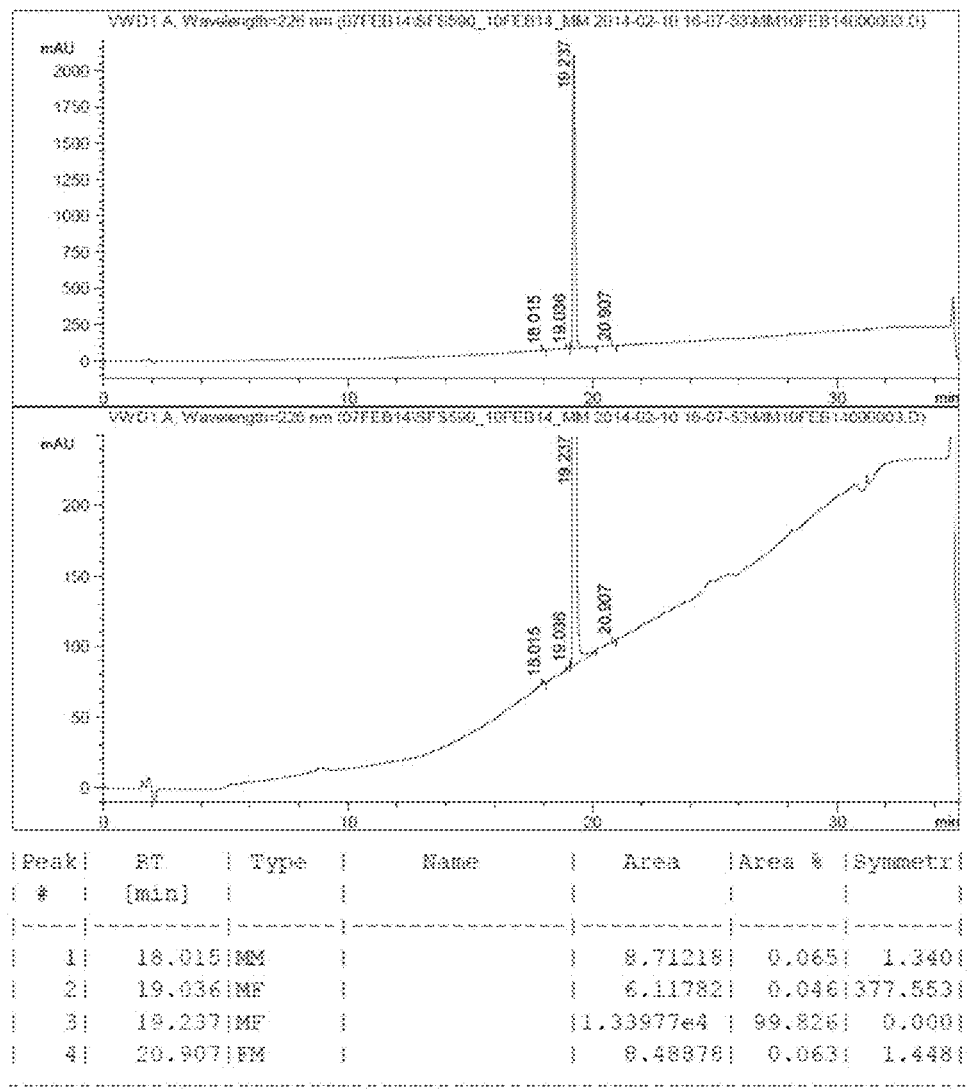
FIG. 104: Form A Compound A bis-mesylate—HPLC Purity Analysis
Figure 105:
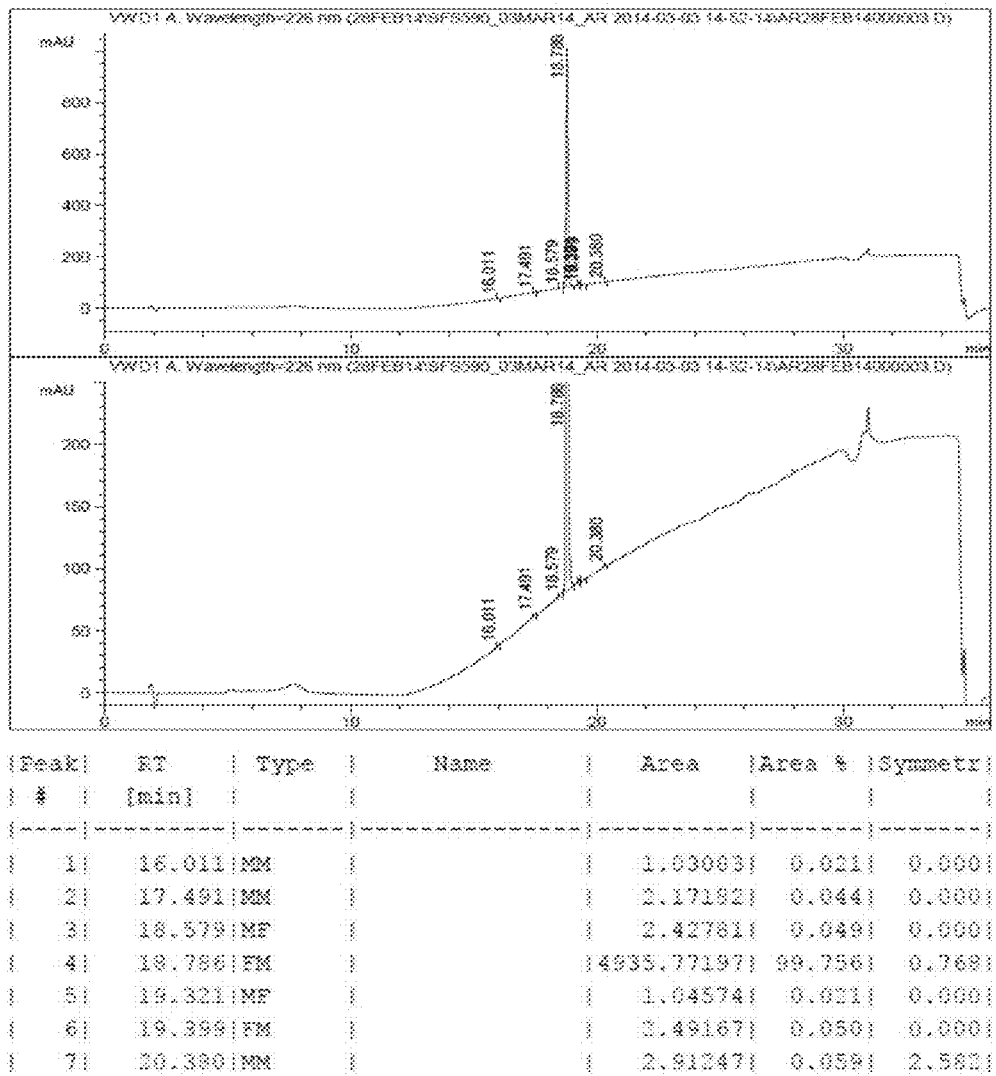
FIG. 105: Form A Compound A bis-mesylate—HPLC Purity: Stability Study at 40° C. and 75% RH
Figure 106:
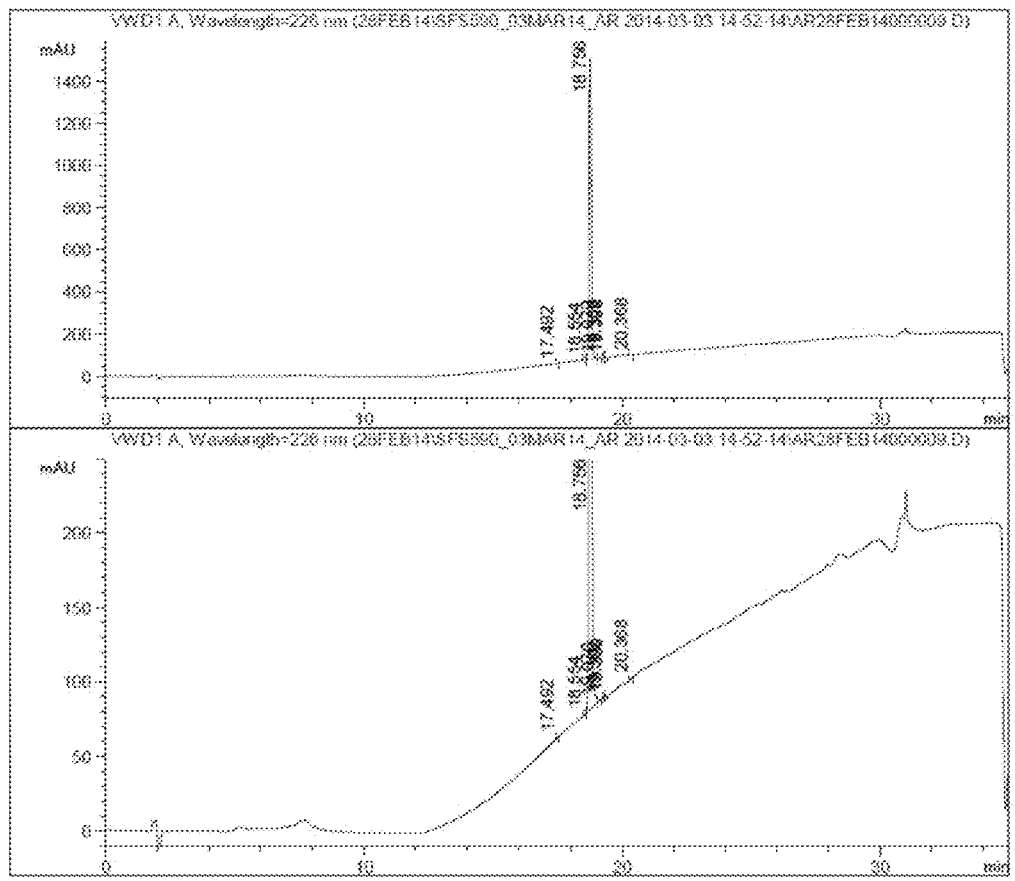
FIG. 106: Form A Compound A bis-mesylate—HPLC Purity: Stability Study at Ambient Temperature
Figure 107:
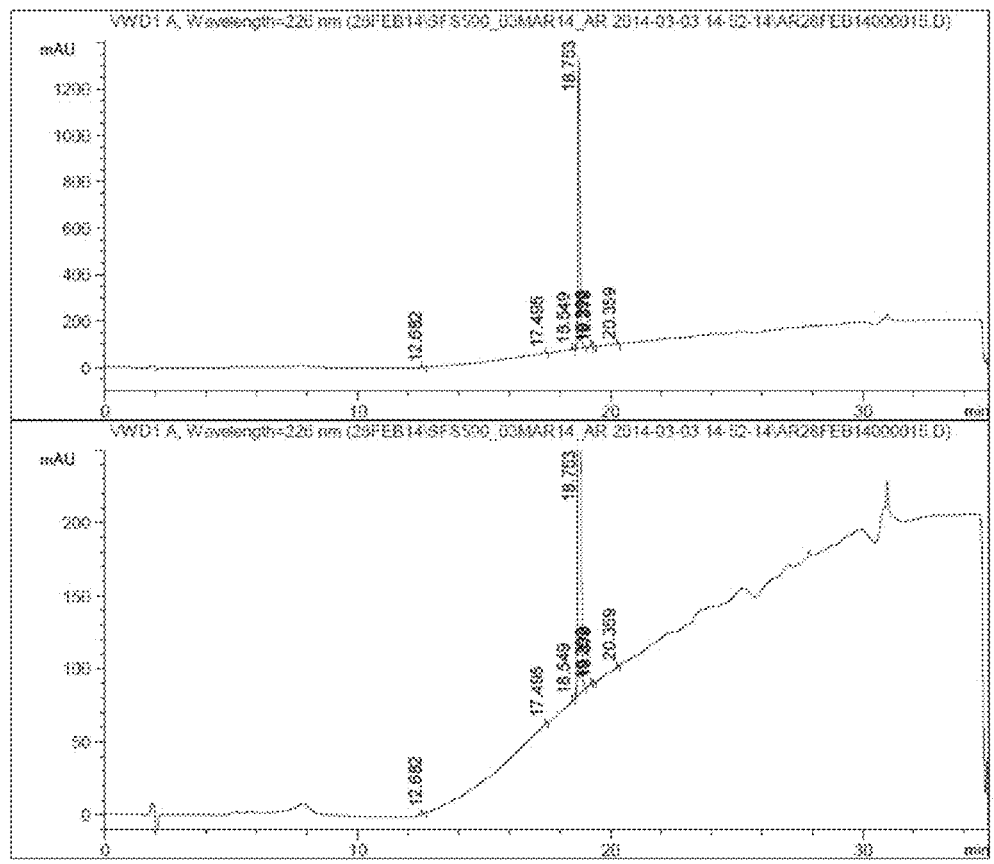
FIG. 107: Form A Compound A bis-mesylate—HPLC Purity: Stability Study at 80° C.
Figure 108:
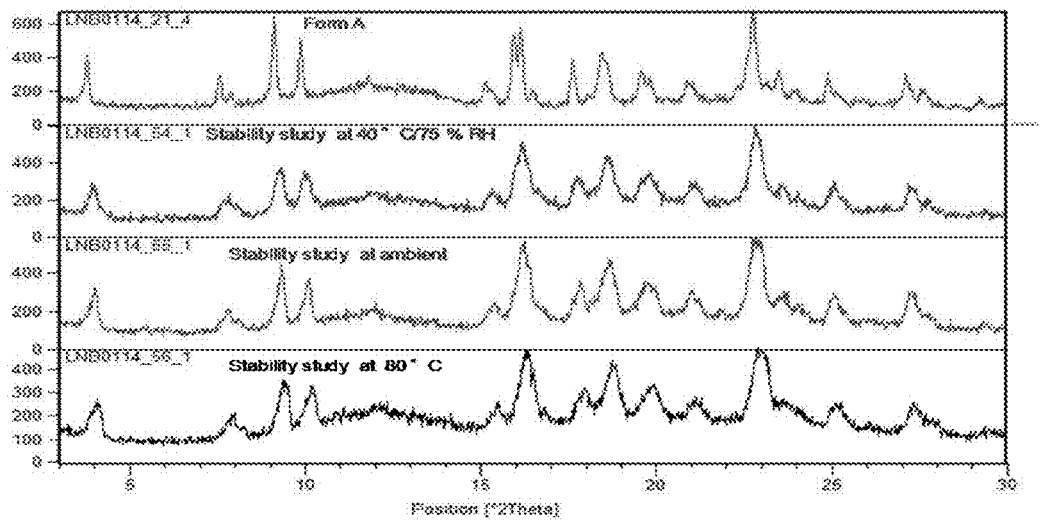
FIG. 108: Form A Compound A bis-mesylate—XRPD Analysis: Stability Testing at 40° C. and 75% RH, Ambient Temperature, and 80° C.
Figure 109:
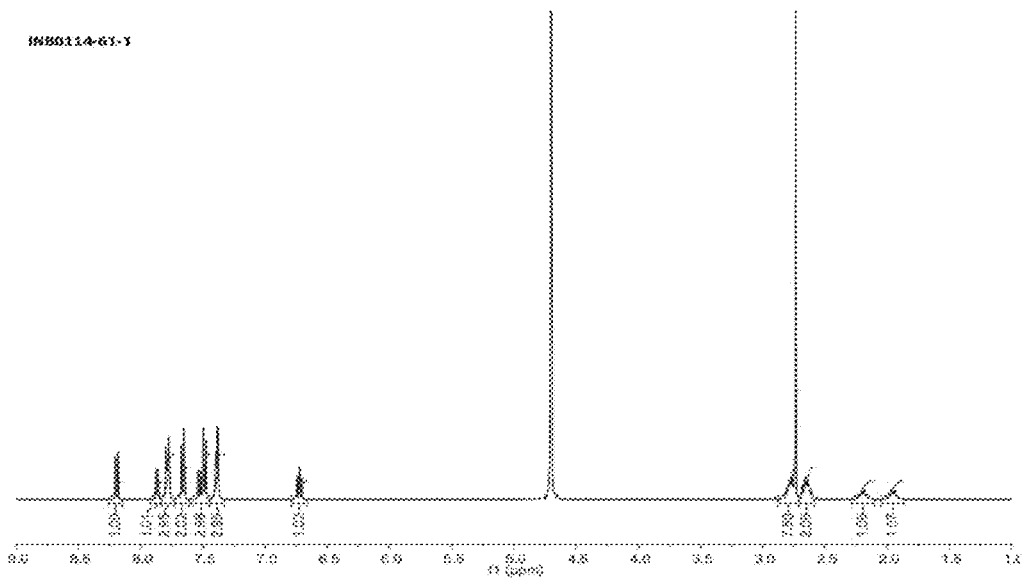
FIG. 109: Form A Compound A bis-mesylate—$^1$H NMR Spectroscopy

A sample of Form B was heated to 235° C. and held for 15 minutes before being cooled to back to ambient temperature. Analysis by XRPD of the solid after heating showed that Form B was no longer present (FIG. 48) and the resulting pattern was consistent with the XRPD of Form A.

Additional characterization of Form C is described below.
PLM analysis indicated that Form C is birefringent with a small block-like morphology.
TG/DTA showed a sharp endotherm at onset about 292.5° C. (peak 294.1° C.), corresponding with a 0.9% weight loss in the TGA trace.
DSC analysis showed a single endothermic event at onset about 291.8° C. (peak 294.6° C.).
A water content of about 0.3% was measured by Karl-Fischer Titration.
An HPLC purity of 99.7% was observed.
HPLC concentration analysis indicated an aqueous solubility of about 367 mg/mL. XRPD analysis on the material after slurrying in deionised water for about 24 hours indicated that Form C converted to Form E.
DVS analysis indicated a total water uptake of about 0.54% up to 90% RH, showing the material to be non-hygroscopic. XRPD analysis carried out after DVS analysis indicated a diffractogram consistent with Form C.
No change in the polymorphic form was observed after stability tests at 40° C./75% RH, 80° C. and at ambient. HPLC analysis indicated a purity of about 99.9% for 40° C./75% RH, about 99.9% for 80° C. and about 99.9% at ambient temperature.
The $^1$H NMR spectrum was observed to be consistent with the received material.

Example 22

Solvent Solubility

The amorphous form of Compound A bis-mesylate salt was used as the input material for the solubility screen. Solubility values were estimated by a solvent addition technique in order to provide approximate values for generating slurries during later experiments. Approximately 15 mg of amorphous material was weighed out into 24 vials. Each solvent was added to the appropriate vial in 10 aliquots of 10 µl, 5 aliquots of 20 µl, 3 aliquots of 100 µl and 1 aliquot of 500 µl or until the material dissolved. In between additions, the sample was heated to 40° C. To vials which already contained 1000 µl of solvent but still had observable solid material, a further aliquot of 1000 µl of solvent was added. If 2000 µl of solvent was added without dissolution of the solid, solubility was calculated to be below this point.

The solvent systems selected for the solubility screen are shown in Table 177-1.

TABLE 17-1

Solvent Systems Selected for Solubility Screening

|  | Solvent System | ICH Class |
|---|---|---|
| 1 | Acetone | 3 |
| 2 | Acetonitrile | 2 |
| 3 | 1-Butanol | 3 |
| 4 | Cyclohexane | 2 |
| 5 | Dichloromethane | 2 |
| 6 | Dimethylsulfoxide | 3 |
| 7 | Diisopropyl ether | Unknown |
| 8 | 1,4-Dioxane | 2 |
| 9 | Ethanol | 3 |
| 10 | 2-Ethoxyethanol | 2 |
| 11 | Ethyl acetate | 3 |
| 12 | n-Heptane | 3 |
| 13 | Isopropyl acetate | 3 |
| 14 | 2-Methyl THF | Unknown |
| 15 | Methanol | 2 |
| 16 | Methylethyl ketone | 3 |
| 17 | Methylisobutyl ketone | 3 |
| 18 | 2-Propanol | 3 |
| 19 | tert-Butylmethyl ether | 3 |
| 20 | Tetrahydrofuran | 2 |
| 21 | Toluene | 2 |
| 22 | Water | N/A |
| 23 | Acetone:Water (90:10) | 3 |
| 24 | 2-Propanol:Water (50:50) | 3 |

The solubility of Compound A bis-mesylate salt is shown in Table 17-2 below.

TABLE 17-2

| Solvent System | Solubility (mg/mL) at 40° C. | |
|---|---|---|
| Acetone | <8 | Some solubility observed based on very pale yellow solution colour |
| Acetonitrile | <8 | Some solubility observed based on very pale yellow solution colour |
| 1-Butanol | <8 | Some solubility observed based on very pale yellow solution colour |
| Cyclohexane | <8 | Colourless solution |
| Dichloromethane | <8 | Colourless solution |
| Dimethylsulfoxide | about 126 | Good solubility |

TABLE 17-2-continued

| Solvent System | Solubility (mg/mL) at 40° C. | |
|---|---|---|
| Diisopropyl ether | <8 | Colourless solution |
| 1,4-Dioxane | <8 | Colourless solution |
| Ethanol | <8 | Some solubility observed based on very pale yellow solution colour |
| 2-Ethoxyethanol | <8 | Some solubility observed based on very pale yellow solution colour |
| Ethyl acetate | <8 | Some solubility observed based on very pale yellow solution colour |
| Heptane | <8 | Colourless solution |
| Isopropyl acetate | <8 | Colourless solution |
| 2-Methyl THF | <8 | Colourless solution |
| Methanol | about 40 | Good solubility |
| Methylethyl ketone | <8 | Colourless solution |
| Methylisobutyl ketone | <8 | Colourless solution |
| 2-Propanol | about 25 | Good solubility |
| tert-Butylmethyl ether | <8 | Colourless solution |
| Tetrahydrofuran | <8 | Some solubility observed based on very pale yellow solution colour |
| Toluene | <8 | Colourless solution |
| Water | about 769 | Good solubility |
| Acetone:water (90:10) | about 16 | Good solubility |
| 2-Propanol:water (50:50) | about 400 | Good solubility |

Example 23

Primary Polymorph Screen

Selected Solvent Systems for Polymorph Screening

The solvent systems listed in Table 18-1 were selected for polymorph screening.

TABLE 18-1

Solvent Systems Selected for Polymorph Screening

| | Solvent System |
|---|---|
| 1 | Acetone |
| 2 | Acetone:Water (95:5) |
| 3 | Acetone:Water (90:10) |
| 4 | Acetone:Water (50:50) |
| 5 | Acetonitrile |
| 6 | Acetonitrile:Water (90:10) |
| 7 | Acetonitrile:Water (50:50) |
| 8 | 1-Butanol |
| 9 | Dimethylsulfoxide |
| 10 | 1,4-Dioxane:Water (80:20) |
| 11 | Ethanol |
| 12 | Ethanol:Water (90:10) |
| 13 | Ethanol:Water (50:50) |
| 14 | 2-Ethoxyethanol |
| 15 | Ethyl acetate |
| 16 | Methanol |
| 17 | Methanol:Water (98:2) |
| 18 | Methanol:Water (80:20) |
| 19 | 1-Propanol |
| 20 | 1-Propanol:Water (90:10) |
| 21 | 1-Propanol:Water (50:50) |
| 22 | 2-Propanol |
| 23 | 2-Propanol:Water (98:2) |
| 24 | 2-Propanol:Water (90:10) |
| 25 | 2-Propanol:Water (50:50) |
| 26 | Tetrahydrofuran |
| 27 | Tetrahydrofuran:Water (95:5) |
| 28 | Tetrahydrofuran:Water (70:30) |
| 29 | Water |

Slow Cooling Experiments

Approximately 150 mg of amorphous Compound A was weighed into each of 29 vials and the appropriate volume of solvent was added to prepare slurries which were stirred at 60° C. for about 48 hours in order to obtain thermodynamically equilibrated systems. The slurries were then filtered and the solutions split into 3 portions. One portion was subjected to slow cooling from about 60° C. to 5° C. at a rate of 0.3° C./min with stirring. Any solid material was then recovered and analyzed by PLM and XRPD. FIGS. 155-160.

Crash Cooling Experiments

Using the saturated solutions, prepared as described in the Slow Cooling Experiments, crash cooling experiments were performed, in each of the 29 selected solvent systems, by placing the solutions in environments of about 2° C. and about −18° C. for a minimum of 72 hours. Any solid material was then recovered and analyzed by PLM and XRPD. FIG. 148-154.

Anti-Solvent Addition Experiments

Anti-solvent addition experiments were conducted at ambient (about 22° C.) by adding anti-solvent (acetone) to saturated, filtered solutions of amorphous Compound A bis-mesylate salt, in each of the 29 selected solvent systems. Addition of anti-solvent was continued until there was no further precipitation or until no more anti-solvent could be added to the vial. Any solid material was recovered and analyzed by PLM and XRPD. FIGS. 161-168.

Evaporation Experiments

Using the saturated solutions, prepared as described in the Slow Cooling Experiments, evaporation experiments were conducted by evaporating the solutions, in each of the 29 solvent systems, at ambient conditions (about 22° C.). Any solid material was then recovered and analyzed by PLM and XRPD after the solvent had evaporated to dryness. FIGS. 169-177.

The results of the polymorph screening are shown in Table 18-2.

TABLE 18-2

| Solvents | Crash Cooling (−18° C.) | Slow Cooling 5° C. | Anti-Solvent Addition | Evaporation |
|---|---|---|---|---|
| Acetone | | | | |
| Acetone:Water (95:5) | | | | Amorphous Solid |
| Acetone:Water (90:10) | Form D | Form D | Form D | Amorphous Solid |
| Acetone:Water (50:50) | Form D | | Form D | Amorphous Solid |
| Acetonitrile | | | | |
| Acetonitrile:Water (90:10) | | | Form D | Form B/Form D |
| Acetonitrile:Water (50:50) | | | Form D | Amorphous Solid |
| 1-butanol | | | | |
| Dimethylsulfoxide | | Form G | | |
| 1,4-dioxane:Water (80:20) | Form D | Form D | Form D | Form D |
| Ethanol | | Form B | | Form B |

TABLE 18-2-continued

| Solvents | Crash Cooling (−18° C.) | Slow Cooling 5° C. | Anti-Solvent Addition | Evaporation |
|---|---|---|---|---|
| Ethanol:Water (90:10) | | Form B | Form B | |
| Ethanol:Water (50:50) | Form D | Form D | Form B/ Form D | Amorphous Solid |
| 2-ethoxyethanol | | | | |
| Ethyl acetate | | | | |
| Methanol | Form A | Form A | Form B | Form A |
| Methanol:Water (98:2) | Form B | Form A | Form B | Form A/ Form B |
| Methanol:Water (80:20) | | Form D | Form B | Amorphous Solid |
| 1-propanol | Form B | Form D | | |
| 1-propanol:Water (90:10) | Form D | Form D | Form D | From B/ Form D |
| 1-propanol:Water (50:50) | Form D | Form D | Form D | Amorphous Solid |
| 2-propanol | | | | |
| 2-propanol:Water (98:2) | | | | Form B/ Form D |
| 2-propanol:Water (90:10) | Form D | Form D | Form B | Form D |
| 2-propanol:Water (50:50) | | Form D | Form D | Form D |
| Tetrahydrofuran | | | | |
| Tetrahydrofuran:Water (95:5) | | | | Form D |
| Tetrahydrofuran:Water (70:30) | Form D | Form D | Form D | Form D |
| Water | | | Form D | |

As indicated in Table 18-2:

Form A was observed in methanol and methanol/water solvent systems from cooling and evaporation experiments.

Form B was observed in ethanol, ethanol/water, methanol, methanol/water, 1-propanol, 1-propanol/water, 2-propanol/water and acetonitrile/water solvent systems from various experiments.

Form D was observed in acetone/water, acetonitrile/water, 1,4-dioxane/water, ethanol/water, methanol/water, 1-propanol, 1-propanol/water, 2-propanol/water, tetrahydrofuran/water and water, from various experiments.

Form G was observed in DMSO from anti-solvent addition, employing acetone as the anti-solvent.

Amorphous material was observed from a number of evaporation experiments.

Example 24

Hydration Screening

The solvents listed in Table 19 were selected for hydration screening based upon chemical diversity.

TABLE 19

Selected Solvents for Hydration Screening

| Solvent | Solvent Class |
|---|---|
| Acetone | 3 |
| Acetonitrile | 2 |
| 2-Propanol | 3 |

The water activities shown in Table 20 were calculated for hydration screening at 10° C., 25° C. and 50° C. in each solvent. The temperatures were selected to cover the expected crystallization temperature range. Separate high (targeted 150 mg/mL) and low (targeted 75 mg/mL) slurry concentration experiments were carried out.

TABLE 20

Water Activities calculated for each solvent at 10° C., 25° C. and 50° C.

| Temperature | Water Activity ($A_w$) | | |
|---|---|---|---|
| ° C. | Acetone | Acetonitrile | 2-Propanol |
| 10 | 0.15 | 0.11 | 0.20 |
| | 0.30 | 0.24 | 0.40 |
| | 0.46 | 0.40 | 0.52 |
| | 0.60 | 0.59 | 0.60 |
| | 0.75 | 0.75 | 0.74 |
| | 0.89 | 0.90 | 0.91 |
| 25 | 0.14 | 0.11 | 0.15 |
| | 0.28 | 0.23 | 0.35 |
| | 0.43 | 0.39 | 0.48 |
| | 0.57 | 0.57 | 0.60 |
| | 0.75 | 0.76 | 0.75 |
| | 0.89 | 0.90 | 0.91 |
| 50 | 0.12 | 0.10 | 0.15 |
| | 0.25 | 0.21 | 0.29 |
| | 0.39 | 0.36 | 0.47 |
| | 0.59 | 0.63 | 0.60 |
| | 0.75 | 0.75 | 0.77 |
| | 0.88 | 0.90 | 0.91 |

Hydration Screening Procedure

Approximately 75-150 mg (solubility dependent) of amorphous Compound A bis-mesylate salt material was weighed into each of 108 vials and slurried in each solvent:water system, with 6 different water activities at 10° C., 25° C. and 50° C. FIGS. 178-189.

Low slurry concentration experiments were carried out first, with up to 1 mL solvent of 0.1 to 0.6 water activity added to 75 mg. For 0.7 to 0.9 water activity, up to 100 μL of solvent was added to 75 mg. High slurry concentration experiments were carried out second, with approximately the same volume of solvent added to 150 mg.

The slurries were stirred at their allocated temperatures for about 48 h, then isolated and allowed to dry under ambient conditions before analysis by XRPD to identify the form of the solid material obtained. The material was more soluble in higher water activity solvent systems; therefore additional solid was added to form a slurry, if required.

Example 25

Alternative Preparation of Form A

Approximately 13.3 mL of dried methanol was added to 1 g of the amorphous form of Compound A bis-mesylate salt to prepare a slurry. The slurry was stirred at about 22° C. for about 2 days before the sample was filtered and allowed to dry at ambient temperature prior to characterization Example 26

Alternative Preparation of Form B

Approximately 13.3 mL of 2-propanol with 0.35 water activity was added to 1 g of the amorphous form of Compound A bis-mesylate salt to prepare a slurry. The slurry was stirred at about 22° C. for about 3 days before the sample was filtered and allowed to dry at ambient temperature prior to characterization.

Example 27

Alternative Preparation of Form C

Approximately 5 mL of 2% aqueous methanol was added to 1 g of Form A of Compound A bis-mesylate to prepare a slurry, which was stirred at about 60° C. for about 3 days. The sample was then filtered and allowed to dry at ambient temperature prior to characterization.

Example 28

Preparation of Form D

Approximately 13.3 mL of 2-propanol with 0.6 water activity was added to 1 g of the amorphous form of Compound A bis-mesylate salt to prepare a slurry. The slurry was stirred at about 22° C. for about 3 days. The sample was then filtered and allowed to dry at ambient prior to characterization.

Example 29

Preparation of Form E

Approximately 1.2 mL of 2-propanol with 0.89 water activity was added to 1 g of the amorphous form of Compound A bis-mesylate salt to prepare a slurry. The slurry was stirred at about 22° C. for about 3 days before the sample was filtered and allowed to dry at ambient temperature prior to characterization.

Example 30

Preparation of Form I

Approximately 5 g of received material Form A of Compound A bis-mesylate salt was dissolved in 50 mL of dried methanol. The solution was then evaporated at about 50° C. in an oven under vacuum, yielding a solid.

Example 31

Stability Testing

Form A, Form B, Form C, Form D, Form E and Form I were exposed to environments of 40° C./75% RH, ambient light (about 22° C.) and elevated temperature (80° C.) for 1 week to determine the stability. The resulting solids were analyzed by XRPD to establish if any form changes had occurred and by HPLC to determine purity.

Example 32

Aqueous Solubility Studies

Slurries of Form A, Form B, Form C, Form D, Form E and Form I were created in deionised water and shaken for about 24 hours at ambient temperature (about 22° C.). The resulting solutions were then analyzed by HPLC and the aqueous solubility was determined. The remaining solids were analyzed by XRPD to determine if any form changes had occurred during slurrying.

Example 33

Characterization of Form D

Figure 190:
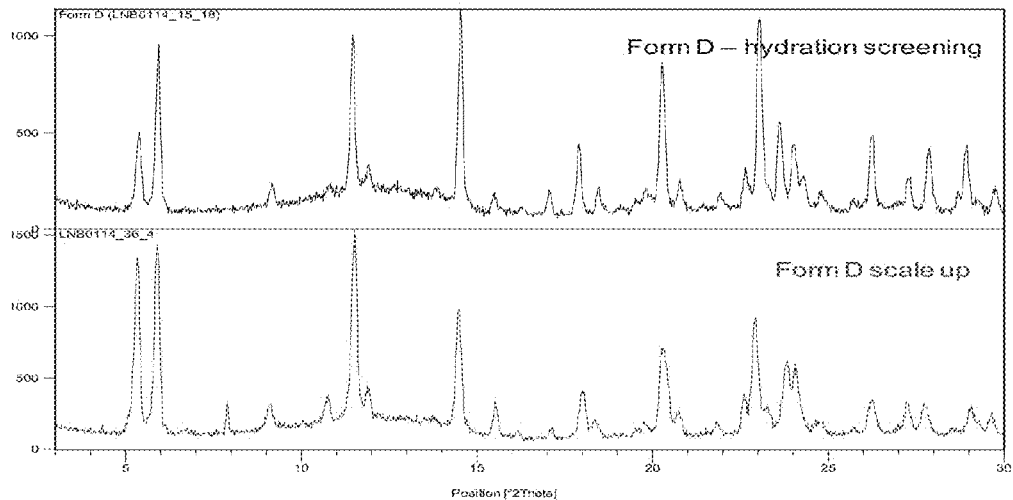
FIG. 190: Form D Compound A bis-mesylate—XRPD Analysis: Hydration Screen and Scale-Up

Form D was scaled up by slurrying amorphous Compound A bis-mesylate salt material in 2-propanol with $A_w$=0.60 at about 22° C. for about 72 hours (FIG. 190).

PLM analysis indicated the material to be birefringent with a flat rod/plate-like morphology (FIG. 191).

Figure 192:
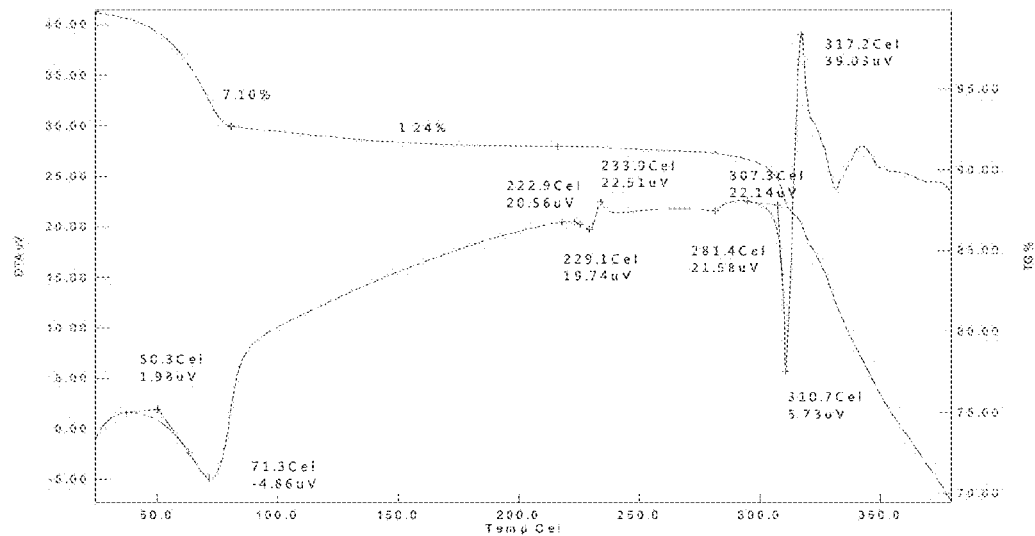
FIG. 192: Form D Compound A bis-mesylate—TG/DTA Analysis after air drying at ambient temperature for about 3 days
Figure 193:
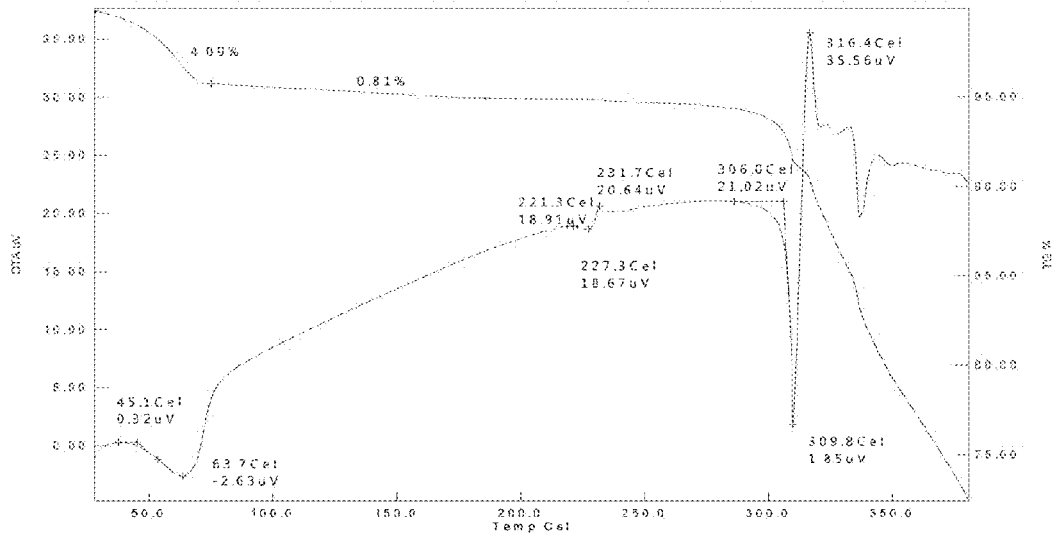
FIG. 193: Form D Compound A bis-mesylate—TG/DTA Analysis after drying under vacuum at ambient temperature for 1 day

After air drying at ambient temperature for about 3 days, TG/DTA showed an initial endotherm at onset about 50.3° C. (peak 71.3° C.) corresponding with a 7.10% weight loss in the TG trace. A further 1.24% gradual weight loss was observed between about 75° C. and 220° C. The DTA trace also showed a small endothermic/exothermic event between about 222° C. and 235° C., a small endotherm at about 281.4° C. and a final sharp endotherm at onset about 307.3° C. (peak 310.7° C.) (FIG. 192). After drying under vacuum at ambient temperature for a further 1 day, TG/DTA showed an initial endotherm at onset about 45.1° C. (peak 63.7° C.) corresponding with a 4.09% weight loss in the TG trace. A further 0.81% gradual weight loss was observed between about 75° C. and 180° C. The DTA trace also showed a small endothermic/exothermic event between about 221° C. and 235° C. and a final sharp endotherm at onset about 306.0° C. (peak 309.8° C.) (FIG. 193).

Figure 195:
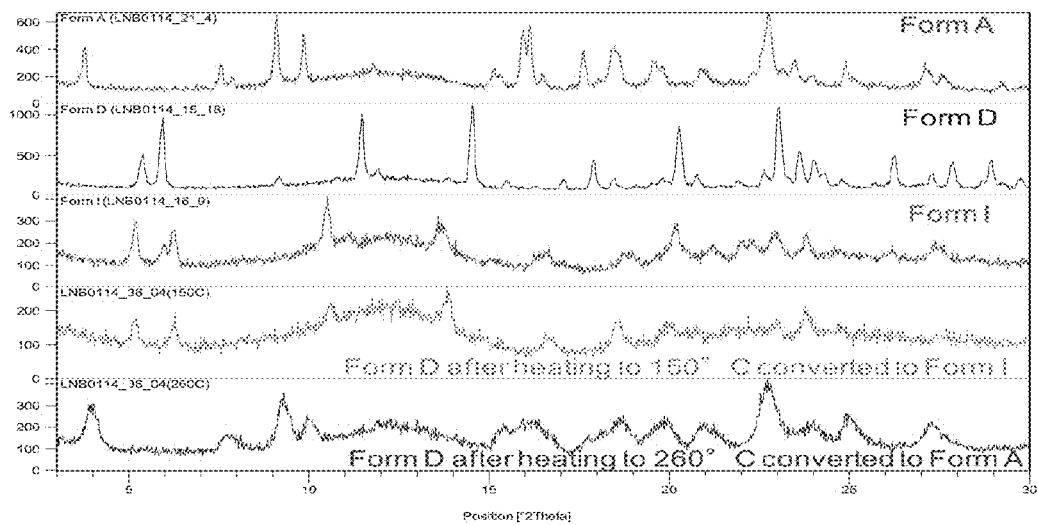
FIG. 195: Form D Compound A bis-mesylate—XRPD Analysis: Form A, Form D, Form I, Form D after heating to 150° C., and Form D after heating to 260° C.

To assess the form obtained after dehydration, as well as after the thermal transition which occurs between about 229° C. and 235° C., a sample of Form D was heated to about 150° C. in one experiment and 260° C. in a second experiment. The post-heating XRPD analyses carried out on the resulting solids gave diffractograms which were consistent with Form I and Form A for the 150° C. and 260° C. experiments, respectively (FIG. 195).

DSC analysis showed an initial broad endotherm at onset about 71.9° C. (peak 103.2° C.). A small endothermic/exothermic event was observed between about 229° C. and 235° C. A final endotherm was observed at onset about 300.9° C. (peak 304.1° C.) (FIG. 194).

A water content of about 3.8% was measured by Karl-Fischer Titration.

An HPLC purity of 99.9% was observed (FIG. 199).

HPLC concentration analysis indicated an aqueous solubility of about 352 mg/mL. XRPD analysis on the material after slurrying in deionised water for about 24 hours indicated that Form D had converted to Form E (FIG. 198).

Figure 196:
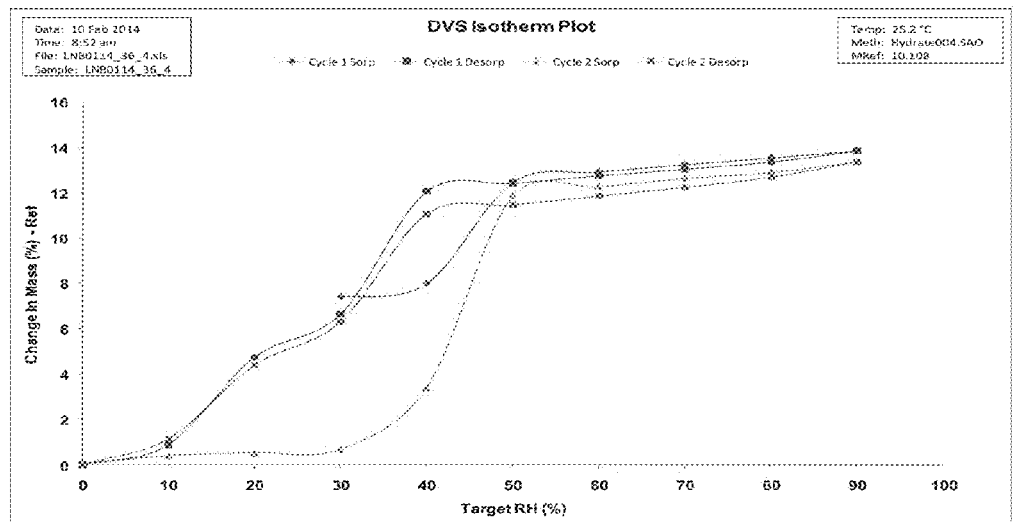
FIG. 196: Form D Compound A bis-mesylate—DVS Analysis

By DVS analysis, after dehydration at 0% RH, the second sorption cycle appeared to indicate rehydration between 30% and 50% RH with about 12% water uptake. The desorption isotherms indicated that when the material was hydrated a gradual loss of water and hence dehydration was observed as the relative humidity was decreased below 40% RH (FIG. 196). XRPD analysis carried out after DVS analysis gave a diffractogram consistent with Form I (FIG. 197).

Figure 201:
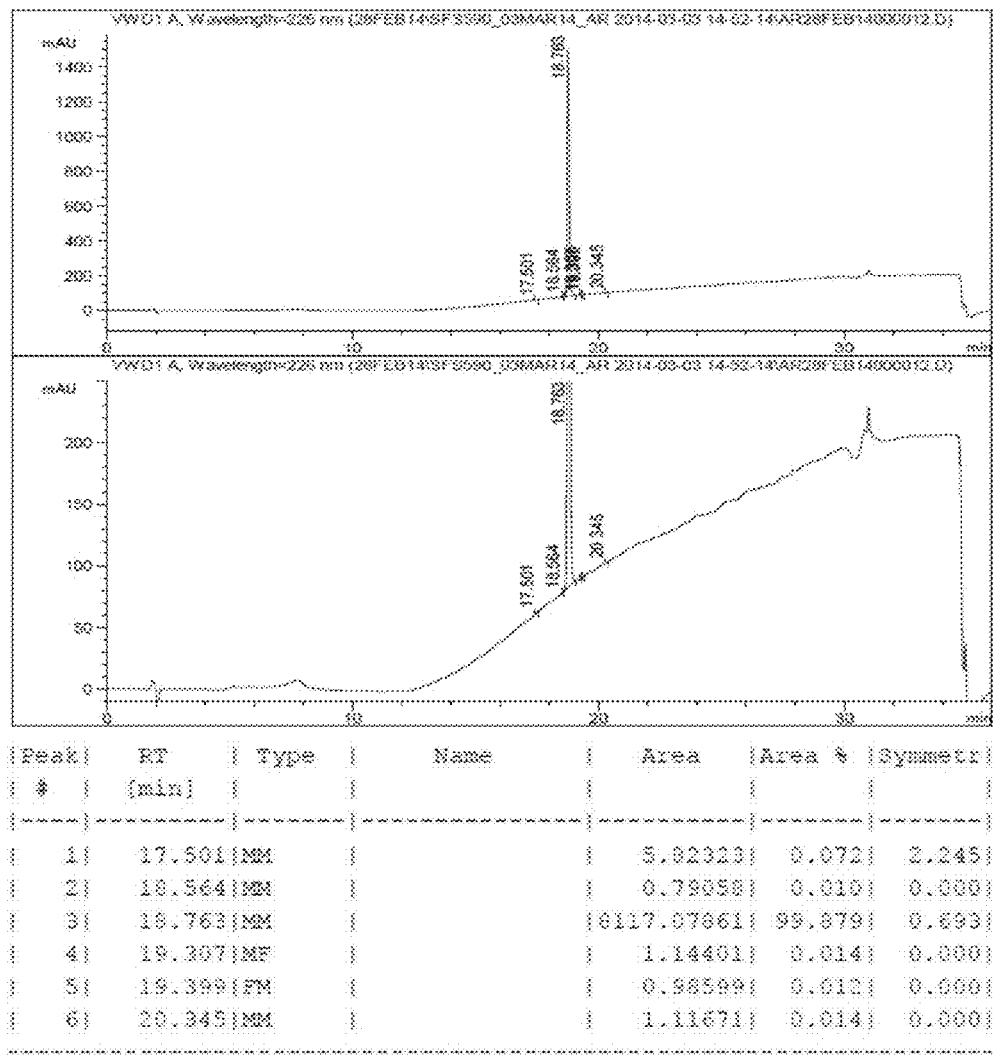
Figure 202:
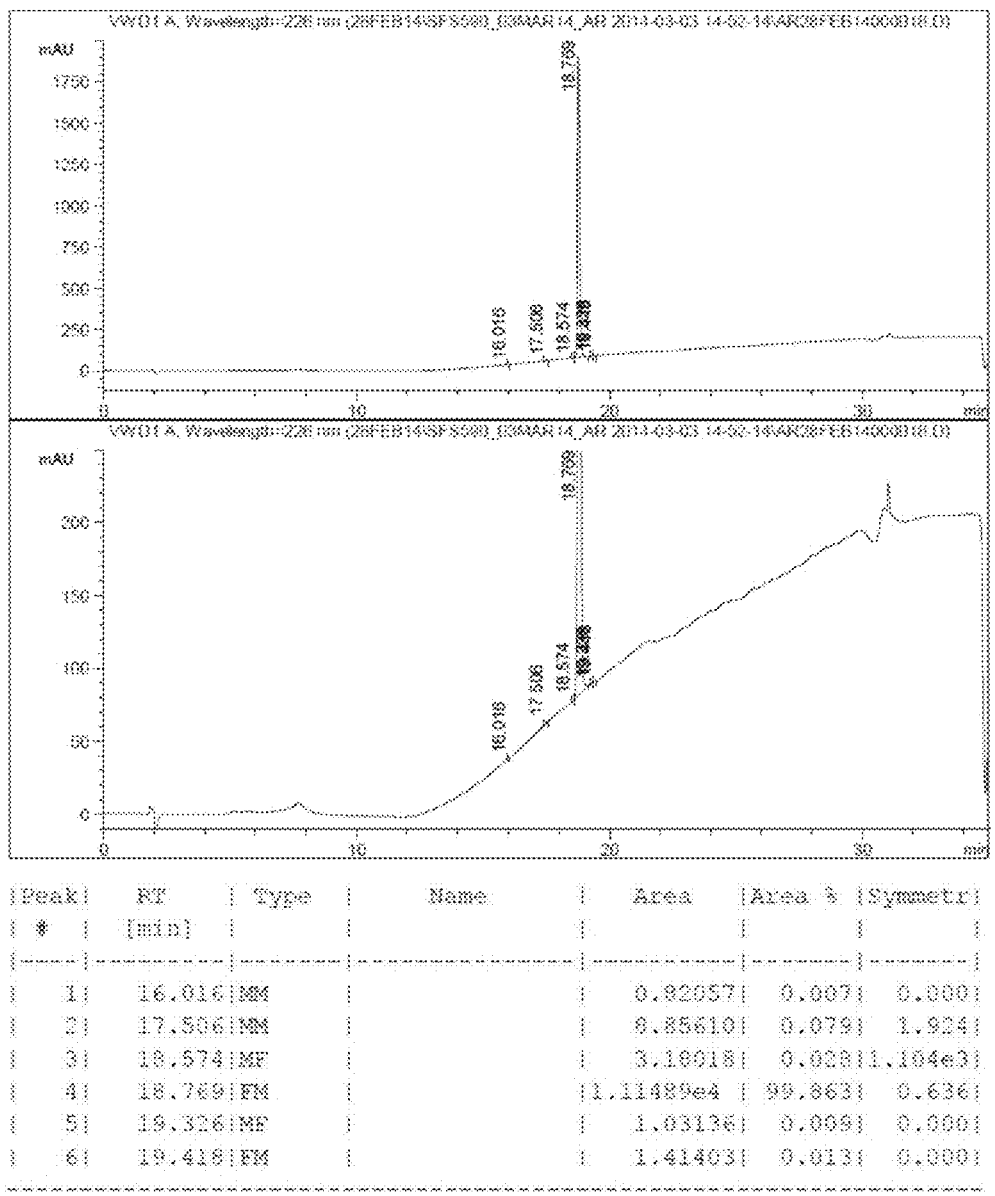

During stability studies, Form D remained unchanged in terms of polymorphic form at ambient temperature but converted to Form J at 40° C./75% RH and Form I at 80° C. (FIG. 203). HPLC analysis indicated a purity of about 99.9% at 40° C./75% RH (FIG. 200), about 99.9% at 80° C. (FIG. 202) and about 99.9% at ambient (FIG. 201).

The $^1$H NMR spectrum was observed to be consistent with the received material, with small amount of 2-propanol present. Ratio of API:2-propanol is about 1:0.25 (FIG. 204).

From the characterization, Form D was therefore observed to be a potential mixed hydrate and solvate.

Example 34

Characterization of Form E

Form E was scaled up by slurrying amorphous Compound A bis-mesylate salt material in acetone with $A_w$=0.89 at about 22° C. for about 72 hours (FIG. 205).

PLM analysis indicated the material to be birefringent with a long, rod-like morphology (FIG. 206).

Figure 207:
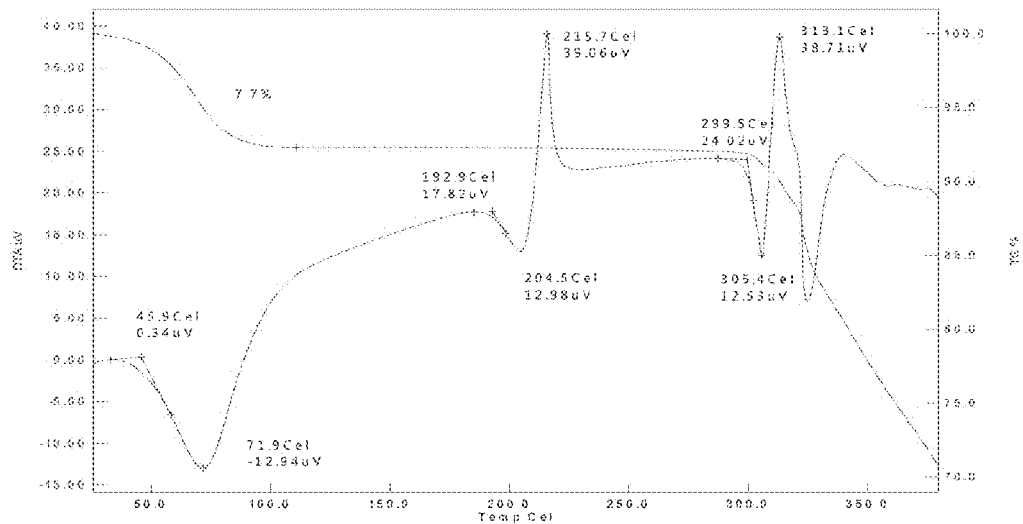
Figure 208:
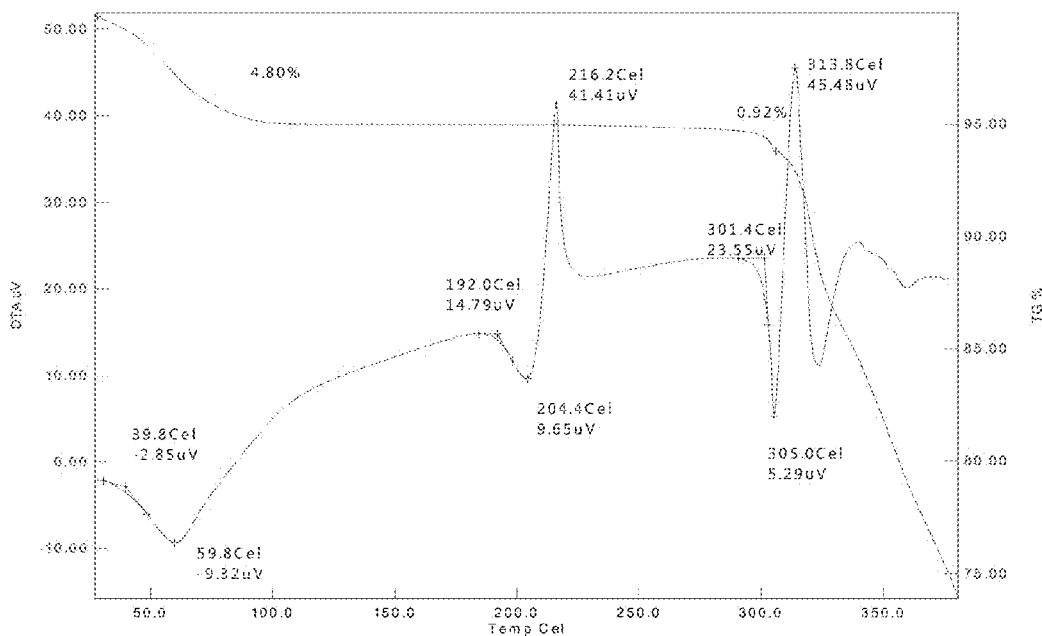

After air drying at ambient temperature for about 3 days, TG/DTA showed an initial endotherm at onset about 45.9° C. (peak 71.9° C.) corresponding with a 7.7% weight loss in the TG trace. The DTA trace also showed an endothermic/exothermic event between about 192° C. and 220° C. and a final sharp endotherm at onset about 299.5° C. (peak 305.4° C.) (FIG. 207). After drying under vacuum at ambient temperature for a further 1 day, TG/DTA showed an initial endotherm at onset about 39.8° C. (peak 59.8° C.) corresponding with a 4.8% weight loss in the TG trace. The DTA trace also showed an endothermic/exothermic event between about 192° C. and 220° C. and a final sharp endotherm at onset about 301.4° C. (peak 305.0° C.) (FIG. 208).

Figure 209:
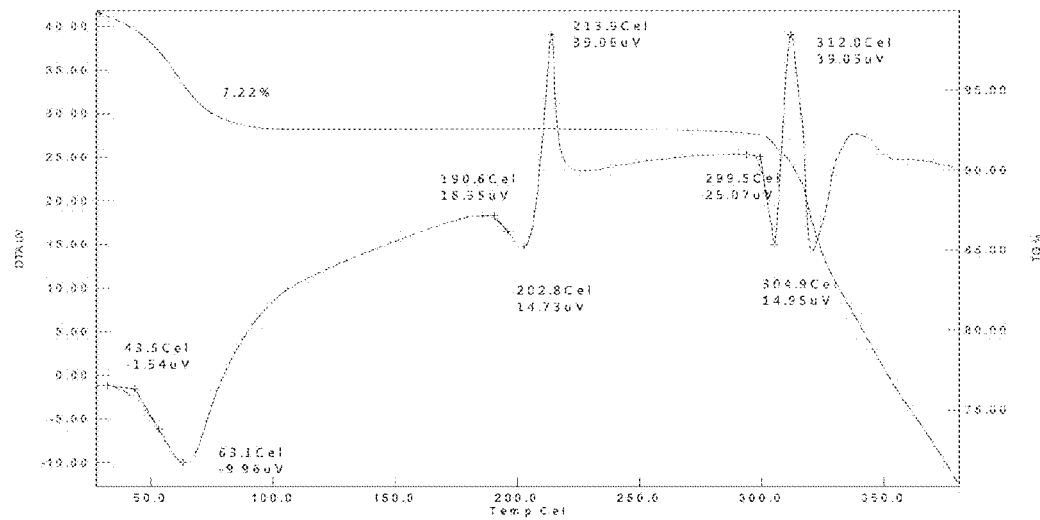

To assess the form obtained after dehydration of Form E, a sample was heated to 150° C. in one experiment and 260° C. in a second experiment. The post-heating XRPD analyses showed that Form E remained unchanged for the 150° C. heating experiment but converted to Form A at 260° C. (FIG. 211). As a result, TG/DTA was again carried out on the sample which had been heated to 150° C. and cooled back down to ambient temperature (FIG. 209). The TG/DTA analysis showed thermal events consistent with the initial Form E sample before vacuum drying. This indicated that after dehydration the material regained water/rehydrated upon exposure to ambient conditions.

DSC analysis showed a broad endotherm at onset about 58.1° C. (peak 86.5° C.). An endothermic/exothermic event was observed between about 189° C. and 215° C. A final endothermic event was present at onset about 299.1° C. (peak 303.7° C.) (FIG. 210).

KF analysis indicated a water content of about 6.2%.

An HPLC purity of 99.8% was observed (FIG. 215).

HPLC concentration analysis indicated an aqueous solubility of about 347 mg/mL.

XRPD analysis on the material after slurrying in deionised water for about 24 hours indicated that Form E remained unchanged (FIG. 214).

During DVS analysis, a first sorption cycle indicated the Form E hydrate to be non-hygroscopic. During the desorption cycle, dehydration occurred below 10% RH. During the second sorption cycle, a water uptake of about 2.78% was observed below 20% RH (corresponding to 1 mole equivalent of water) (FIGS. 212 and 213). A further 5.5% water was then rapidly taken up between 20% and 40% RH, likely indicating further hydration.

Figure 217:
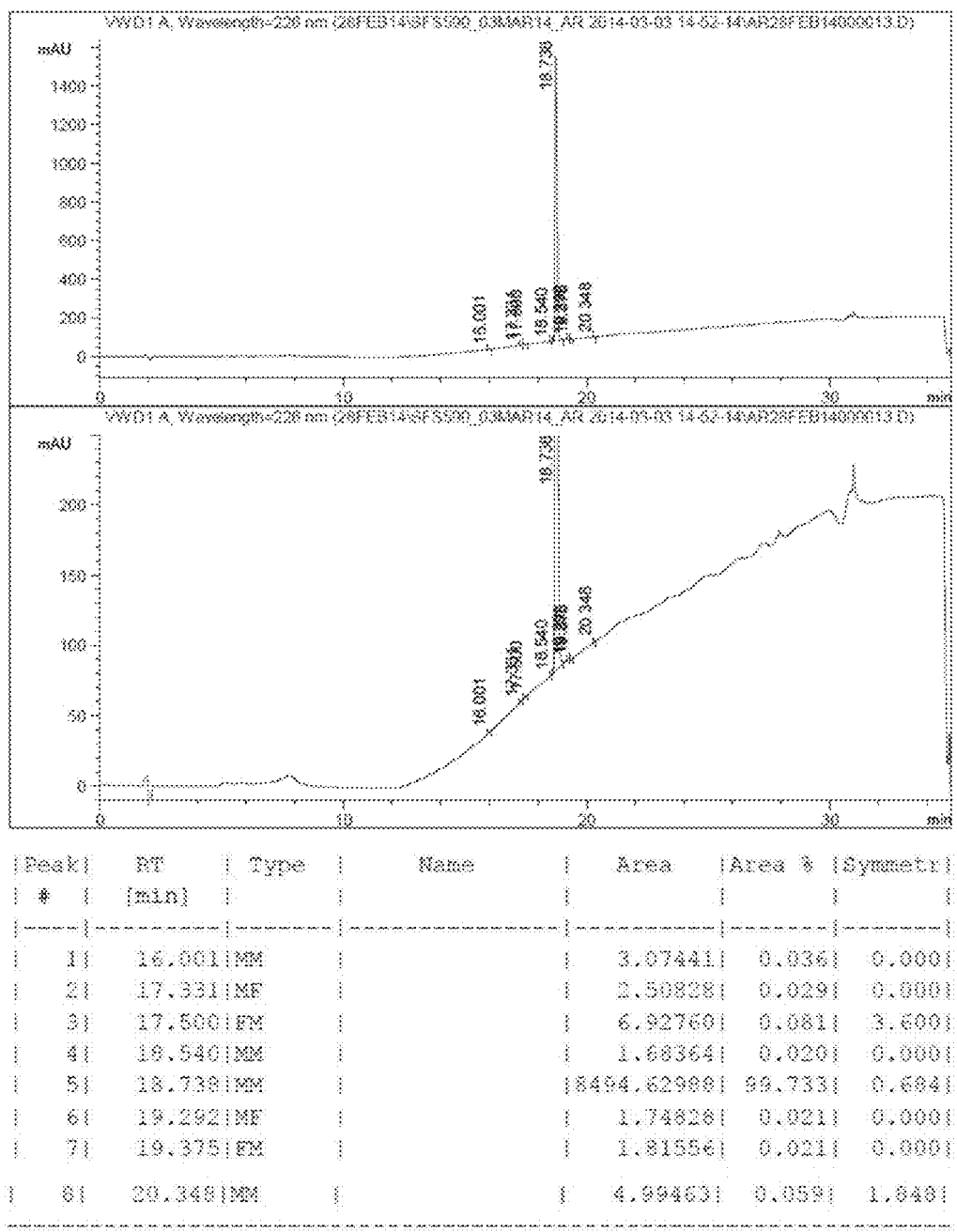
Figure 218:
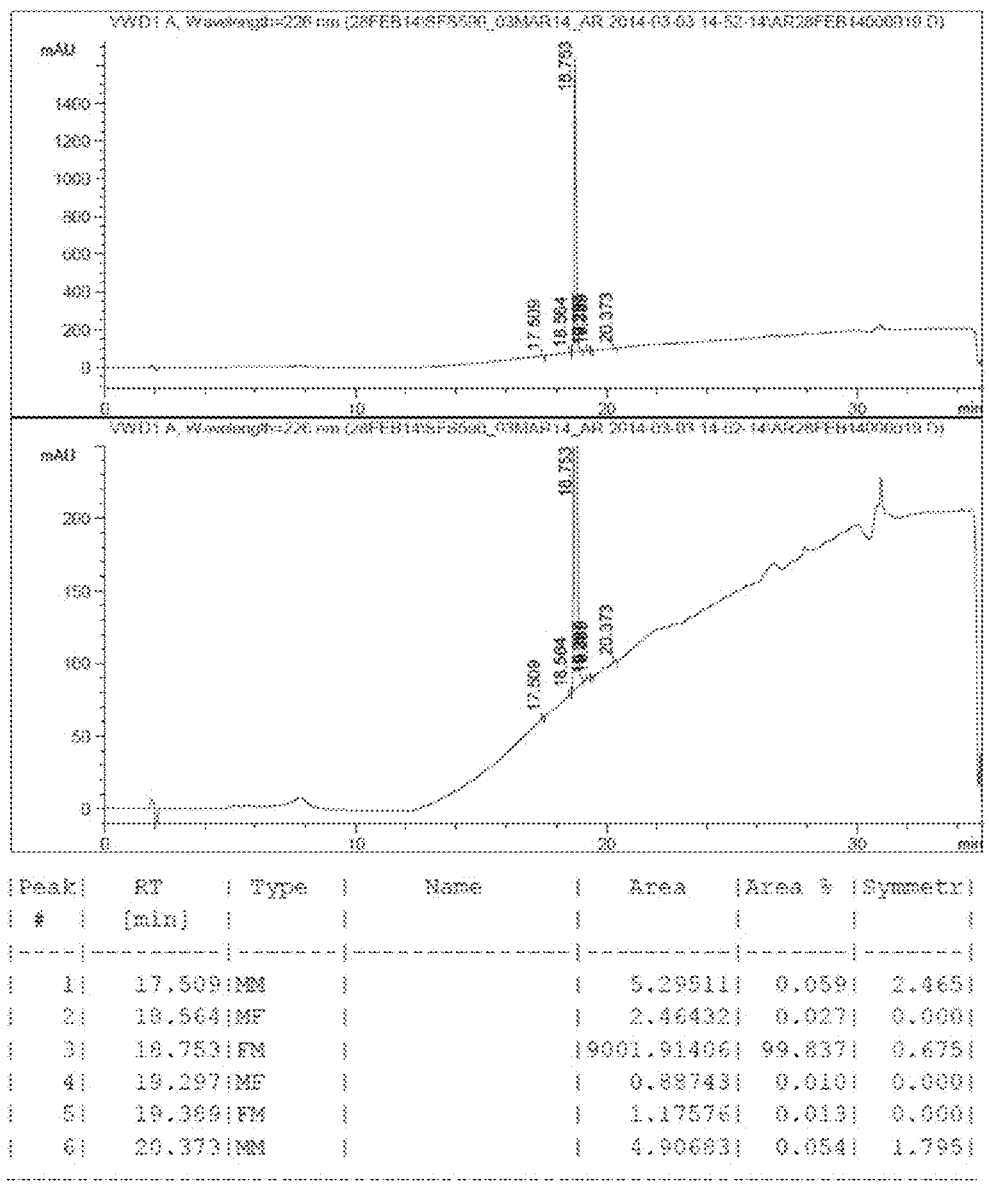

During stability studies Form E remained unchanged in terms of polymorphic form at 40° C./75% RH and ambient. After 80° C. storage, some differences were observed by XRPD analysis in comparison to Form E, likely due to dehydration during storage (FIG. 219). HPLC analyses indicated a purity of about 99.8% at 40° C./75% RH (FIG. 216), about 99.8% at 80° C. (FIG. 218) and about 99.7% at ambient temperature (FIG. 217).

The $^1$H NMR spectrum was observed to be consistent with the received material (FIG. 220).

From the characterization, Form E was therefore observed to be a hydrate.

Example 35

Characterization of Form F

Form F was observed during hydration screening in acetonitrile with a 0.76 water activity at 25° C. The Form F sample from the hydration screen was analyzed by TG/DTA: TG/DTA of Form F from the hydration screen showed an initial weight loss of 6.53% between about 25 and 120° C. Multiple endothermic and exothermic events are observed in the DTA (FIG. 221).

From the limited characterization, Form F is likely to be a potential solvate/hydrate.

Example 36

Characterization of Form G

Form G was observed in DMSO from anti-solvent (acetone) addition during polymorph screening. The Form G sample from the polymorph screen was analyzed by TG/DTA: TG/DTA of Form G from the polymorph screen showed a weight loss of 10.66% between about 25 and 200° C. Very small endothermic events were observed in the DTA between 150-180° C. (FIG. 222).

From the data, Form G is likely a DMSO solvate.

Example 37

Characterization of Form H

Form H was observed during hydration screening in acetonitrile with a 0.21 water activity at 50° C. The Form H sample from the hydration screen was analyzed by TG/DTA: TG/DTA of Form H from the hydration screen showed an initial weight loss of about 3.58% between about 25 and 60° C. A further weight loss of about 0.95% was observed between 60 and 240° C. The DTA trace showed an initial endotherm at about 45.8° C., an exotherm at about 202° C. and a final endotherm at onset about 306.6° C. (peak 309.8° C.) (FIG. 223).

From the limited characterization, Form H is likely to be a solvate/hydrate.

Example 38

Characterization of Form I

Form I was scaled up by evaporation of a methanol solution of Form A of Compound A bis-mesylate salt at about 50° C. under vacuum (FIG. 224).

PLM analysis indicated the material to be birefringent with a rod-like morphology (FIG. 225).

Figure 226:
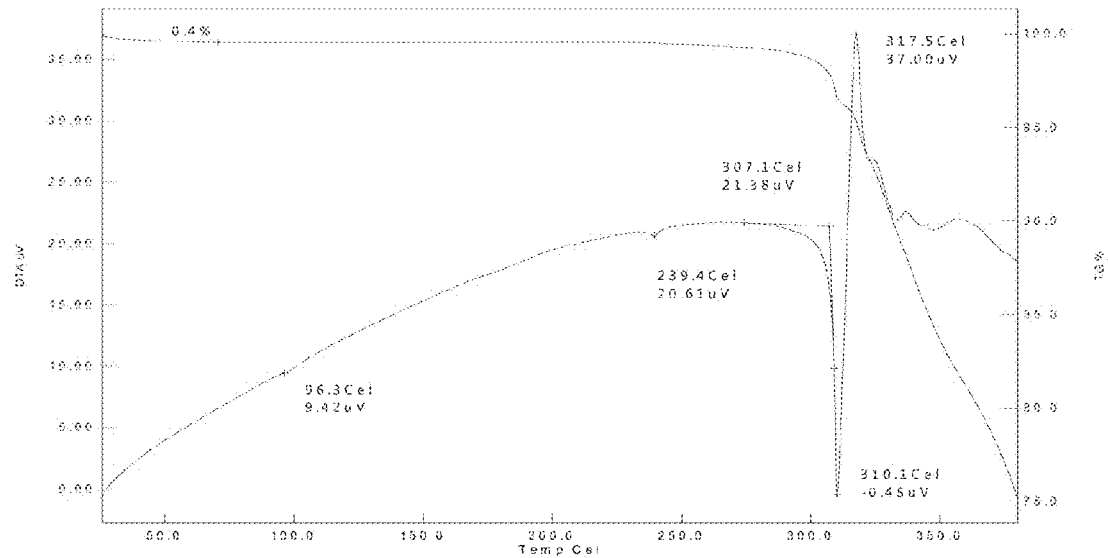

TG/DTA showed two very small endothermic events, at about 96.3° C. and about 239.4° C. A final endotherm was then observed at onset about 307.1° C. (peak 310.1° C.). A small 0.4% weight loss was observed below about 60° C., likely due to unbound solvent/water (FIG. 226).

DSC analysis showed a small endothermic event at onset about 231.9° C. (peak 235.7° C.), followed by a final endotherm at onset about 303.7° C. (peak 306.3° C.) (FIG. 227).

A water content of about 0.8% was measured by Karl-Fischer Titration.

An HPLC purity of 99.6% was observed (FIG. 231).

Figure 230:
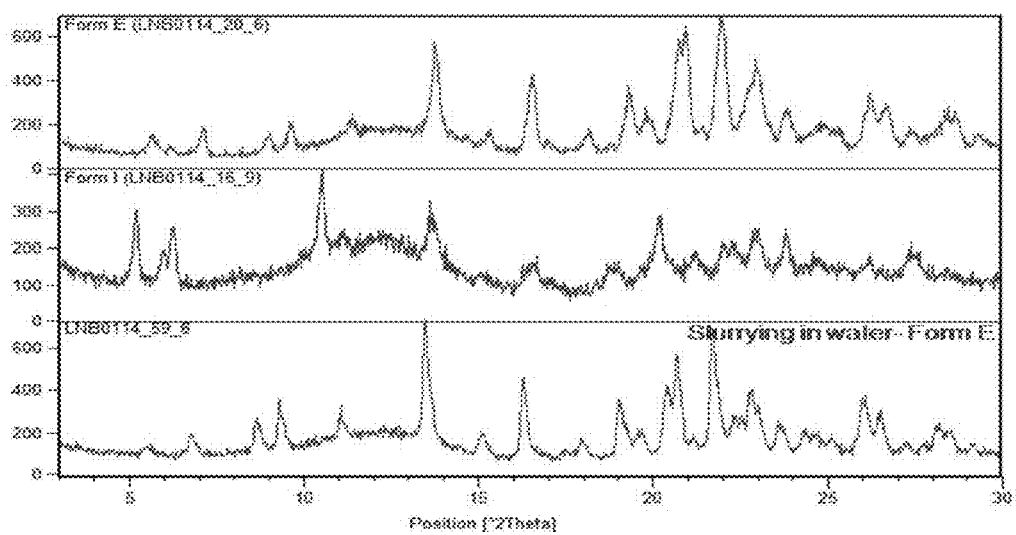

HPLC concentration analysis indicated an aqueous solubility of about 368 mg/mL. XRPD analysis on the material after slurrying in deionised water for about 24 hours indicated that Form I had converted to Form E (FIG. 230).

Figure 228:
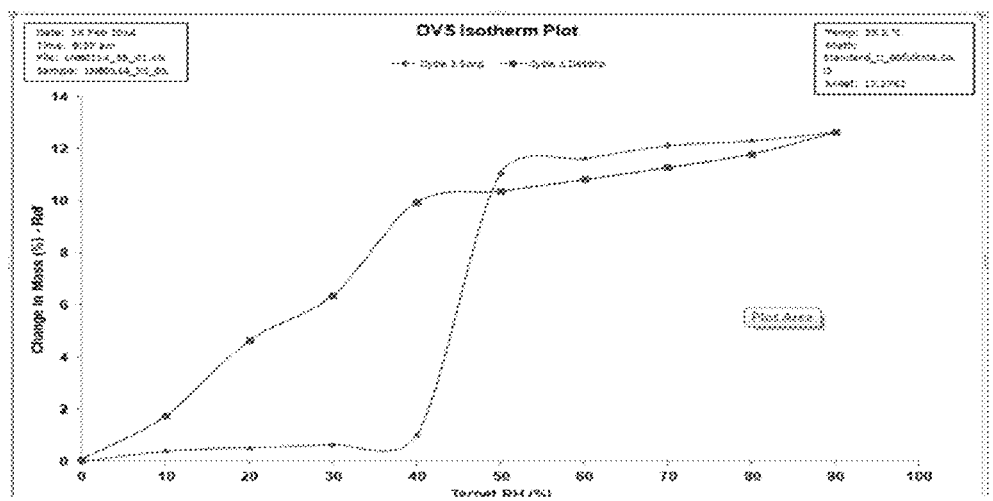
Figure 229:
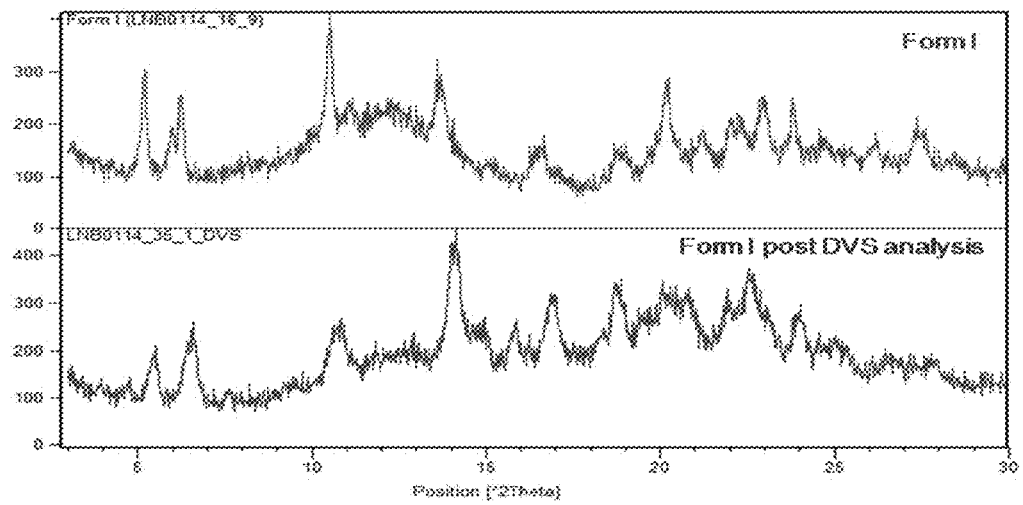

By DVS analysis, the sorption cycle appeared to indicate hydration above 40% RH with about 10% water uptake between 40% and 50% RH. The desorption cycle indicated a gradual loss of water/dehydration below 50% RH (FIGS. 228-229).

Figure 233:
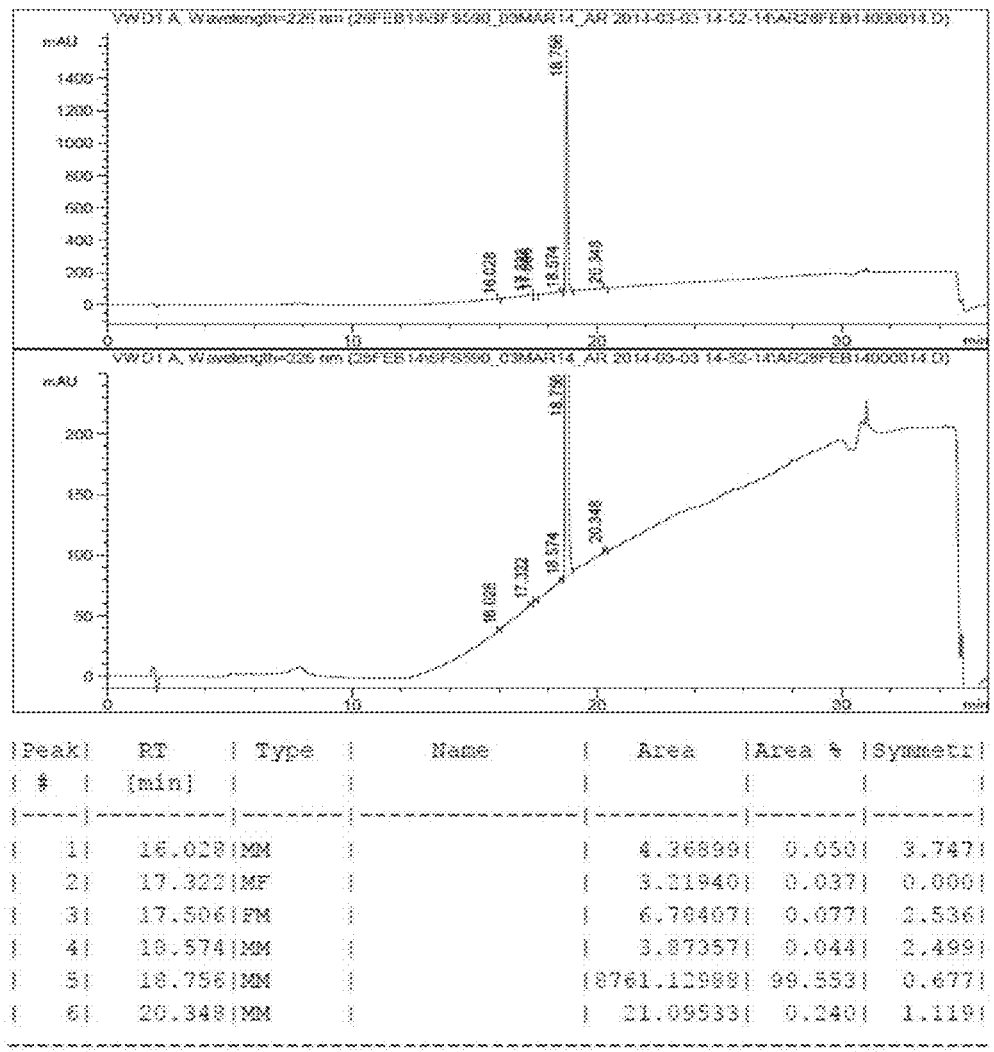
Figure 234:
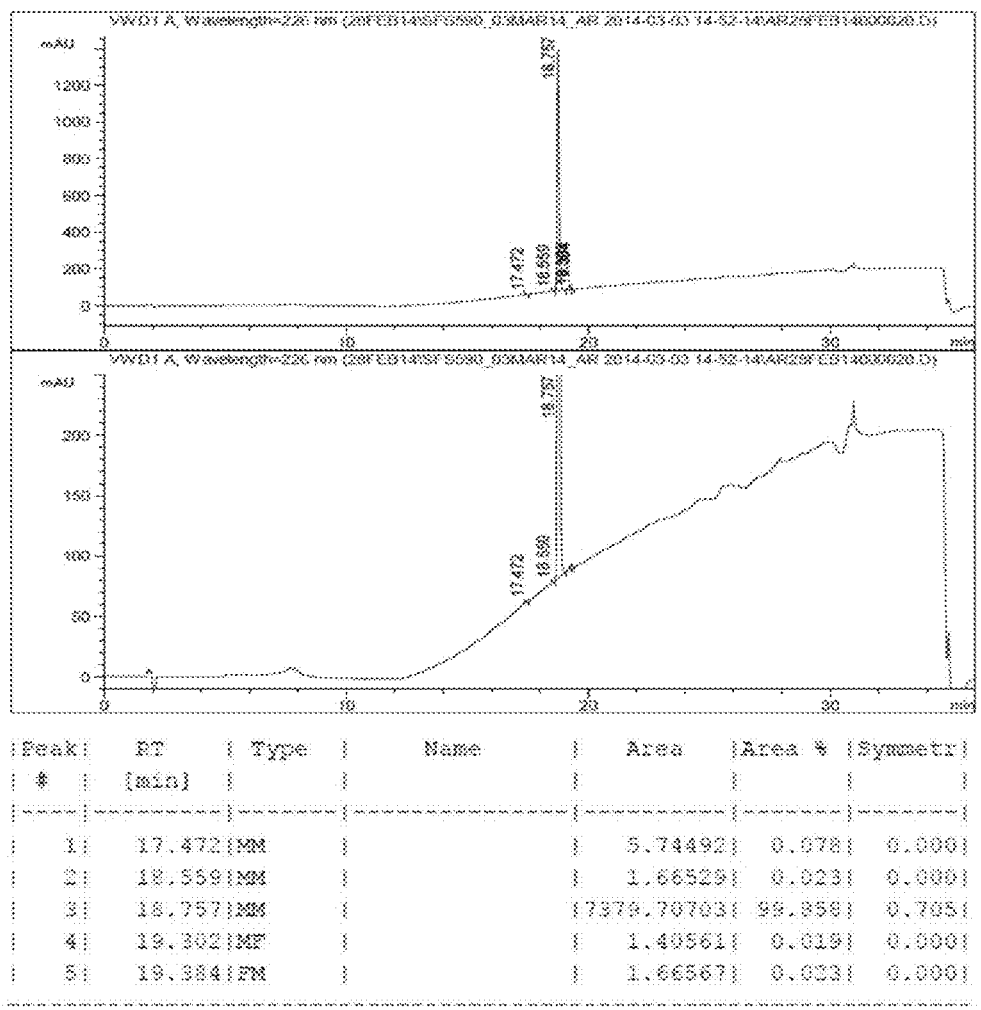

During stability studies, Form I remained unchanged in terms of polymorphic form at ambient and 80° C. storage, but conversion to Form J was observed for 40° C./75% RH storage (FIG. 235). HPLC analysis indicated a purity of about 99.8% at 40° C./75% RH (FIG. 232), about 99.9% at 80° C. (FIG. 234) and about 99.6% at ambient temperature (FIG. 233).

The $^1$H NMR spectrum was observed to be consistent with received material (FIG. 236).

From the characterization, Form I was therefore observed to be anhydrous.

Example 39

Characterization of Form J

A further polymorphic form was observed after DVS analysis of Form B. This form was assigned as Form J (FIG. 237).

TGA showed about 2.76% weight loss below about 90° C. The DTA trace showed an initial endothermic event at peak about 76.3° C. and a small endothermic event at peak about 227.3° C. followed by an exothermic event at peak about 233.3° C. A sharp endotherm was then observed at onset about 306.5° C. (peak 309.6° C.) (FIG. 238).

From the limited characterization, Form J is likely to be a hydrate.

Example 40

Summary of Each Characterized Form

A summary of the characterization of the successfully prepared forms is presented in Table 21 below.

temperatures above about 107° C., which was assigned as Form K.

The invention claimed is:
1. A polymorph of a mesylate salt of Compound A:

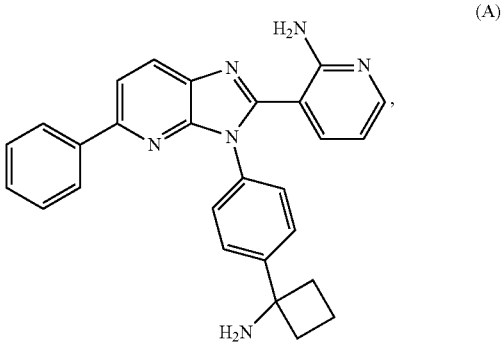 [SMILES: Nc1ncccc1-c1nc2ccc(-c3ccccc3)nc2n1-c1ccc(C2(N)CCC2)cc1]

(A)

selected from Form A, Form B, Form C, Form D, Form E, Form F, Form G, Form H, Form I, Form J, and Form K, wherein:
the Form A is characterized by having X-ray powder diffraction peaks at approximately 9.4 and 23.0° 2θ using Cu Kα radiation, or at 9.1 and 22.8° 2θ using Cu Kα radiation,
the Form B is characterized by having X-ray powder diffraction peaks at approximately 6.2 and 14.3° 2θ using Cu Kα radiation, or at 6.0 and 14.6° 2θ using Cu Kα radiation,

TABLE 21

A Summary of characterization of polymorphs

| Analysis | Form A | Form B | Form C | Form D | Form E | Form I |
|---|---|---|---|---|---|---|
| XRPD (Crystallity) | Crystalline | Crystalline | Crystalline | Crystalline | Crystalline | Partially Crystalline |
| PLM (Morphology) | Needle-like | Small rod/needle-like | Small block-like | Flat rod/plate-like | Long, rod-like | Rod-like |
| Nature of Solid Form | Anhydrous | Potential mixed solvate/hydrate | Anhydrous | Potential mixed solvate/hydrate | Hydrate | Anhydrous |
| KF (Water content) | 1.1% | 2.4% | 0.3% | 3.8% | 6.2% | 0.8% |
| Aqueous Solubility | 383 mg/mL Converted to Form E | 360 mg/mL Converted to Form E | 367 mg/mL Converted to Form E | 352 mg/mL Converted to Form E | 347 mg/mL Form E | 368 mg/mL Converted to Form E |
| HPLC (Purity) | 99.8% | 99.7% | 99.7% | 99.9% | 99.8% | 99.6% |
| $^1$H NMR | Consistent with received materials | Consistent with received materials with 2-propanol present | Consistent with received material | Consistent with received materials with 2-propanol present | Consistent with received material | Consistent with received material |
| Hot Stage Microscopy | Melting was observed at 315° C. No other thermal events were observed. | Melting was observed at 305° C. No other thermal events were observed. | Melting was observed at 305° C. No other thermal events were observed. | Melting was observed at 320° C. No other thermal events were observed. | Melting was observed at 211° C. Recrystallised at 250° C. | Melting was observed at 300° C. No other thermal events were observed. |
| DVS and post-DVS XRPD | Moderately hygroscopic Form A post analysis | Gradual uptake between 0 and 90% RH. Converted to Form J post analysis | Non-hygroscopic Form C post analysis | Hydration occurs between 30 and 50% RH Converted to Form I post analysis | Two hydration steps below 30% RH Form E post analysis | Hydration occurs between 40 and 50% RH Form I post analysis |

The characterization of the various forms resulted in an additional form being identified after DVS analysis of Form B, which was assigned as Form J. Variable temperature XRPD analysis of Form A also indicated a different form at the Form C is characterized by having X-ray powder diffraction peaks at approximately 20.3 and 22.8° 2θ using Cu Kα radiation, or at 20.1 and 22.6° 2θ using Cu Kα radiation, the Form D is characterized by having X-ray powder diffraction peaks at approximately 14.5 and 23.0° 2θ using Cu Kα radiation,
the Form E is characterized by having X-ray powder diffraction peaks at approximately 20.9 and 21.9° 2θ using Cu Kα radiation,
the Form F is characterized by having X-ray powder diffraction peaks at approximately 16.7 and 17.0° 2θ using Cu Kα radiation,
the Form G is characterized by having X-ray powder diffraction peaks at approximately 5.8 and 22.1° 2θ using Cu Kα radiation,
the Form H is characterized by having X-ray powder diffraction peaks at approximately 10.9 and 22.8° 2θ using Cu Kα radiation,
the Form I is characterized by having X-ray powder diffraction peaks at approximately 5.2 and 10.5° 2θ using Cu Kα radiation,
the Form J is characterized by having X-ray powder diffraction peaks at approximately 17.0 and 22.8° 2θ using Cu Kα radiation, and
the Form K is characterized by having X-ray powder diffraction peaks at approximately 9.2 and 10.0° 2θ using Cu Kα radiation.

2. The Form A polymorph of claim 1, characterized by having X-ray powder diffraction peaks at approximately 9.4, 15.5, 18.8, and 23.0° 2θ using Cu Kα radiation.

3. The Form A polymorph of claim 1, characterized by having X-ray powder diffraction peaks at approximately 9.1, 15.1, 16.0, 18.5, 22.8, and 22.9° 2θ using Cu Kα radiation.

4. The Form B polymorph of claim 1, characterized by having X-ray powder diffraction peaks at approximately 6.2, 6.6, 14.3, and 15.3° 2θ using Cu Kα radiation.

5. The Form B polymorph of claim 1, characterized by having X-ray powder diffraction peaks at approximately 6.0, 6.4, 11.1, 14.6, 15.1, and 23.7° 2θ using Cu Kα radiation.

6. The Form C polymorph of claim 1, characterized by having X-ray powder diffraction peaks at approximately 17.6, 18.4, 19.3, 19.7, and 22.8° 2θ using Cu Kα radiation.

7. The Form C polymorph of claim 1, characterized by having X-ray powder diffraction peaks at approximately 17.5, 18.2, 19.0, 19.6, 20.1, and 22.6° 2θ using Cu Kα radiation.

8. The Form E polymorph of claim 1, characterized by having X-ray powder diffraction peaks at approximately 13.7, 20.6, 20.9, 21.9, and 23.0° 2θ using Cu Kα radiation.

9. The Form F polymorph of claim 1, characterized by having X-ray powder diffraction peaks at approximately 16.7, 17.0, 19.5, 20.3, and 24.4° 2θ using Cu Kα radiation.

10. The Form G polymorph of claim 1, characterized by having X-ray powder diffraction peaks at approximately 5.8, 14.9, 16.3, 22.1, and 23.7° 2θ using Cu Kα radiation.

11. The Form H polymorph of claim 1, characterized by having X-ray powder diffraction peaks at approximately 6.1, 10.9, 12.4, 15.9, and 22.8° 2θ using Cu Kα radiation.

12. The Form I polymorph of claim 1, characterized by having X-ray powder diffraction peaks at approximately 5.2, 6.2, 10.5, 20.2, and 23.0° 2θ using Cu Kα radiation.

13. The Form J polymorph of claim 1, characterized by having X-ray powder diffraction peaks at approximately 14.6, 17.0, 21.9, 22.8, and 24.8° 2θ using Cu Kα radiation.

14. The Form K polymorph of claim 1, characterized by having X-ray powder diffraction peaks at approximately 9.2, 10.0, 15.7, 20.0, and 23.8° 2θ using Cu Kα radiation.

15. A polymorph of the free base of Compound A:

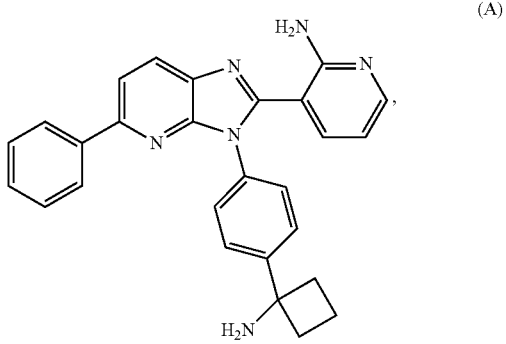 [SMILES: Nc1ncccc1-c1nc2ccc(-c3ccccc3)nc2n1-c1ccc(C2(N)CCC2)cc1]

selected from Form 1, Form 2, Form 3, and Form 4, wherein:
the Form 1 is characterized by having X-ray powder diffraction peaks at approximately 22.0 and 25.0° 2θ using Cu Kα radiation,
the Form 2 is characterized by having X-ray powder diffraction peaks at approximately 18.4 and 19.3° 2θ using Cu Kα radiation,
the Form 3 is characterized by having X-ray powder diffraction peaks at approximately 15.1 and 23.4° 2θ using Cu Kα radiation, and
the Form 4 is characterized by having X-ray powder diffraction peaks at approximately 17 and 23° 2θ using Cu Kα radiation.

16. The Form 1 polymorph of claim 15, is characterized by having X-ray powder diffraction peaks at approximately 8.3, 17.1, 22.0, and 25.0° 2θ using Cu Kα radiation.

17. The Form 2 polymorph of claim 15, is characterized by having X-ray powder diffraction peaks at approximately 15.8, 18.4, 19.3, and 20.1° 2θ using Cu Kα radiation.

18. The Form 3 polymorph of claim 15, is characterized by having X-ray powder diffraction peaks at approximately 15.1, 18.8, 21.0, and 23.4° 2θ using Cu Kα radiation.

19. The Form 4 polymorph of claim 15, is characterized by having X-ray powder diffraction peaks at approximately 15, 17, 23, and 26° 2θ using Cu Kα radiation.

20. A method of modulating AKT in a subject in need thereof, comprising administering to the subject a therapeutically effective amount of any of the Form A, Form B, Form C, Form D, Form E, Form F, Form G, Form H, Form I, Form J, or Form K polymorph of claim 1.

21. A method of modulating AKT in a subject in need thereof, comprising administering to the subject a therapeutically effective amount of any of the Form 1, Form 2, Form 3, or Form 4 polymorph of claim 15.

22. The Form A polymorph of claim 1, characterized by having X-ray powder diffraction peaks at approximately 4.1, 7.8, 9.4, 10.1, 12.1, 15.5, 16.2, 18.8, 19.9, 21.1, 23.0, 25.1 and 27.4° 2θ using Cu Kα radiation.

23. The Form A polymorph of claim 1, characterized by having X-ray powder diffraction peaks at approximately 3.8, 7.6, 9.1, 9.9, 15.1, 16.0, 16.1, 18.5, 22.8, 22.9, and 23.2° 2θ using Cu Kα radiation.

24. The Form B polymorph of claim 1, characterized by having X-ray powder diffraction peaks at approximately 6.2, 6.6, 11.3, 14.3, 15.3, 22.8, and 26.9° 2θ using Cu Kα radiation.

25. The Form B polymorph of claim 1, characterized by having X-ray powder diffraction peaks at approximately 6.0, 6.4, 11.1, 14.6, 15.1, 17.3, 22.5, 22.7, 23.7, and 27.0° 2θ using Cu Kα radiation.

26. The Form C polymorph of claim 1, characterized by having X-ray powder diffraction peaks at approximately 6.2, 8.9, 9.8, 10.1, 13.7, 18.4, 19.3, 19.7, 22.8, and 26.8° 2θ using Cu Kα radiation.

27. The Form C polymorph of claim 1, characterized by having X-ray powder diffraction peaks at approximately 12.5, 16.6, 17.5, 18.2, 19.0, 19.6, 20.1, 21.7, 22.6, 23.0, 23.6, 24.0, 26.6, and 27.2° 2θ using Cu Kα radiation.

28. The Form D polymorph of claim 1, characterized by having X-ray powder diffraction peaks at approximately 5.9, 11.5, 14.5, 20.3, and 23.0° 2θ using Cu Kα radiation.

29. The Form D polymorph of claim 1, characterized by having X-ray powder diffraction peaks at approximately 5.4, 5.9, 11.5, 14.5, 17.9, 20.3, 23.0, 23.6, 24.0, 26.2, 27.8, and 28.9° 2θ using Cu Kα radiation.

30. The Form E polymorph of claim 1, characterized by having X-ray powder diffraction peaks at approximately 8.9, 11.3, 13.7, 16.5, 19.3, 20.6, 20.9, 21.9, 23.0, 23.8, and 26.2° 2θ using Cu Kα radiation.

31. The Form F polymorph of claim 1, characterized by having X-ray powder diffraction peaks at approximately 4.8, 7.2, 15.6, 16.7, 17.0, 19.5, 20.3, 21.7, 24.0, and 24.4° 2θ using Cu Kα radiation.

32. The Form G polymorph of claim 1, characterized by having X-ray powder diffraction peaks at approximately 5.8, 10.8, 14.9, 16.3, 17.7, 22.1, 23.1, 23.7, 24.5, and 26.5° 2θ using Cu Kα radiation.

33. The Form H polymorph of claim 1, characterized by having X-ray powder diffraction peaks at approximately 6.1, 10.1, 10.9, 12.4, 15.7, 15.9, 16.4, 20.4, 20.8, and 22.8° 2θ using Cu Kα radiation.

34. The Form I polymorph of claim 1, characterized by having X-ray powder diffraction peaks at approximately 5.2, 6.2, 10.5, 11.1, 13.6, 20.2, 22.0, 22.3, 23.0, and 23.8° 2θ using Cu Kα radiation.

35. The Form J polymorph of claim 1, characterized by having X-ray powder diffraction peaks at approximately 14.6, 17.0, 19.7, 20.4, 21.9, 22.8, 24.8, 25.3, 26.7, and 27.7° 2θ using Cu Kα radiation.

36. The Form K polymorph of claim 1, characterized by having X-ray powder diffraction peaks at approximately 4.1, 9.2, 10.0, 15.7, 17.5, 19.3, 20.0, 21.5, 23.2, and 23.8° 2θ using Cu Kα radiation.

37. The Form 1 polymorph of claim 15, characterized by having X-ray powder diffraction peaks at approximately 8.3, 9.5, 12.9, 14.1, 15.2, 16.6, 17.1, 19.2, 19.4, 19.6, 21.2, 22.0, 22.4 and 25.0° 2θ using Cu Kα radiation.

38. The Form 2 polymorph of claim 15, characterized by having X-ray powder diffraction peaks at approximately 8.3, 8.8, 11.6, 13.3, 15.8, 18.4, 19.3, 20.1, 20.9, 21.4, 23.2, 25.9 and 26.6° 2θ using Cu Kα radiation.

39. The Form 3 polymorph of claim 15, characterized by having X-ray powder diffraction peaks at approximately 6.4, 7.6, 8.4, 11.7, 15.1, 16.7, 18.8, 21.0, and 23.4° 2θ using Cu Kα radiation.

40. The Form 4 polymorph of claim 15, characterized by having X-ray powder diffraction peaks at approximately 8, 14, 15, 17, 22, 23, and 26° 2θ using Cu Kα radiation.

* * * * *